(12) United States Patent
Campbell et al.

(10) Patent No.: US 11,957,671 B2
(45) Date of Patent: Apr. 16, 2024

(54) BENZODIOXANE MODULATORS OF LEUKOTRIENE A4 HYDROLASE (LTA4H) FOR PREVENTION AND TREATMENT OF AGING-ASSOCIATED DISEASES

(71) Applicant: Alkahest, Inc., San Carlos, CA (US)

(72) Inventors: Meghan Kerrisk Campbell, San Francisco, CA (US); Eva Czirr, Foster City, CA (US); Reema Harish, Redwood City, CA (US)

(73) Assignee: Alkahest, Inc., San Carlos, CA (US)

( * ) Notice: Subject to any disclaimer, the term of this patent is extended or adjusted under 35 U.S.C. 154(b) by 0 days.

(21) Appl. No.: 17/977,687

(22) Filed: Oct. 31, 2022

(65) Prior Publication Data

US 2023/0146135 A1   May 11, 2023

Related U.S. Application Data

(60) Provisional application No. 63/342,572, filed on May 16, 2022, provisional application No. 63/327,496, filed on Apr. 5, 2022, provisional application No. 63/293,560, filed on Dec. 23, 2021, provisional application No. 63/274,222, filed on Nov. 1, 2021.

(51) Int. Cl.
*A61K 31/453* (2006.01)
*A61P 25/28* (2006.01)

(52) U.S. Cl.
CPC ............ *A61K 31/453* (2013.01); *A61P 25/28* (2018.01)

(58) Field of Classification Search
CPC .................................................. A61K 31/453
USPC ....................................................... 514/321
See application file for complete search history.

(56) References Cited

U.S. PATENT DOCUMENTS

| | | |
|---|---|---|
| 4,185,156 A | 1/1980 | Umezawa et al. |
| 4,281,180 A | 7/1981 | Umezawa et al. |
| 4,918,092 A | 4/1990 | Frenette et al. |
| 5,120,758 A | 6/1992 | Satoh |
| 5,700,816 A | 12/1997 | Isakson et al. |
| 6,180,637 B1 | 1/2001 | Shindler et al. |
| 7,098,222 B2 | 8/2006 | Altenbach et al. |
| 7,429,665 B2 | 9/2008 | Verhoset et al. |
| 7,674,802 B2 | 3/2010 | Sandanayaka et al. |
| 8,278,302 B2 | 10/2012 | Grundl et al. |
| 8,551,982 B2 | 10/2013 | Abeywardane et al. |
| 8,680,280 B2 | 3/2014 | Duran et al. |
| 8,742,115 B2 | 6/2014 | Frank et al. |
| 8,946,203 B2 | 2/2015 | Abeywardane et al. |
| 9,233,950 B2 | 1/2016 | Frank et al. |
| 10,213,421 B2 | 2/2019 | Fetscher et al. |
| 10,245,285 B2 | 4/2019 | Braithwaite et al. |
| 10,357,513 B2 | 7/2019 | Braithwaite et al. |
| 2002/0132822 A1 | 9/2002 | Noe et al. |
| 2005/0272051 A1 | 12/2005 | Helgadottir et al. |
| 2006/0019269 A1 | 1/2006 | Helgadottir et al. |
| 2006/0223792 A1 | 10/2006 | Butler et al. |
| 2006/0227392 A1 | 10/2006 | Fukusaka |
| 2007/0066820 A1 | 3/2007 | Sandanayaka et al. |
| 2007/0149544 A1 | 6/2007 | Sandanayaka et al. |
| 2013/0196973 A1 | 8/2013 | Abeywardane et al. |
| 2013/0236468 A1 | 9/2013 | Bylock |
| 2013/0244996 A1 | 9/2013 | Abeywardane et al. |
| 2014/0031339 A1 | 1/2014 | Abeywardane et al. |
| 2015/0018333 A1 | 1/2015 | Abeywardane et al. |
| 2015/0018334 A1 | 1/2015 | Abeywardane et al. |
| 2016/0272649 A1 | 9/2016 | Arnaiz et al. |
| 2017/0319567 A1 | 11/2017 | Nivens et al. |
| 2018/0110839 A1 | 4/2018 | Bell et al. |
| 2018/0117014 A1 | 5/2018 | Springman et al. |
| 2018/0127424 A1 | 5/2018 | Guilford |
| 2019/0105314 A1 | 4/2019 | Braithwaite et al. |
| 2019/0111042 A1 | 4/2019 | Braithwaite et al. |
| 2019/0151300 A1 | 5/2019 | Fetscher et al. |
| 2019/0167719 A1 | 6/2019 | Braithwaite et al. |

FOREIGN PATENT DOCUMENTS

| | | |
|---|---|---|
| CA | 2076573 | 2/1993 |
| CA | 2280727 | 8/1998 |
| CL | 201601255 | 11/2016 |
| CL | 201702017 | 4/2018 |
| WO | WO1996010999 A2 | 4/1996 |
| WO | WO1996011192 A1 | 4/1996 |
| WO | WO2004029237 A1 | 4/2004 |
| WO | WO2004056369 A1 | 7/2004 |
| WO | WO2005011736 A1 | 2/2005 |
| WO | WO2007040682 A1 | 4/2007 |
| WO | WO2008052086 A1 | 5/2008 |

(Continued)

OTHER PUBLICATIONS

Jung et al, Cerebral autosomal dominant arteriopathy with subcortical infarcts and leukoencephalopathy: a clinicopathological and genetic study of a Swiss family, Journal of Neurology, Neurosurgery, and Psychiatry, (1995), 59: pp. 138-143.

Jagtap et al, Biomarkers in vascular dementia: A recent update, Biomarkers and Genomic Medicine, (2015), 7, pp. 43-56.

Chao et al., Protective effects of pinostilbene, a resveratrol methylated derivative, against 6-hydroxydopamine-induced neurotoxicity in SH-SY5Y cells, J Nutr Biochem, Jun. 2010; 21(6):482-9.

Brigham and Womens Hospital, Neurosurgery, Von Hippel-Lindau Disease Treatment Hemangioblastomas Information, http://www.brighamandwomens.org/Departments_and_Services/neurosurgery/patient/VHLclinicalfacts.aspx, accessed on Feb. 17, 2016.

Chaichian et al., Targeted Therapies in Systemic Lupus Erythematosus: A State-of-the Art Review, J Clin Cell Immunol, 2013, S6.

(Continued)

*Primary Examiner* — Taofiq A Solola
(74) *Attorney, Agent, or Firm* — Todd W. Esker; Bret E. Field; Bozicevic, Field & Francis LLP

(57) ABSTRACT

This invention pertains to the prevention and treatment of aging-associated disease. The invention relates to the use of benzodioxane inhibitors of leukotriene production through modulation of leukotriene A4 hydrolase ("LTA4H") to treat and/or prevent conditions associated with aging such as cognitive disorders, motor disorders, and neuroinflammation.

13 Claims, 109 Drawing Sheets

(56) References Cited

FOREIGN PATENT DOCUMENTS

| WO | WO2009032870 A2 | 3/2009 |
|---|---|---|
| WO | WO2010115836 A1 | 10/2010 |
| WO | WO2011032050 A2 | 3/2011 |
| WO | WO2011114220 A1 | 9/2011 |
| WO | WO2012045803 A1 | 4/2012 |
| WO | WO2012125598 A1 | 9/2012 |
| WO | WO2013012844 A1 | 1/2013 |
| WO | WO2013134226 A1 | 9/2013 |
| WO | WO2013149926 A1 | 10/2013 |
| WO | WO2013149986 A1 | 10/2013 |
| WO | WO2013149987 A1 | 10/2013 |
| WO | WO2014014874 A1 | 1/2014 |
| WO | WO2017189919 A2 | 11/2017 |
| WO | WO2018034712 A1 | 2/2018 |
| WO | WO2018064373 A1 | 4/2018 |
| WO | WO2018187503 A1 | 10/2018 |
| WO | WO2018200560 A1 | 11/2018 |
| WO | WO2019075351 A1 | 4/2019 |
| WO | WO2019222265 A1 | 11/2019 |

OTHER PUBLICATIONS

Damia et al., Contemporary pre-clinical development of anticancer agents—what are the optimal preclinical models?, Eur J Cancer. Nov. 2009; 45(16):2768-81.

Davies et al., Discovery of leukotriene A4 hydrolase inhibitors using metabolomics biased fragment crystallography, J Med Chem. Aug. 13, 2009; 52(15):4694-715.

Garrido et al., Experimental models of sepsis and septic shock: an overview, Special Article, Acta Cir. Bras. 19 (2), Apr. 2004.

Grice et al., Current status of leukotriene A4 hydrolase inhibitors, Expert Opinion on Therapeutic Patents, 18:12, 1333-1350, Published online: Nov. 18, 2008.

Healthline, Inflammatory Bowel Disease: Types, Causes & Risk Factors, https://www.healthline.com/health/inflammatory-bowel-disease, accessed on Sep. 10, 2015.

Iversen et al., Significance of Leukotriene-A4 Hydrolase in the Pathogenesis of Psoriasis, Skin Pharmacology, 1997, vol. 10, pp. 169-177.

Johnson et al., Relationships between drug activity in NCI preclinical in vitro and in vivo models and early clinical trials, Br J Cancer. May 18, 2001; 84(10):1424-31.

Medical Dictionary "Active Ingredient" excerpt accessed from medical-dictionary.thefreedictionary.com on Mar. 2, 2022 (Year: 2022).

Minami et al., Molecular cloning of a cDNA coding for human leukotriene A4 hydrolase. Complete primary structure of an enzyme involved in eicosanoid synthesis, J Biol Chem. Oct. 15, 1987;262(29):13873-6.

Ocana et al., Preclinical development of molecular-targeted agents for cancer, Dec. 2010, Nature Reviews Clinical Oncology 8(4):200-9.

Practical Fragments: Fragments in the Clinic: DG-051; Blog 2010 https:/practicalfragments.blogspot.com/2010/01/fragments-in-clinic-dg-051.html, accessed on Feb. 17, 2016 (clean version enclosed).

Sandanayaka et al., Discovery of novel leukotriene A4 hydrolase inhibitors based on piperidine and piperazine scaffolds, Bioorg Med Chem Lett. May 1, 2010; 20(9):2851-4.

Sandanayaka et al., Discovery of 4-[(2S)-2-{[4-(4-chlorophenoxy)phenoxy]methyl}-1-pyrrolidinyl]butanoic acid (DG-051) as a novel leukotriene A4 hydrolase inhibitor of leukotriene B4 biosynthesis, J Med Chem. Jan. 28, 2010;5 3(2):573-85.

Sharma et al., Cell line-based platforms to evaluate the therapeutic efficacy of candidate anticancer agents, Mar. 2010, Nature reviews. Cancer 10(4):241-53.

Simone, V. Part XIV, Oncology: Introduction, Cecil Textbook of Medicine 20$^{th}$ Edition, 1996, vol. 1, p. 1004-1010.

Skrupky et al., Advances in the Management of Sepsis and in the Understanding of Key Immunologic Defects of the Disorder, Anesthesiology. Dec. 2011; 115(6): 1349-1362.

Thangapandian et al., Molecular Docking and Pharmacophore Filtering in the Discovery of Dual-Inhibitors for Human Leukotriene A4 Hydrolase and Leukotriene C4 Synthase, J. Chem. Inf. Model. 2011, 51, 1, 33-44.

| ID | source | term_id | term_size | term_name | p_value |
|---|---|---|---|---|---|
| 1 | GO: BP | GO:0001568 | 651 | blood vessel development | 8.72E-17 |
| 2 | GO: BP | GO:0001944 | 682 | vasculature development | 1.47E-16 |
| 3 | GO: BP | GO:0048514 | 557 | blood vessel morphogenesis | 3.87E-16 |
| 4 | GO: BP | GO:0035239 | 819 | tube morphogenesis | 1.56E-14 |
| 5 | GO: BP | GO:0001525 | 455 | angiogenesis | 2.29E-14 |
| 6 | GO: BP | GO:0035456 | 59 | response to interferon-beta | 9.21E-13 |
| 7 | GO: BP | GO:0034097 | 999 | response to cytokine | 1.85E-10 |
| 8 | GO: BP | GO:0034341 | 131 | response to interferon-gamma | 4.22E-10 |
| 9 | GO: BP | GO:0030155 | 707 | regulation of cell adhesion | 2.47E-09 |
| 10 | GO: BP | GO:0030334 | 870 | regulation of cell migration | 1.22E-08 |
| 11 | GO: BP | GO:0035458 | 50 | cellular response to interferon-beta | 1.29E-08 |
| 12 | GO: BP | GO:0010942 | 623 | positive regulation of cell death | 1.99E-08 |
| 13 | GO: BP | GO:0098542 | 944 | defense response to other organism | 4.42E-08 |
| 14 | GO: BP | GO:2000145 | 926 | regulation of cell motility | 1.29E-07 |
| 15 | GO: BP | GO:0071345 | 913 | cellular response to cytokine stimulus | 1.48E-07 |
| 16 | GO: BP | GO:0043069 | 909 | negative regulation of programmed cell death | 1.97E-07 |
| 17 | GO: BP | GO:0040012 | 971 | regulation of locomotion | 2.51E-07 |
| 18 | GO: BP | GO:0043066 | 889 | negative regulation of apoptotic process | 2.68E-07 |
| 19 | GO: BP | GO:0019882 | 106 | antigen processing and presentation | 3.70E-07 |
| 20 | GO: BP | GO:0045765 | 276 | regulation of angiogenesis | 4.46E-07 |

FIG. 89B

| ID | source | term_id | term_size | term_name | p_value |
|---|---|---|---|---|---|
| 1 | GO: BP | GO:0050808 | 449 | synapse organization | 8.46E-15 |
| 2 | GO: BP | GO:0099536 | 859 | synaptic signaling | 4.68E-13 |
| 3 | GO: BP | GO:0099537 | 827 | trans-synaptic signaling | 1.24E-12 |
| 4 | GO: BP | GO:0007416 | 182 | synapse assembly | 3.58E-12 |
| 5 | GO: BP | GO:0034330 | 703 | cell junction organization | 7.81E-12 |
| 6 | GO: BP | GO:0098916 | 820 | anterograde trans-synaptic signaling | 1.25E-11 |
| 7 | GO: BP | GO:0007268 | 820 | chemical synaptic transmission | 1.25E-11 |
| 8 | GO: BP | GO:0042391 | 429 | regulation of membrane potential | 1.48E-10 |
| 9 | GO: BP | GO:0007610 | 691 | behavior | 1.37E-08 |
| 10 | GO: BP | GO:0098655 | 690 | cation transmembrane transport | 1.55E-08 |
| 11 | GO: BP | GO:0050804 | 625 | modulation of chemical synaptic transmission | 4.74E-08 |
| 12 | GO: BP | GO:0120039 | 647 | plasma membrane bounded cell projection morphogenesis | 4.90E-08 |
| 13 | GO: BP | GO:0099177 | 626 | regulation of trans-synaptic signaling | 5.00E-08 |
| 14 | GO: BP | GO:0048858 | 652 | cell projection morphogenesis | 6.30E-08 |
| 15 | GO: BP | GO:0034220 | 835 | ion transmembrane transport | 6.60E-08 |
| 16 | GO: BP | GO:0032990 | 682 | cell part morphogenesis | 7.82E-08 |
| 17 | GO: BP | GO:0098660 | 660 | inorganic ion transmembrane transport | 8.11E-08 |
| 18 | GO: BP | GO:0048812 | 634 | neuron projection morphogenesis | 9.14E-08 |
| 19 | GO: BP | GO:0034329 | 409 | cell junction assembly | 1.12E-07 |
| 20 | GO: BP | GO:0098662 | 607 | inorganic cation transmembrane transport | 1.51E-07 |

FIG. 90B

| ID | source | term_id | term_size | term_name | p_value |
|---|---|---|---|---|---|
| 1 | GO: BP | GO:0050808 | 449 | synapse organization | 1.20E-15 |
| 2 | GO: BP | GO:0050803 | 254 | regulation of synapse structure or activity | 3.55E-13 |
| 3 | GO: BP | GO:0050807 | 247 | regulation of synapse organization | 8.77E-12 |
| 4 | GO: BP | GO:0099537 | 827 | trans-synaptic signaling | 2.31E-11 |
| 5 | GO: BP | GO:0007268 | 820 | chemical synaptic transmission | 6.05E-11 |
| 6 | GO: BP | GO:0098916 | 820 | anterograde trans-synaptic signaling | 6.05E-11 |
| 7 | GO: BP | GO:0034330 | 703 | cell junction organization | 1.07E-10 |
| 8 | GO: BP | GO:0099536 | 859 | synaptic signaling | 1.13E-10 |
| 9 | GO: BP | GO:0048667 | 590 | cell morphogenesis involved in neuron differentiation | 1.17E-10 |
| 10 | GO: BP | GO:0099173 | 187 | postsynapse organization | 1.46E-10 |
| 11 | GO: BP | GO:0035418 | 82 | protein localization to synapse | 3.51E-10 |
| 12 | GO: BP | GO:0048812 | 634 | neuron projection morphogenesis | 3.88E-10 |
| 13 | GO: BP | GO:0099003 | 231 | vesicle-mediated transport in synapse | 4.07E-10 |
| 14 | GO: BP | GO:0120039 | 647 | plasma membrane bounded cell projection morphogenesis | 8.08E-10 |
| 15 | GO: BP | GO:0007416 | 182 | synapse assembly | 8.46E-10 |
| 16 | GO: BP | GO:0048858 | 652 | cell projection morphogenesis | 1.07E-09 |
| 17 | GO: BP | GO:0099504 | 206 | synaptic vesicle cycle | 1.17E-09 |
| 18 | GO: BP | GO:0032990 | 682 | cell part morphogenesis | 5.29E-09 |
| 19 | GO: BP | GO:0050804 | 625 | modulation of chemical synaptic transmission | 5.53E-09 |
| 20 | GO: BP | GO:0099177 | 626 | regulation of trans-synaptic signaling | 5.83E-09 |

FIG. 91B

| ID | source | term_id | term_size | term_name | p_value |
|---|---|---|---|---|---|
| 1 | GO: BP | GO:0034330 | 449 | synapse organization | 9.54E-21 |
| 2 | GO: BP | GO:0007267 | 859 | synaptic signaling | 2.82E-19 |
| 3 | GO: BP | GO:0099536 | 827 | trans-synaptic signaling | 7.46E-19 |
| 4 | GO: BP | GO:0098916 | 820 | chemical synaptic transmission | 1.03E-17 |
| 5 | GO: BP | GO:0099537 | 820 | anterograde trans-synaptic signaling | 1.03E-17 |
| 6 | GO: BP | GO:0016043 | 703 | cell junction organization | 3.02E-16 |
| 7 | GO: BP | GO:0016043 | 187 | postsynapse organization | 1.88E-13 |
| 8 | GO: BP | GO:0050803 | 247 | regulation of synapse organization | 1.00E-12 |
| 9 | GO: BP | GO:0065008 | 254 | regulation of synapse structure or activity | 2.27E-12 |
| 10 | GO: BP | GO:0065008 | 429 | regulation of membrane potential | 3.12E-12 |
| 11 | GO: BP | GO:0007268 | 625 | modulation of chemical synaptic transmission | 3.66E-12 |
| 12 | GO: BP | GO:0010646 | 626 | regulation of trans-synaptic signaling | 3.90E-12 |
| 13 | GO: BP | GO:0007399 | 182 | synapse assembly | 6.91E-12 |
| 14 | GO: BP | GO:0006812 | 690 | cation transmembrane transport | 4.80E-11 |
| 15 | GO: BP | GO:0008150 | 691 | behavior | 2.02E-10 |
| 16 | GO: BP | GO:0048858 | 647 | plasma membrane bounded cell projection morphogenesis | 4.04E-10 |
| 17 | GO: BP | GO:0000902 | 652 | cell projection morphogenesis | 5.36E-10 |
| 18 | GO: BP | GO:0032989 | 682 | cell part morphogenesis | 7.38E-10 |
| 19 | GO: BP | GO:0031175 | 634 | neuron projection morphogenesis | 7.54E-10 |
| 20 | GO: BP | GO:0098655 | 607 | inorganic cation transmembrane transport | 1.91E-09 |

FIG. 92B

| ID | source | term_id | term_size | term_name | p_value |
|---|---|---|---|---|---|
| 1 | GO: BP | GO:0050808 | 449 | synapse organization | 3.97E-18 |
| 2 | GO: BP | GO:0048812 | 634 | neuron projection morphogenesis | 4.12E-15 |
| 3 | GO: BP | GO:0034330 | 703 | cell junction organization | 4.75E-15 |
| 4 | GO: BP | GO:0050803 | 254 | regulation of synapse structure or activity | 6.27E-15 |
| 5 | GO: BP | GO:0120039 | 647 | plasma membrane bounded cell projection morphogenesis | 1.02E-14 |
| 6 | GO: BP | GO:0048858 | 652 | cell projection morphogenesis | 1.45E-14 |
| 7 | GO: BP | GO:0048667 | 590 | cell morphogenesis involved in neuron differentiation | 1.92E-14 |
| 8 | GO: BP | GO:0050807 | 247 | regulation of synapse organization | 1.99E-14 |
| 9 | GO: BP | GO:0032990 | 682 | cell part morphogenesis | 1.06E-13 |
| 10 | GO: BP | GO:0032989 | 766 | cellular component morphogenesis | 4.00E-12 |
| 11 | GO: BP | GO:0007416 | 182 | synapse assembly | 7.63E-12 |
| 12 | GO: BP | GO:0099003 | 231 | vesicle-mediated transport in synapse | 9.47E-12 |
| 13 | GO: BP | GO:0000904 | 746 | cell morphogenesis involved in differentiation | 2.01E-11 |
| 14 | GO: BP | GO:1902414 | 111 | protein localization to cell junction | 8.98E-11 |
| 15 | GO: BP | GO:0034329 | 409 | cell junction assembly | 1.18E-10 |
| 16 | GO: BP | GO:0099537 | 827 | trans-synaptic signaling | 2.87E-10 |
| 17 | GO: BP | GO:0035418 | 82 | protein localization to synapse | 6.69E-10 |
| 18 | GO: BP | GO:0098916 | 820 | anterograde trans-synaptic signaling | 7.24E-10 |
| 19 | GO: BP | GO:0007268 | 820 | chemical synaptic transmission | 7.24E-10 |
| 20 | GO: BP | GO:0099536 | 859 | synaptic signaling | 1.33E-09 |

BENZODIOXANE MODULATORS OF LEUKOTRIENE A4 HYDROLASE (LTA4H) FOR PREVENTION AND TREATMENT OF AGING-ASSOCIATED DISEASES

I. CROSS-REFERENCE TO RELATED APPLICATIONS

Pursuant to 35 U.S.C. § 119(e), this application claims priority to the filing dates of: U.S. Provisional Patent Application No. 63/274,222, filed Nov. 1, 2021; U.S. Provisional Patent Application No. 63/293,560, filed Dec. 23, 2021; U.S. Provisional Patent Application No. 63/327,496, filed Apr. 5, 2022; and U.S. Provisional Patent Application No. 63/342,572, filed May 16, 2022; the disclosures of which applications are herein incorporated by reference.

II. INTRODUCTION

Field

This invention pertains to the prevention and treatment of aging-associated disease. The invention relates to the use of benzodioxane inhibitors of leukotriene production through modulation of leukotriene A4 hydrolase ("LTA4H") to treat and/or prevent conditions associated with aging such as cognitive disorders, motor disorders, and neuroinflammation.

Background

The following is offered as background information only and is not admitted as prior art to the present invention.

Aging is an important risk factor for multiple human diseases including cognitive impairment, cancer, arthritis, vision loss, osteoporosis, diabetes, cardiovascular disease, and stroke. In addition to normal synapse loss during natural aging, synapse loss is an early pathological event common to many neurodegenerative conditions and is the best correlate to the neuronal and cognitive impairment associated with these conditions. As such, aging remains the single most dominant risk factor for dementia-related neurodegenerative diseases such as Alzheimer's disease (AD) (Bishop N. A. et al., *Neural mechanisms of ageing and cognitive decline*. Nature 464(7288), 529-535 (2010); Heeden T. et al., *Insights into the ageing mind: a view from cognitive neuroscience*. Nat. Rev. Neurosci. 5(2), 87-96 (2004); Mattson, M. P., et al., *Ageing and neuronal vulnerability*. Nat. Rev. Neurosci. 7(4), 278-294 (2006)). Similarly, a decline in motor skills correlates with aging. (Hoogendam Y Y, et al., *Older Age Relates to Worsening of Fine Motor Skills: A Population-Based Study of Middle-Aged and Elderly Persons*. Front. Aging Neurosci. 6 (2014)). Additionally, neuroinflammation has been associated with aging in both healthy brains and in diseased brains such as in AD. (Lynch M A, *Age-related neuroinflammatory changes negatively impact on neuronal function*. Front. Aging Neurosci. 1(6), 1-8 (2010)). Aging affects all tissues and functions of the body including the central nervous system, and neurodegeneration and a decline in functions such as cognition or motor skills, can severely impact quality of life. Treatment for cognitive decline, motor impairment, neuroinflammation, and neurodegenerative disorders has had limited success in preventing and reversing impairment. It is therefore important to identify new treatments for maintaining cognitive and motor integrity by protecting against, countering, or reversing the effects of aging.

Leukotriene $A_4$ hydrolase ("$LTA_4H$" or "LTA4H") is a soluble, monomeric enzyme that converts lipid metabolite leukotriene $A_4$ ("$LTA_4$" or "LTA4") to leukotriene $B_4$ ("$LTB_4$" or "LTB4"). The $LTA_4H$ enzyme through its ability to produce the LTB4 lipid metabolite has been characterized as pro-inflammatory. Additionally, LTB4 lipid metabolite is associated with neutrophil recruitment. Thus, the LTA4H enzyme has been implicated in such diseases as atherosclerosis, atherosclerotic coronary artery disease, rheumatoid arthritis, cystic fibrosis, chronic obstructive pulmonary disease, sepsis, adult respiratory distress syndrome, inflammatory bowel disease, and asthma. (Snelgrove R J, *Leukotriene A4 Hydrolase: An Anti-Inflammatory Role for A Proinflammatory Enzyme*, Thorax 66:550-51 (2011); Shim Y M, et al., *Leukotriene A4 Hydrolase—An Evolving Therapeutic Target*, Inflammatory Diseases—Immunopathology, Clinical and Pharmacological Bases (Dr. Mahin Khatami (Ed.)), 253-278, (2012)).

The LTA4H enzyme has recently been characterized as having an additional catalytic activity. LTA4H not only exhibits the epoxide hydrolase activity converting LTA4 to LTB4, but an additional aminopeptidase activity (or "peptidase" activity), cleaving Pro-Gly-Pro peptides (P-G-P) to Pro+Gly-Pro. This aminopeptidase activity is thought to contribute an anti-inflammatory role for LTA4H by reducing accumulation of P-G-P. (Snelgrove, et al. *A critical role for LTA4H in limiting chronic pulmonary neutrophilic inflammation*, Science 330(6000):90-4 (2010)). This discovery may provide insights into the clinical failures of LTA4H inhibitors within inflammatory diseases. Modulators of the LTA4H enzyme have been described, including small molecule inhibitors. These include small molecules that: bind both the epoxide hydrolase pocket and the aminopeptidase active site, such as SC-57461A; and selectively bind the epoxide hydrolase binding pocket of LTA4H, such as pinostilbene hydrate (Low C M et al., *The development of novel LTA4H modulators to selectively target LTB4 generation*. Sci. Rep. 7, 44449 (2017)).

A class of benzodioxane inhibitors of leukotriene production through inhibition of LTA4H are described herein. These benzodioxane inhibitors exhibit an unexpectedly robust effect on improving cognition in aged mice as well as mouse models for neuroinflammation.

III. SUMMARY

The present invention recognizes that as people age, the amounts of certain plasma proteins also increase. The present invention recognizes that such proteins can be referred to as "pro-aging factors," and modulation of their activity or concentration in the blood circulation can protect or even reverse certain aging-related symptoms and/or disease. The present invention is also based on work demonstrating that the LTA4H enzyme and its product LTB4 occur at higher concentrations in older subjects than in younger subjects. The present invention shows that LTA4H is significantly increased in human plasma with worsening Alzheimer's disease diagnosis from subjective cognitive decline (SCD) to mild cognitive impairment (MCI) to Alzheimer's Disease (AD). Further the present invention also shows that human LTA4H plasma levels are significantly correlated with a worsening cognitive score on the mini-mental state exam (MMSE).

The present invention is based on targeting the LTA4H enzyme with benzodioxane compounds disclosed herein for treating and/or preventing age-related disorders, such as cognitive impairment conditions, age-related dementia, impairment of motor function, neuroinflammation, and neurodegenerative disease. The present invention recognizes, among other things, the need for new therapies and new mechanisms of action for the treatment and/or prevention of cognitive impairment, age-related dementia, motor impairment, neuroinflammation, and neurodegenerative disease. The present compositions of the invention relate to a solution for the failures and shortcomings of current therapies through utilization of benzodioxane inhibitors of the LTA4H enzyme in the treatment and/or prevention of cognitive impairment, age-related dementia, motor impairment, neuroinflammation, and neurodegenerative disease.

An embodiment of the invention includes treating a subject diagnosed with a cognitive impairment by administering to the subject an effective amount of one or more of the benzodioxane compounds that are inhibitory agents to the activity of LTA4H. Another embodiment of the invention includes administering the effective amount of one or more benzodioxane compounds and subsequently monitoring the subject for improved cognitive function. Another embodiment of the invention includes treating a subject diagnosed with a cognitive impairment by administering to the subject an effective amount of one or more of the benzodioxane compounds wherein the one or more benzodioxane compounds are administered in a manner resulting in improved cognitive function, improved neurogenesis, or reduced neuroinflammation. Another embodiment of the invention includes treating subject diagnosed with a cognitive impairment by administering to the subject an effective amount of one or more the benzodioxane compounds systemically.

An embodiment of the invention includes treating a subject diagnosed with a neurodegenerative motor disorder such as, by way of example and not limitation, Parkinson's Disease, by administering to the subject an effective amount of one or more of the benzodioxane compounds. Another embodiment of the invention includes administering the effective amount of one or more of the benzodioxane compounds and subsequently monitoring the subject for improved motor function. Another embodiment of the invention includes treating a subject diagnosed with a neurodegenerative motor disorder by administering to the subject an effective amount of one or more of the benzodioxane compounds wherein the one or more benzodioxane compounds are administered in a manner resulting in improved motor function, neurogenesis, or reduced neuroinflammation.

An additional embodiment of the invention includes treating a subject diagnosed with cerebral autosomal dominant arteriopathy with sub-cortical infarcts and leukoencephalopathy (CADASIL) by administering to the subject an effective amount of one or more of the benzodioxane compounds. Another embodiment of the invention includes administering the effective amount of one or more of the benzodioxane compounds and subsequently monitoring the subject for improved cognitive function, neurogenesis, or reduced neuroinflammation.

Another embodiment of the invention includes treating a subject diagnosed with neuroinflammation or a neuroinflammation-associated disorder by administering to the subject an effective amount of the one or more benzodioxane compounds. Another embodiment of the invention includes administering the effective amount of one or more of the benzodioxane compounds and subsequently monitoring the subject for reduced neuroinflammation. Another embodiment of the invention includes treating a subject diagnosed with neuroinflammation or a neuroinflammation-associated disorder by administering to the subject an effective amount of one or more of the benzodioxane compounds wherein the one or more benzodioxane compounds are administered in a manner resulting in reduced neuroinflammation.

Another embodiment of the invention includes treating a subject diagnosed with a cognitive impairment, impaired motor function, or neuroinflammation or a decline in neurogenesis by administering to the subject an effective amount of one or more of the benzodioxane compounds, with the subject following an exercise regimen after the administration. Another embodiment of the invention includes following an exercise regimen that is prescribed to the subject. Another embodiment of the invention includes the subject exercising at a higher intensity and/or greater frequency than the subject exercised preceding the administration. Another embodiment of the invention includes the subject exercising at a similar intensity and/or frequency as the subject exercised preceding the administration.

IV. INCORPORATION BY REFERENCE

All publications and patent applications mentioned in this specification are herein incorporated by reference to the same extent as if each individual publication or patent application was specifically and individually indicated to be incorporated by reference. By way of example and not limitation, U.S. patent application Ser. Nos. 13/418,377, 13/785,097, and 13/974,879, U.S. Pat. Nos. 8,551,982, 9,133,146, and 9,662,339, and PCT Patent Publication Nos. WO/2012/125598 and WO/2013/131901.

V. BRIEF DESCRIPTION OF THE DRAWINGS

FIG. 1 shows LTA4H levels in individual human plasma from patients diagnosed with subjective cognitive decline (SCD), mild cognitive impairment (MCI), or possible/probably Alzheimer's disease (AD) measured by SomaLogic SomaScan assay in relative fluorescence units (RFU).

FIG. 2 reports plasma levels of LTA4H measured in RFU by SomaLogic SomaScan assay correlated with mini-mental state (MMSE) score.

Figure 6:
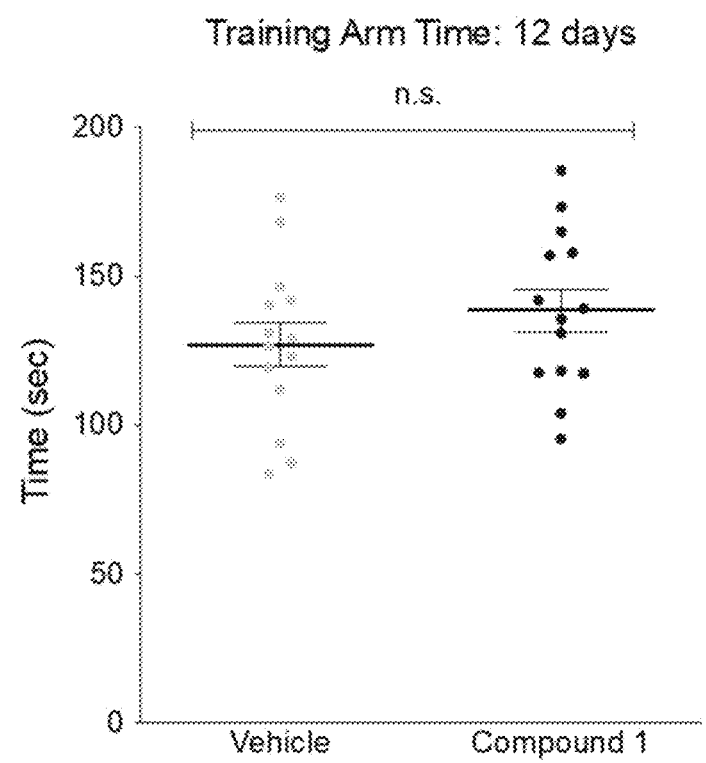

FIG. 6 reports the average time mice spent in seconds (sec) during training in the familiar arm of a Y-Maze hippocampus-dependent memory test after 12 days of dosing.

Figure 7:
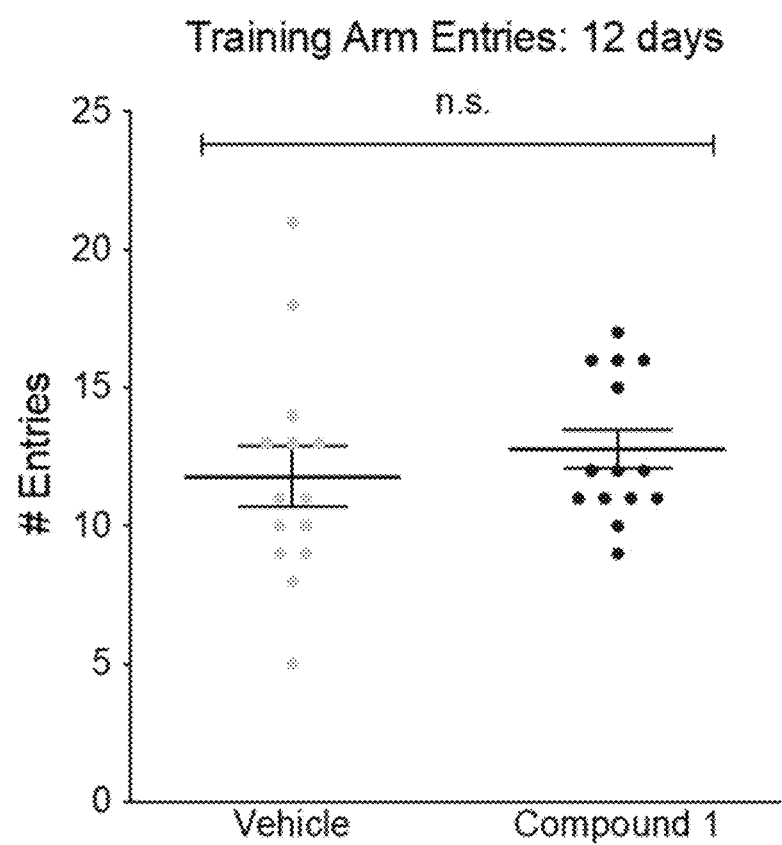

FIG. 7 reports the average number of entries by mice during training in the familiar arm of a Y-Maze hippocampus-dependent memory test after 12 days of dosing.

Figure 8:
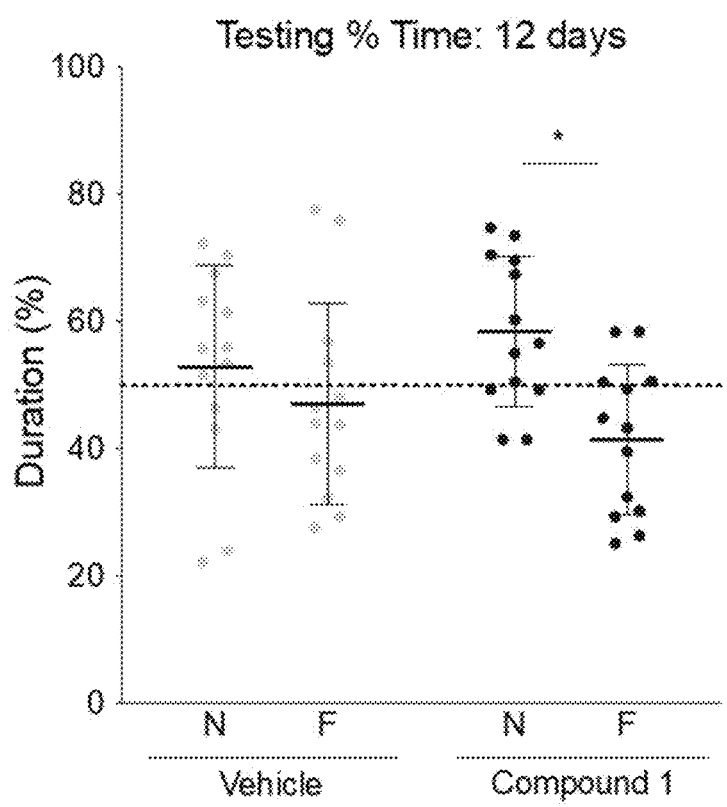

FIG. 8 reports the average percent time mice spent in the novel (N) or familiar (F) arm of total time spent in either arm during Y-Maze hippocampus-dependent memory testing after 12 days of dosing.

Figure 9:
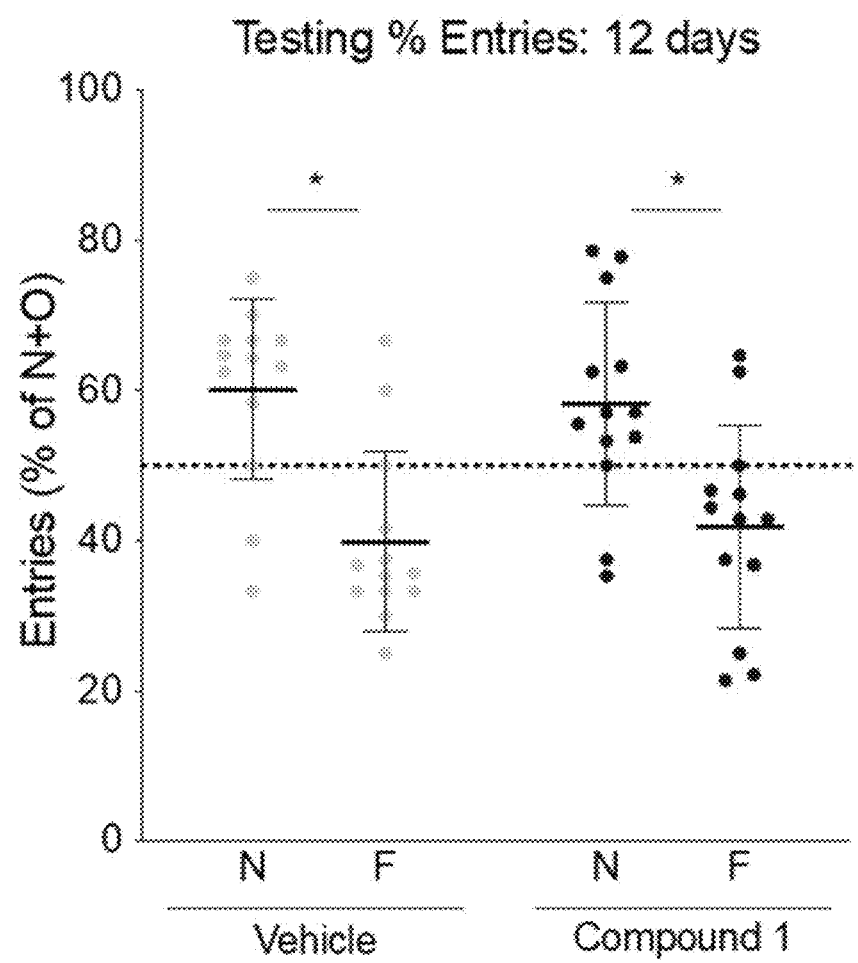

FIG. 9 reports the average percent of total number of entries made by mice into either the novel (N) or familiar (F) arm of total entries made into each arm during testing after 12 days of dosing.

Figure 10:
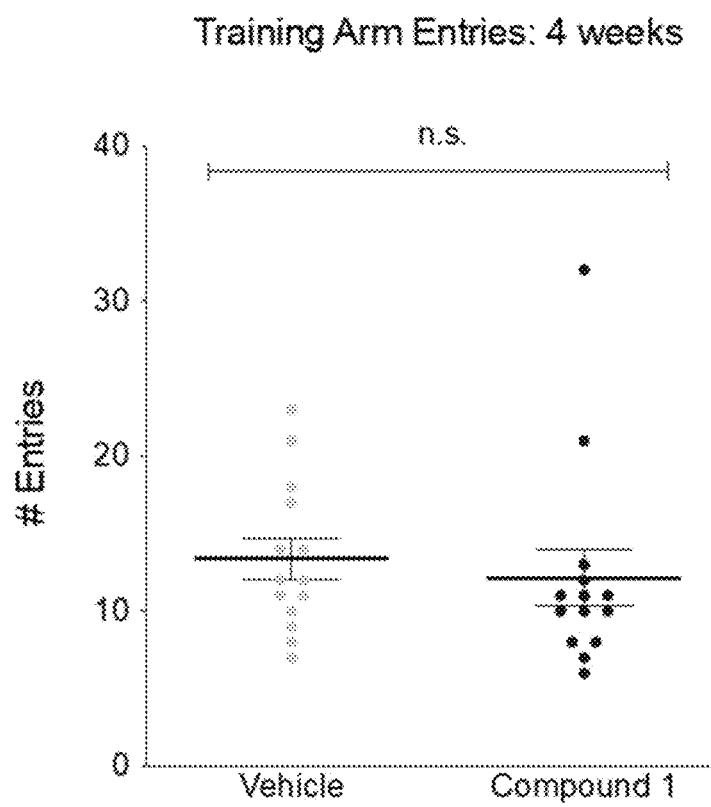

FIG. 10 reports the average time spent in seconds (sec) by mice during training in the familiar arm of Y-Maze hippocampus-dependent memory testing after 26 days of dosing.

Figure 11:
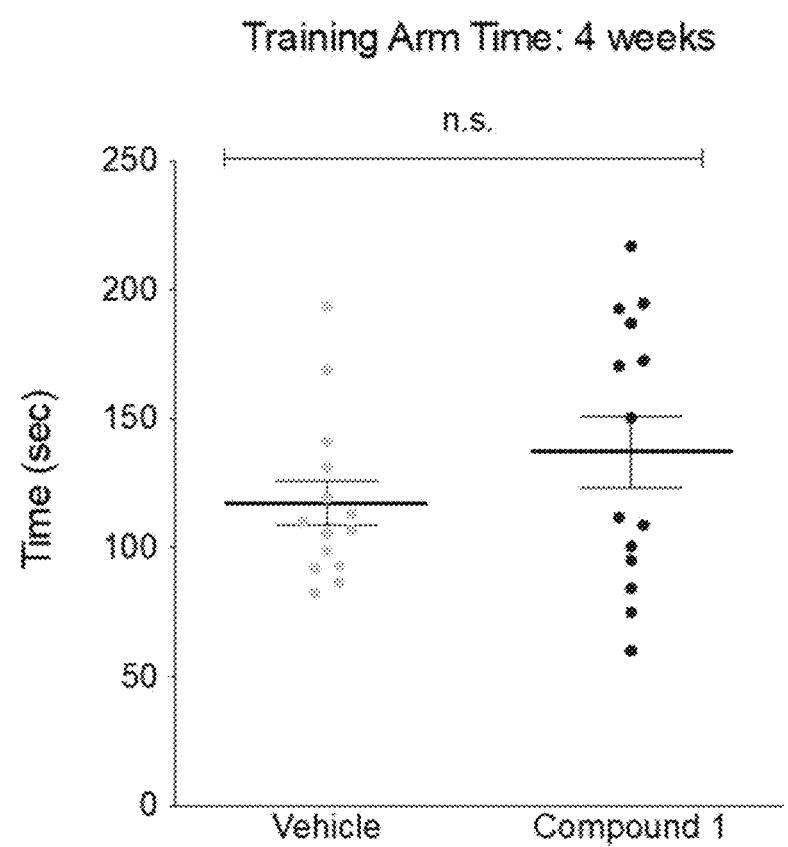

FIG. 11 reports the average number of entries made by mice during training into the familiar arm of Y-Maze hippocampus-dependent memory testing after 26 days of dosing.

Figure 12:
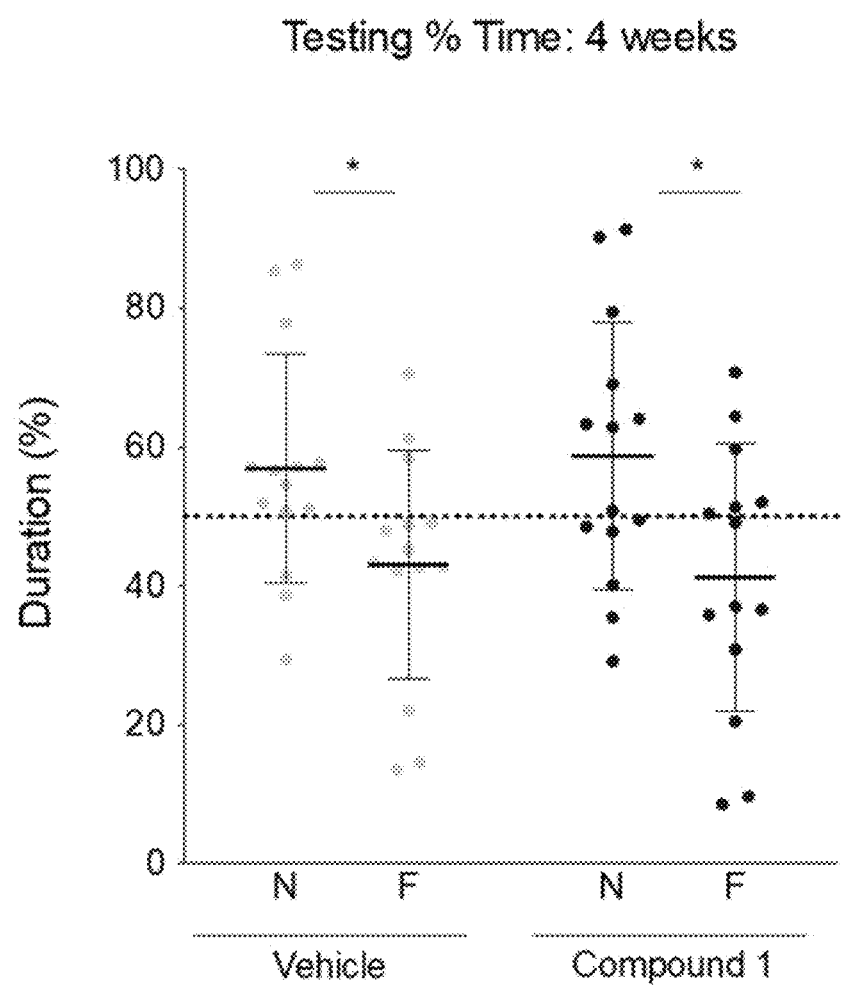

FIG. 12 reports the average percent time spent by mice in the novel (N) or familiar (F) arm of total time spent in either arm during Y-Maze hippocampus-dependent memory testing after 26 days of dosing.

Figure 13:
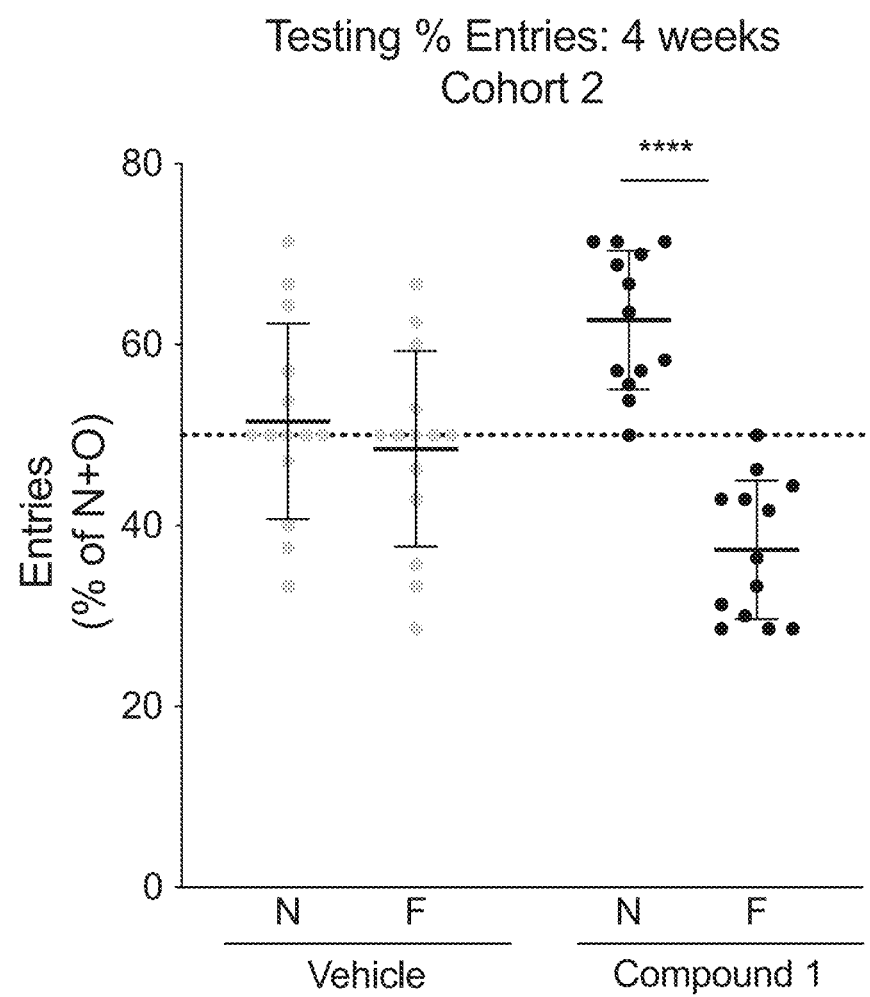

FIG. 13 reports the average percent of total number of entries made by mice into either the novel (N) or familiar (F) arm of total entries made into each arm during Y-Maze hippocampus-dependent memory testing after 26 days of dosing.

Figure 14:
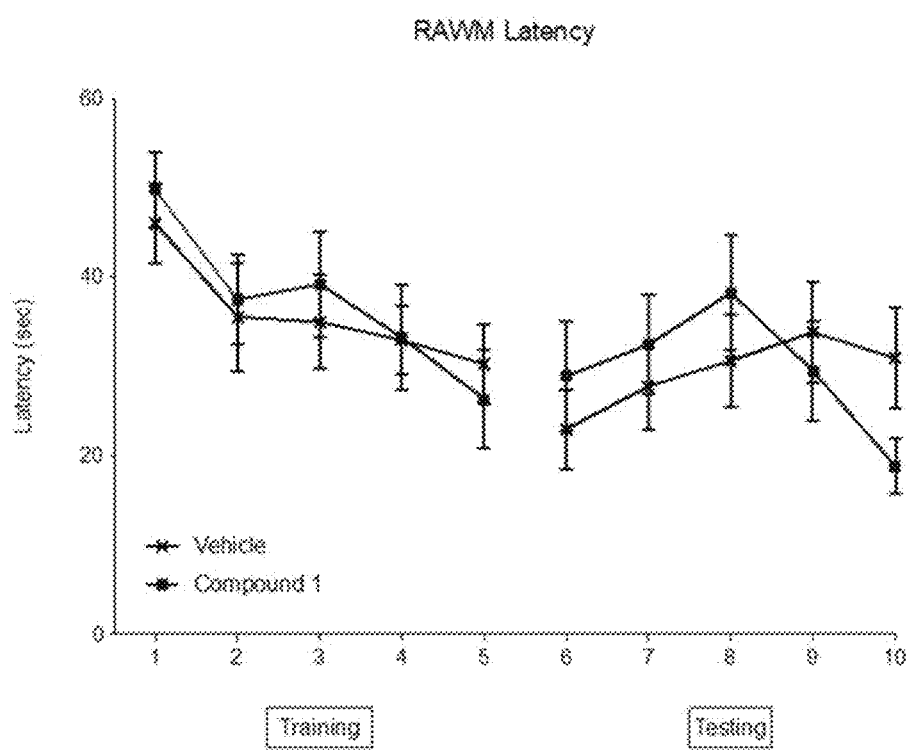

FIG. 14 reports the average latency of mice across all training and testing trials in a radial arm water maze (RAWM) after 29 days of dosing.

Figure 15:
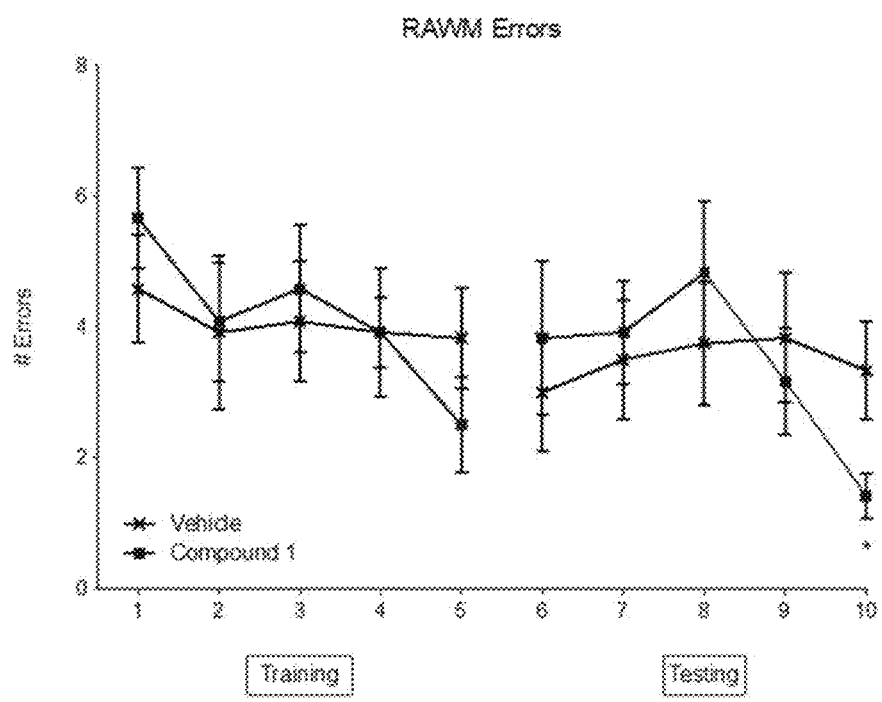

FIG. 15 reports the average number of errors made by mice across all training and testing trials in a radial arm water maze (RAWM) after 29 days of dosing.

Figure 16:
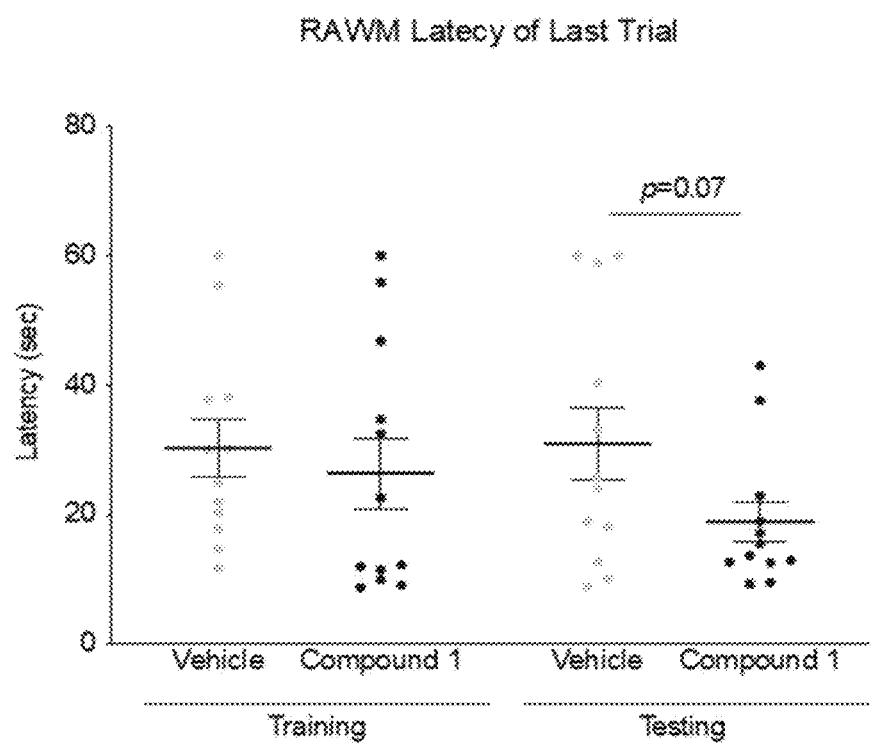

FIG. 16 reports the average latency by mice in the last training trial and last testing trial in a radial arm water maze (RAWM) after 29 days of dosing.

Figure 17:
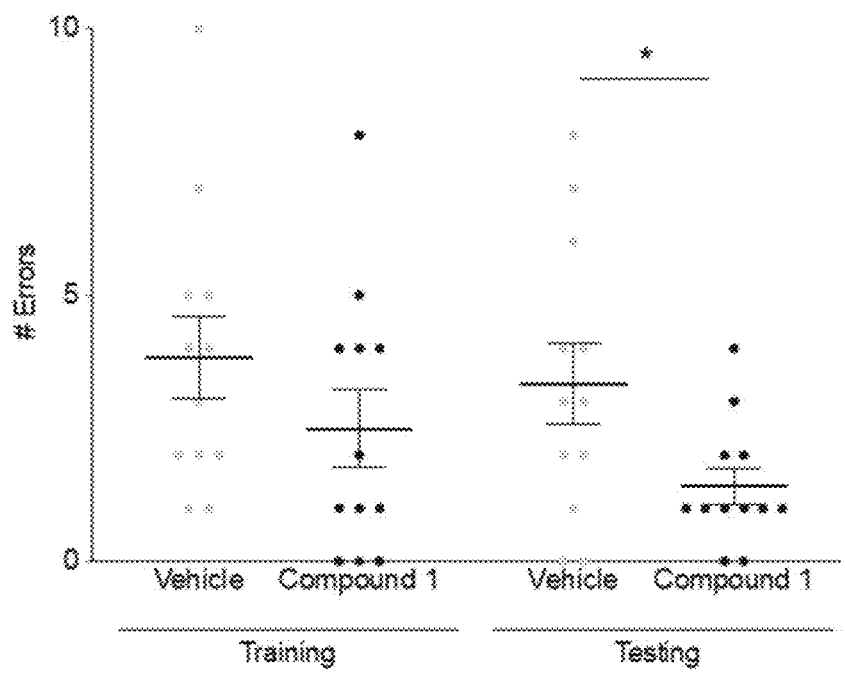

FIG. 17 reports the average number of errors made by mice in the last training and last testing trials in a radial arm water maze (RAWM) after 29 days of dosing.

Figure 18:
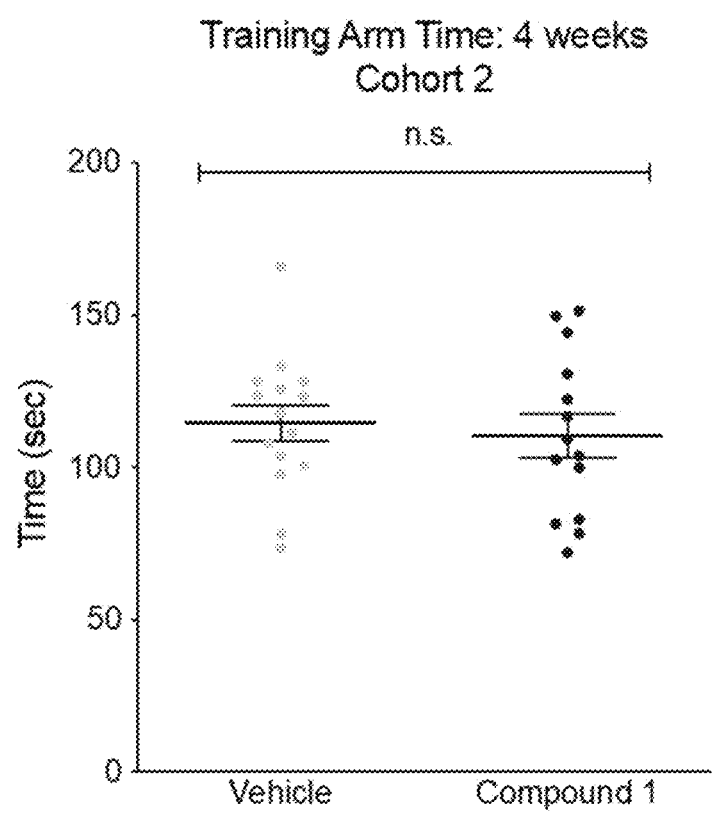

FIG. 18 reports the average time spent in seconds (sec) by mice in the familiar arm during training in the Y-Maze hippocampus-dependent memory test after 18 days of dosing.

Figure 19:
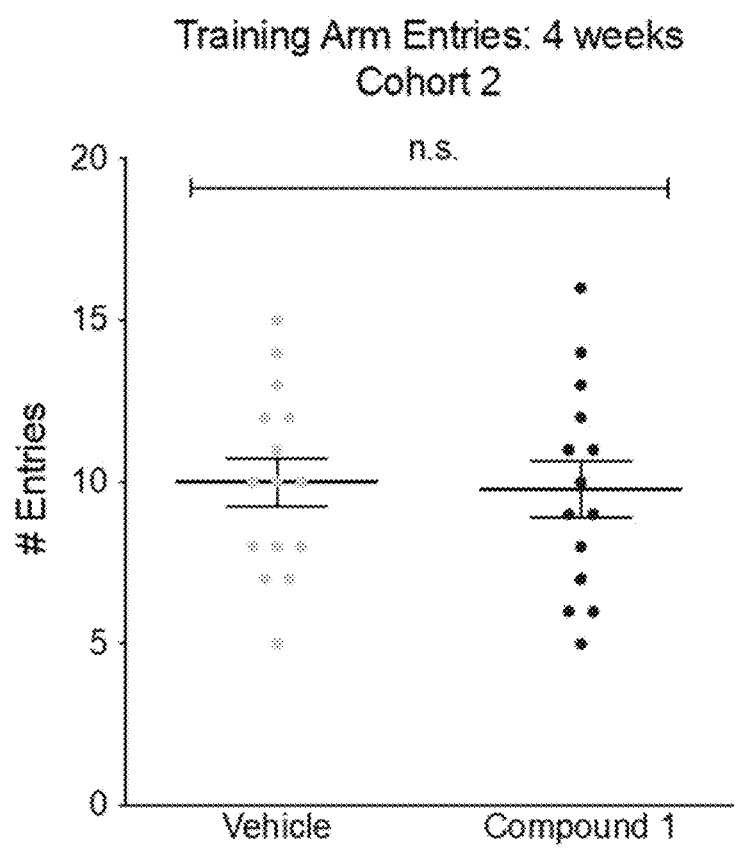

FIG. 19 reports the average number of entries made by mice during mice in the familiar arm during training in the Y-Maze hippocampus-dependent memory test after 18 days of dosing.

Figure 20:
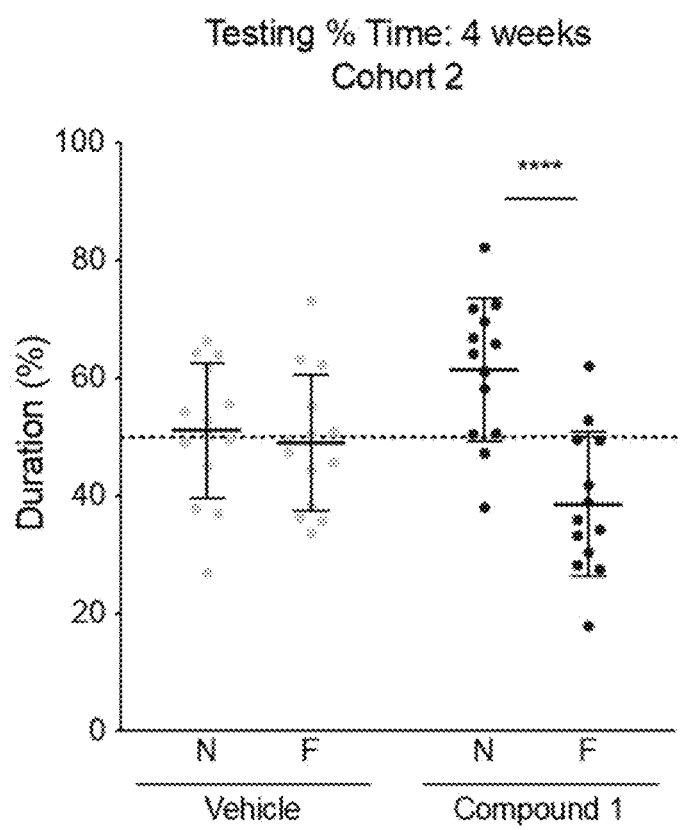

FIG. 20 reports the average percent time spent by mice in the novel (N) or familiar (F) arm of total time spent in either arm during testing in the Y-Maze hippocampus-dependent memory test after 18 days of dosing.

Figure 21:
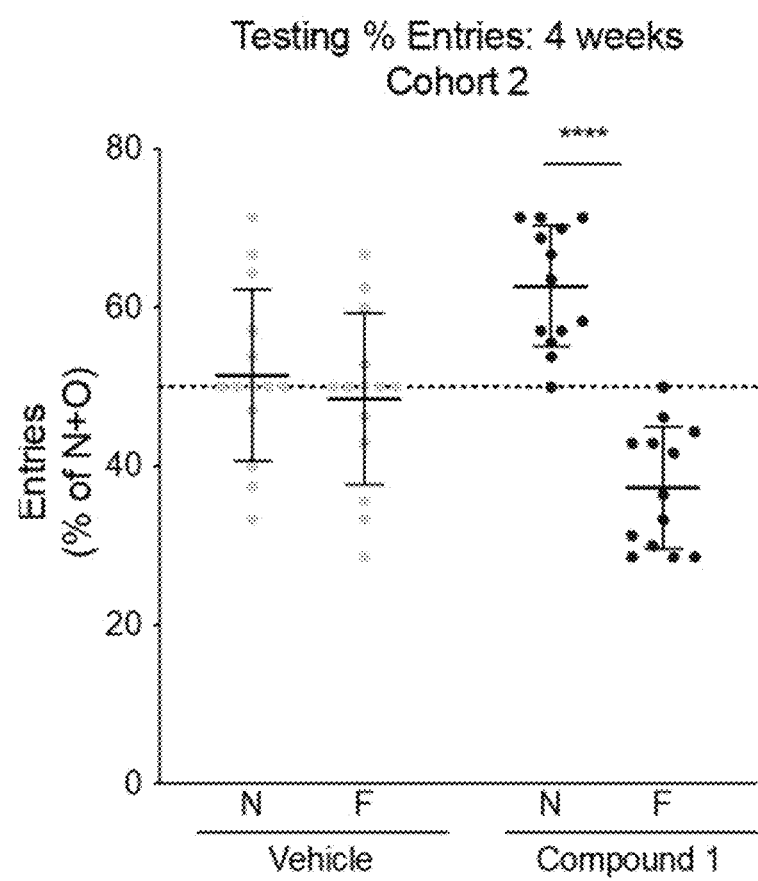

FIG. 21 reports the average percent of total number of entries made by mice into either the novel (N) or familiar (F) arm of total entries made into each arm during testing in the Y-Maze hippocampus-dependent memory test after 18 days of dosing.

Figure 22:
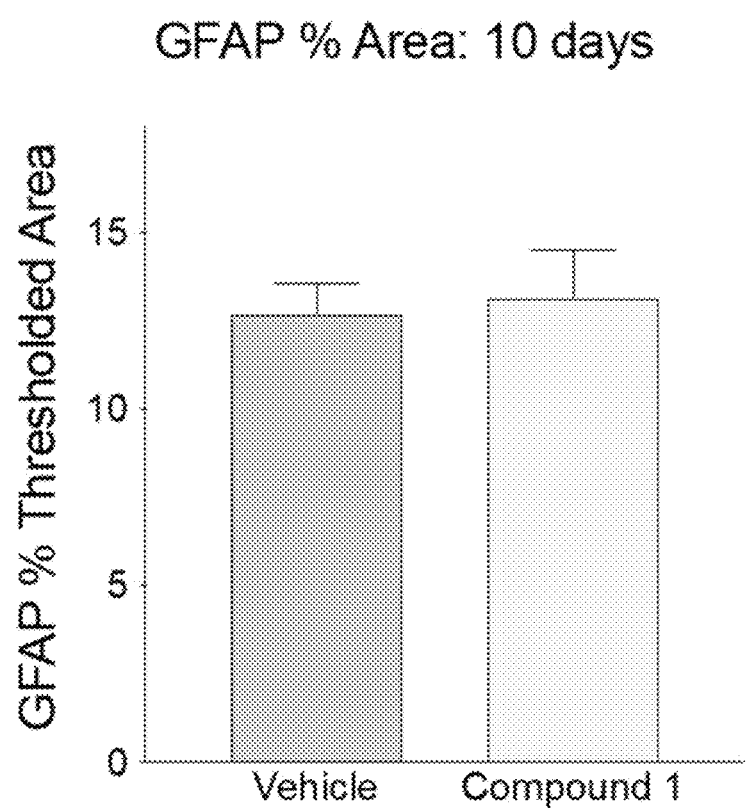

FIG. 22 shows the effect of LTA4H inhibition by Compound 1 on astrocyte activation by measuring average glial fibrillary acidic protein (GFAP) percent thresholded area in mouse brains 10 days after treatment.

Figure 23:
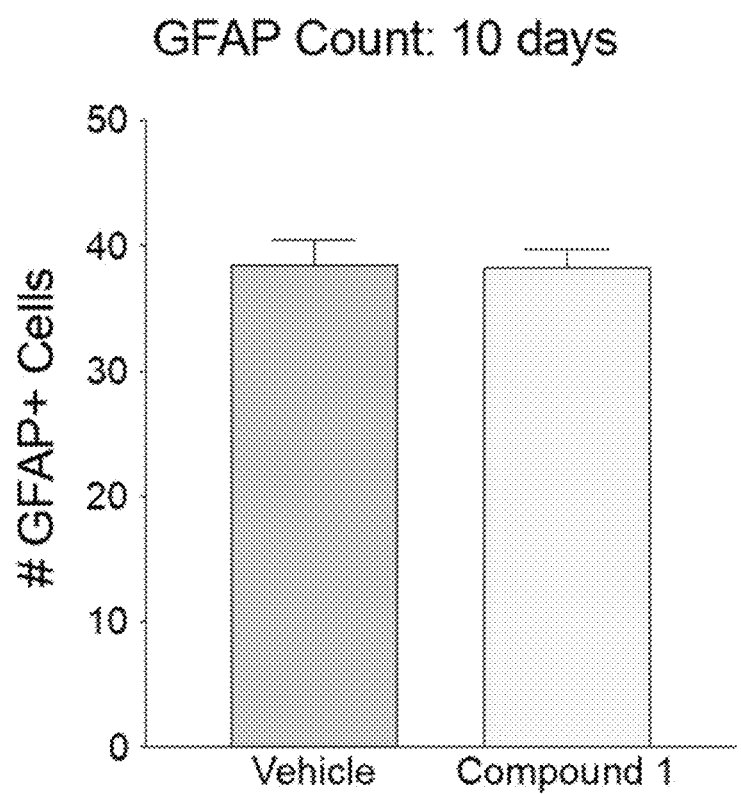

FIG. 23 shows the effect of LTA4H inhibition by Compound 1 on astrocyte activation by measuring the average number of GFAP positive cells 10 days after treatment.

Figure 24:
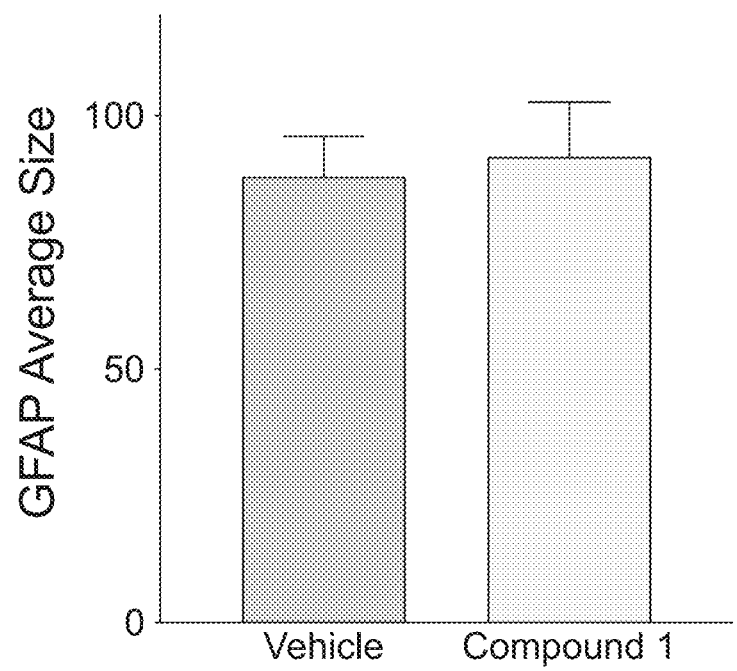

FIG. 24 shows the effect of LTA4H inhibition by Compound 1 on astrocyte activation by measuring average size of GFAP positive cells 10 days after treatment.

Figure 25:
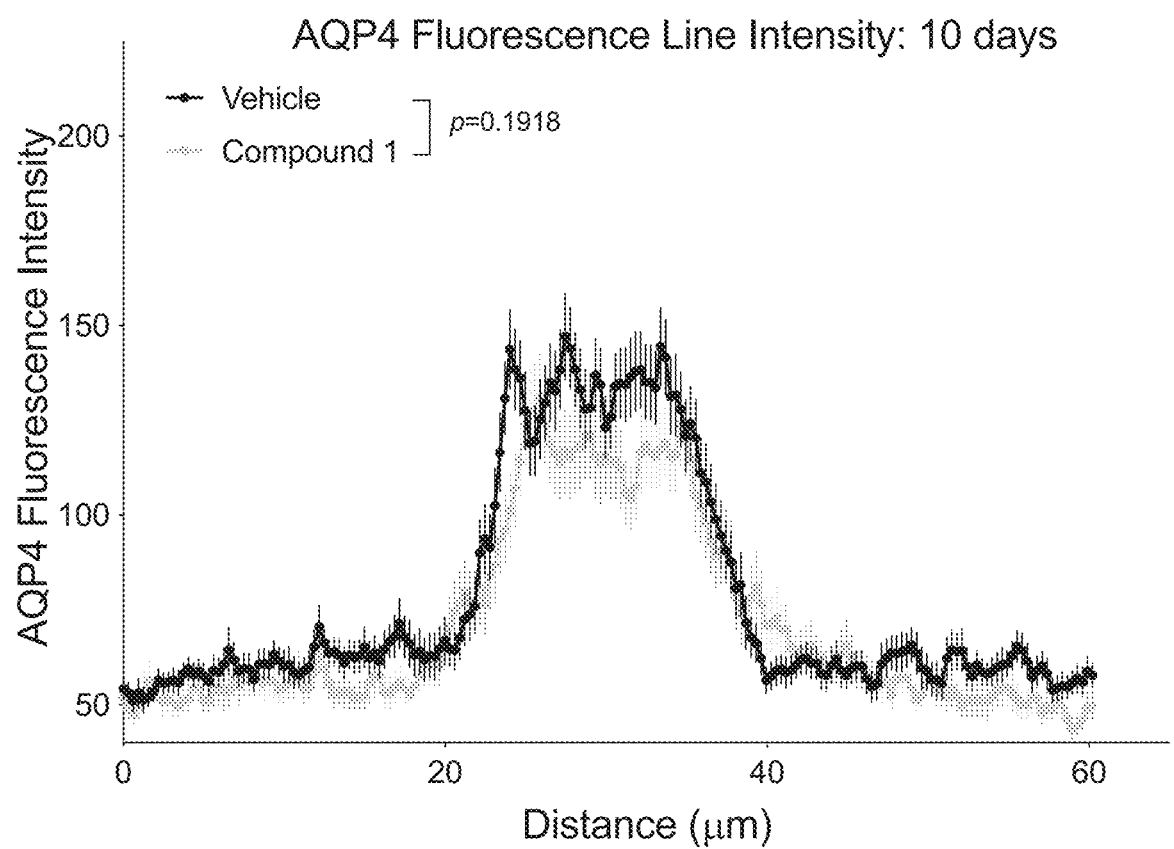

FIG. 25 shows the effect of LTA4H inhibition by Compound 1 on astrocyte activation by measuring the average line intensity profiles of aquaporin 4 (AQP4) across large descending vessels of the CA1 region of the hippocampus 10 days after treatment.

Figure 26:
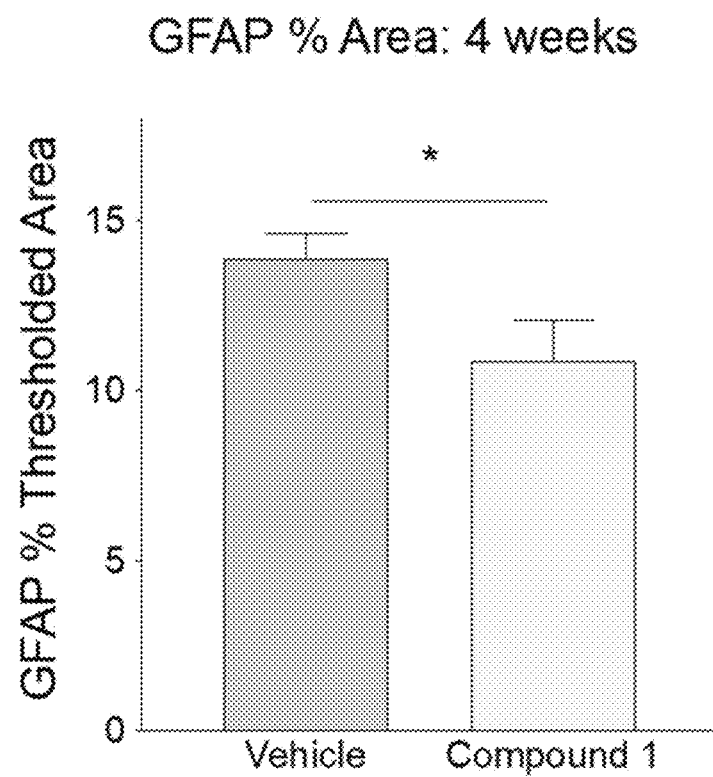

FIG. 26 shows the effect of LTA4H inhibition by Compound 1 on astrocyte activation by measuring the average GFAP percent thresholded area 4 weeks after treatment.

Figure 27:
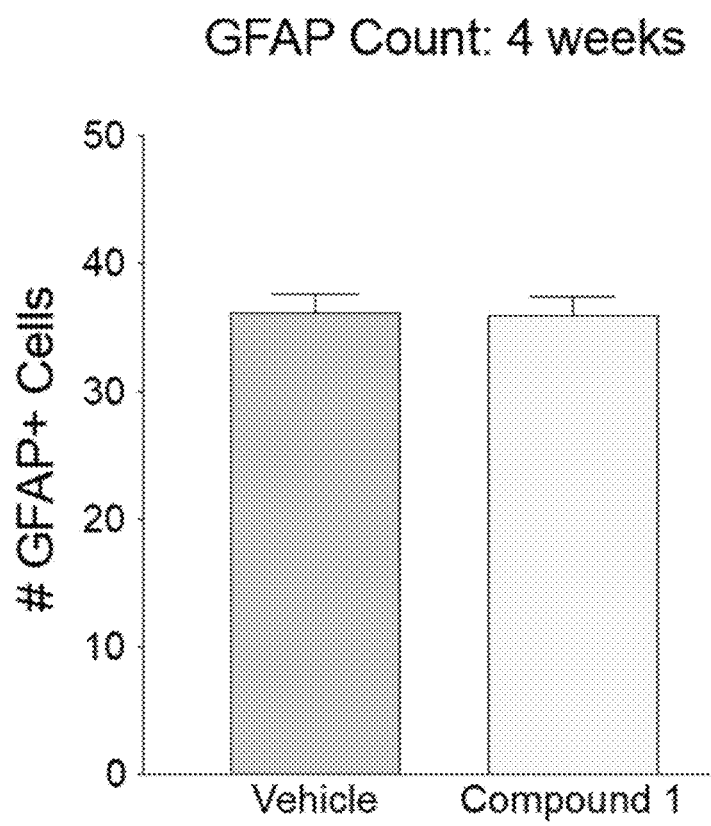

FIG. 27 shows the effect of LTA4H inhibition by Compound 1 on astrocyte activation by measuring the average number of GFAP positive cells 4 weeks after treatment.

Figure 28:
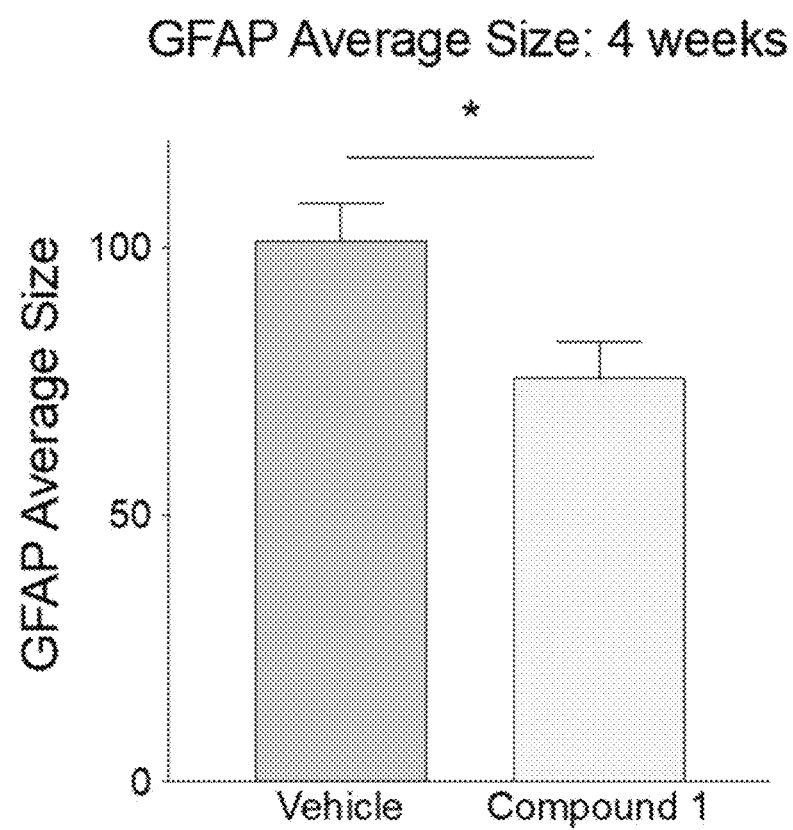

FIG. 28 shows the effect of LTA4H inhibition by Compound 1 on astrocyte activation by measuring average size of GFAP positive cells 4 weeks after treatment.

Figure 29:
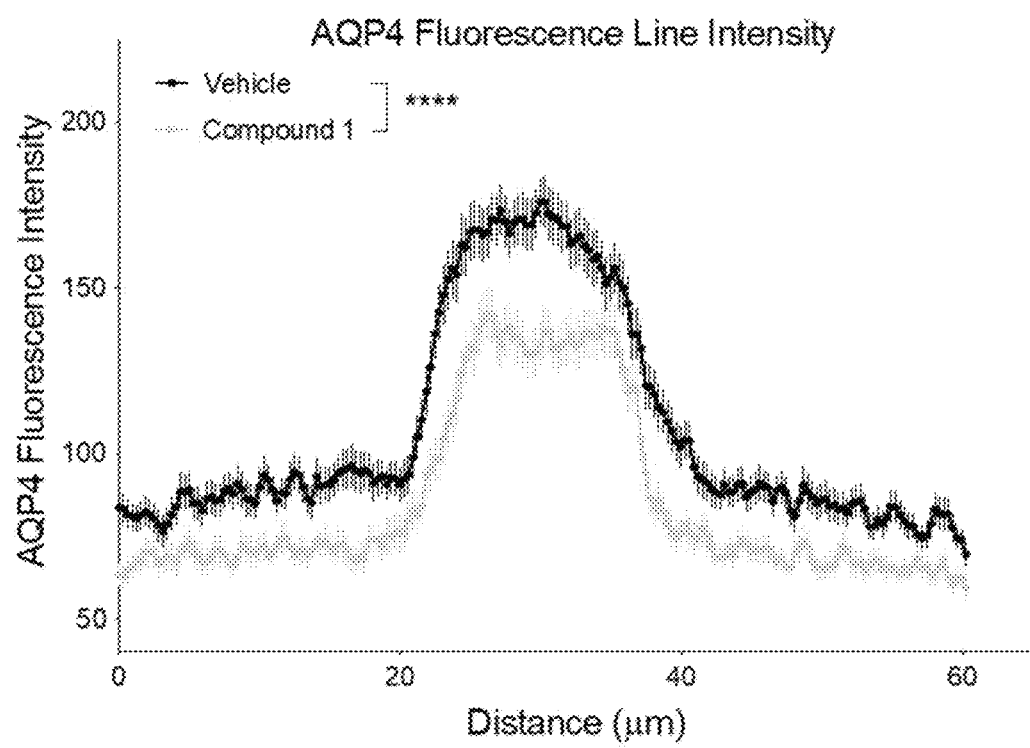

FIG. 29 shows the effect of LTA4H inhibition by Compound 1 on astrocyte activation by measuring the average line intensity profiles of AQP4 across large descending vessels of the CA1 region of the hippocampus 4 weeks after treatment.

Figure 30:
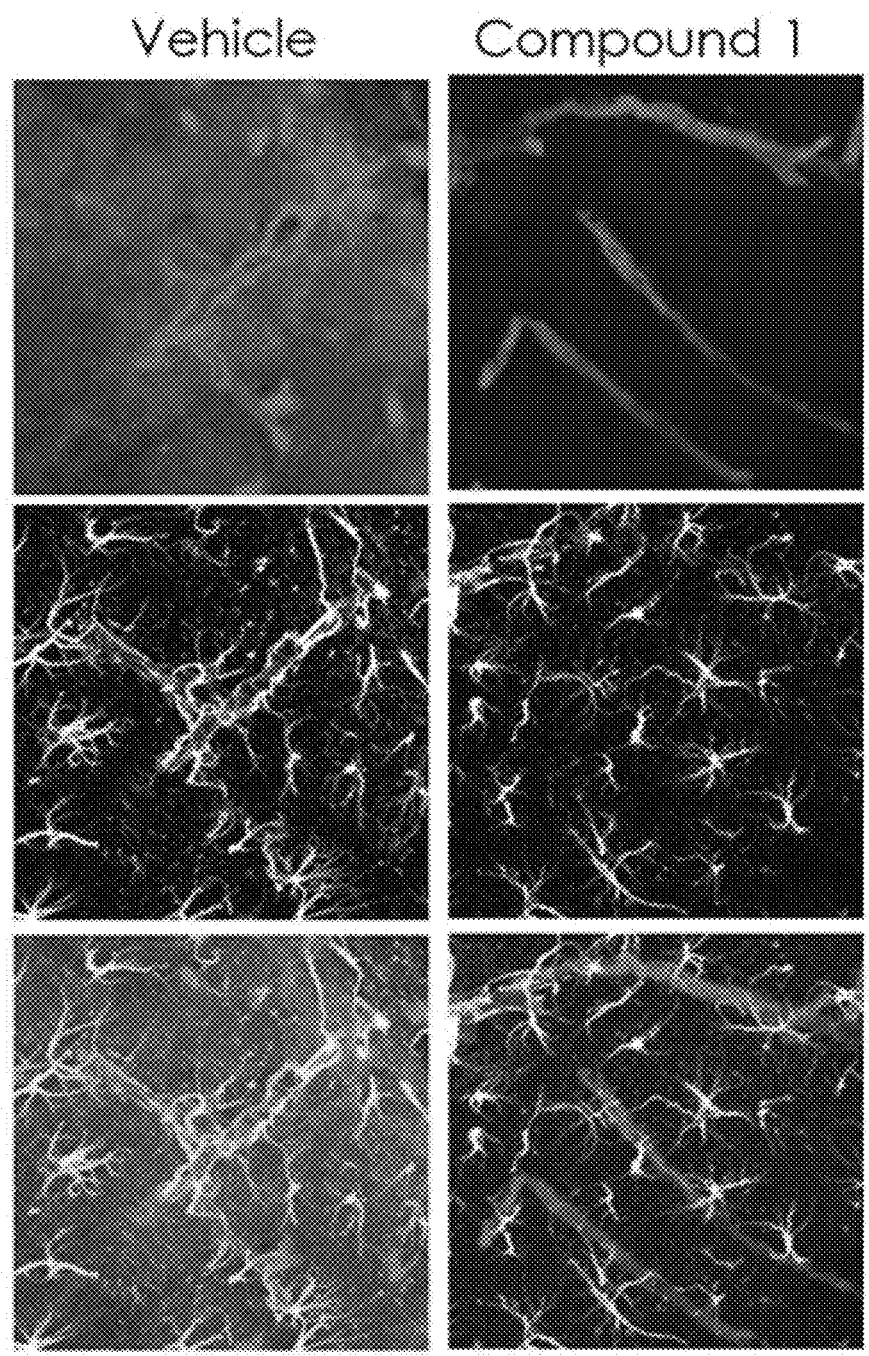

FIG. 30 shows representative confocal microscopy images of AQP4 (purple) top row, GFAP (white) middle row, and AQP4-GFAP merged images bottom row in the CA1 region of the hippocampus of mice treated with vehicle (left column of images) or Compound 1 (right column of images).

Figure 31:
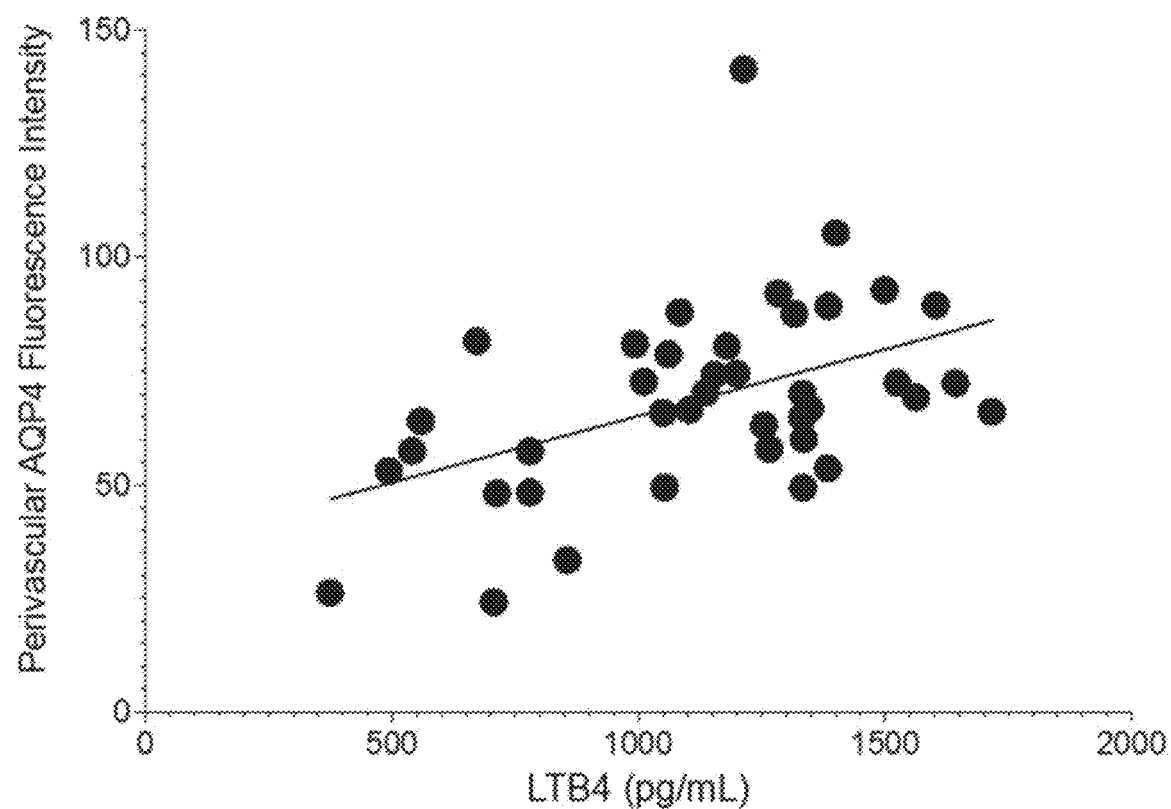

FIG. 31 reports that AQP4 intensity levels as measured by fluorescence intensity (x-axis) are correlated with plasma levels of LTB4 (a product of LTA4H enzymatic activity) in the perivascular space of large descending blood vessels in the CA1 region of the hippocampus in mouse brain.

Figure 32:
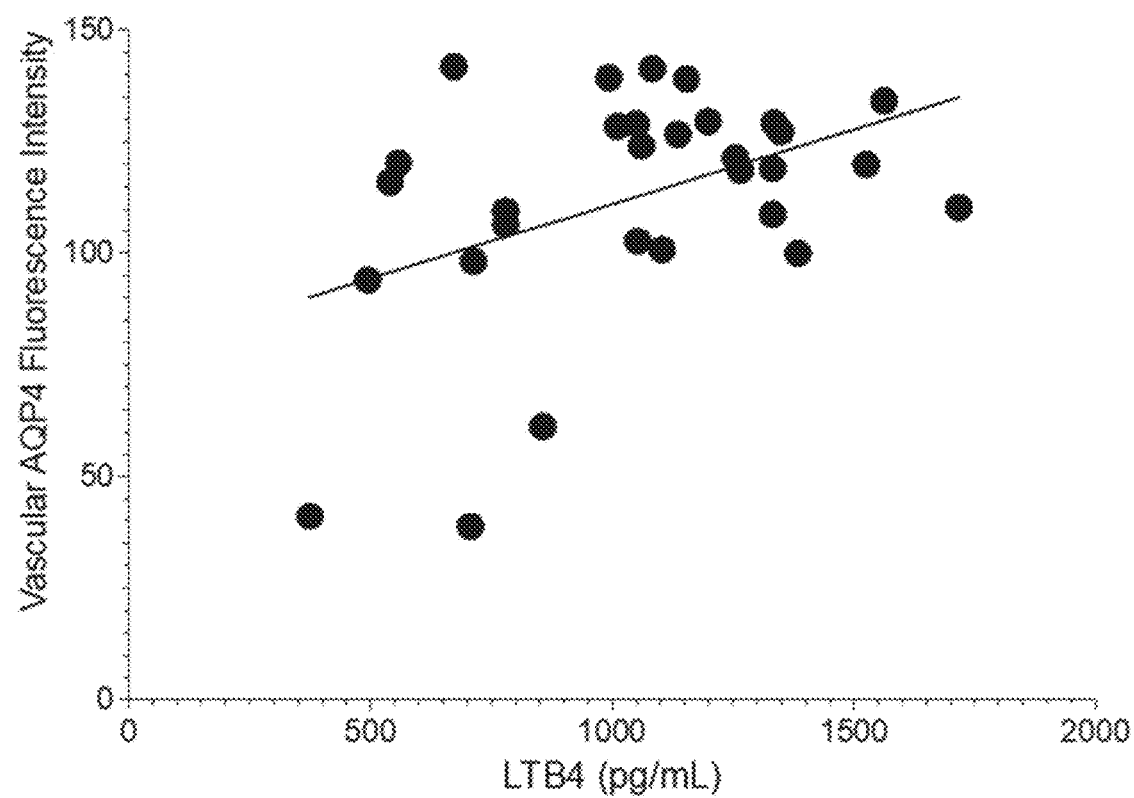

FIG. 32 reports that AQP4 intensity levels as measured by fluorescence intensity (x-axis) are correlated with plasma levels of LTB4 (a product of LTA4H enzymatic activity) in the vasculature space of large descending blood vessels in the CA1 region of the hippocampus in mouse brain.

Figure 33:
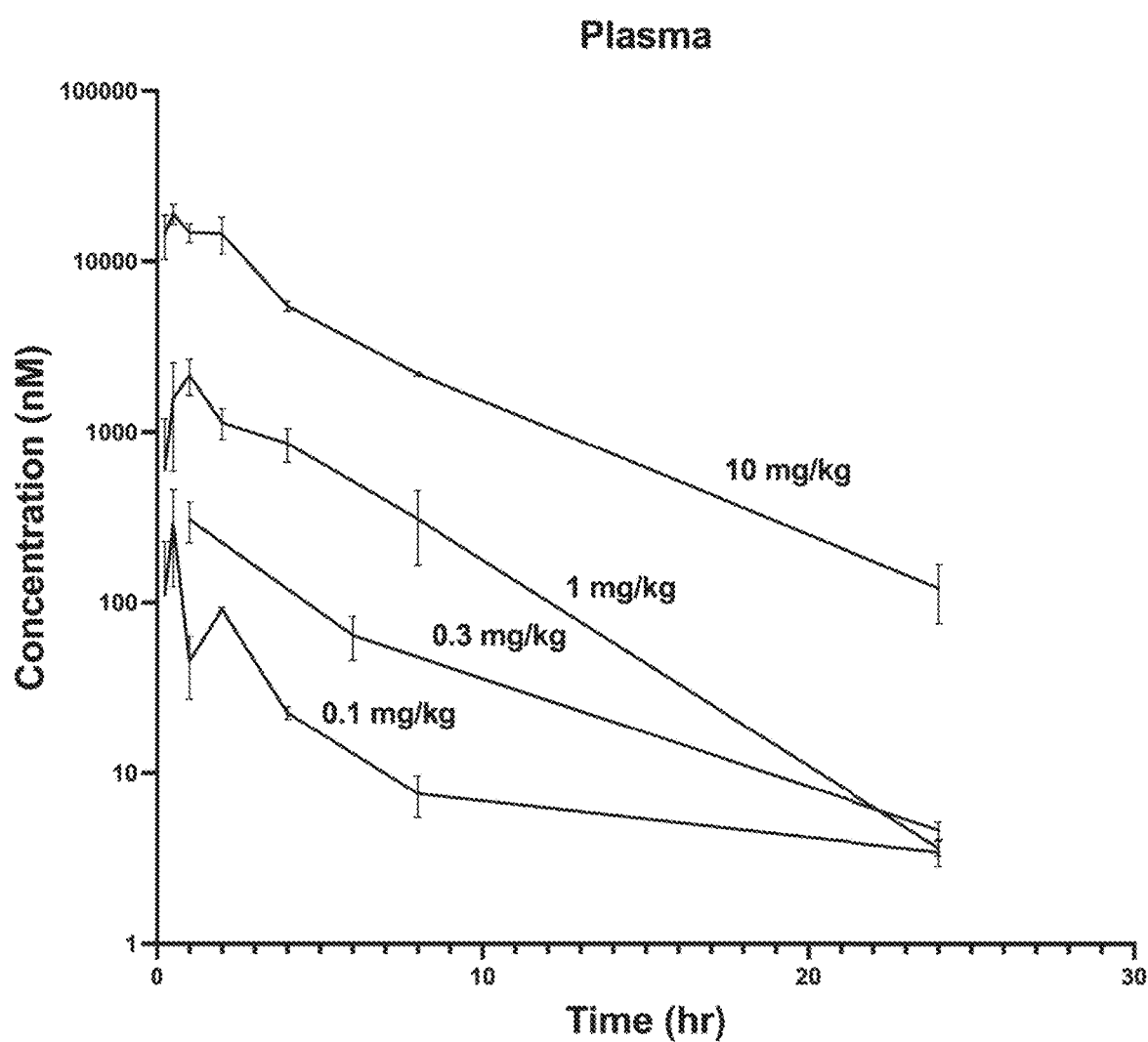

FIG. 33 reports pharmacokinetic data of Compound 1 in the form of plasma levels in C57BL/6 mice treated with a single oral gavage dose of Compound 1 at 10 mg/kg, 1 mg/kg, 0.3 mg/kg, and 0.1 mg/kg at multiple timepoints following dosing.

Figure 34:
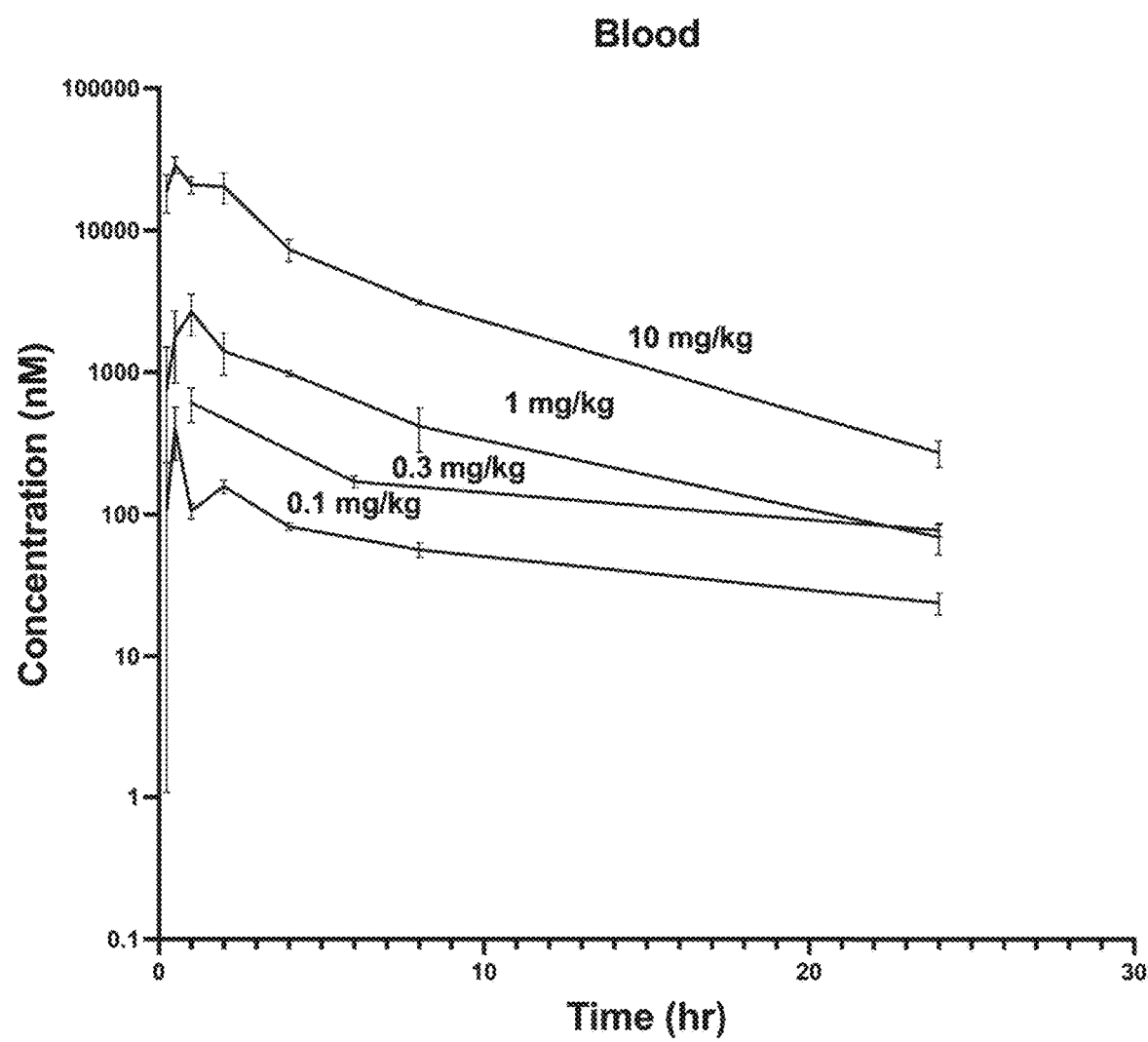

FIG. 34 reports pharmacokinetic data of Compound 1 in the form of blood levels in C57BL/6 mice treated with a single oral gavage dose of Compound 1 at 10 mg/kg, 1 mg/kg, 0.3 mg/kg, and 0.1 mg/kg at multiple timepoints following dosing.

Figure 35:
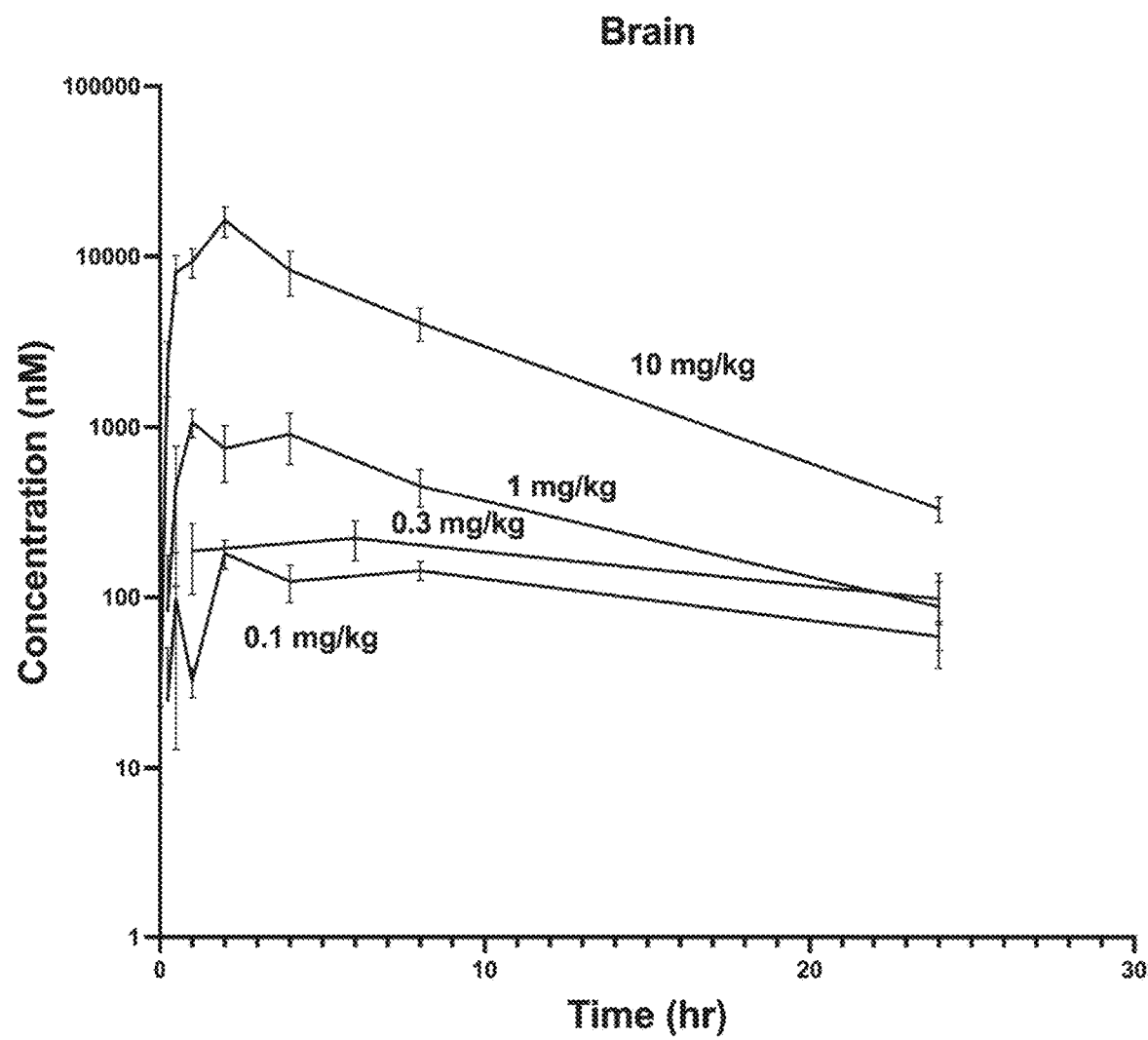

FIG. 35 reports pharmacokinetic data of Compound 1 in the form of brain levels in C57BL/6 mice treated with a single oral gavage dose of Compound 1 at 10 mg/kg, 1 mg/kg, 0.3 mg/kg, and 0.1 mg/kg at multiple timepoints following dosing.

Figure 36:
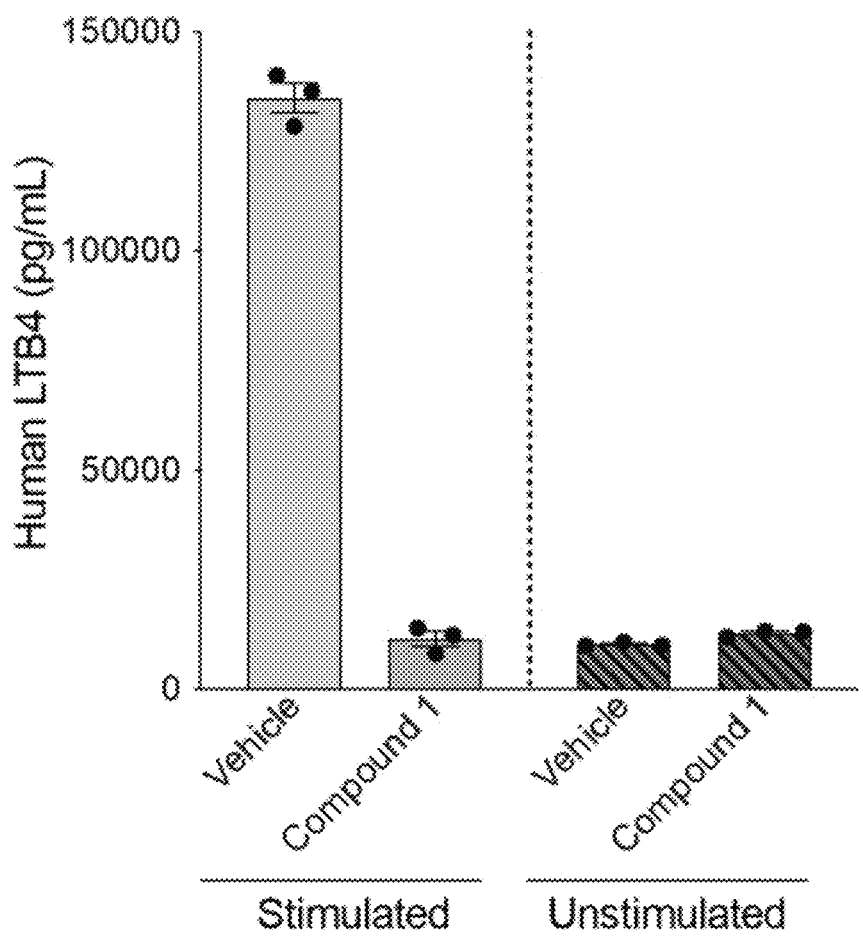

FIG. 36 shows the effects of LTA4H inhibition using Compound ex vivo in human blood. Calcimycin stimulation increases detectable levels of LTB4 in human plasma, which is reduced when incubated with Compound 1.

Figure 37:
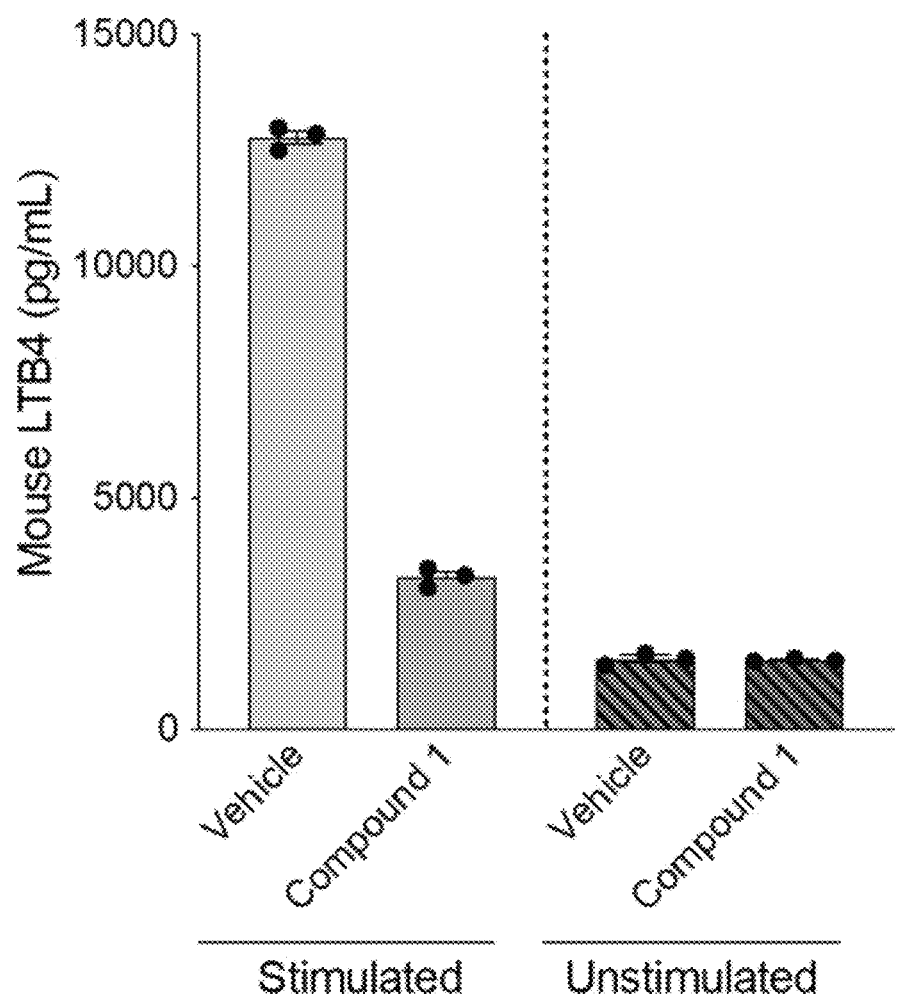

FIG. 37 shows the effects of LTA4H inhibition using Compound 1 ex vivo in mouse blood. Calcimycin stimulation increases detectable levels of LTB4 in mouse plasma, which is reduced when incubated with Compound 1.

Figure 38:
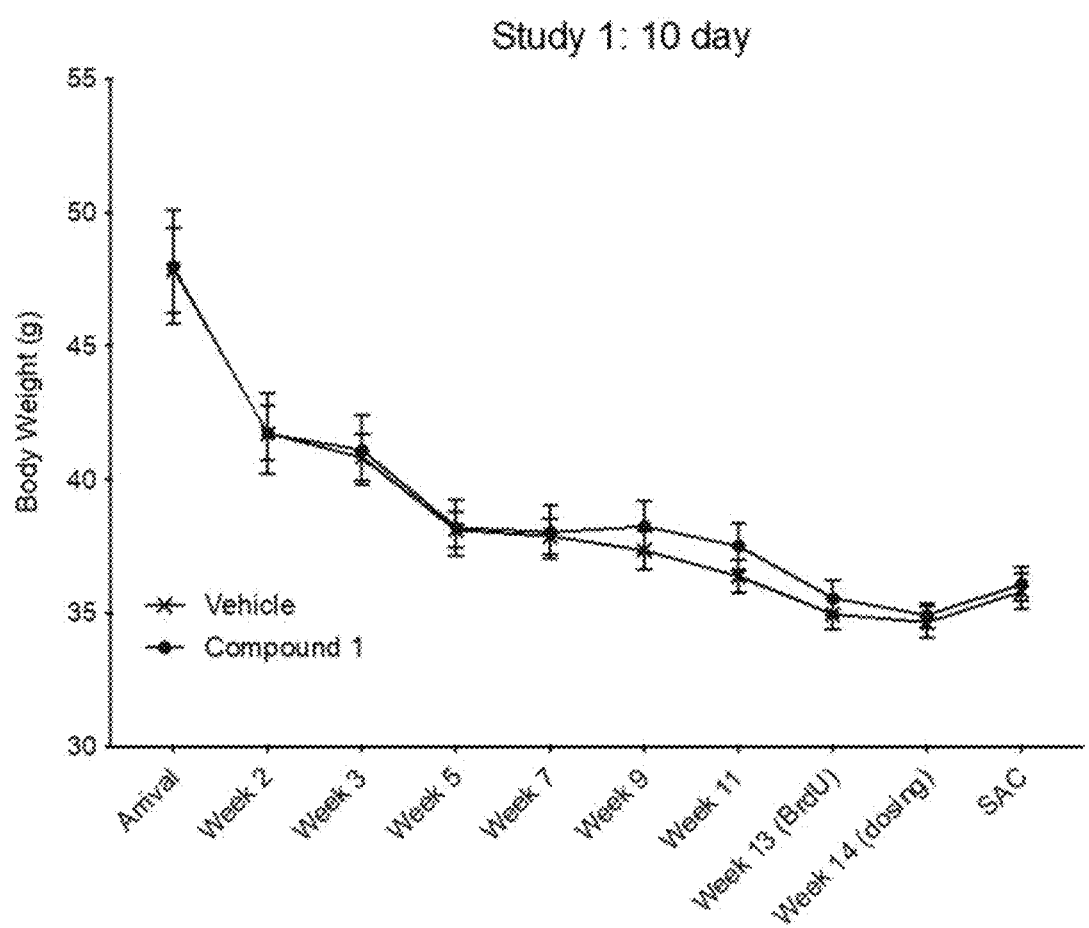

FIG. 38 shows change in body weights in grams (g) of vehicle and Compound 1 treated groups of mice after 10 days of dosing. No significant difference was observed in this group (Study 1 Group).

Figure 39:
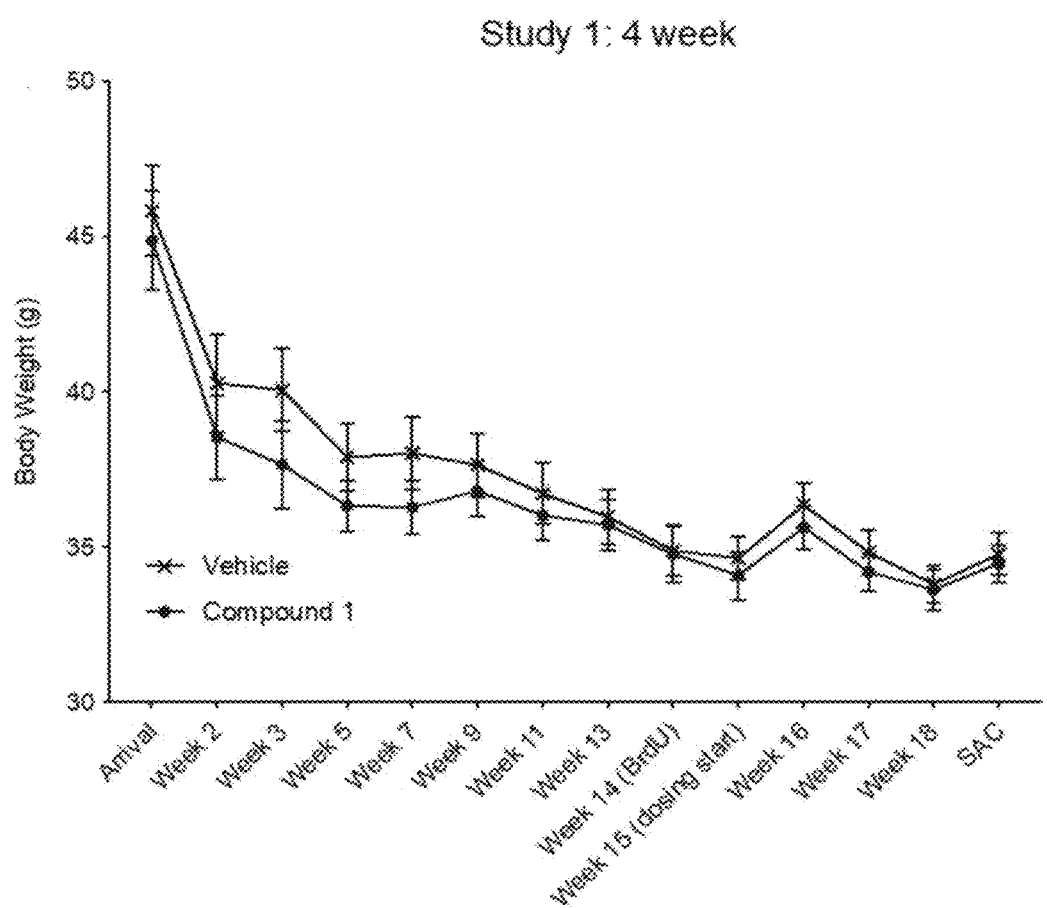

FIG. 39 shows change in body weights in grams (g) of vehicle and Compound 1 treated groups of mice after 4 weeks of dosing. No significant difference was observed in this group (Study 1 Group).

Figure 40:
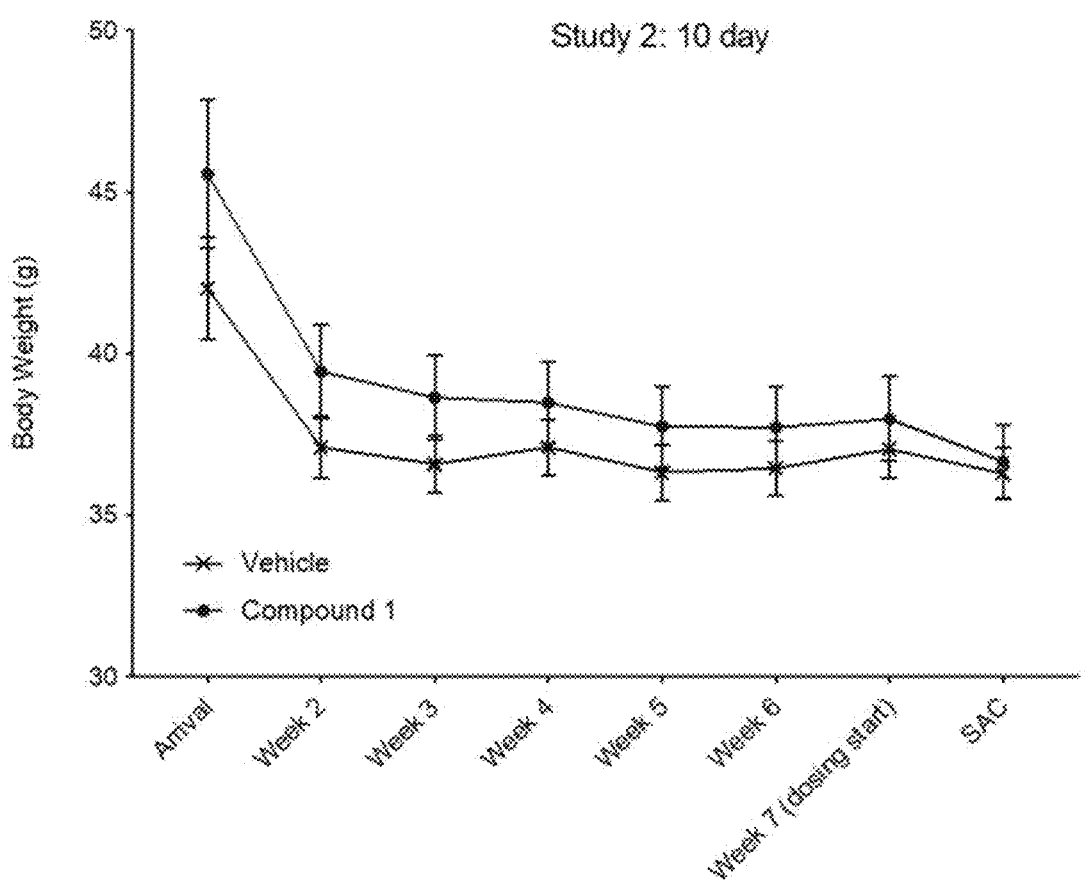

FIG. 40 shows change in body weights in grams (g) of vehicle and Compound 1 treated groups of mice after 10 days of dosing. No significant difference was observed in this group (Study 2 Group).

Figure 41:
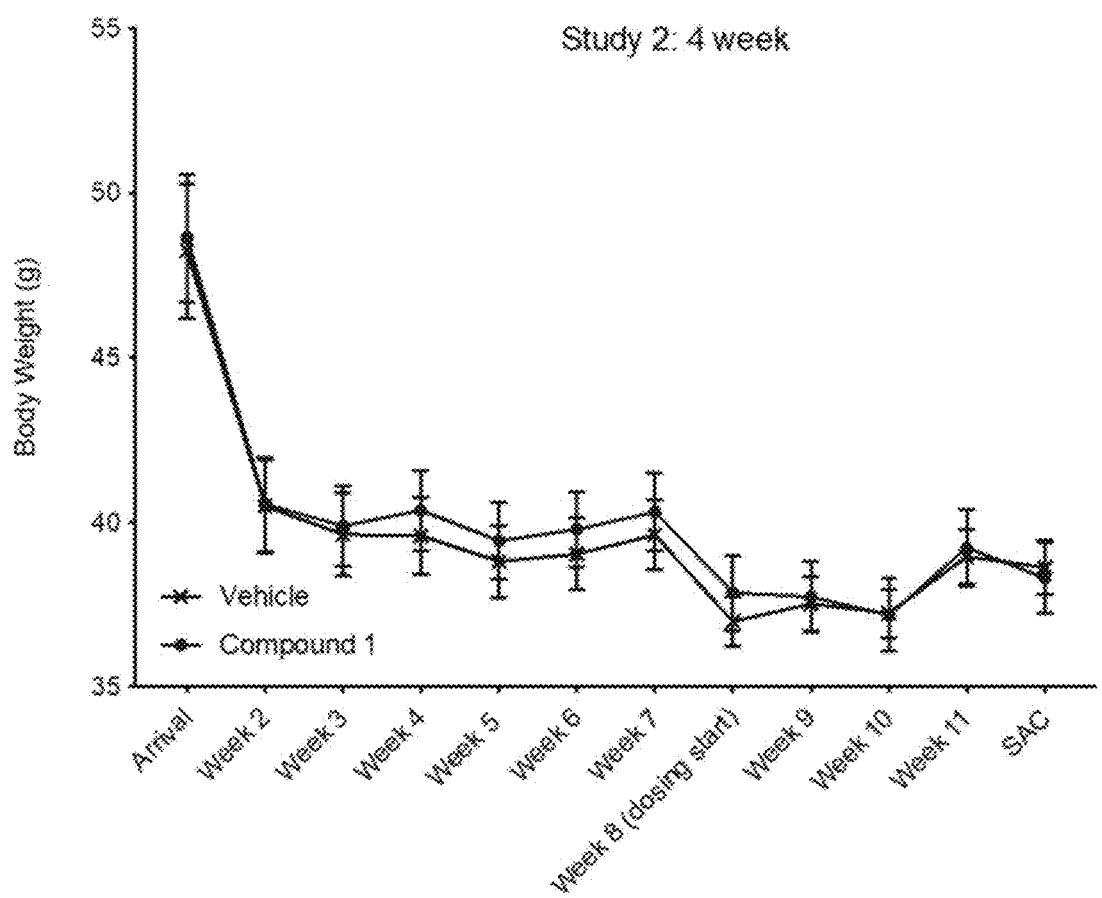

FIG. 41 shows change in body weights in grams (g) of vehicle and Compound 1 treated groups of mice after 4 weeks of dosing. No significant difference was observed in this group (Study 2 Group).

Figure 42:
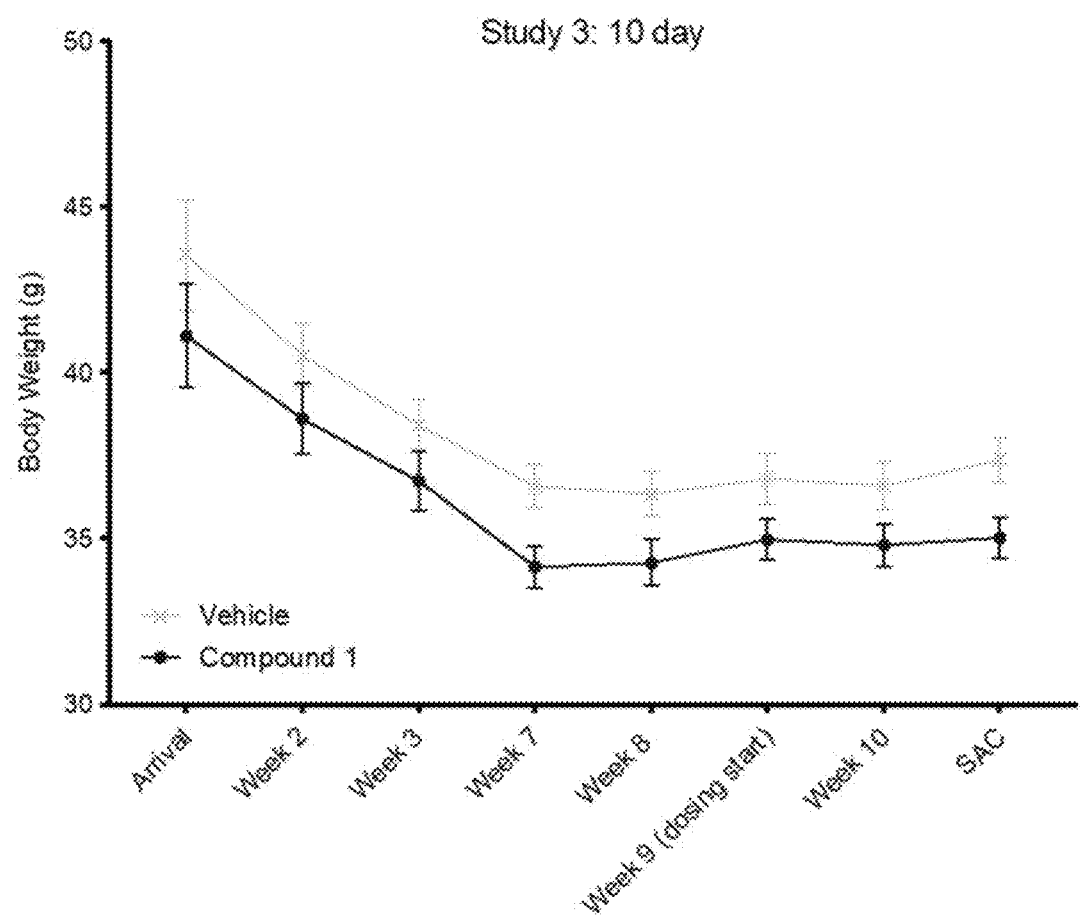

FIG. 42 shows change in body weights in grams (g) of vehicle and Compound 1 treated groups of mice after 10 days of dosing. No significant difference was observed in this group (Study 3 Group).

Figure 43:
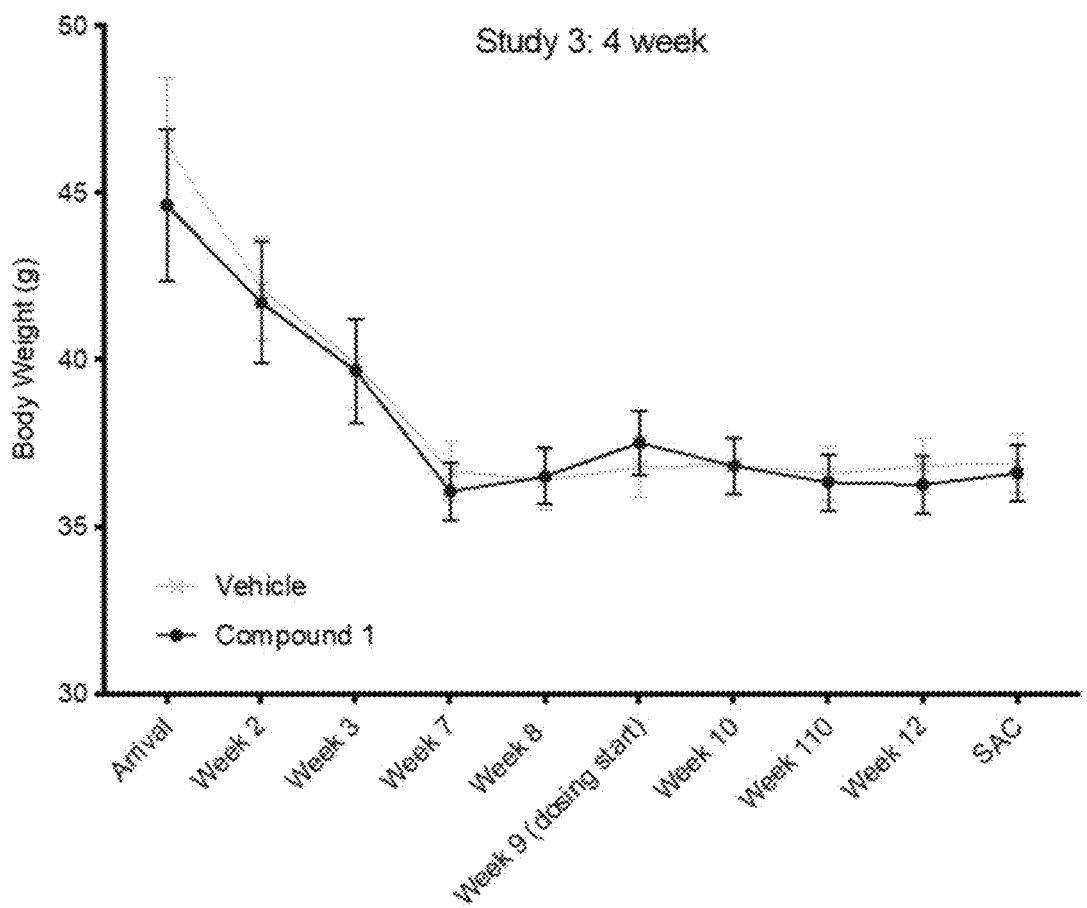

FIG. 43 shows change in body weights in grams (g) of vehicle and Compound 1 treated groups of mice after 4 weeks of dosing. No significant difference was observed in this group (Study 3 Group).

Figure 44:
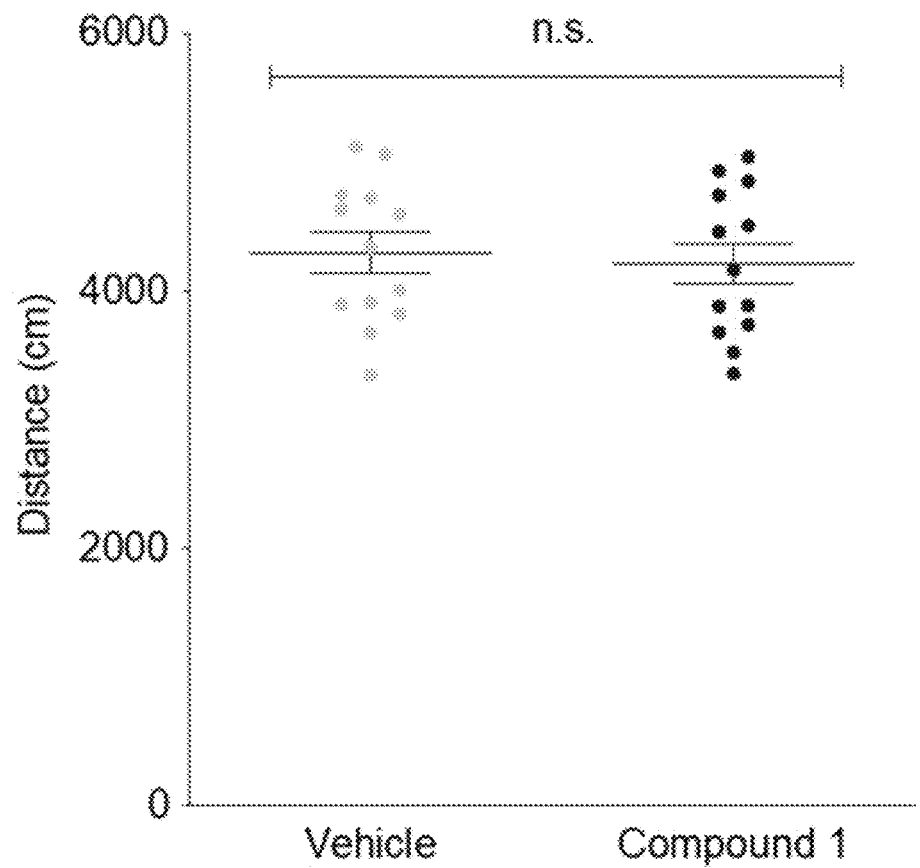

FIG. 44 reports the total distance traveled in an Open Field test in vehicle and Compound 1 treated groups of mice after 10 days of dosing.

Figure 45:
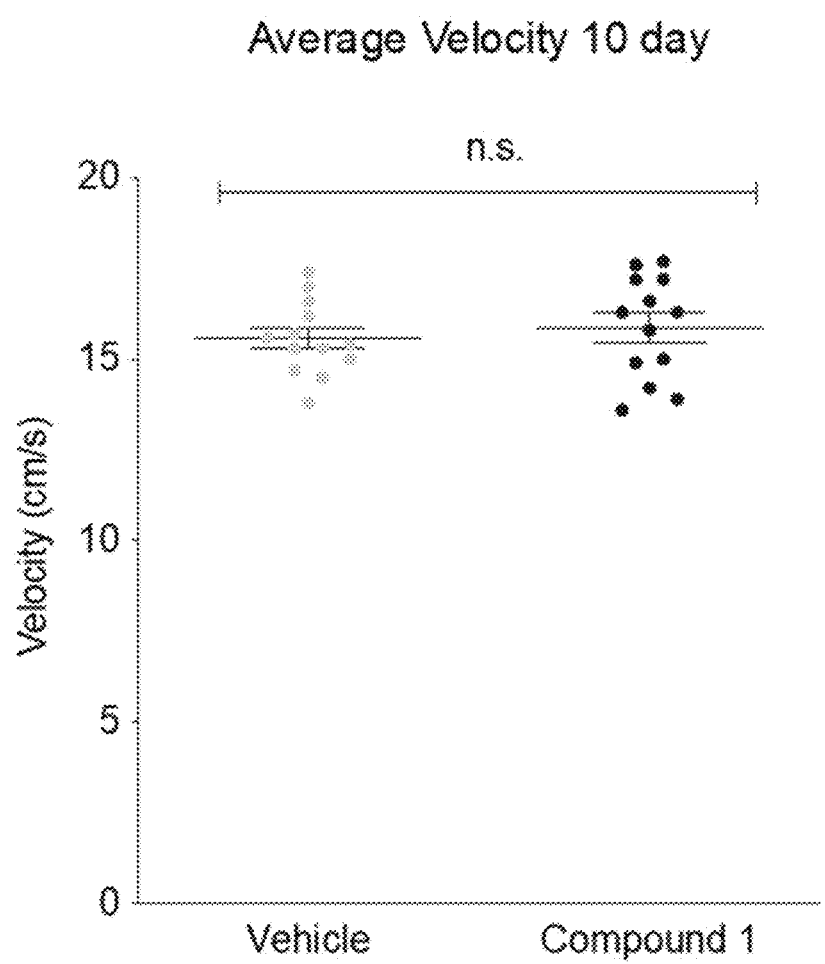

FIG. 45 reports the average velocity traveled in an Open Field test in vehicle and Compound 1 treated groups of mice after 10 days of dosing.

Figure 46:
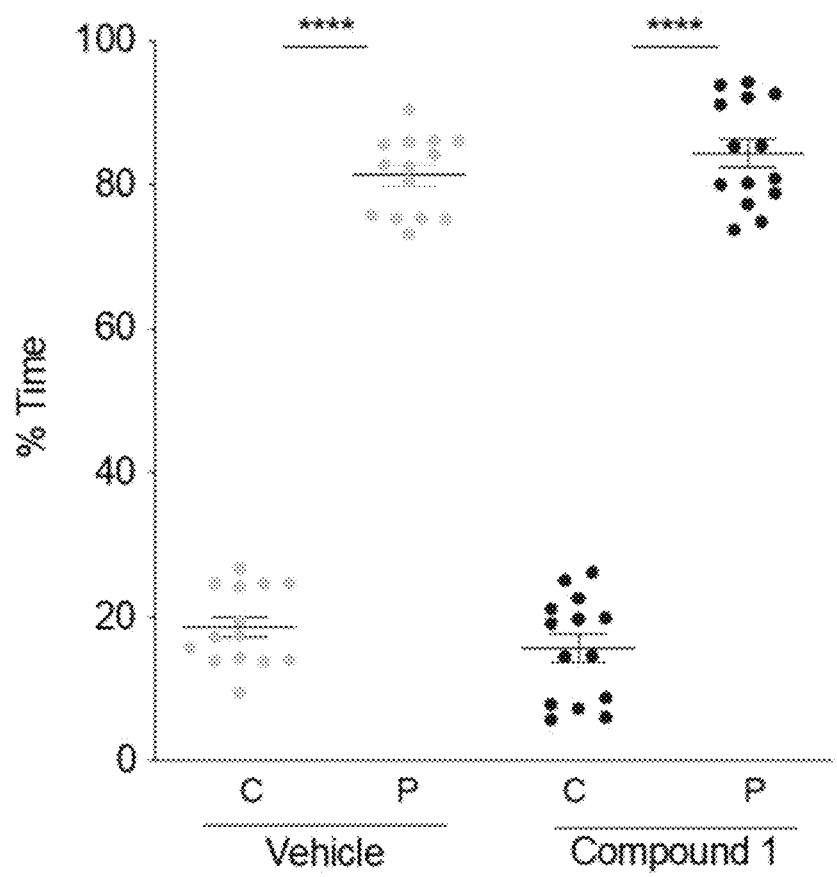

FIG. 46 reports the percent time spent in the center (C) versus the periphery (P) in an Open Field test in vehicle and Compound 1 treated groups of mice after 10 days of dosing.

Figure 47:
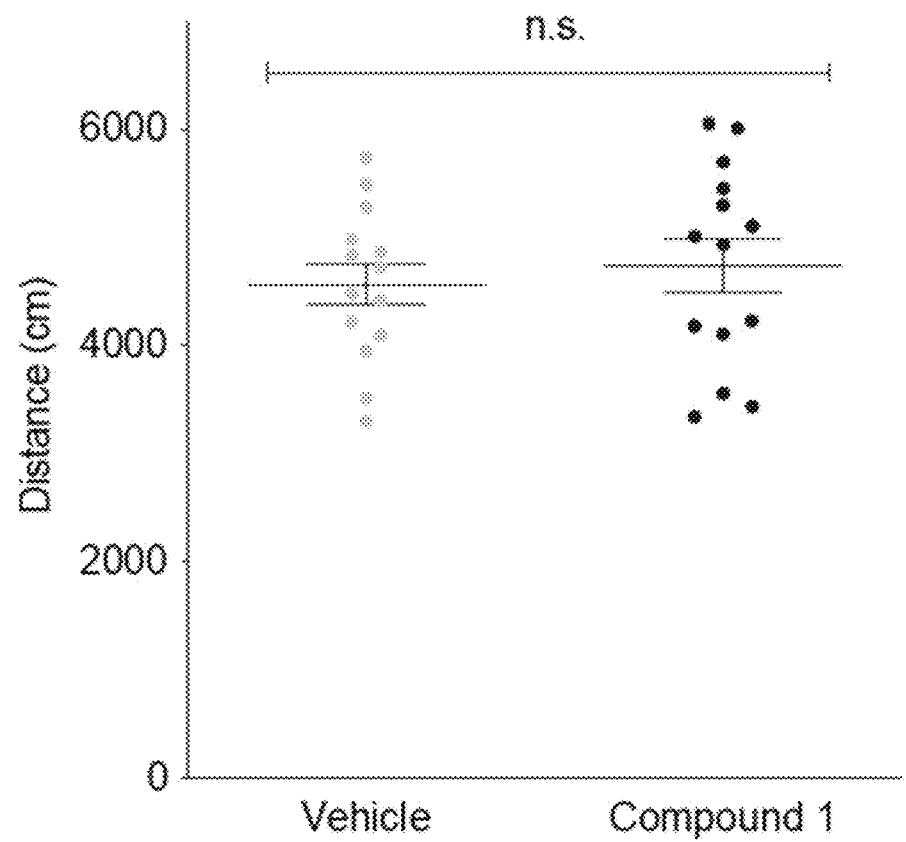

FIG. 47 reports the total distance traveled in an Open Field test in vehicle and Compound 1 treated groups of mice after 4 weeks of dosing.

Figure 48:
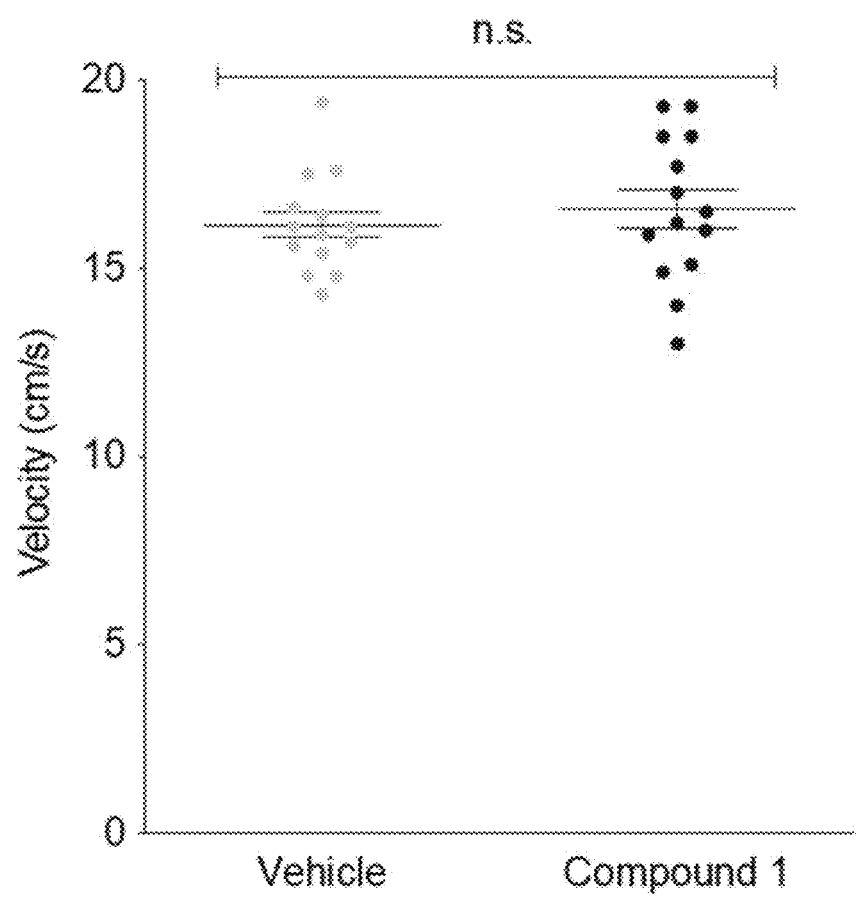

FIG. 48 reports the average velocity traveled in an Open Field test in vehicle and Compound 1 treated groups of mice after 4 weeks of dosing.

Figure 49:
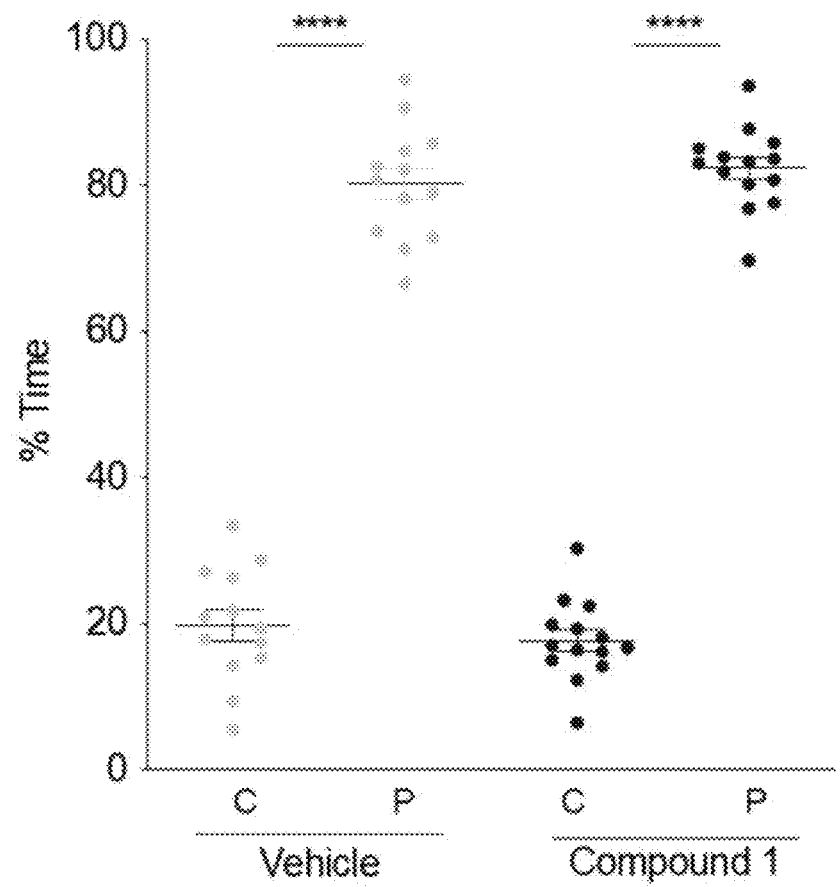

FIG. 49 reports the percent time spent in the center (C) versus the periphery (P) in an Open Field test in vehicle and Compound 1 treated groups of mice after 4 weeks of dosing.

Figure 50:
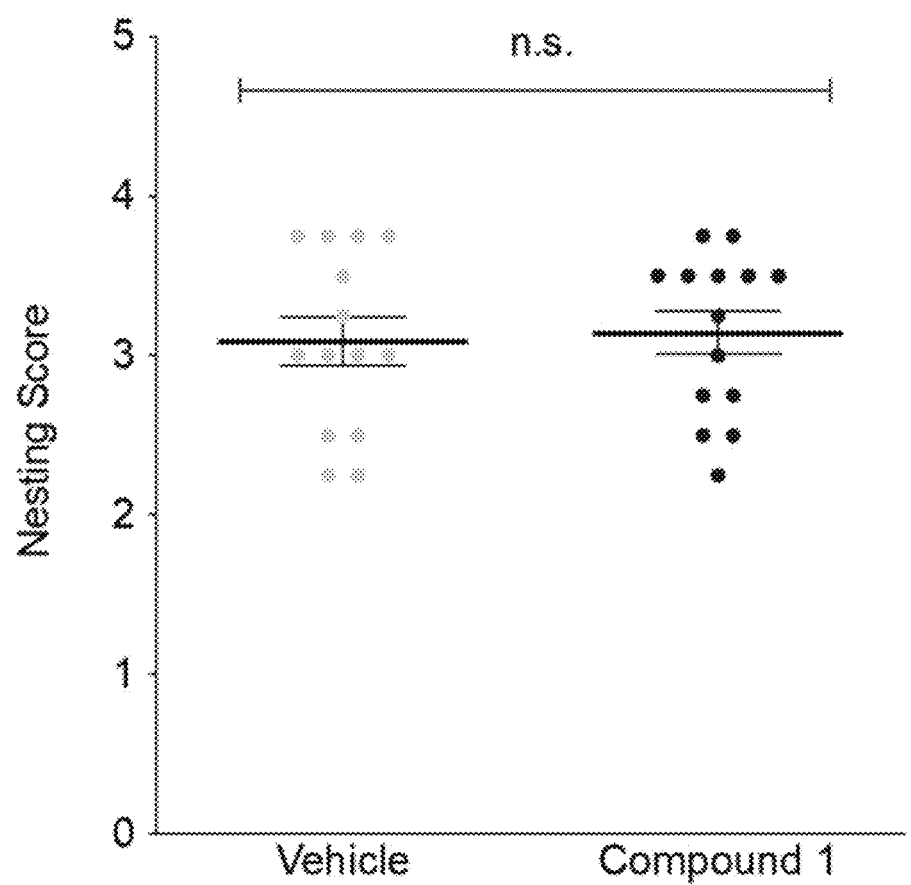

FIG. 50 reports the average nesting score in vehicle and Compound 1 treated groups of mice after 8 days of dosing.

Figure 51:
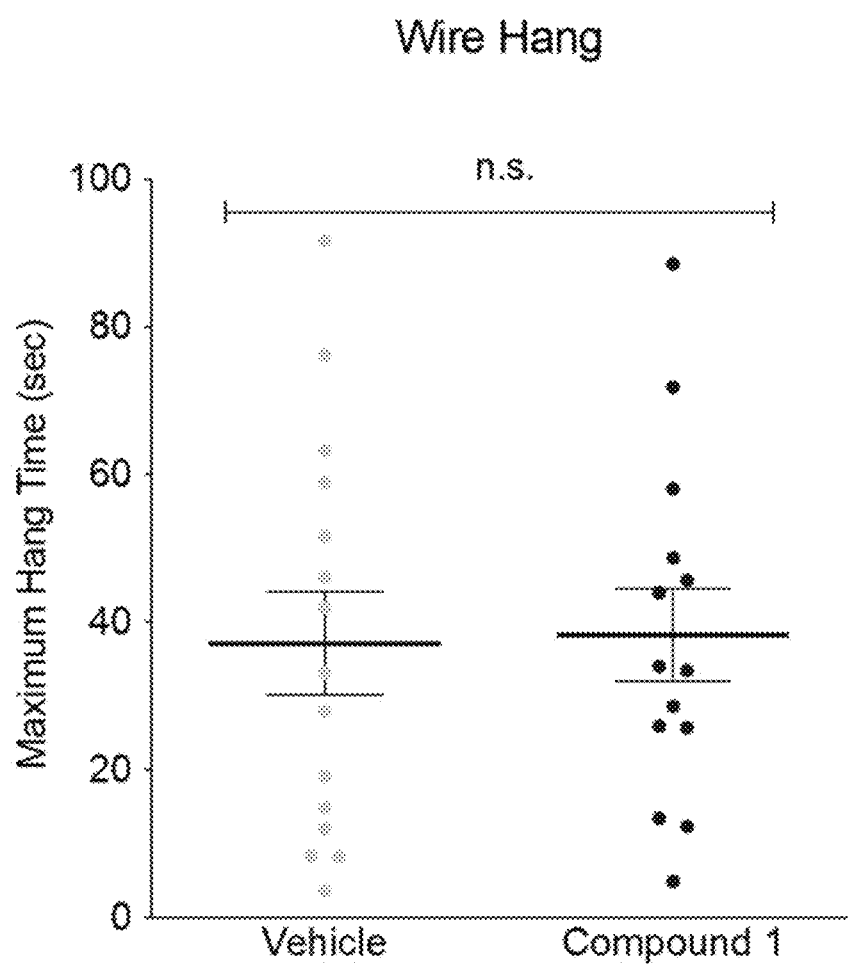

FIG. 51 reports the maximum hang time (sec, seconds) of vehicle and Compound 1 treated groups of mice in a wire hang task after 12 days of dosing.

Figure 52:
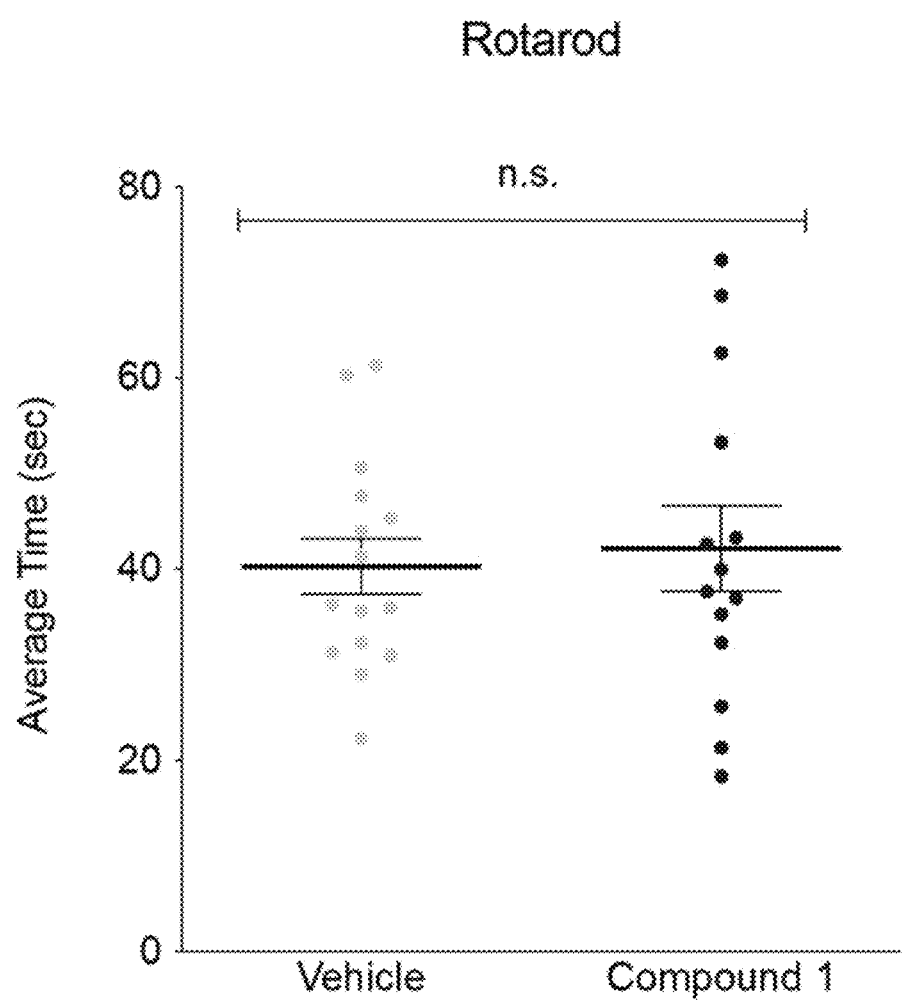

FIG. 52 reports the average time (sec, seconds) before falling in a rotarod task of vehicle and Compound 1 treated groups of mice tested after 19 days of dosing.

Figure 53:
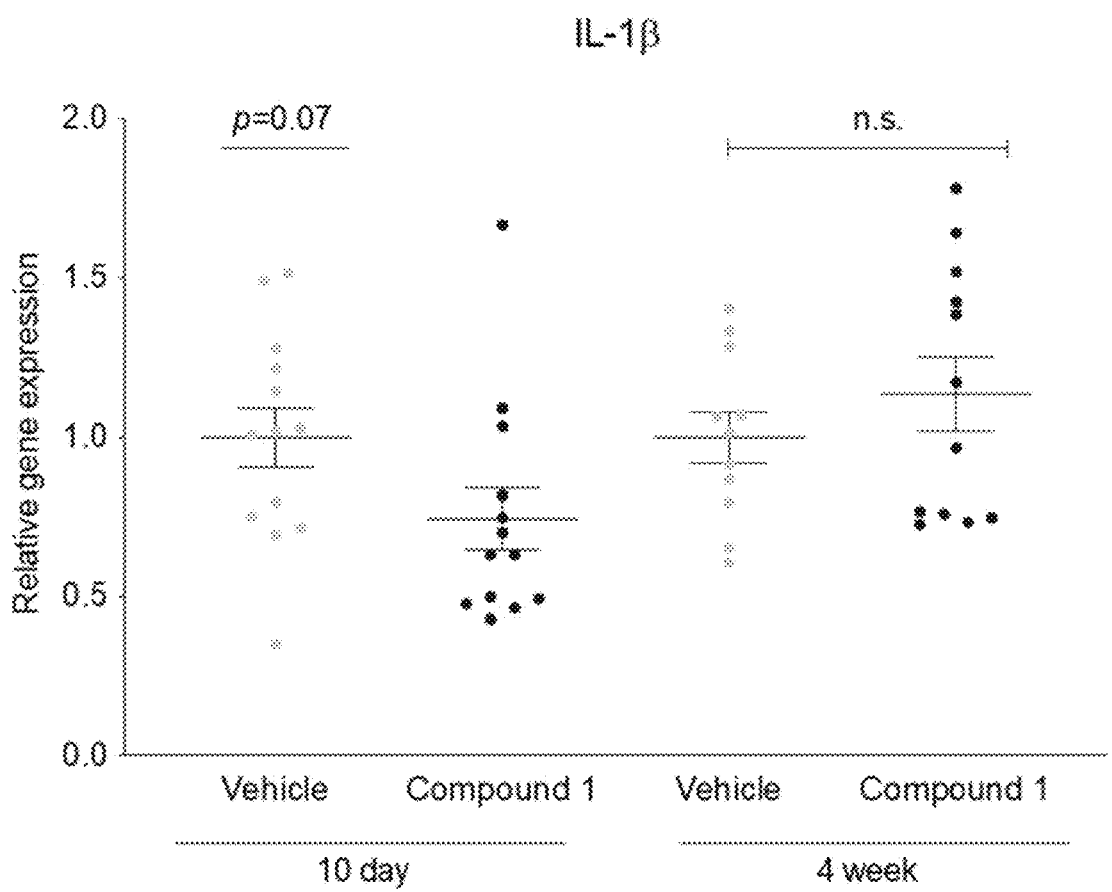

FIG. 53 shows the average ddCT levels of hippocampal interleukin-1-beta (IL-10) mRNA in vehicle and Compound 1 treated groups of mice after 10 days and 4 weeks of treatment. mRNA expression was normalized to vehicle by TaqMan qPCR.

Figure 54:
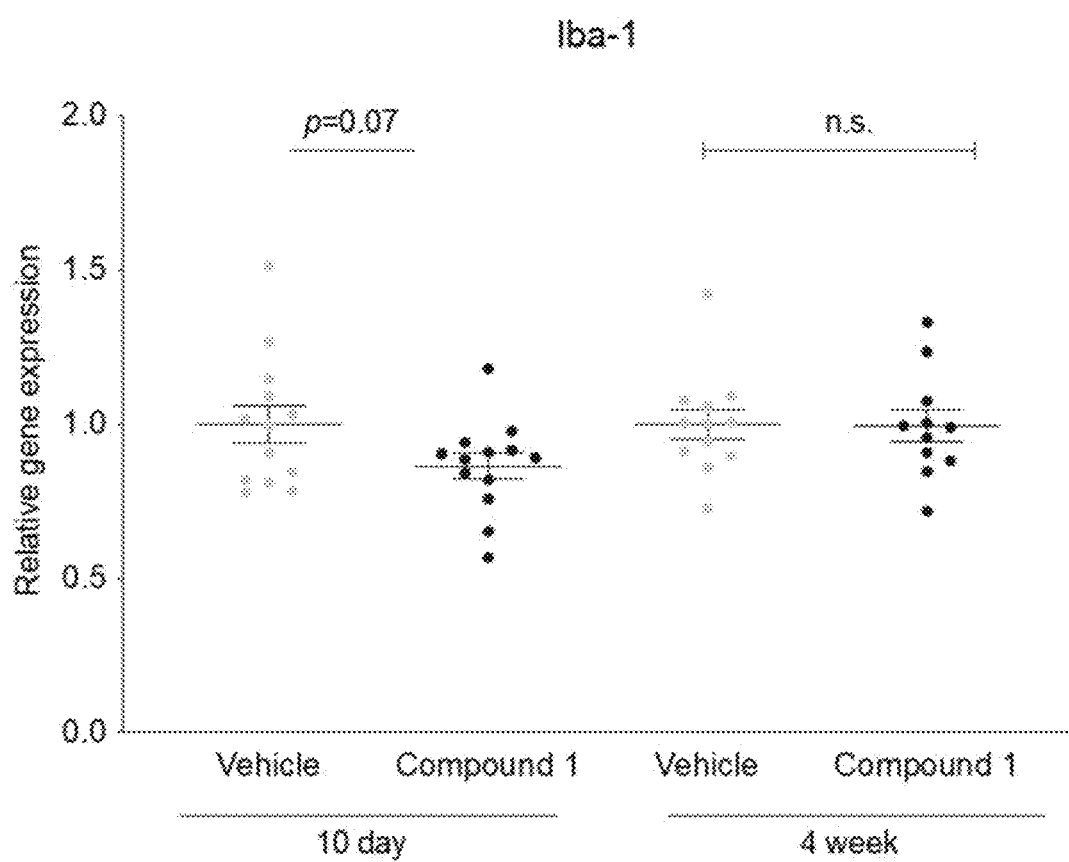

FIG. 54 shows the average ddCT levels of hippocampal ionized calcium-binding adaptor molecule1 (Iba-1) mRNA in vehicle and Compound 1 treated groups of mice after 10 days and 4 weeks of treatment. mRNA expression was normalized to vehicle by TaqMan qPCR. Iba1 is a microglial marker.

Figure 55:
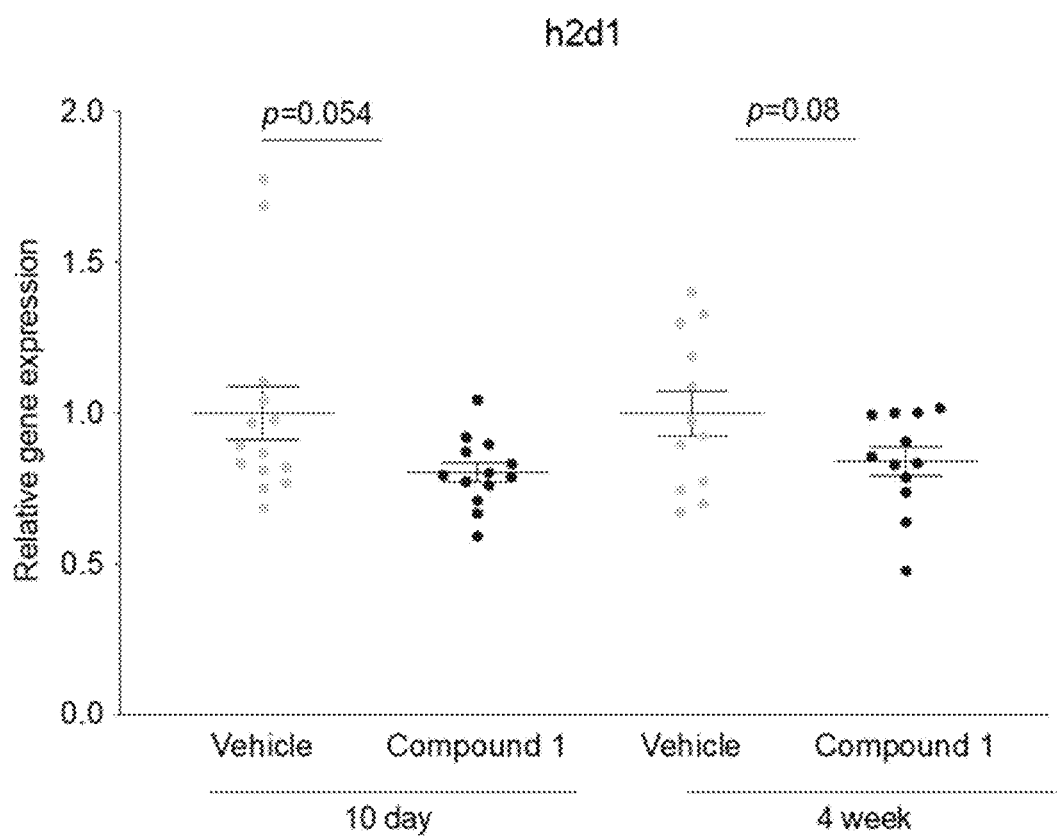

FIG. 55 shows the average ddCT levels of hippocampal histocompatibility 2, D region locus 1 (h2d1) mRNA in vehicle and Compound 1 treated groups of mice after 10 days and 4 weeks of treatment. mRNA expression was normalized to vehicle by SYBR Green qPCR.

Figure 56:
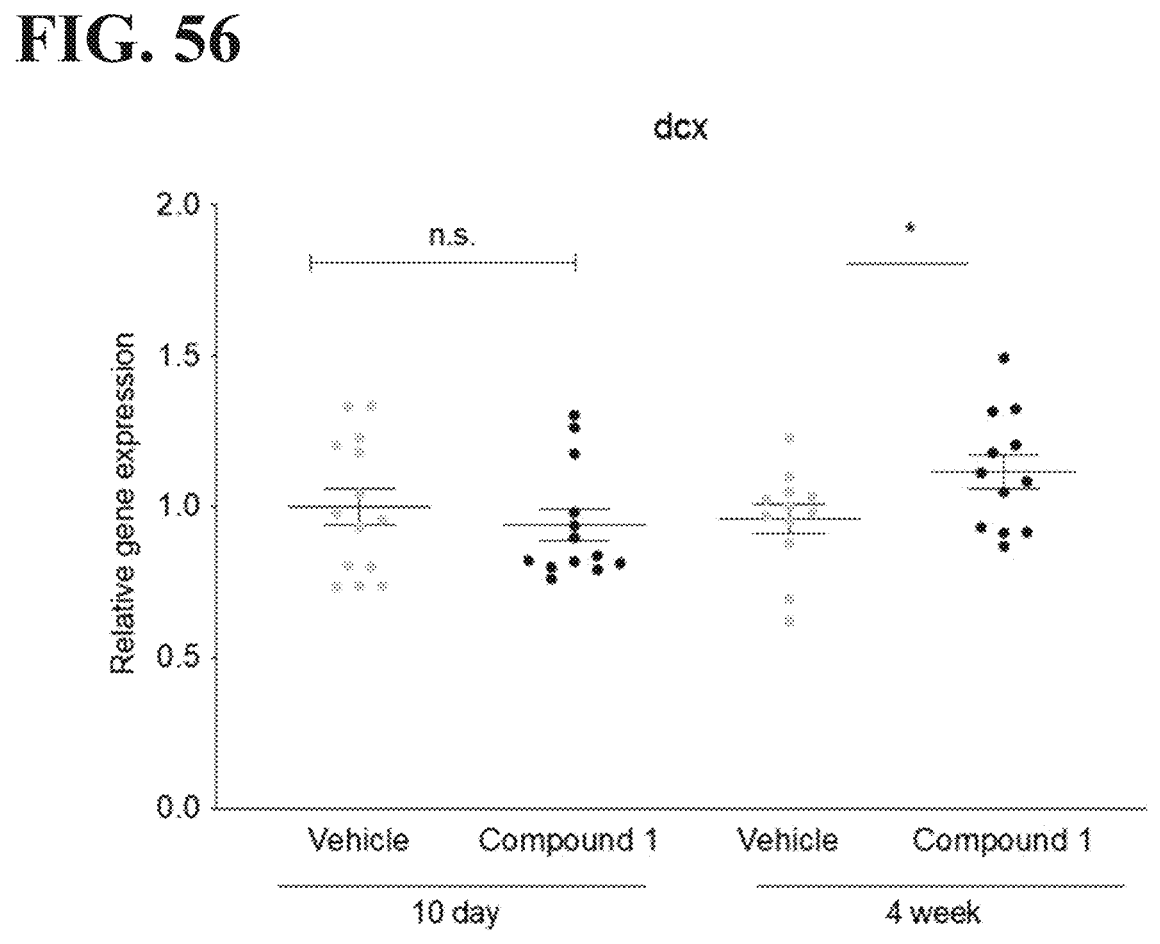

FIG. 56 shows the average ddCT levels of hippocampal doublecortin (dcx) mRNA in vehicle and Compound 1 treated groups of mice after 10 days and 4 weeks of treatment. mRNA expression was normalized to vehicle by SYBR Green qPCR. Doublecortin is a marker of neurogenesis.

Figure 57:
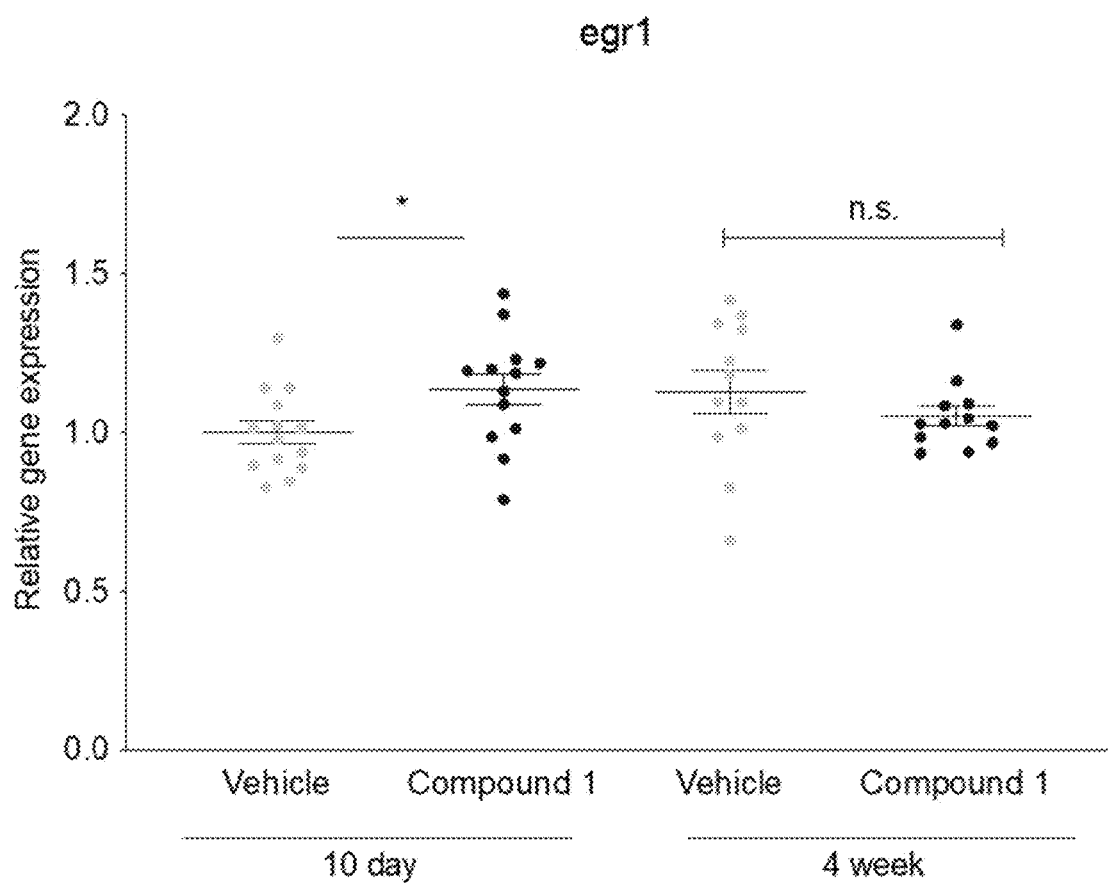

FIG. 57 shows the average ddCT levels of hippocampal early growth response protein 1 (egr1) mRNA in vehicle and Compound 1 treated groups of mice after 10 days and 4 weeks of treatment. mRNA expression was normalized to vehicle by SYBR Green qPCR. Egr1 is a marker of neuronal activity.

Figure 58:
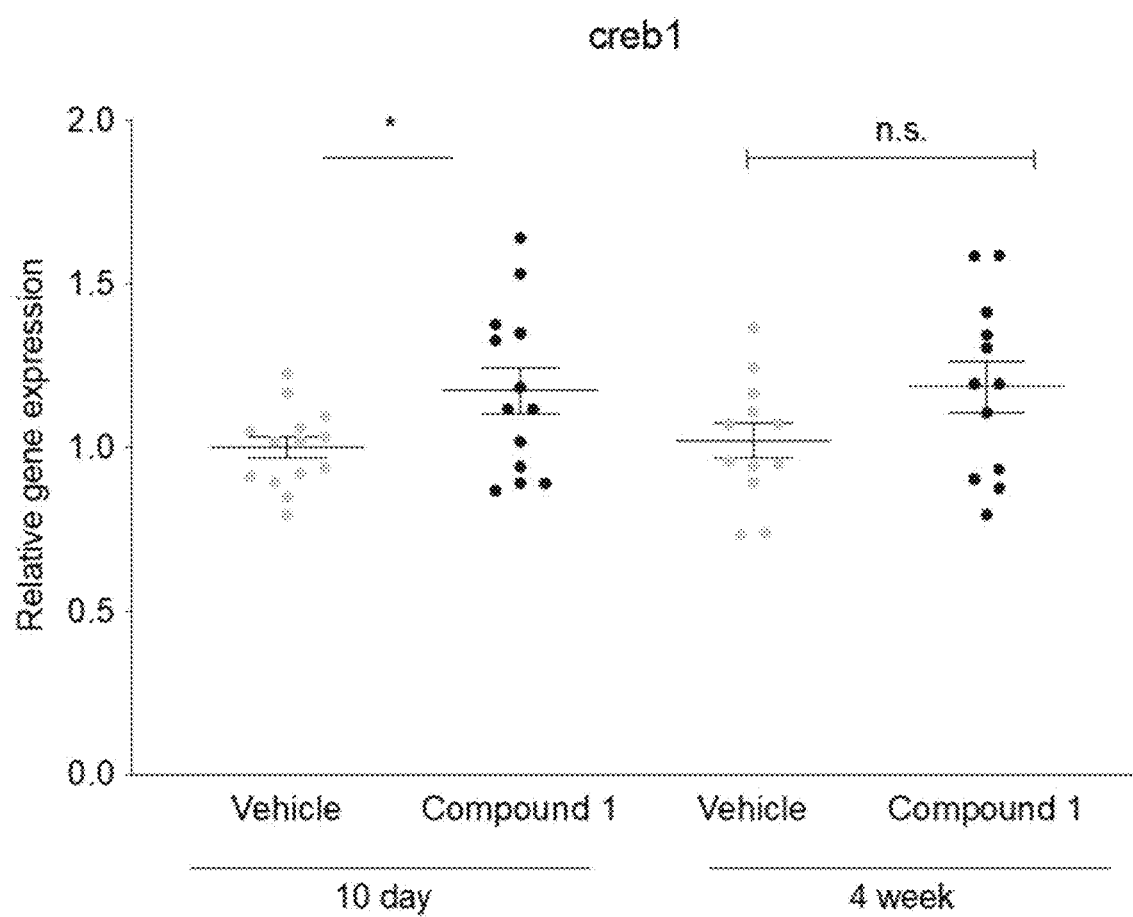

FIG. 58 shows the average ddCT levels of hippocampal cAMP responsive element binding protein 1 (creb1) mRNA in vehicle and Compound 1 treated groups of mice after 10 days and 4 weeks of treatment. mRNA expression was normalized to vehicle by SYBR Green qPCR. Creb1 is considered a marker for cognitive function in cognitive disorders.

Figure 59:
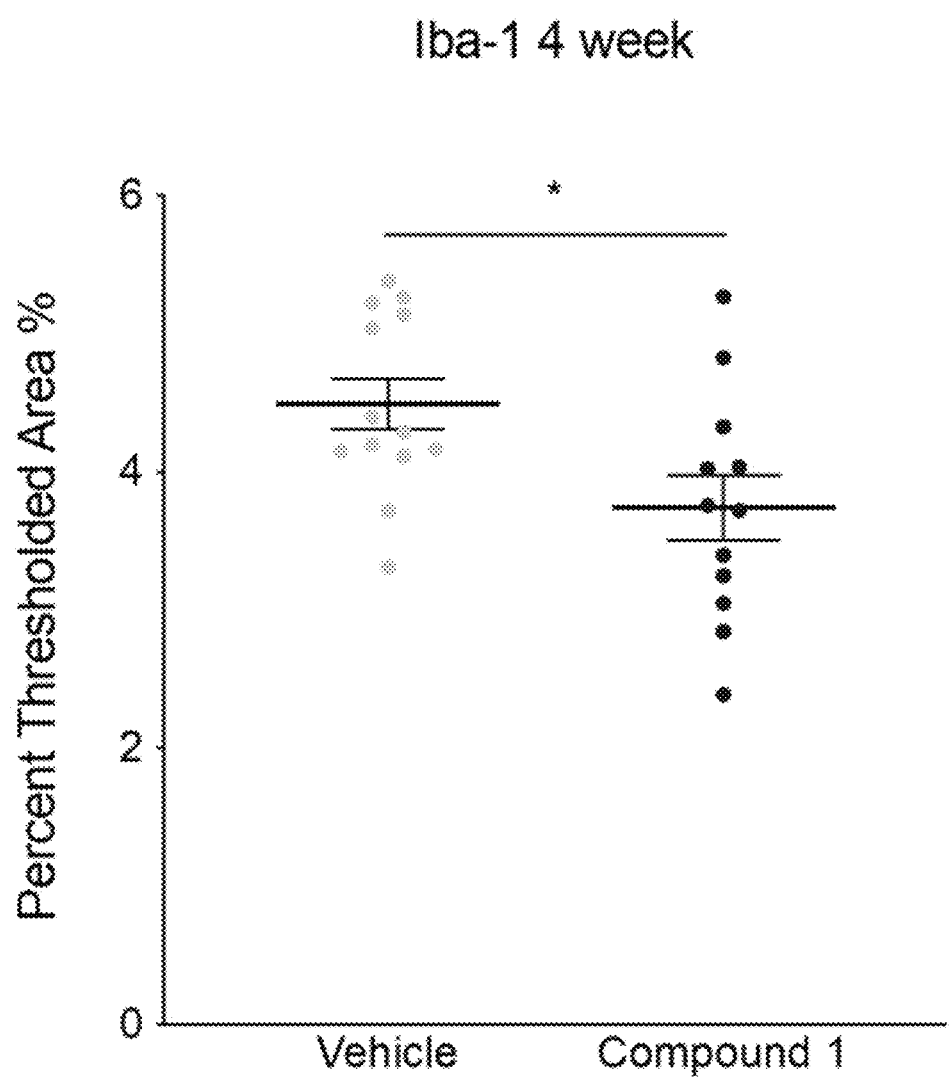

FIG. 59 shows the average Iba-1 percent thresholded area in the hippocampus of groups of mice treated with either vehicle or Compound 1 after 4 weeks of dosing.

Figure 60:
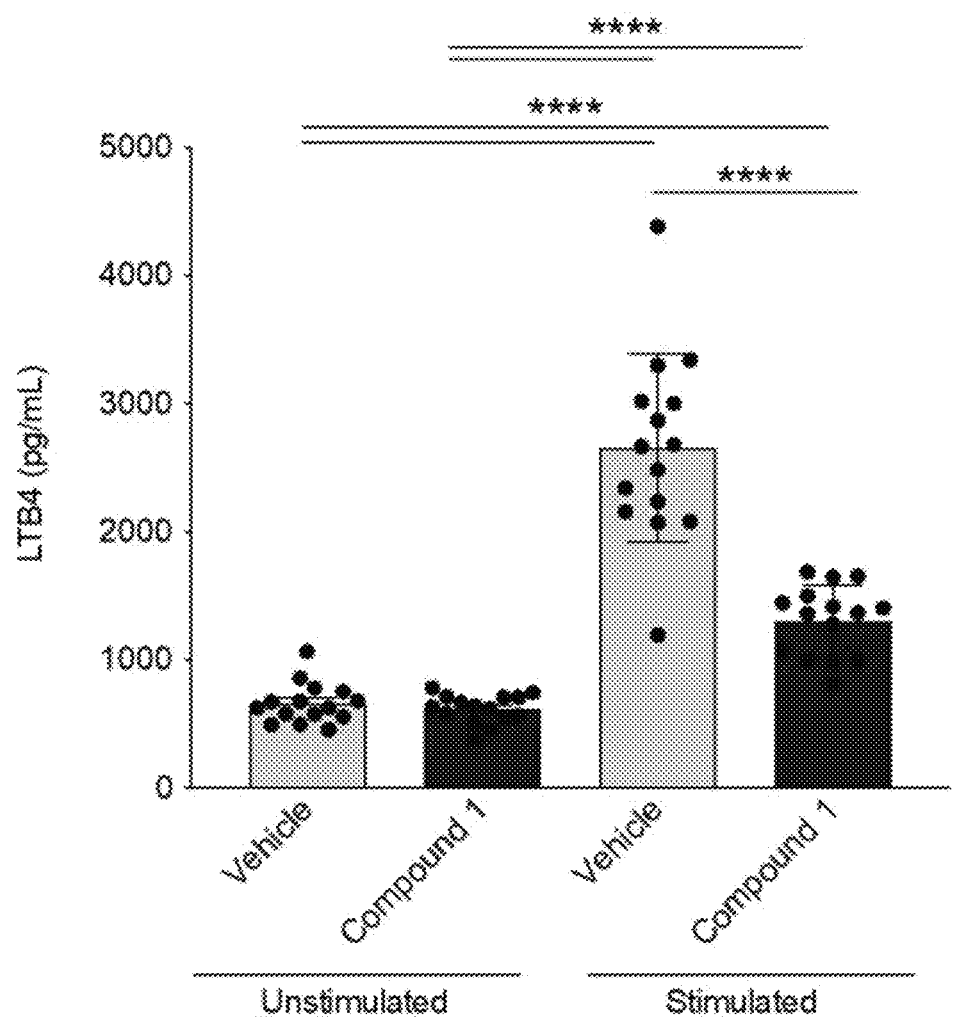

FIG. 60 reports the levels of LTB4 measured by ELISA in pg/mL from plasma collected from mouse blood either stimulated or unstimulated with calcimycin after 10 days of dosing the mice with either vehicle or Compound 1.

Figure 61:
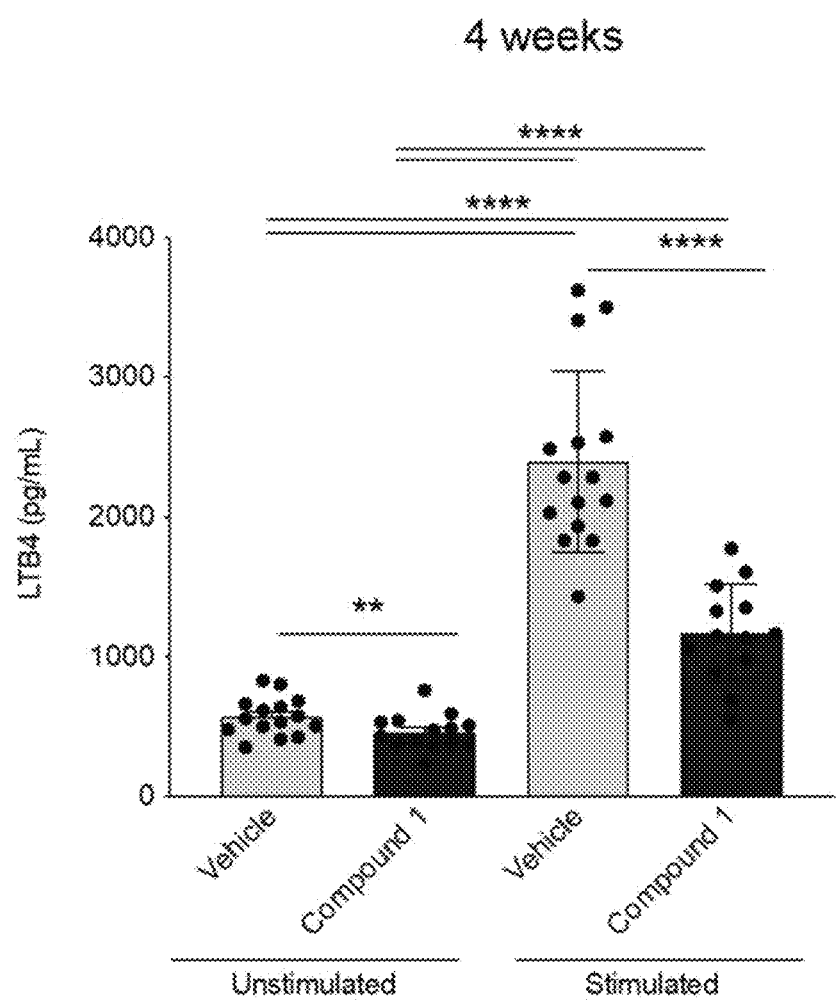

FIG. 61 reports the levels of LTB4 measured by ELISA in pg/mL from plasma collected from mouse blood either stimulated or unstimulated with calcimycin after 4 weeks of dosing the mice with either vehicle or Compound 1.

Figure 62:
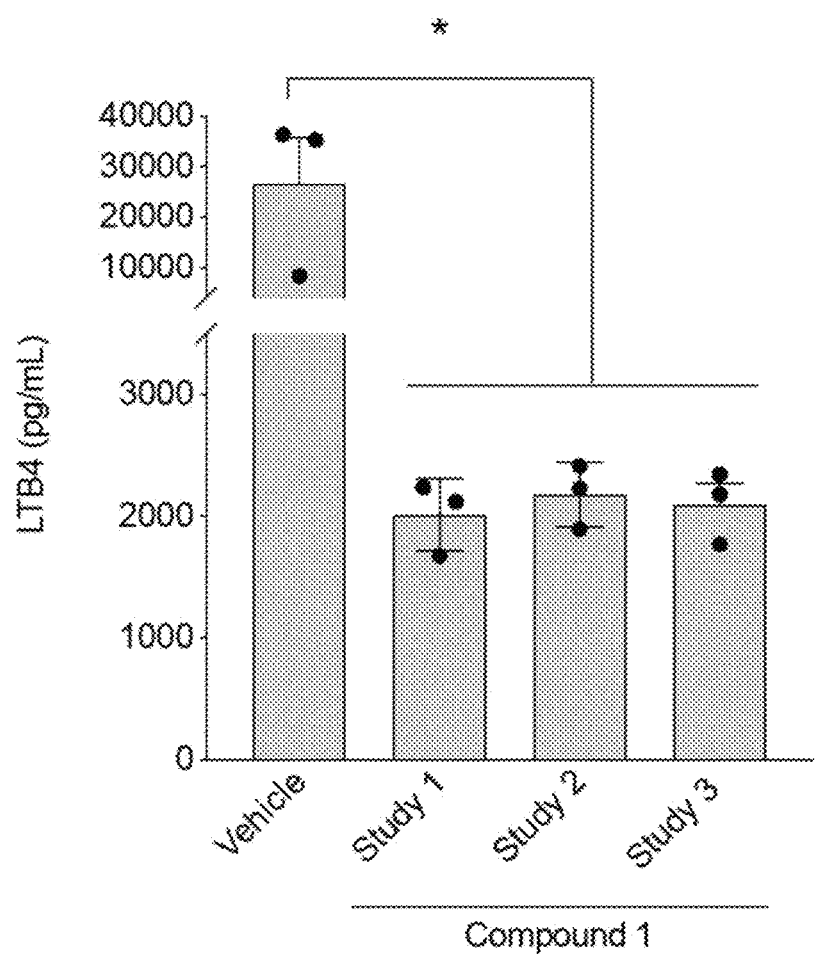

FIG. 62 reports the levels of LTB4 measured by ELISA in pg/mL from plasma collected from young mouse blood either stimulated or unstimulated with calcimycin after 2 hours of a single dose to the mice with either vehicle or Compound 1. Data is reported for three independent study groups.

Figure 63:
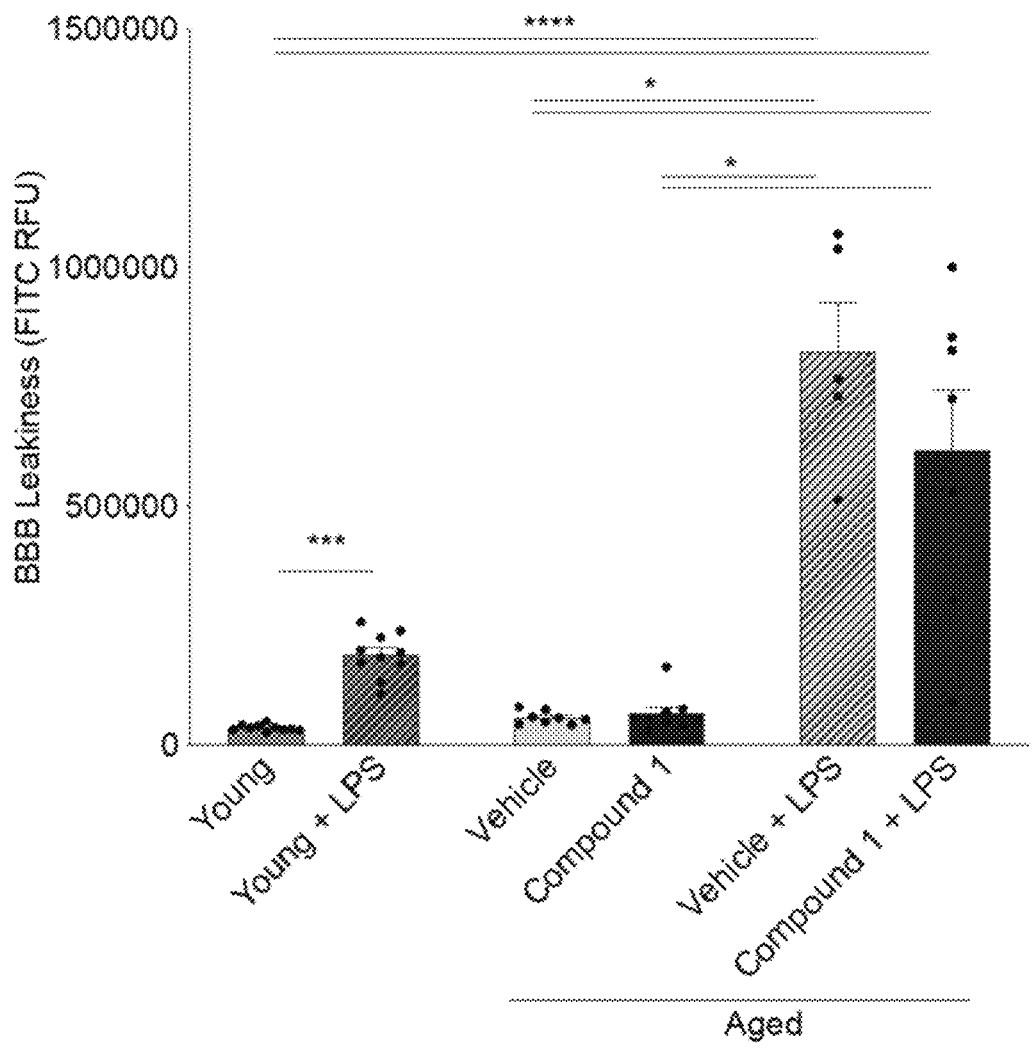

FIG. 63 shows the effects of vehicle and Compound 1 on an LPS model for blood-brain barrier (BBB) breakdown. BBB leakiness was measured in relative fluorescent units (RFU) of sodium fluorescein (FITC) from brain homogenates across age (Young and Aged groups), LPS, and either vehicle or Compound 1 treatment.

Figure 64:
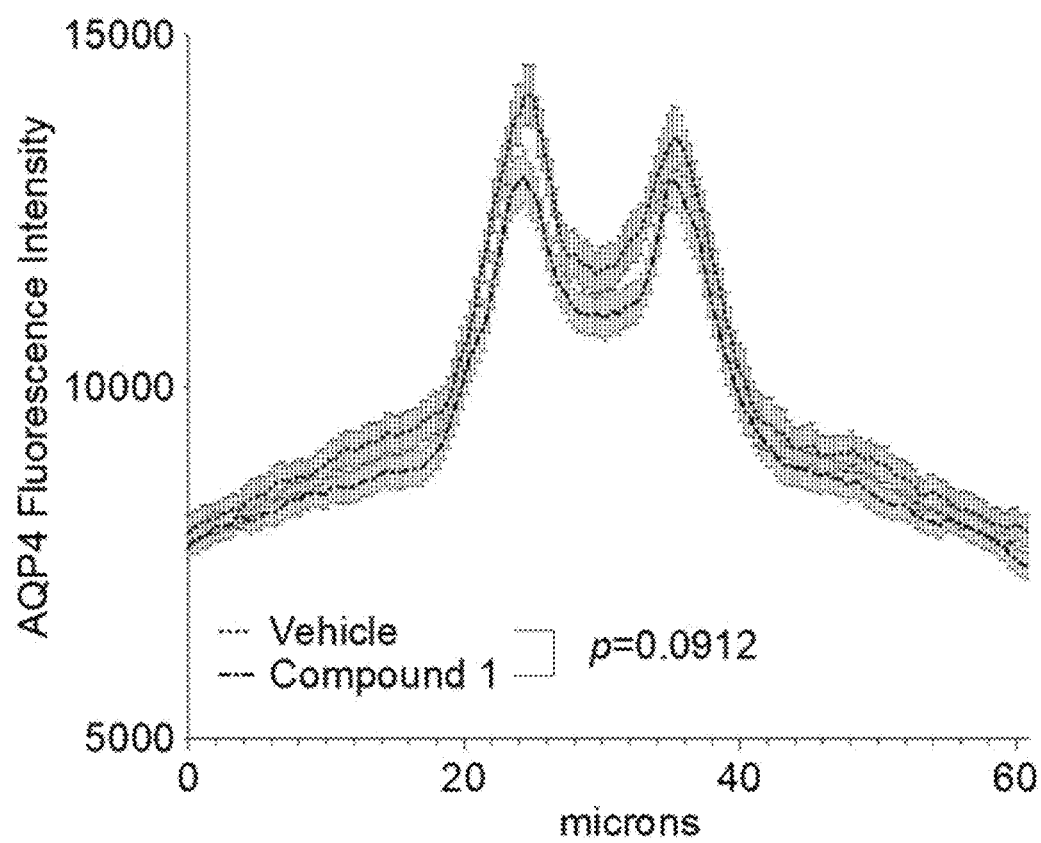

FIG. 64 shows the average AQP4 intensity across descending blood vessels in CA1 hippocampus in mice treated with vehicle or Compound 1 followed by an acute, high dose of LPS to induce BBB leakiness. Line graphs depict average AQP4 intensity across a 60 μm line, 6-8 vessels per mouse.

Figure 65:
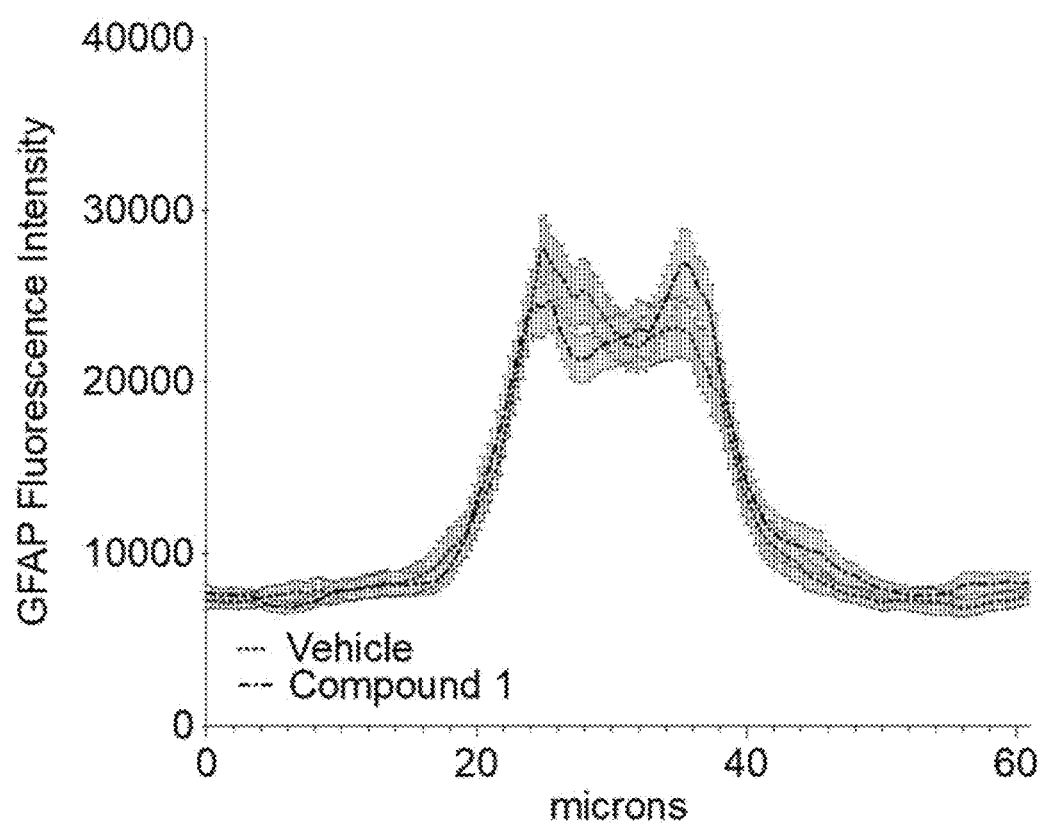

FIG. 65 shows the average GFAP intensity across descending blood vessels in CA1 hippocampus in mice treated with vehicle or Compound 1 followed by an acute, high dose of LPS to induce BBB leakiness. Line graphs depict average GFAP intensity across a 60 μm line, 6-8 vessels per mouse.

Figure 66:
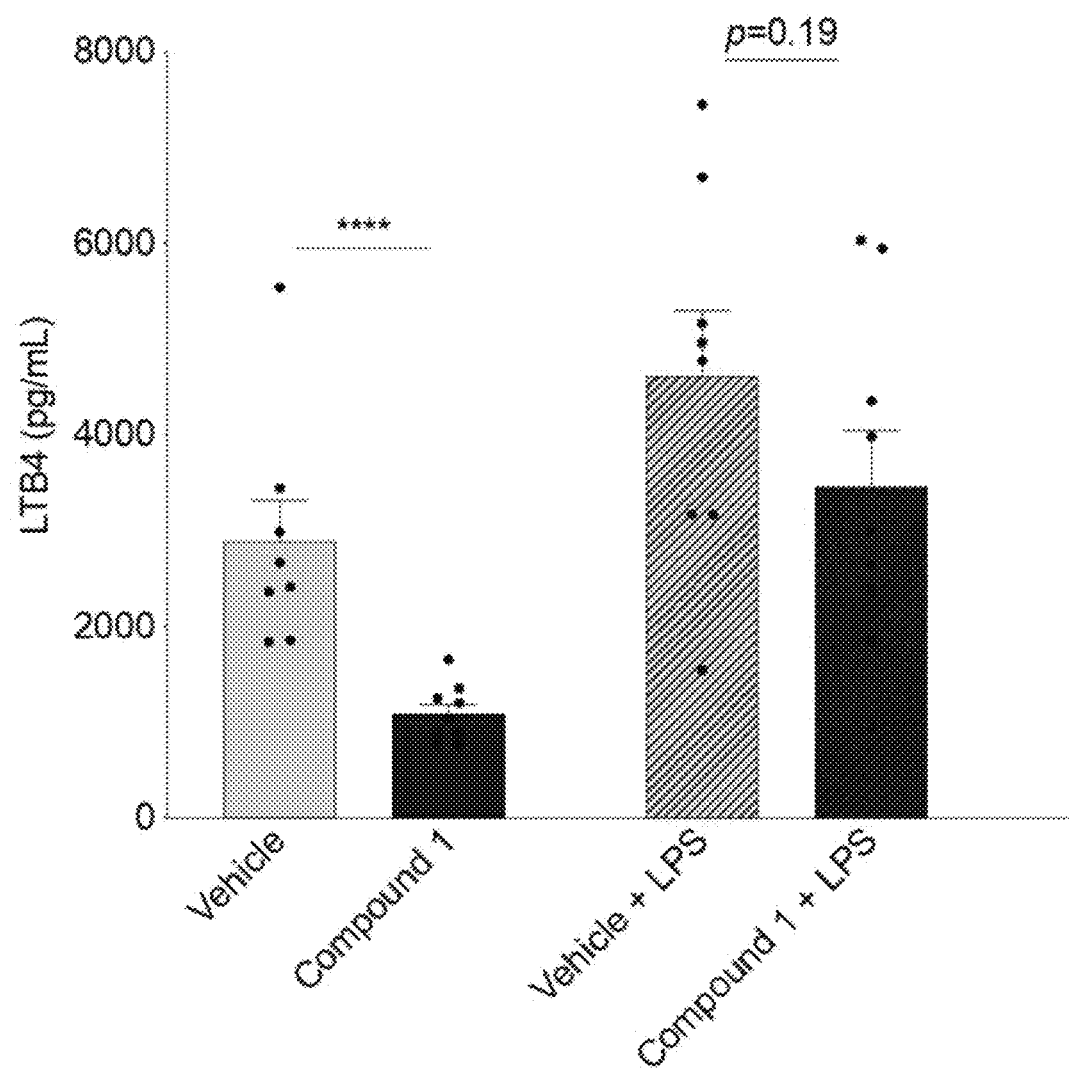

FIG. 66 reports the terminal plasma levels of LTB4 in mice treated with vehicle or Compound 1 followed by an acute, high dose of LPS to induce BBB leakiness. LTB4 levels were measured by ELISA in pg/mL following calcimycin stimulation.

Figure 67:
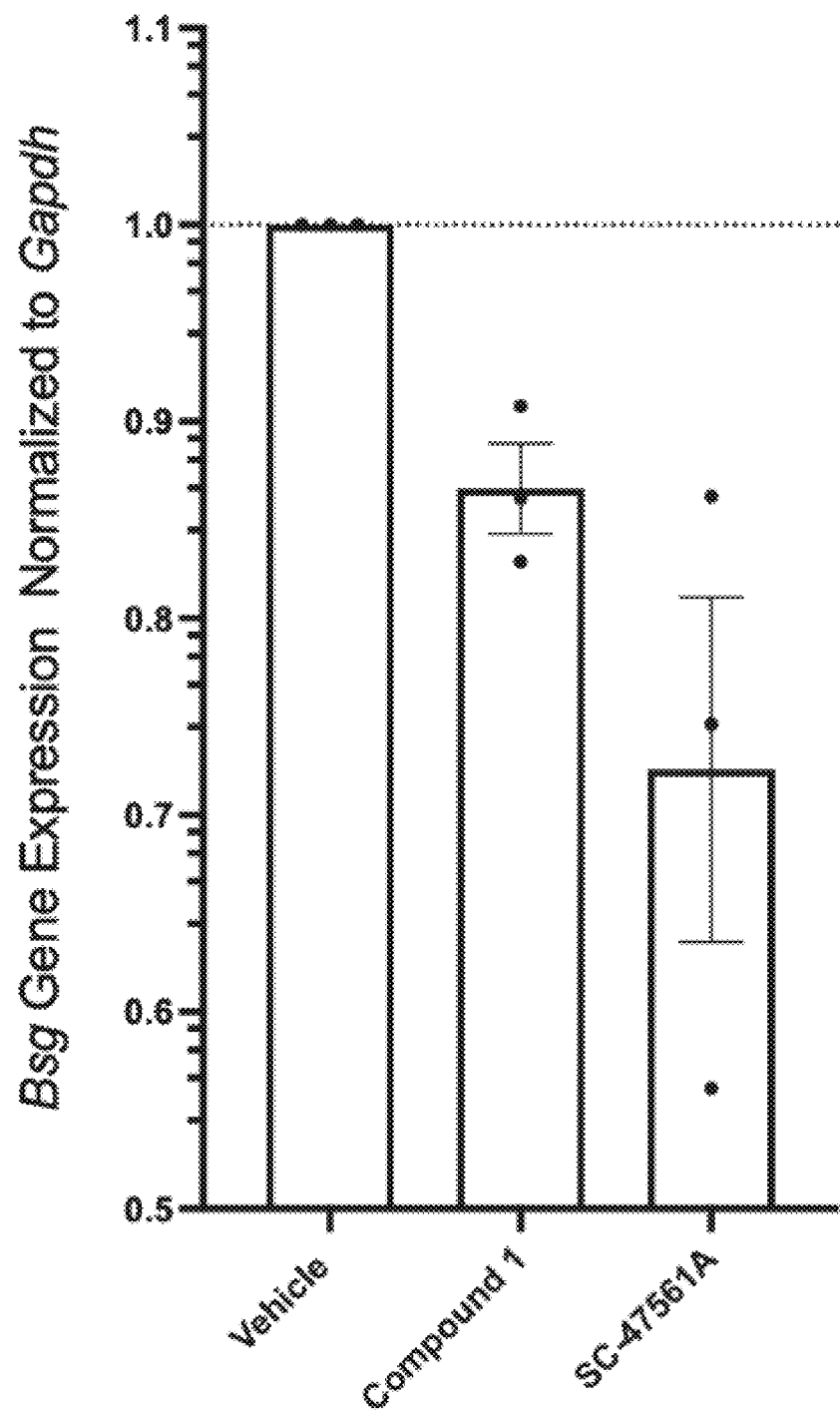

FIG. 67 shows levels of downregulation of the Bsg detrimental gene in the cortex of vehicle, Compound 1, and SC-47561A-treated mice.

Figure 68:
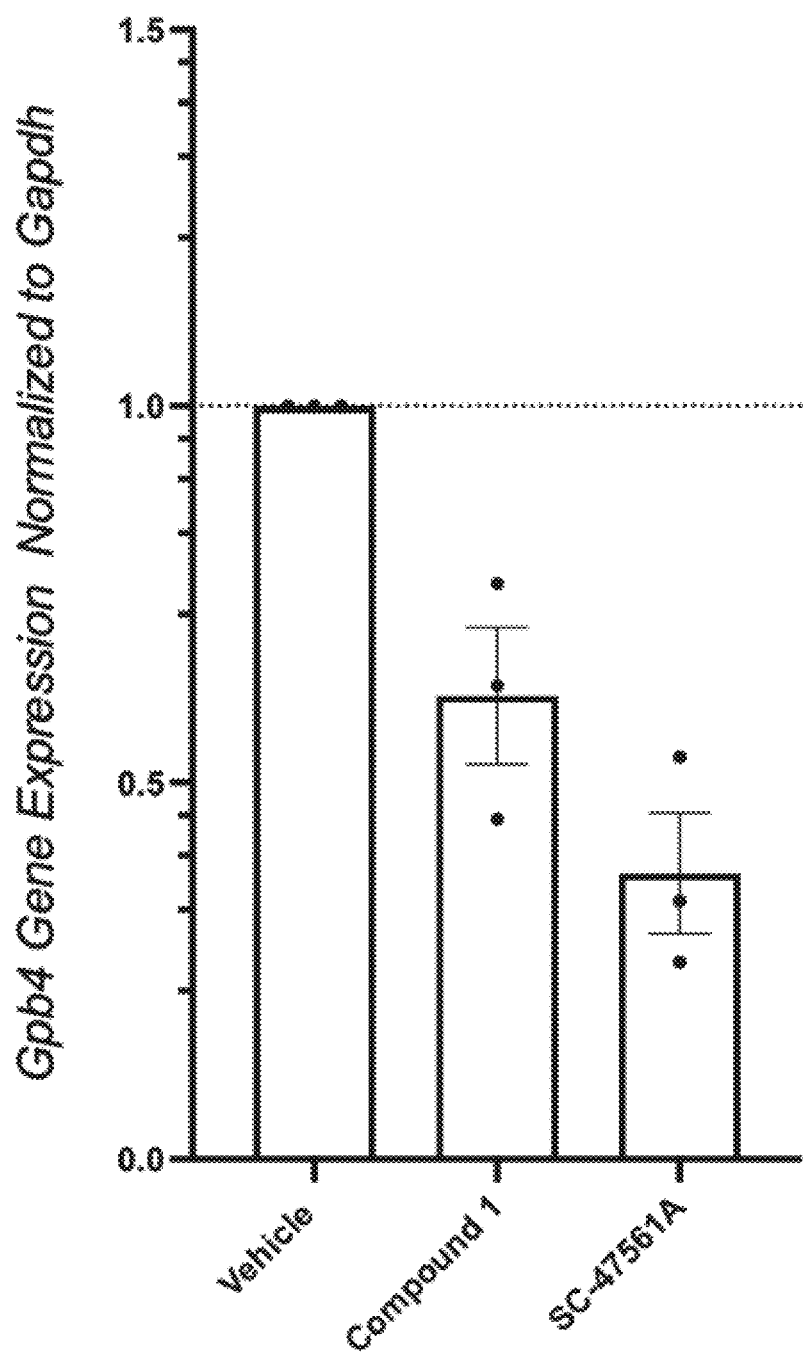

FIG. 68 shows levels of downregulation of the Gpb4 detrimental gene in the cortex of vehicle, Compound 1, and SC-47561A-treated mice.

Figure 69:
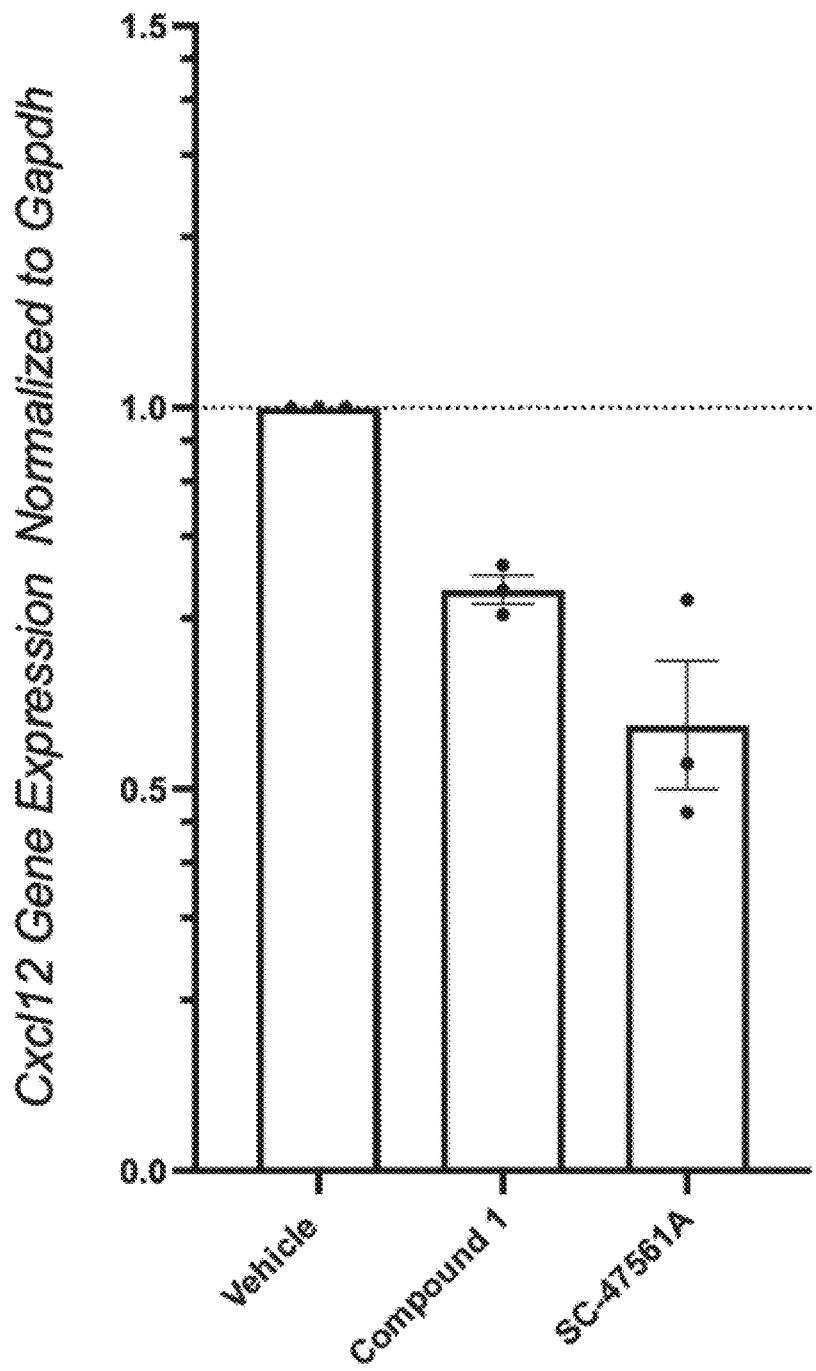

FIG. 69 shows levels of downregulation of the CXCL12 detrimental gene in the cortex of vehicle, Compound 1, and SC-47561A-treated mice.

Figure 70:
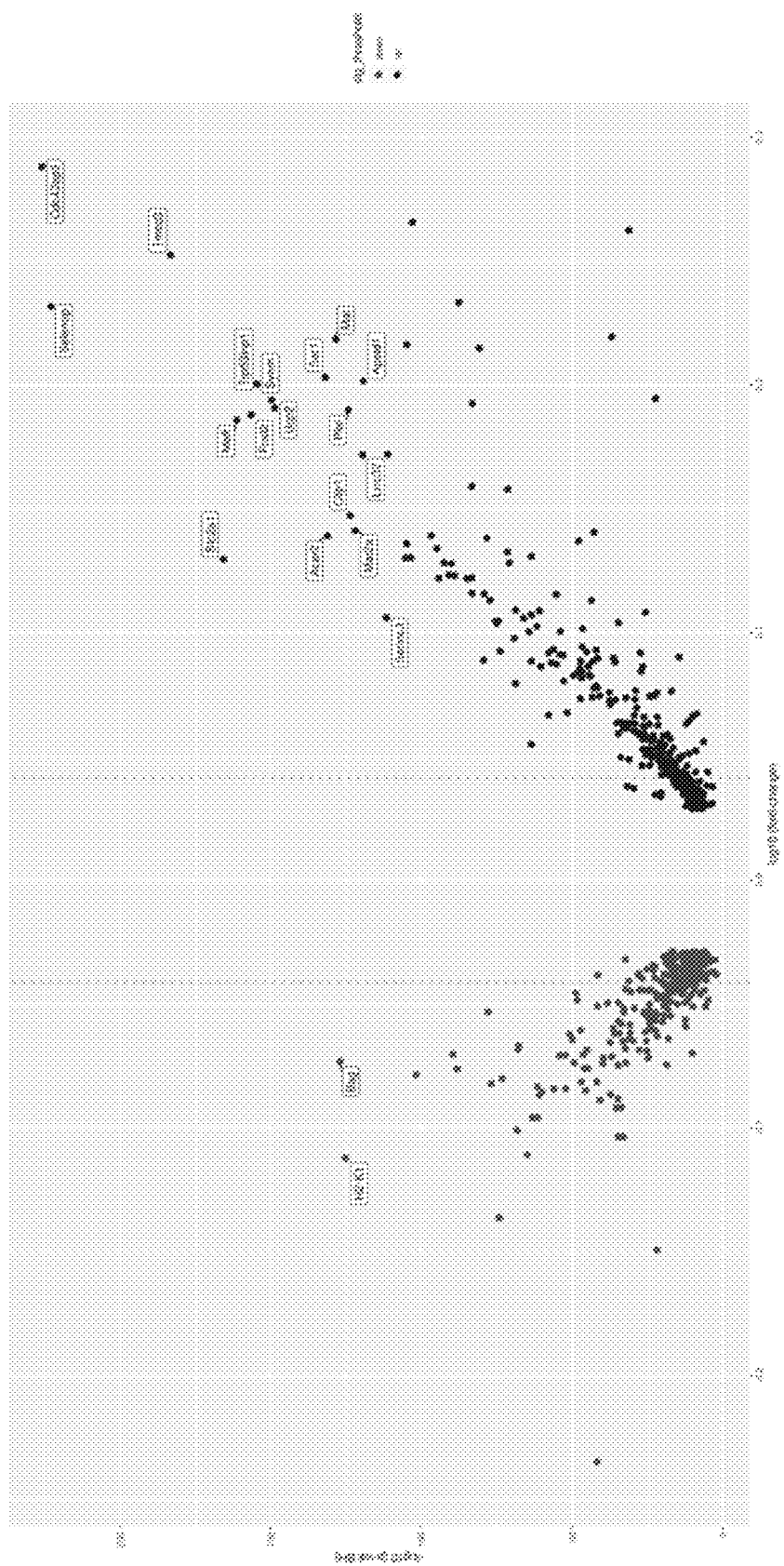

FIG. 70 is a volcano plot of endothelial cell gene changes from unbiased single cell RNA sequencing of brain tissue from aged mice treated with SC-57461A LTA4H inhibitor.

Figure 71:
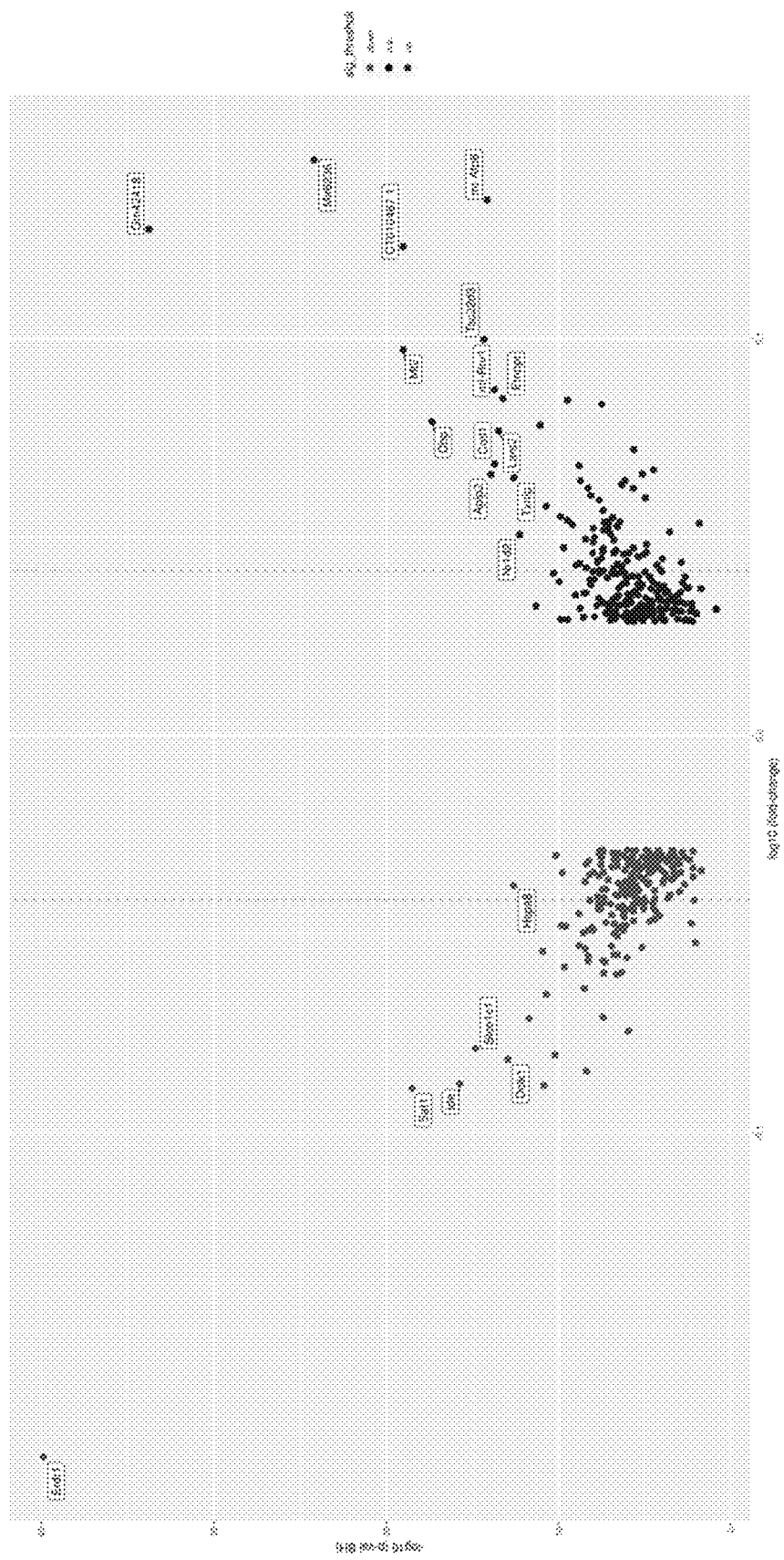

FIG. 71 is a volcano plot of astrocyte gene changes from unbiased single cell RNA sequencing of brain tissue from aged mice treated with SC-57461A LTA4H inhibitor.

Figure 72:
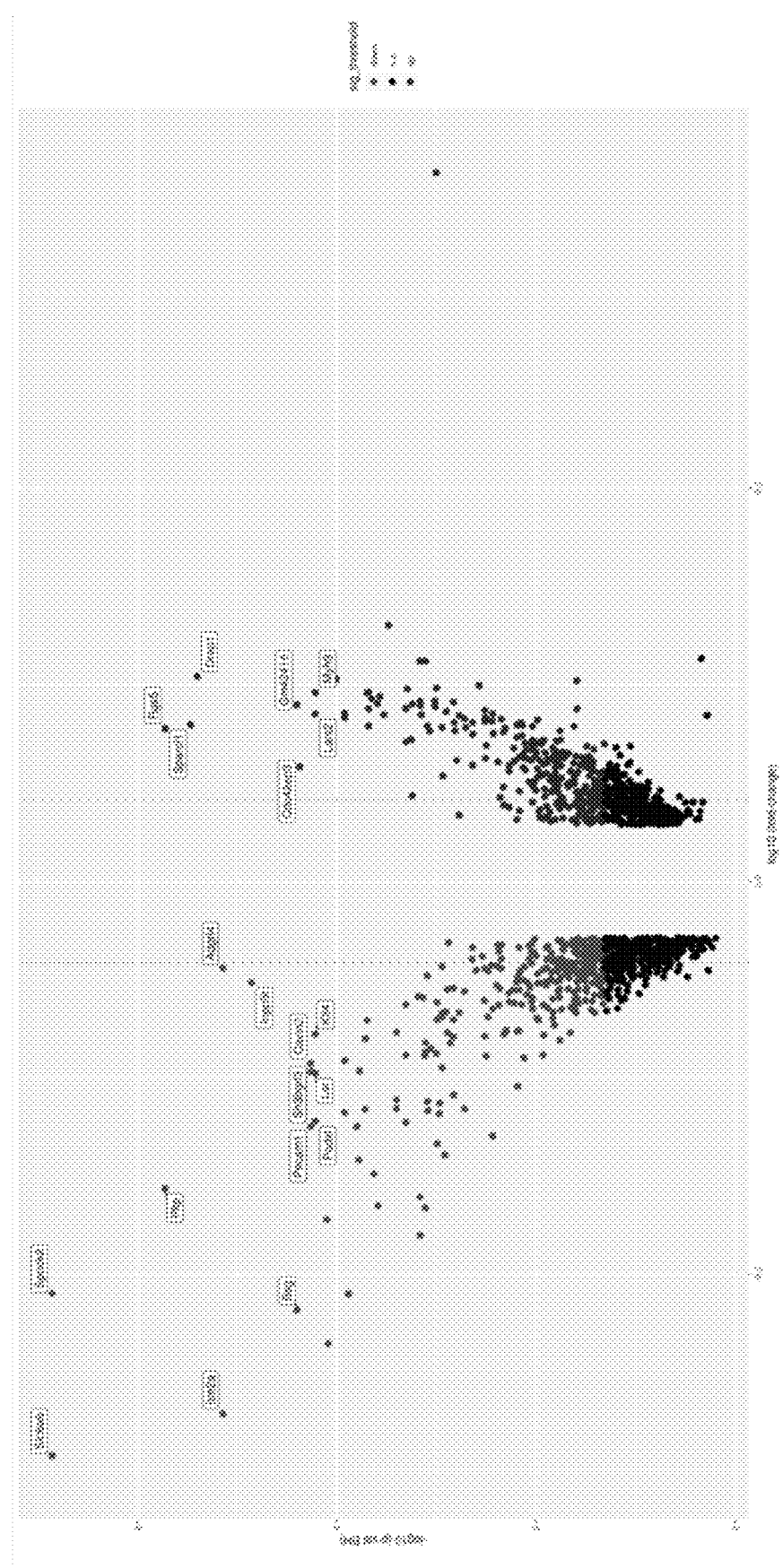

FIG. 72 is a volcano plot of pericyte gene changes from unbiased single cell RNA sequencing of brain tissue from aged mice treated with SC-57461A LTA4H inhibitor.

Figure 73:
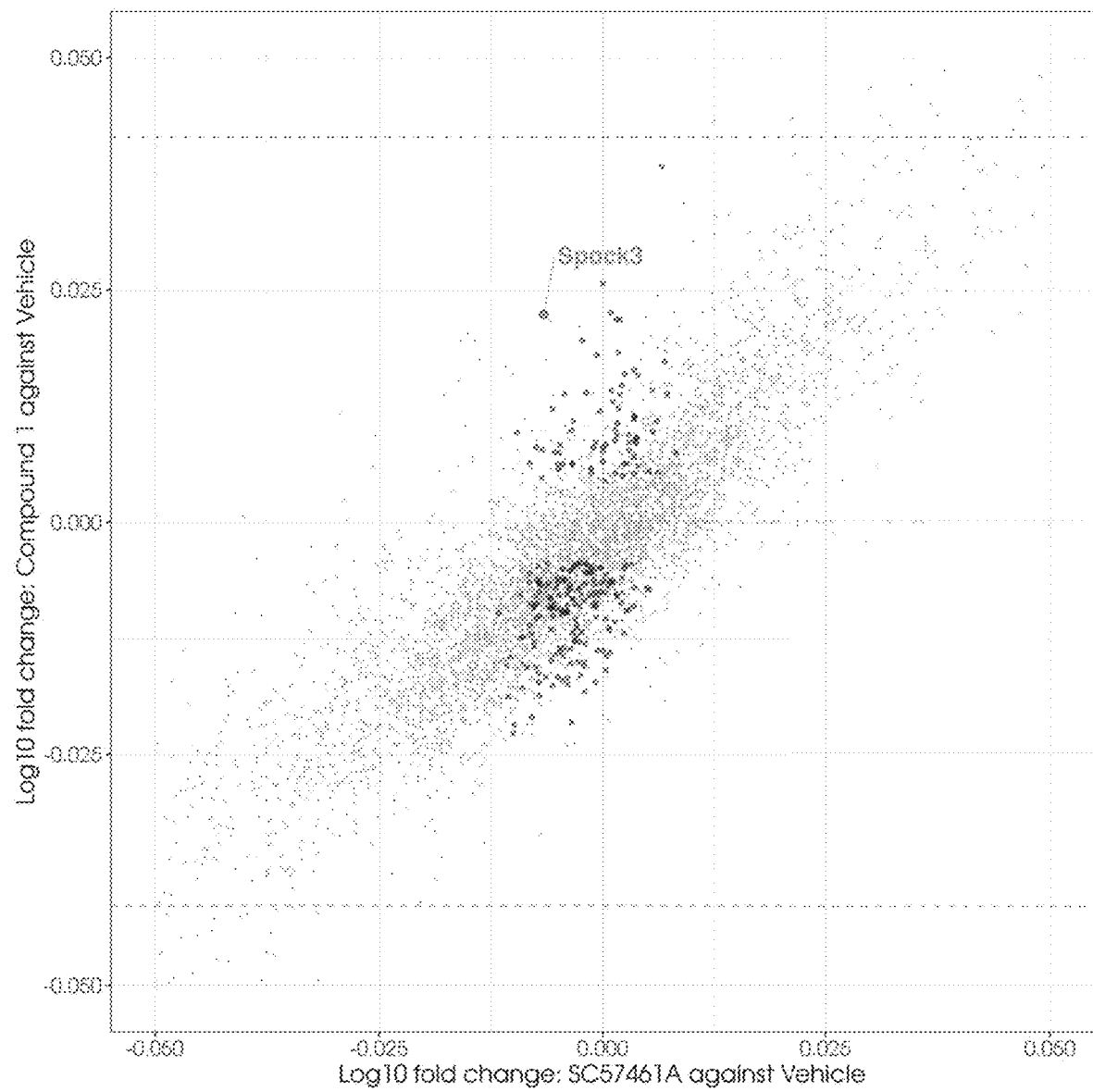

FIG. 73 shows the upregulation of the Spock3 gene in purified neurons from the dentate gyrus of the hippocampus of mice treated with Compound 1 compared to vehicle treated mice. This gene is not impacted by SC-57461A treatment. Graph depicts log 10 fold change comparing mice treated with vehicle to either the LTA4H inhibitor SC57461A (x-axis) or Compound 1 (y-axis). Black dots represent genes that are significantly up- or down-regulated with Compound 1 treatment but were unchanged with SC57461A treatment. Arrow points to one of the top upregulated genes Spock3.

Figure 74:
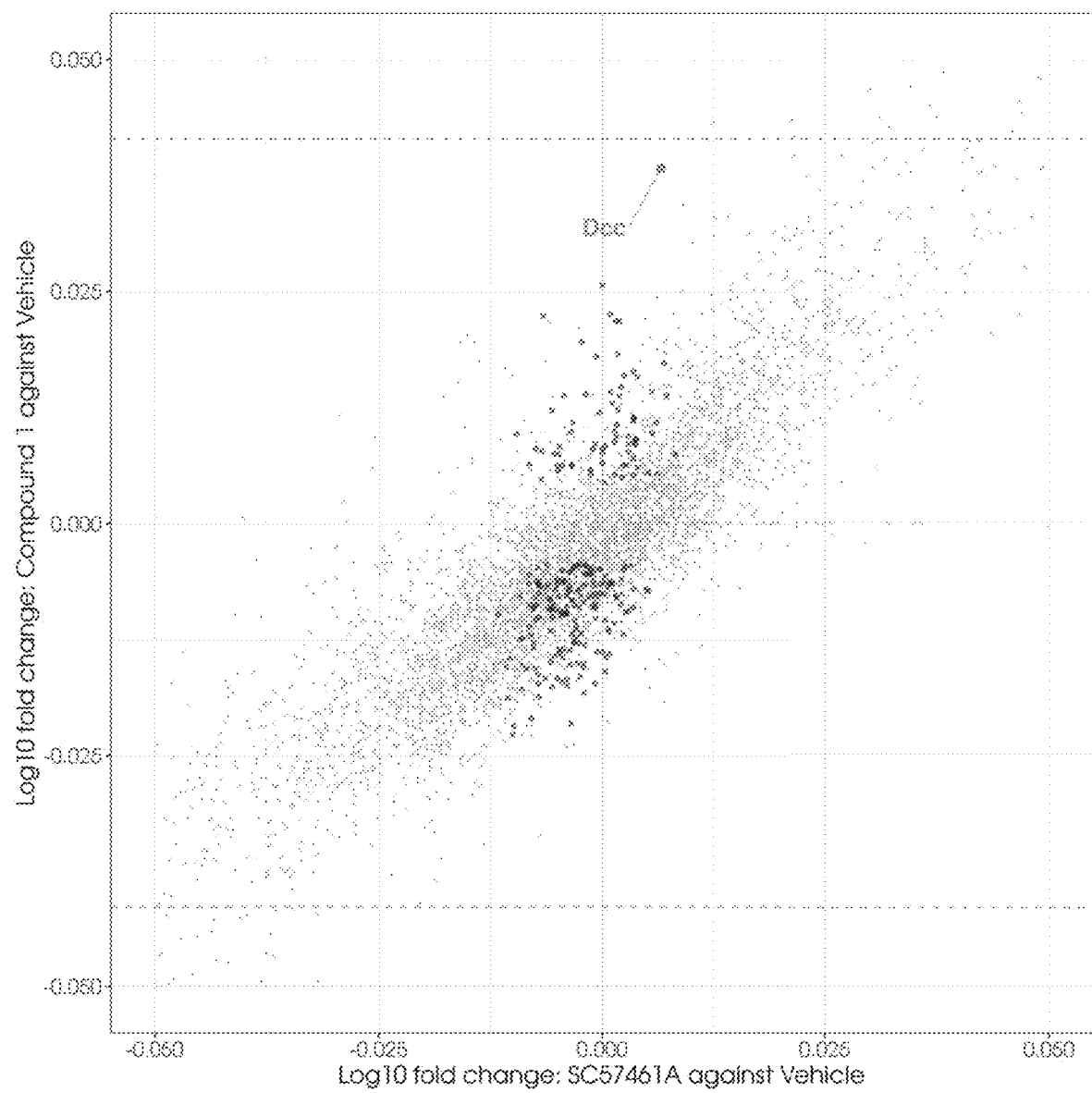

FIG. 74 shows the upregulation of Dcc gene in purified neurons from the dentate gyrus of the hippocampus of mice treated with Compound 1 compared to vehicle treated mice. This gene is not impacted by SC-57461A treatment. Graph depicts log 10 fold change comparing mice treated with vehicle to either the LTA4H inhibitor SC57461A (x-axis) or Compound 1 (y-axis). Black dots represent genes that are significantly up- or down-regulated with Compound 1 treatment but were unchanged with SC57461A treatment. Arrow points to one of the top upregulated genes Dcc.

Figure 75:
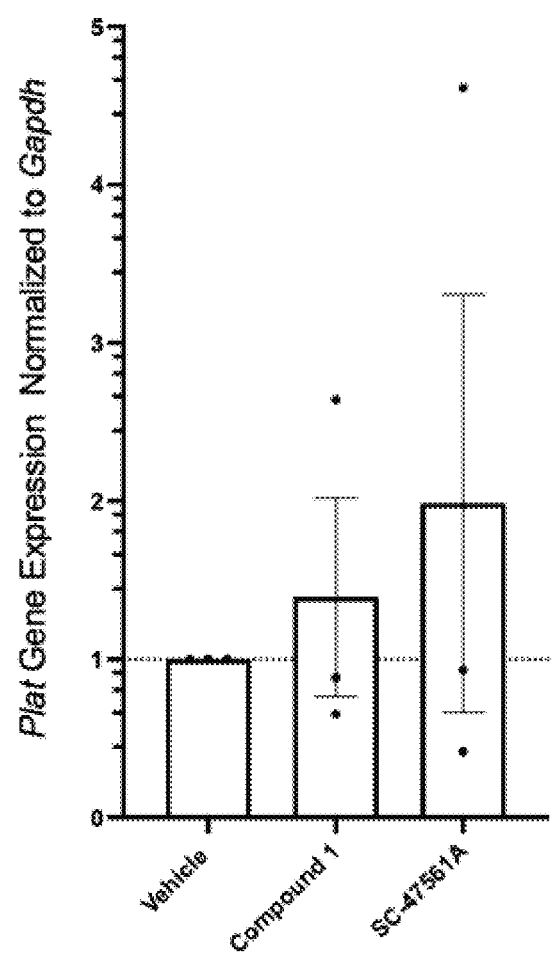

FIG. 75 shows levels of upregulation of the Plat beneficial gene in purified endothelial cells from the cortex of vehicle, Compound 1, and SC-47561A-treated mice.

Figure 76:
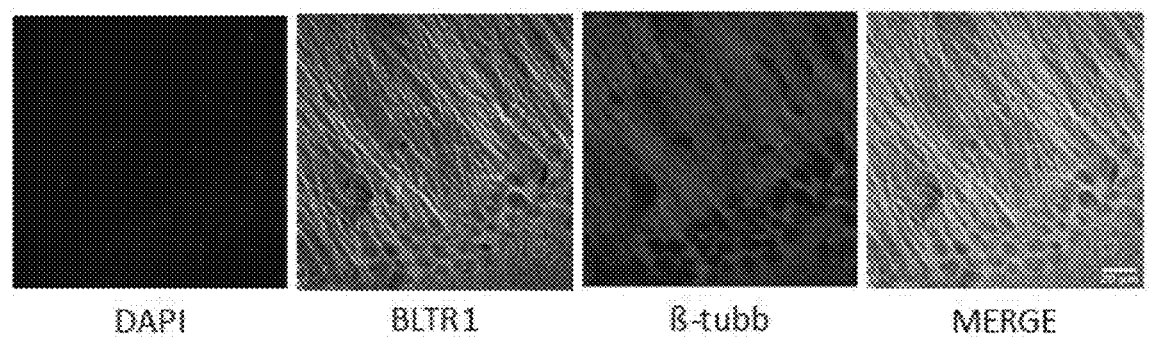

FIG. 76 reports the histology of the LTB4 receptor BLTR1 with beta-tubulin in the dendrites of neurons of the hippocampus. DAPI is in blue, BLTR1 is in white, beta-tubulin is in purple. Scale bar is 20 µm.

Figure 77:
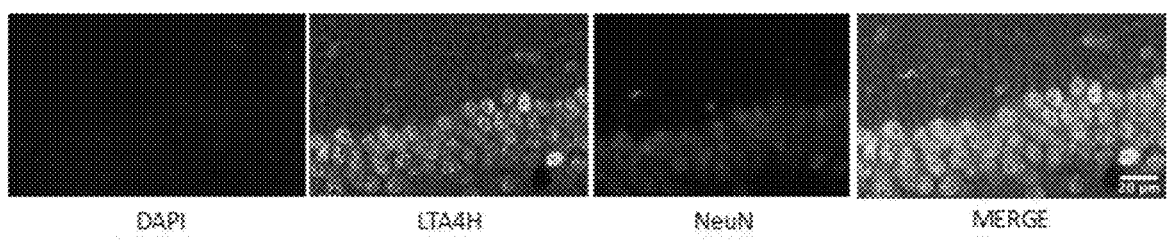

FIG. 77 reports the histology of the LTA4H with NeuN in the nucleus of neurons of the hippocampus. DAPI is in blue, LTA4H is in white, NeuN is in purple. Scale bar is 20 µm.

Figure 78:
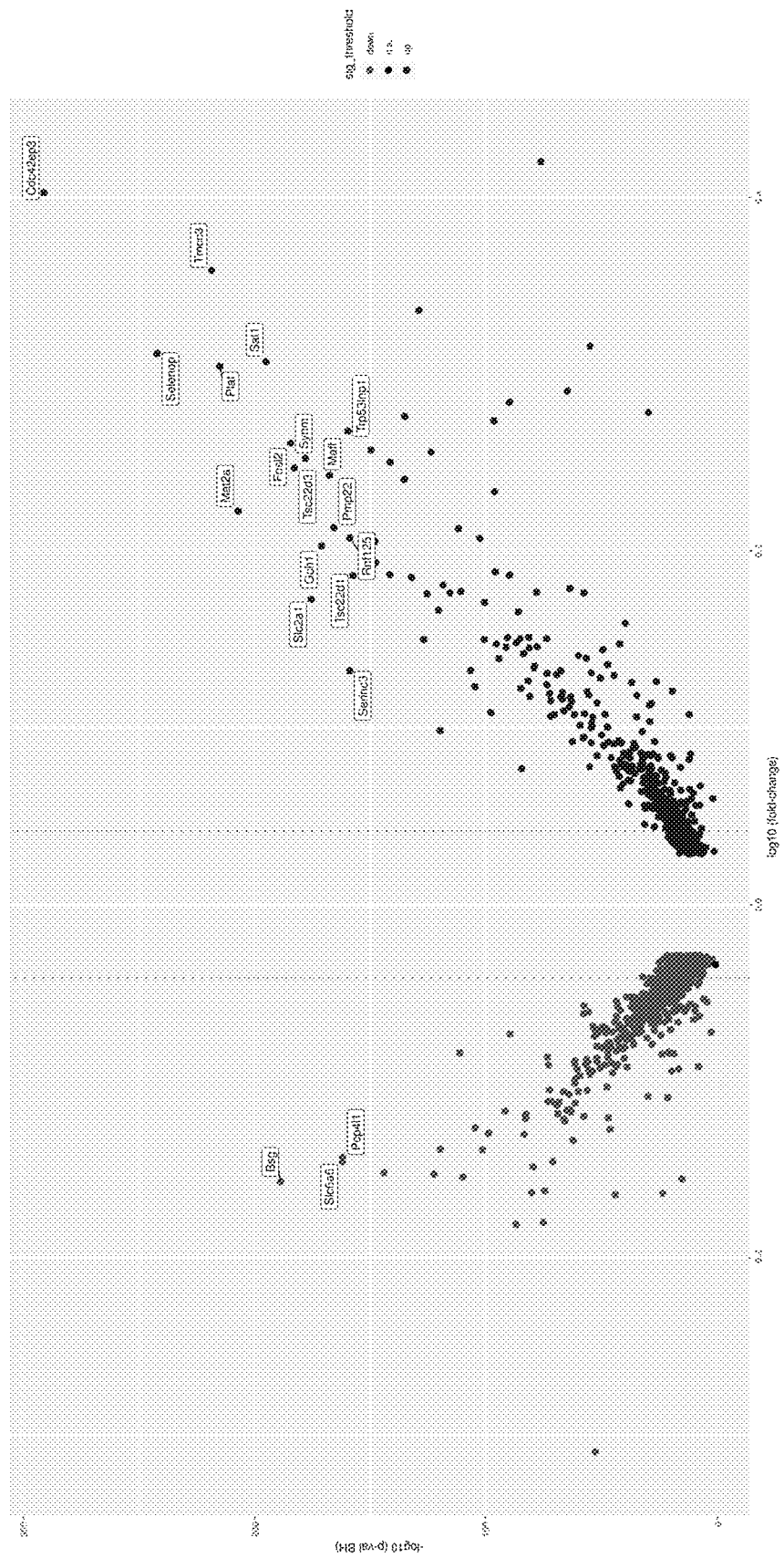

FIG. 78 is a volcano plot of endothelial cells gene changes from single cell RNA sequencing performed on brain endothelial cells enriched from aged mice treated with SC-57461A LTA4H inhibitor compared to vehicle treated mice.

Figure 79:
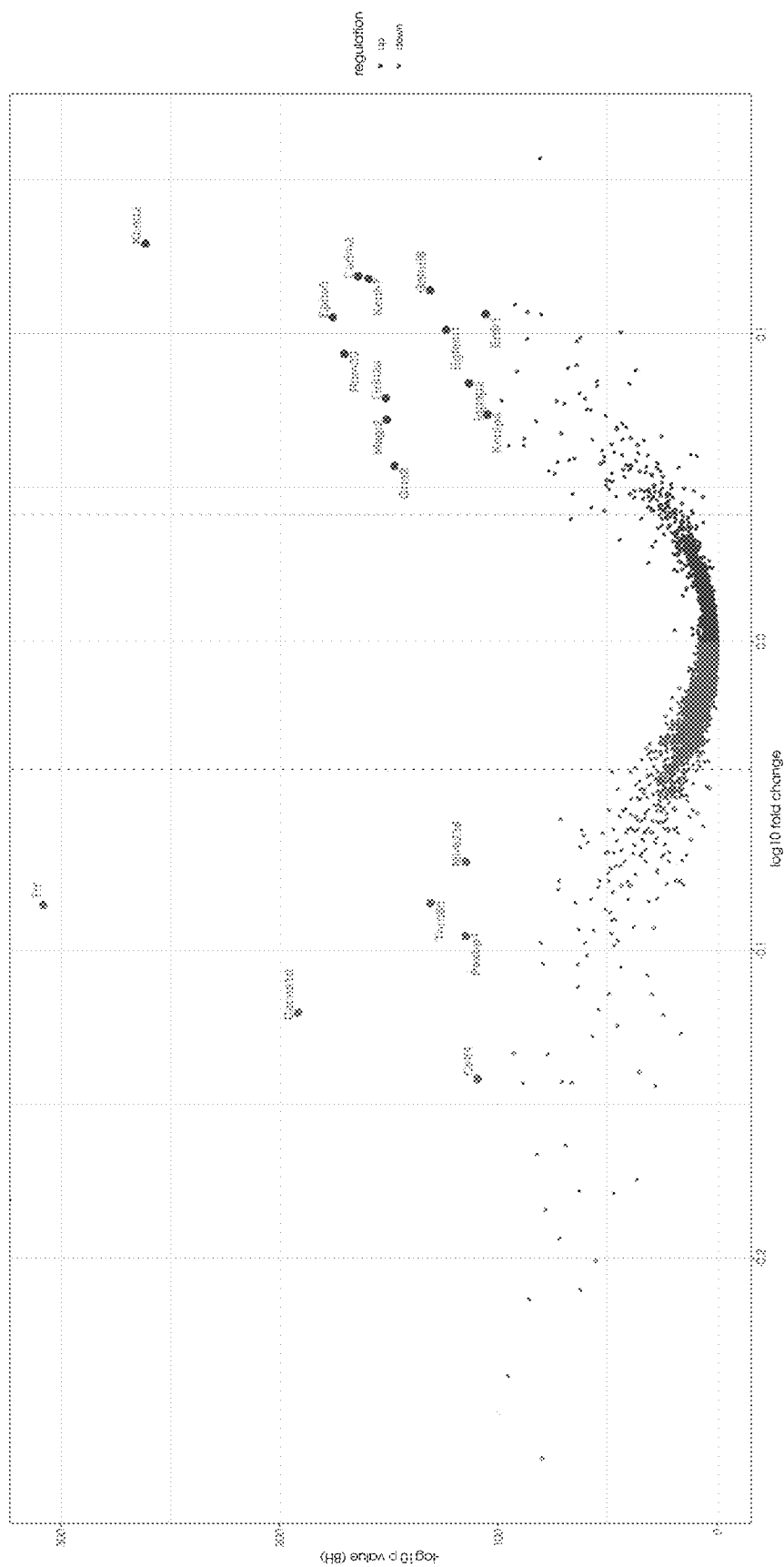

FIG. 79 is a volcano plot of CA1 neuronal gene changes from single cell RNA sequencing performed on NeuN+ nuclei enriched from aged mice treated with Compound 1 LTA4H inhibitor compared to vehicle treated mice.

Figure 80:
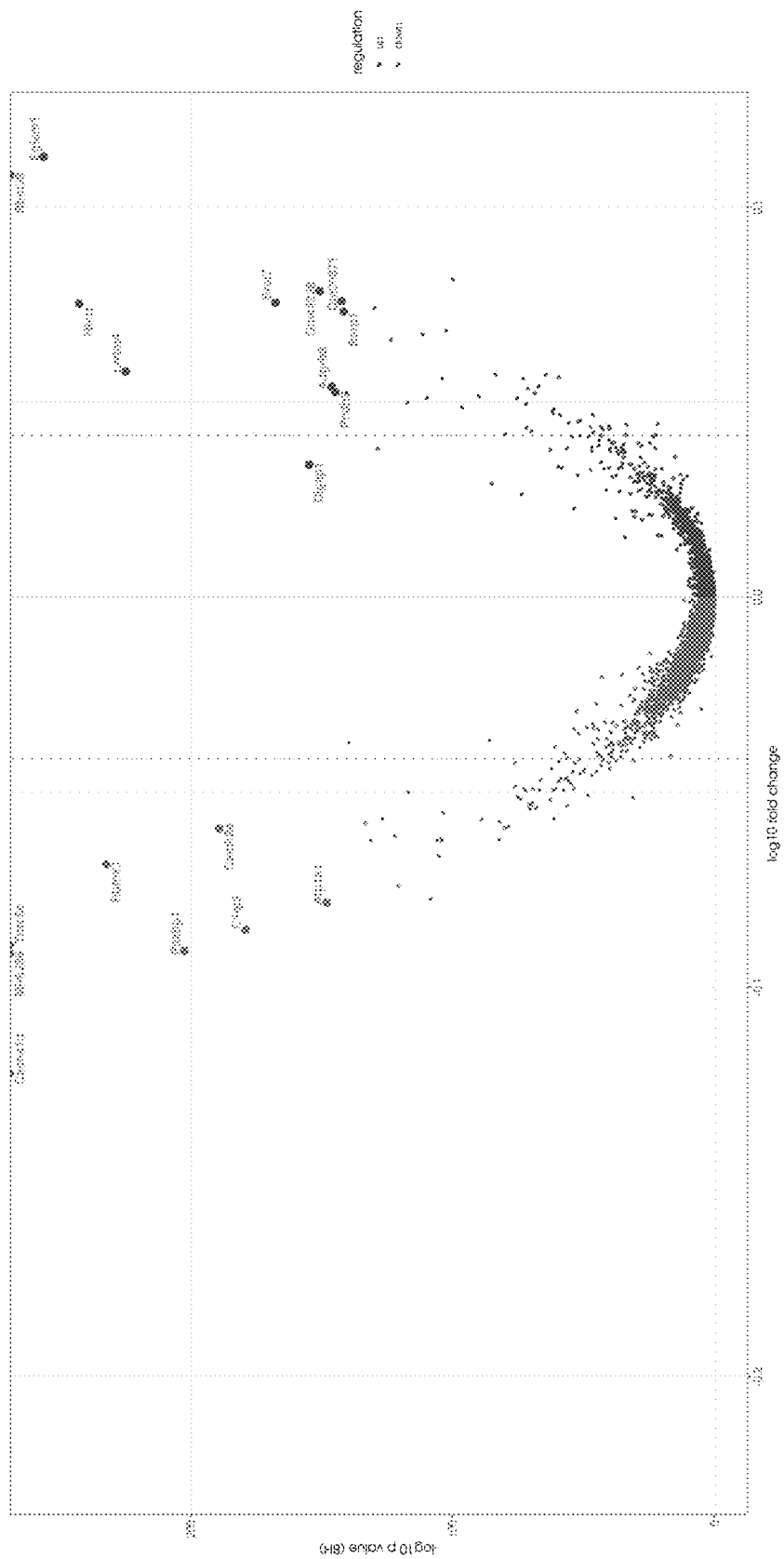

FIG. 80 is a volcano plot of DG neuronal gene changes from single cell RNA sequencing performed on NeuN+ nuclei enriched from aged mice treated with Compound 1 LTA4H inhibitor compared to vehicle treated mice.

Figure 81:
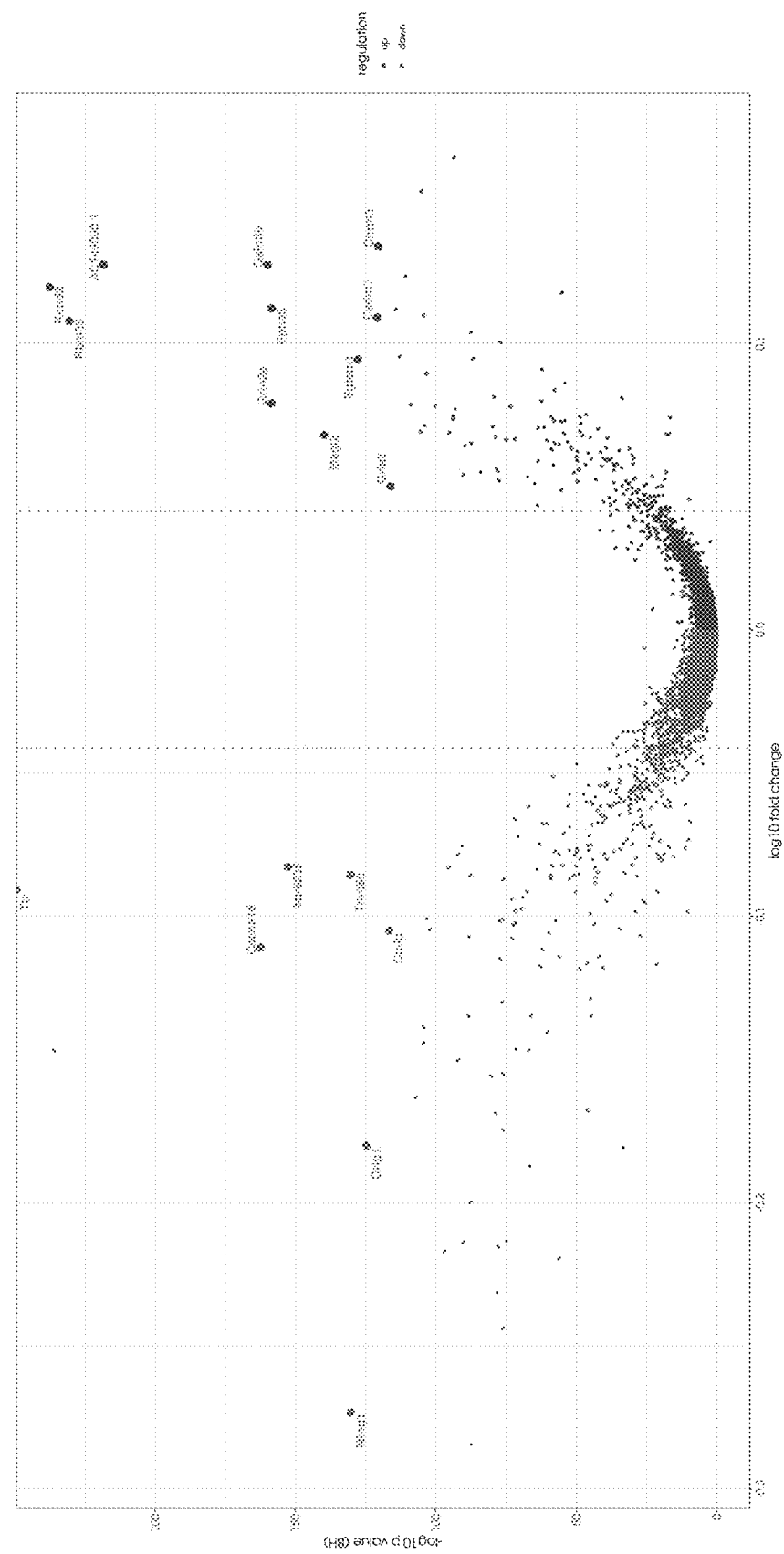

FIG. 81 is a volcano plot of CA1 neuronal gene changes from single cell RNA sequencing performed on NeuN+ nuclei enriched from aged mice treated with SC-57461A LTA4H inhibitor compared to vehicle treated mice.

Figure 82:
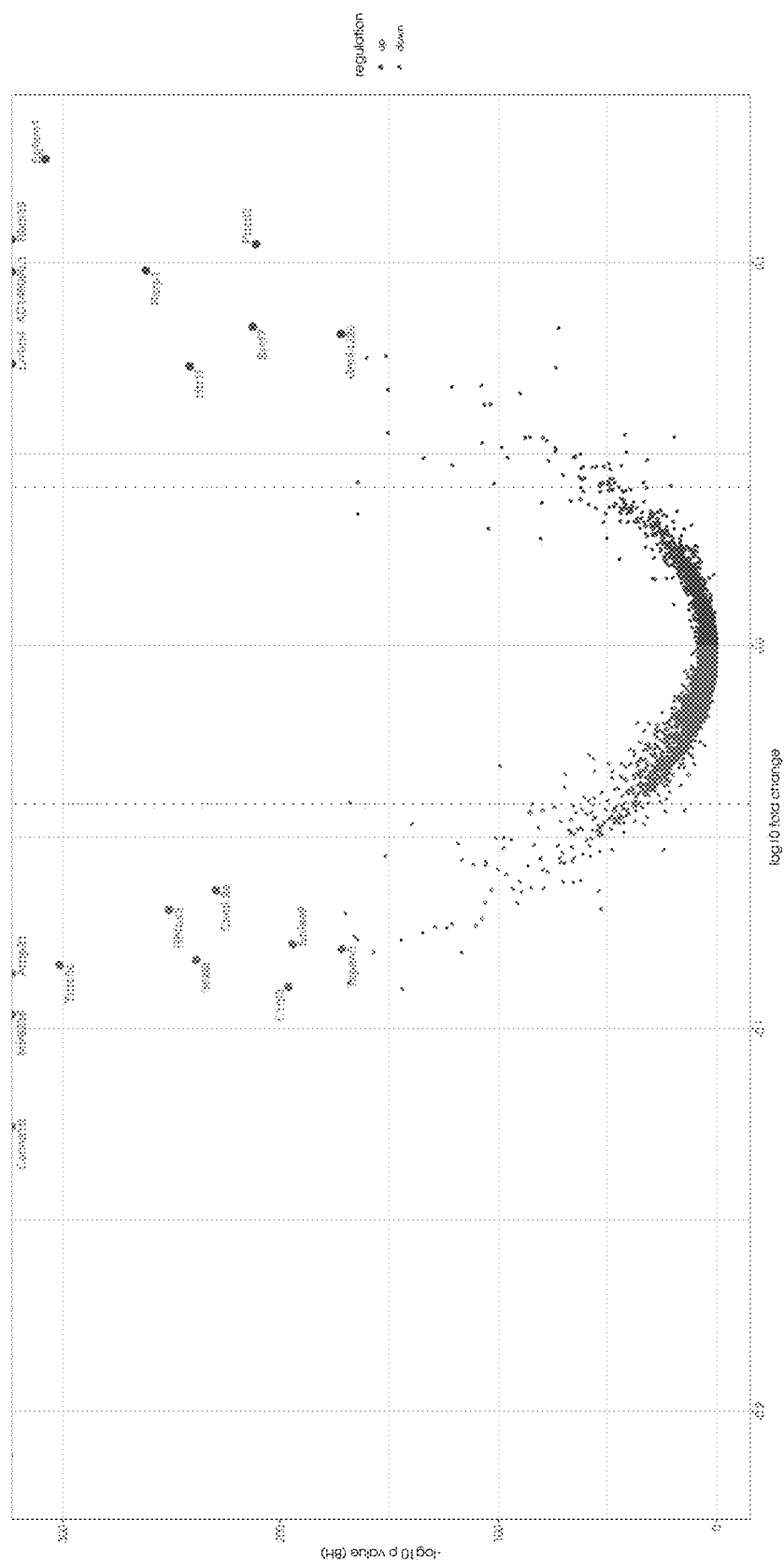

FIG. 82 is a volcano plot of DG neuronal gene changes from single cell RNA sequencing performed on NeuN+ nuclei enriched from aged mice treated with SC-57461A LTA4H inhibitor compared to vehicle treated mice.

Figure 83:
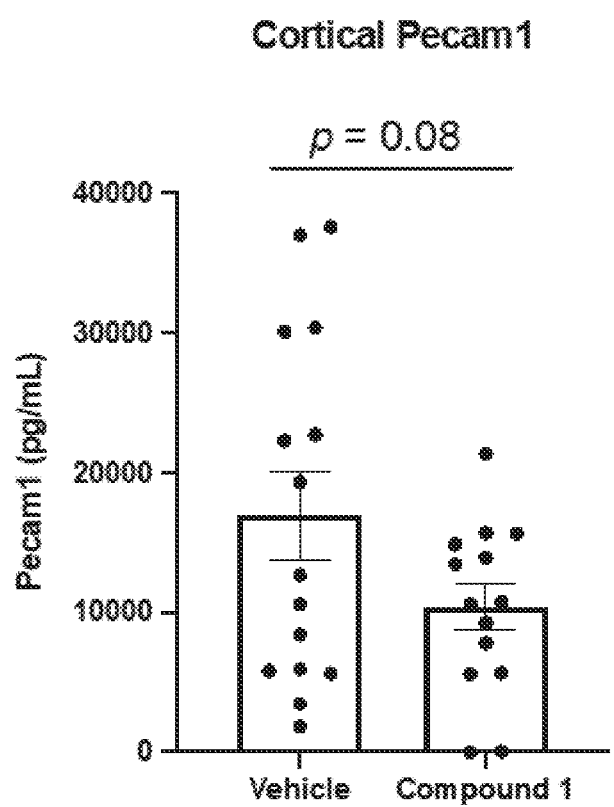

FIG. 83 shows a reduction in Pecam-1 from cortical brain lysate from aged mice treated with Compound 1 LTA4H inhibitor compared to vehicle treated mice.

Figure 84:
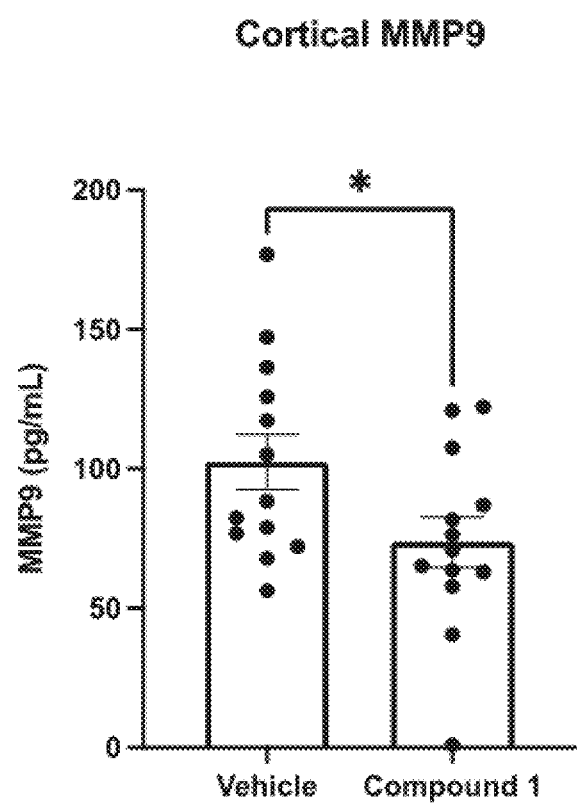

FIG. 84 shows a reduction in MMP9 from cortical brain lysate from aged mice treated with Compound 1 LTA4H inhibitor compared to vehicle treated mice.

Figure 85:
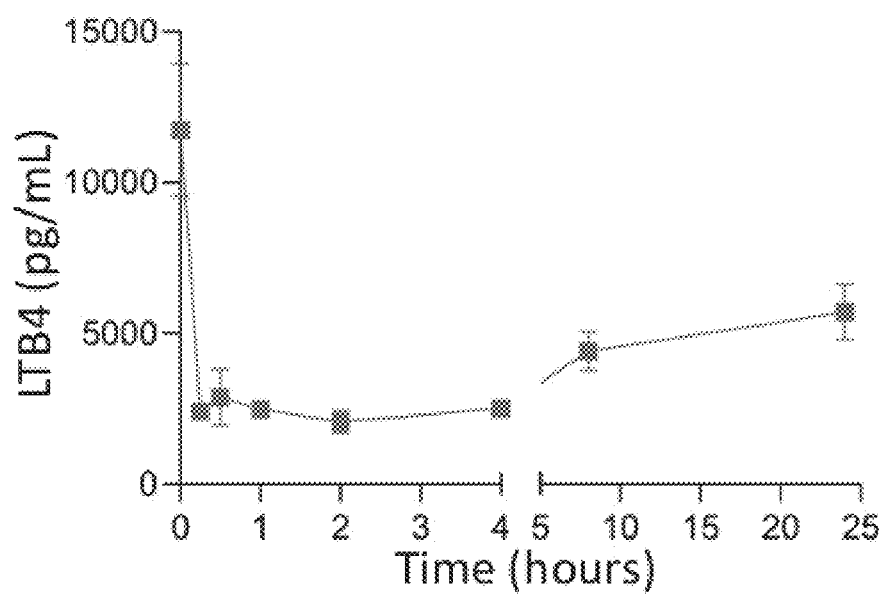

FIG. 85 reports pharmacodynamic data of Compound 1 in the form of plasma levels of LTB4 in C57BL/6 mice treated with a single oral gavage dose of Compound 1 at 1 mg/kg at multiple timepoints following dosing.

Figure 86:
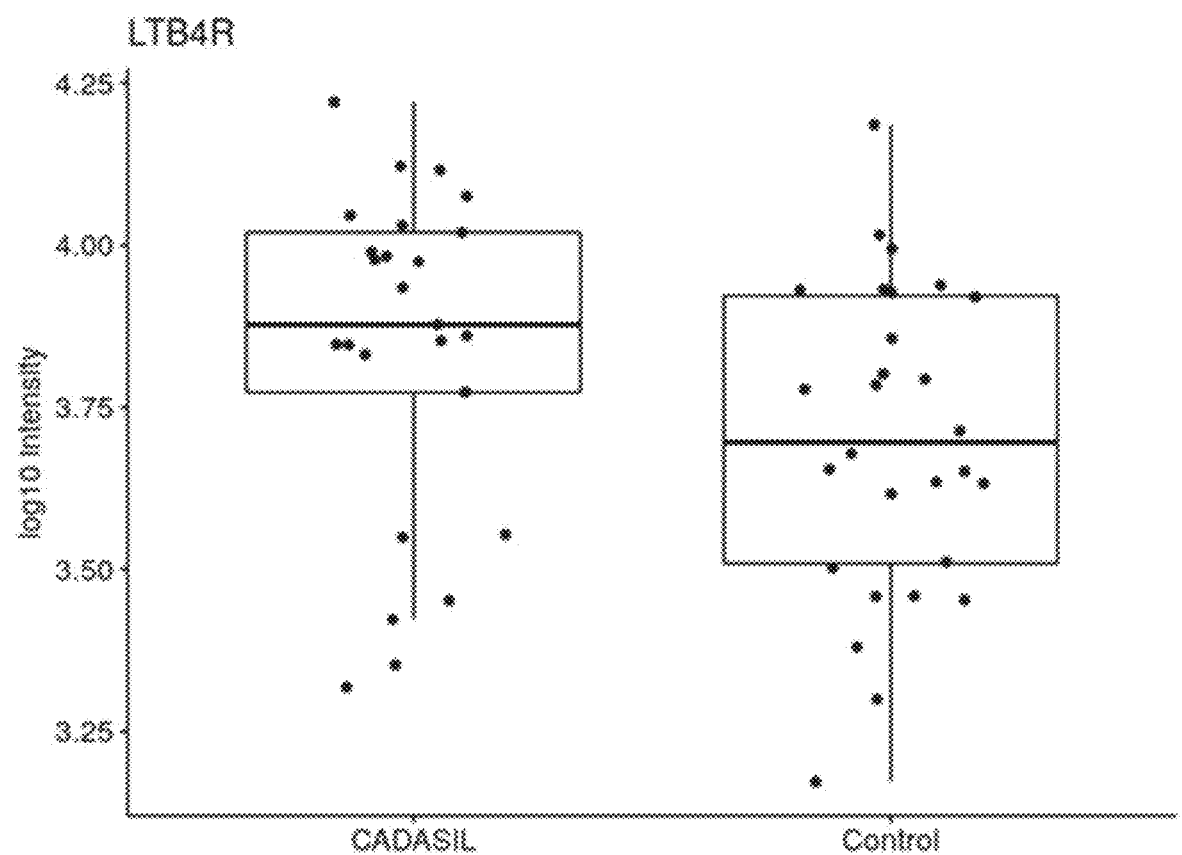

FIG. 86 shows an increase in plasma level of the LTB4 receptor (LTB4R) in the plasma of human CADASIL patients compared to healthy controls measured by SomaLogic SomaScan.

Figure 87:
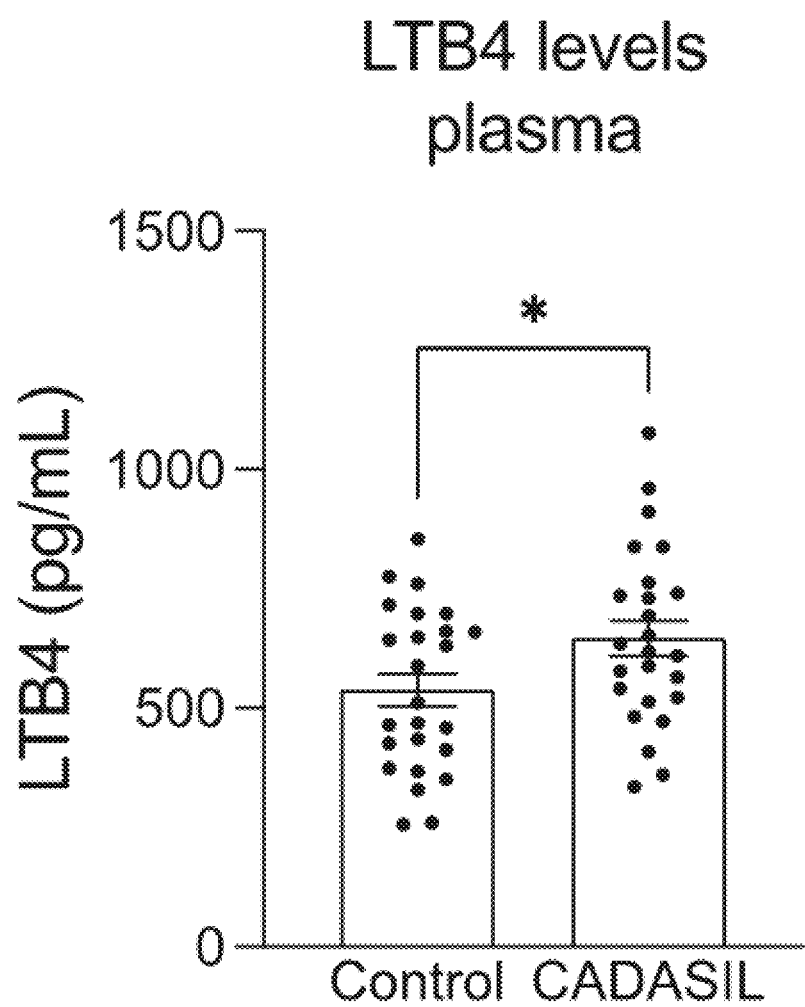

FIG. 87 shows an increase in plasma level of the LTB4 in human CADASIL patients compared to healthy controls measured by ELISA.

Figure 88A:
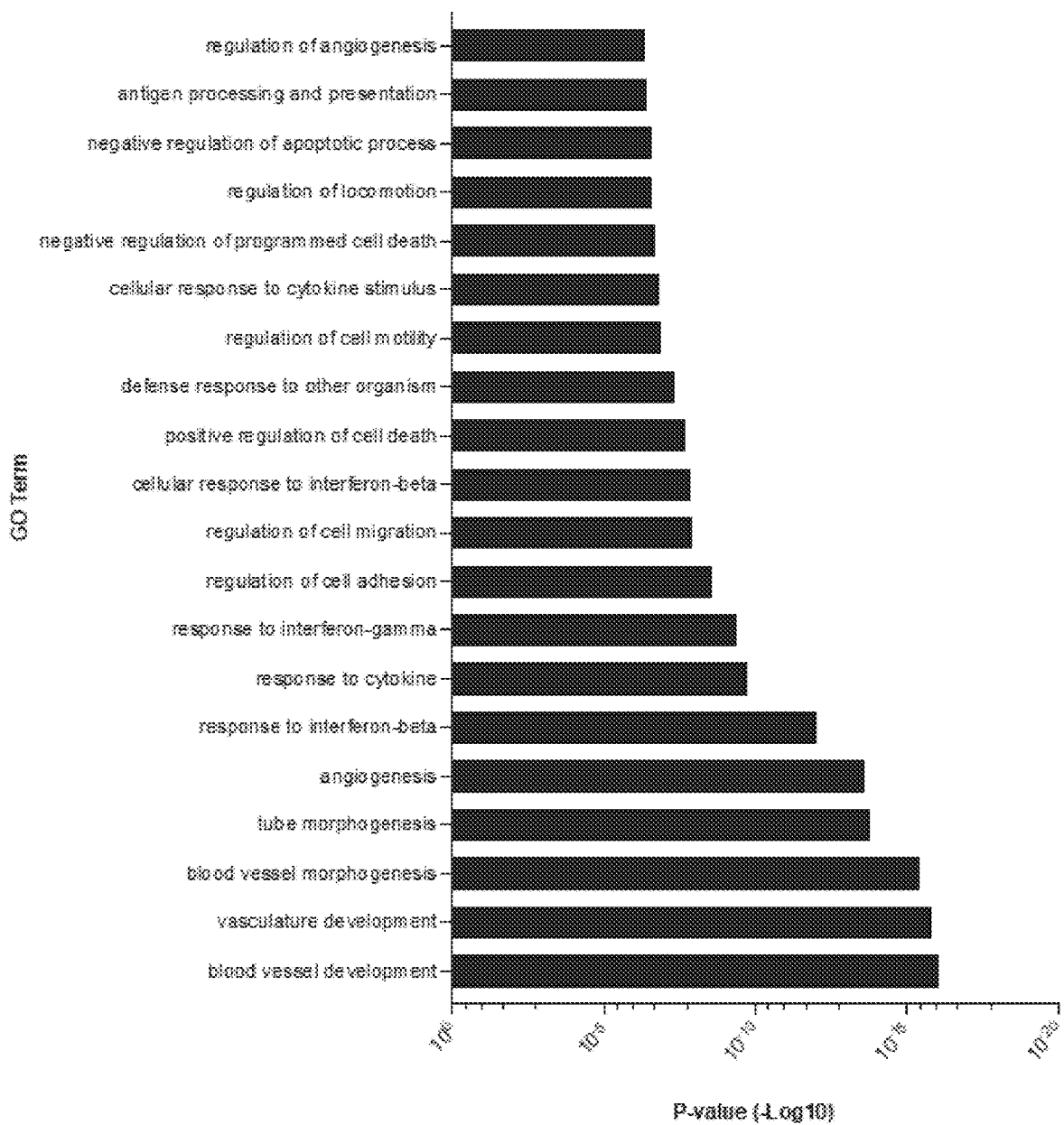

FIG. 88A is a bar graph showing the top 20 significant Biological Process Gene Ontology (GO) terms from single cell sequencing of brain endothelial cells isolated from aged mice treated long-term with vehicle or the SC-57461A LTA4H inhibitor compared to vehicle treated mice.

Figure 89A:
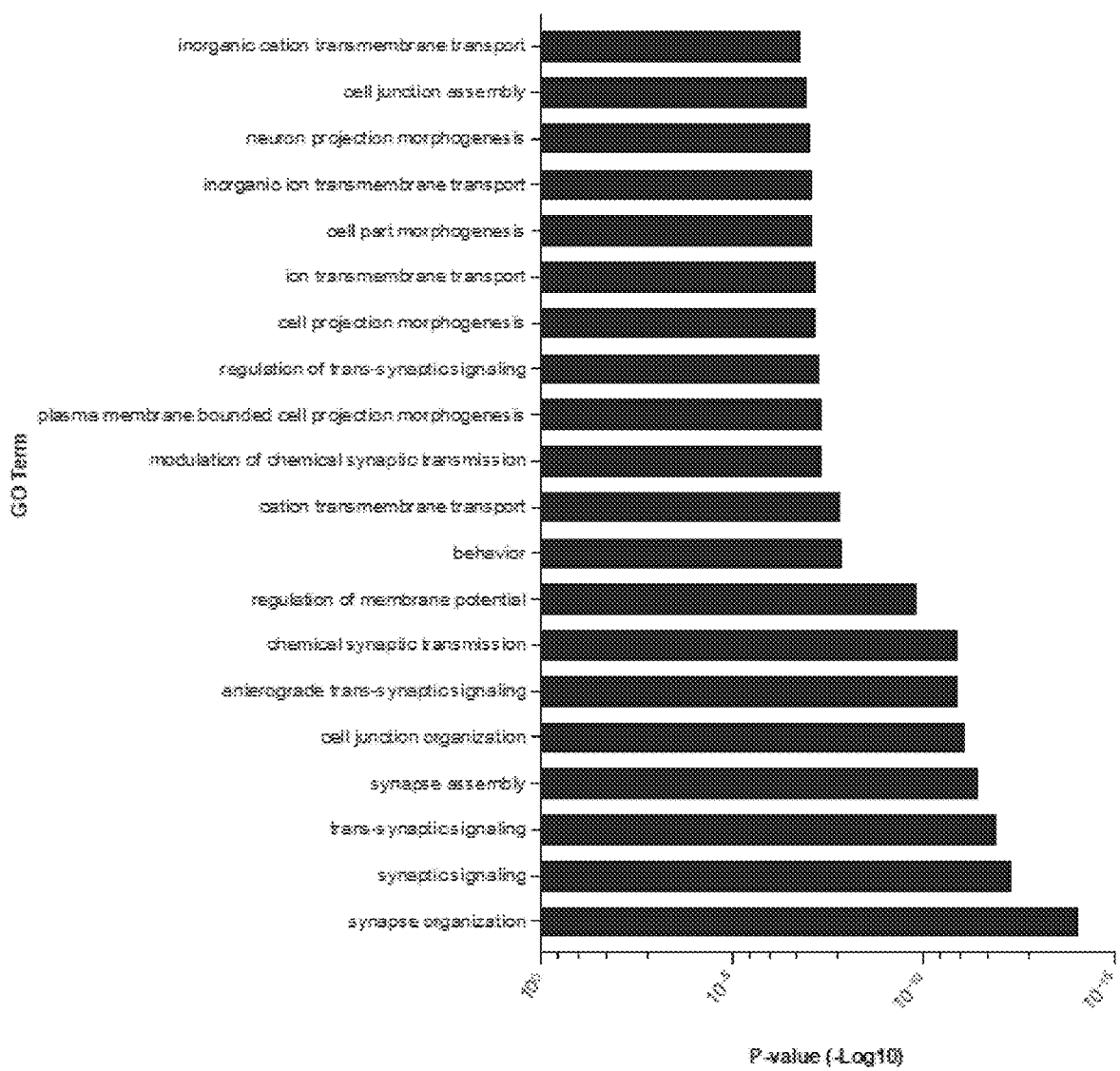

FIG. 88B is a table listing detailed information for the top 20 significant GO terms as described in FIG. 88A FIG. 89A is a bar graph showing the top 20 significant Biological Process GO terms from single cell sequencing of CA1 hippocampal neurons isolated from aged mice treated long-term with vehicle or the Compound 1 LTA4H inhibitor compared to vehicle treated mice.

FIG. 89B is a table listing detailed information for the top 20 significant GO terms as described in FIG. 89A.

Figure 90A:
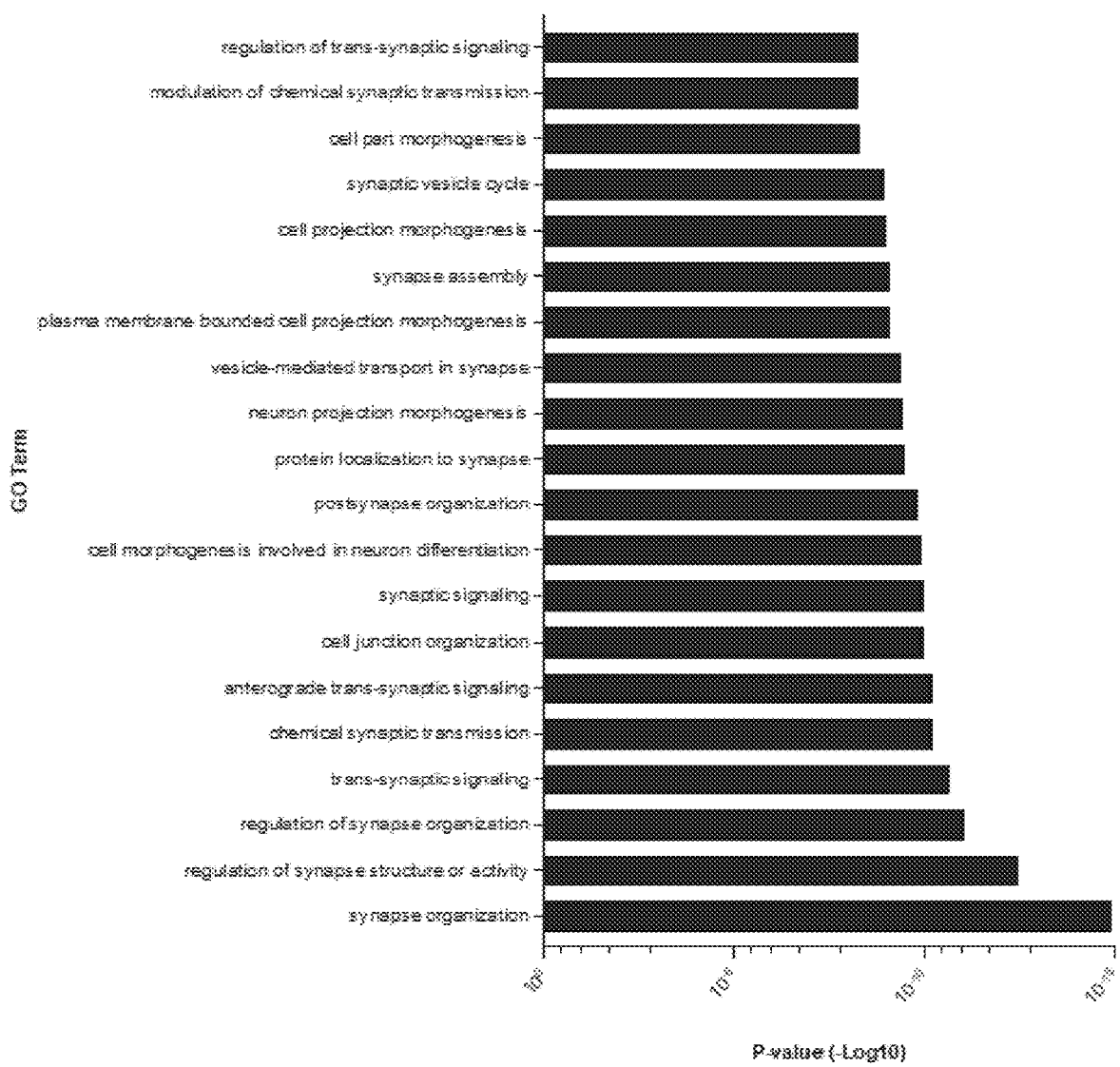

FIG. 90A is a bar graph showing the top 20 significant Biological Process GO terms from single cell sequencing of DG hippocampal neurons isolated from aged mice treated long-term with vehicle or the Compound 1 LTA4H inhibitor compared to vehicle treated mice.

FIG. 90B is a table listing detailed information for the top 20 significant GO terms as described in FIG. 90A.

Figure 91A:
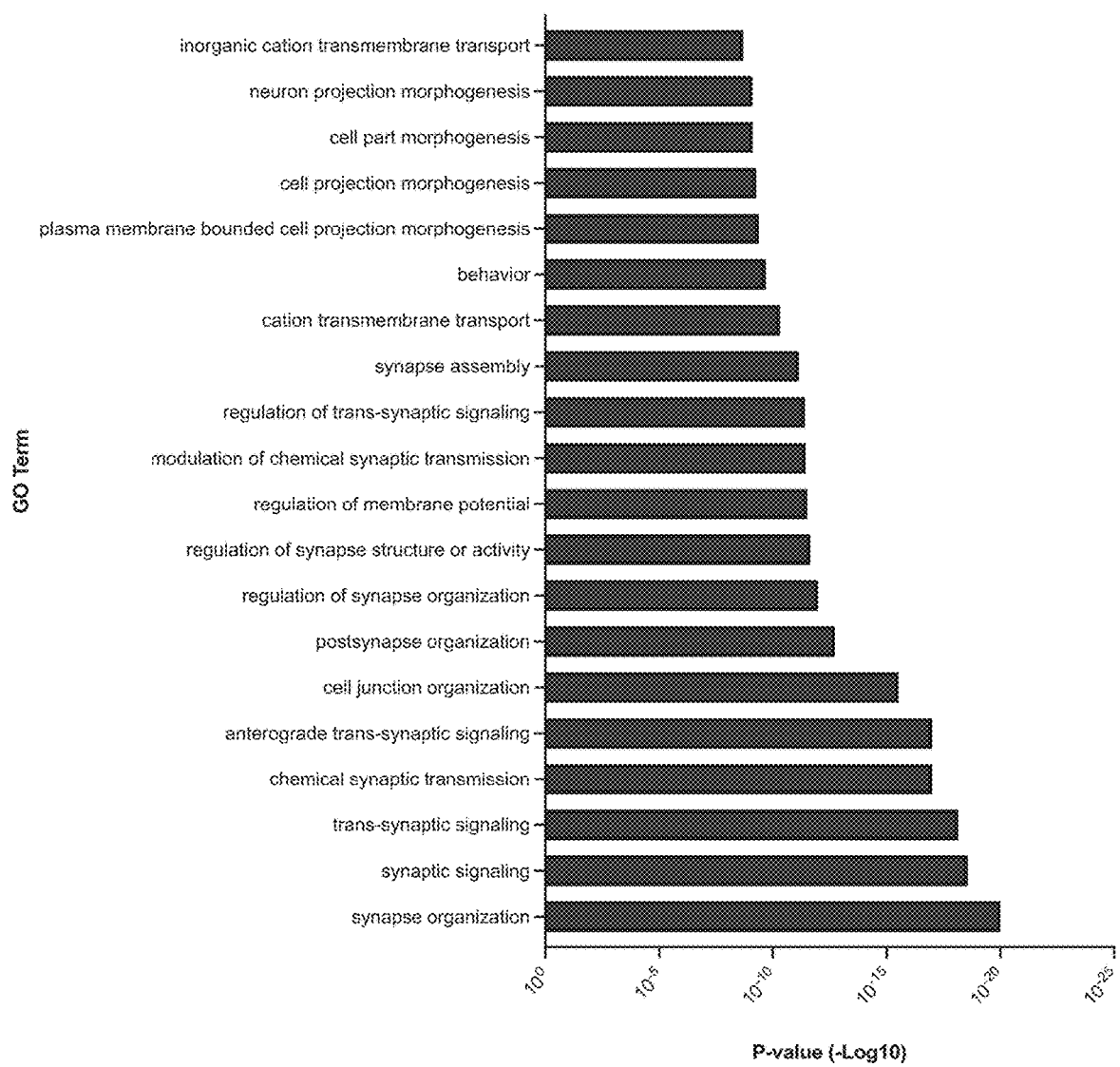

FIG. 91A is a bar graph showing the top 20 significant Biological Process GO terms from single cell sequencing of CA1 hippocampal neurons isolated from aged mice treated long-term with vehicle or the SC-57461A LTA4H inhibitor compared to vehicle treated mice.

FIG. 91B is a table listing detailed information for the top 20 significant GO terms as described in FIG. 91A.

Figure 92A:
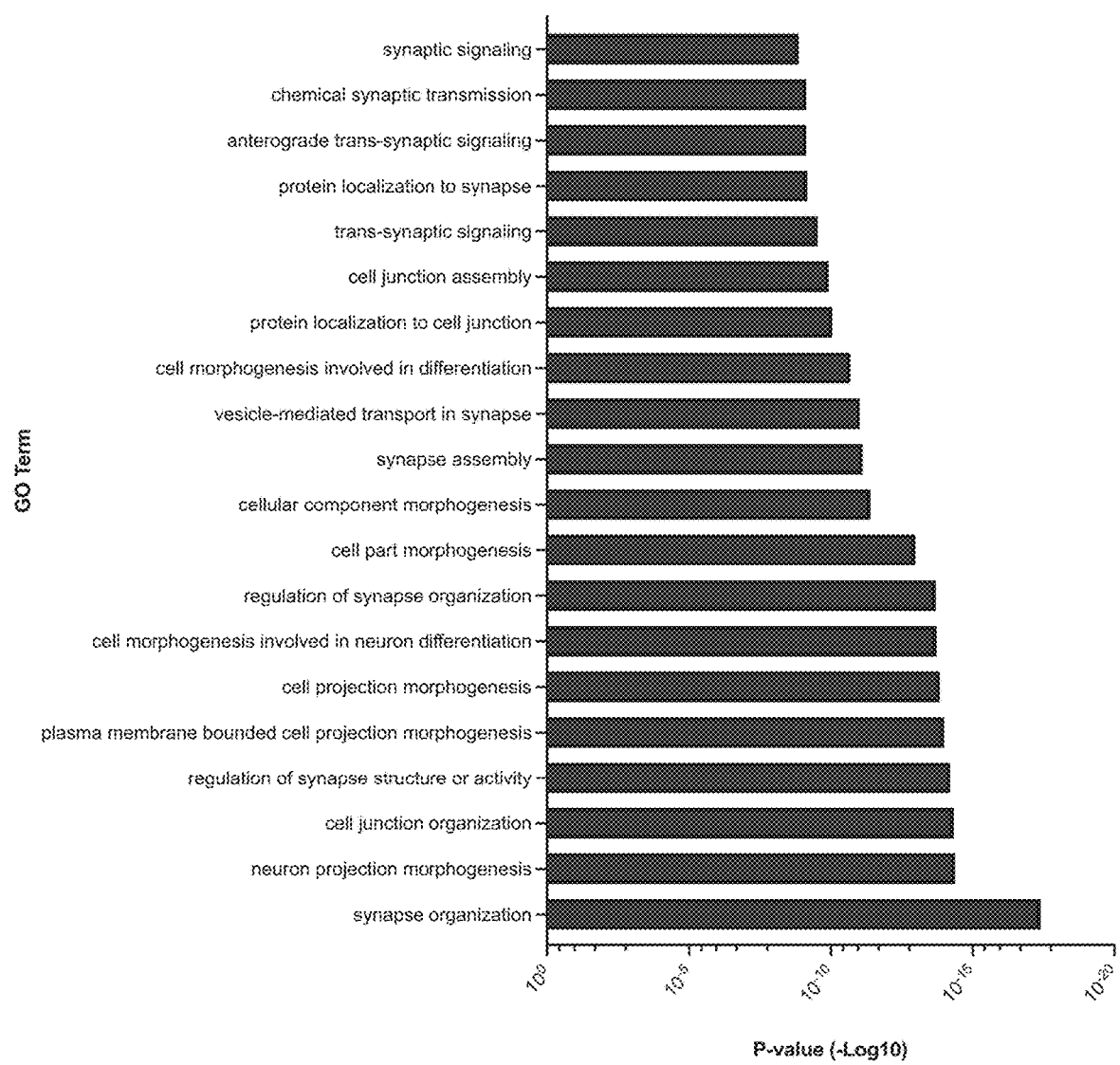

FIG. 92A is a bar graph showing the top 20 significant Biological Process GO terms from single cell sequencing of DG hippocampal neurons isolated from aged mice treated with vehicle or the LTA4H inhibitor SC-57461A compared to vehicle treated mice.

FIG. 92B is a table listing detailed information for the top 20 significant GO terms as described in FIG. 92A.

Figure 93A:
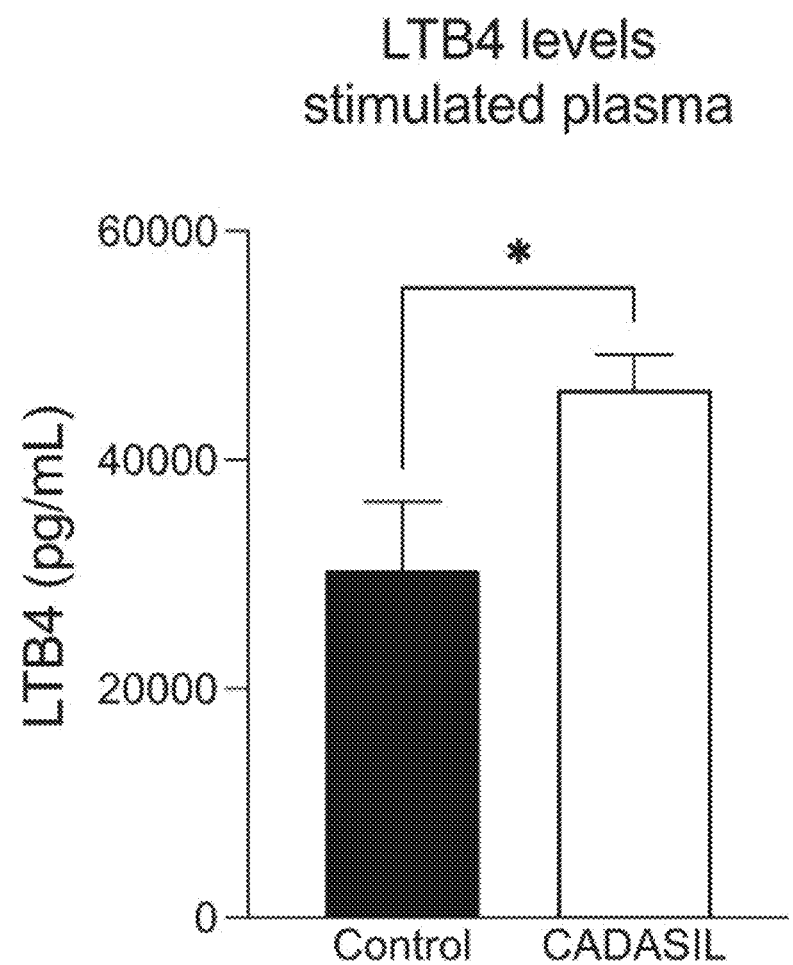

FIG. 93A shows the increase in LTB4 levels in CADASIL human subjects, measured in stimulated plasma compared with age-matched controls.

Figure 93B:
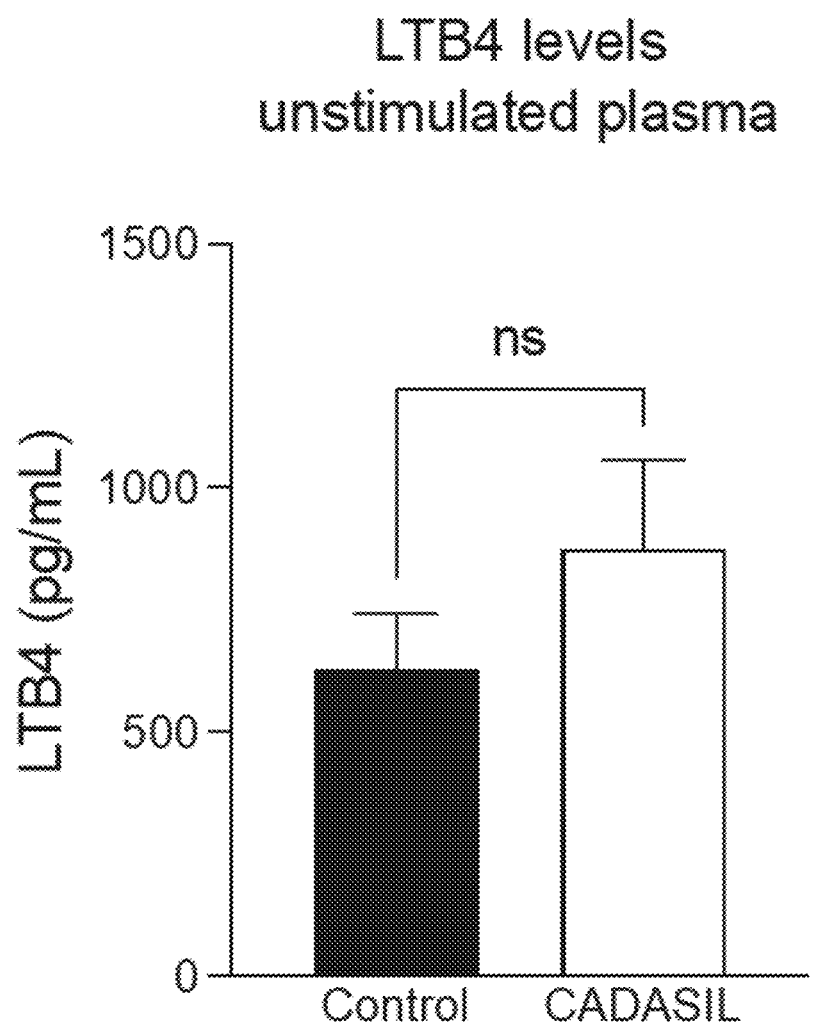

FIG. 93B shows that unstimulated plasma LTB4 levels trend towards an increase in CADSIL human subjects versus age-matched controls.

Figure 94A:
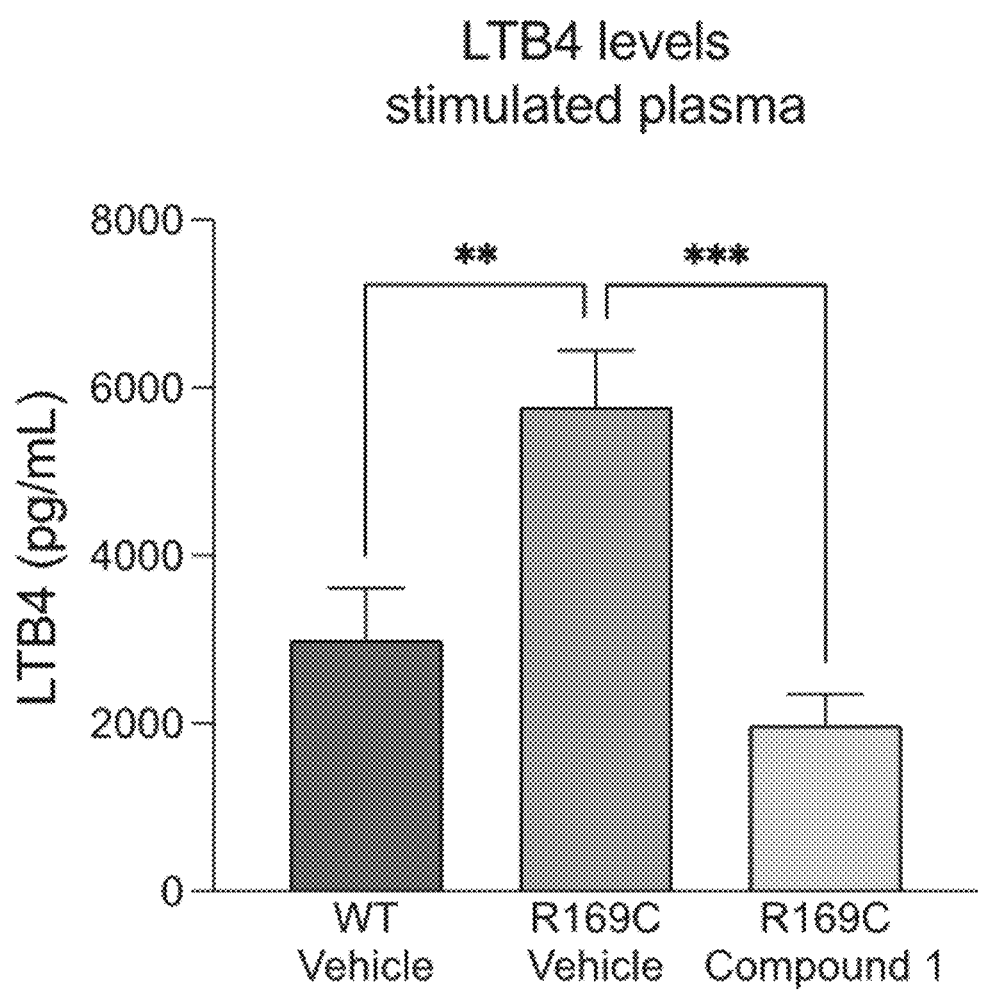

FIG. 94A shows the significant increase in LTB4 levels in the CADASIL model NOTCH3$^{R169C}$ transgenic mice (R169C), measured in stimulated plasma.

Figure 94B:
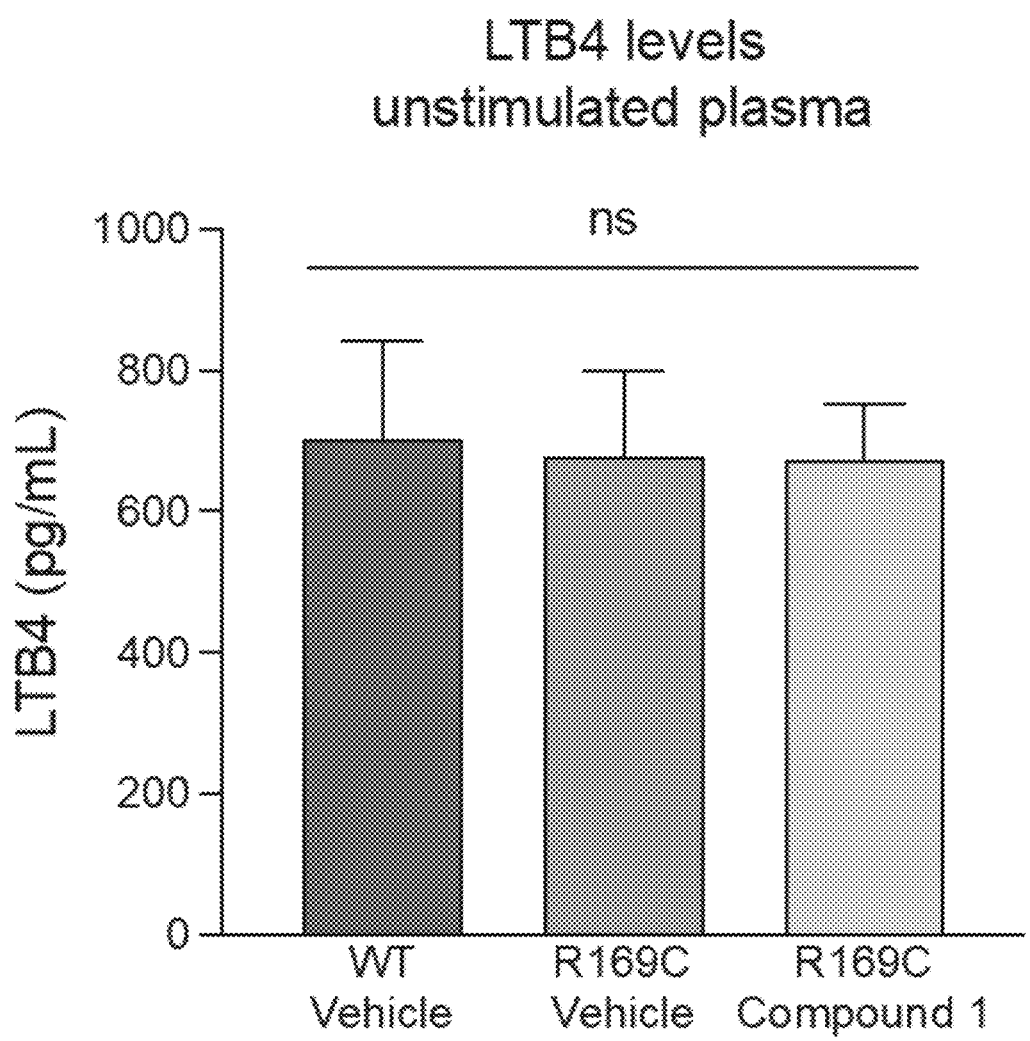

FIG. 94B shows that there is no change in LTB4 levels detected between groups with unstimulated plasma.

Figure 95A:
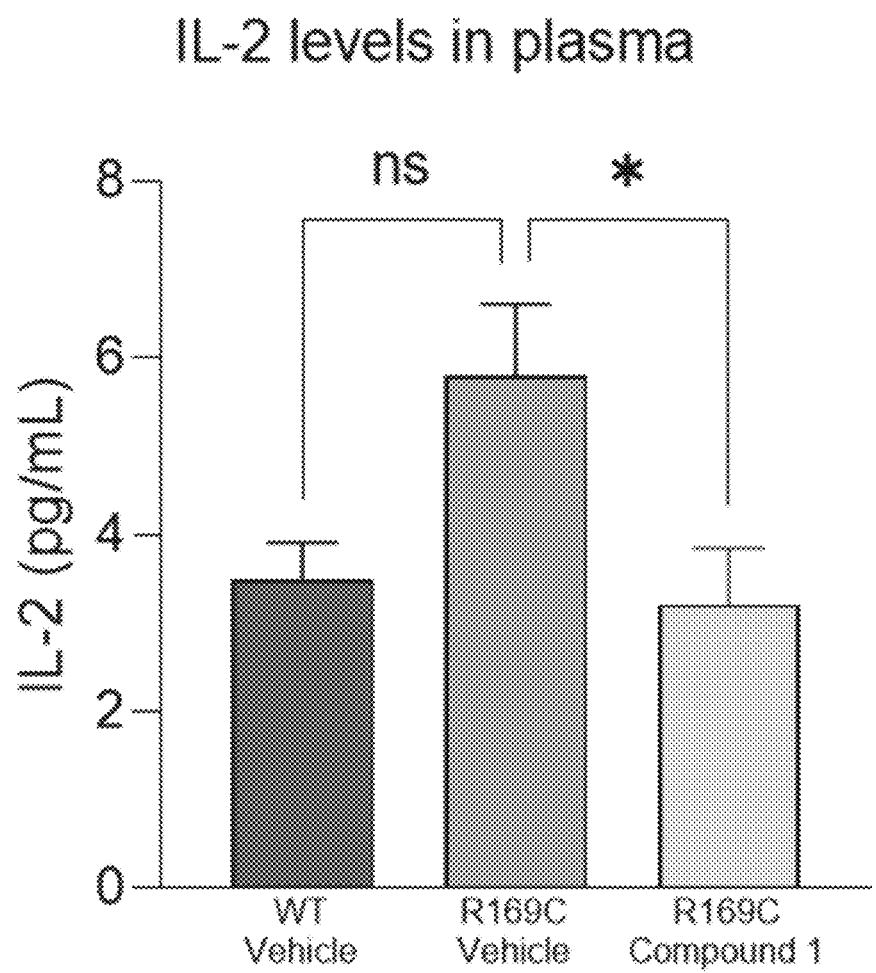

FIG. 95A shows a trending increase in IL-2 in plasma of the CADASIL model NOTCH3$^{R169C}$ transgenic mice (R169C) treated with vehicle while IL-2 levels are significantly reduced in those treated with Compound 1.

Figure 95B:
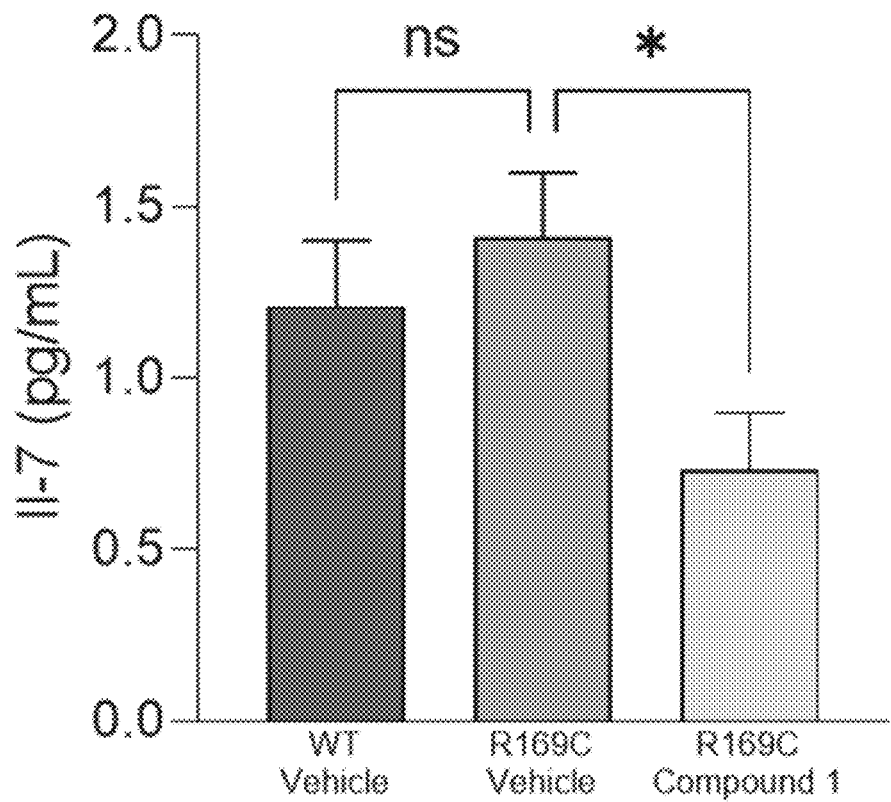

FIG. 95B shows a trending increase in IL-7 levels in brain cortex lysate in the CADASIL model NOTCH3$^{R169C}$ transgenic mice (R169C) treated with vehicle while IL-7 levels are reduced significantly in those treated with Compound 1.

Figure 96:
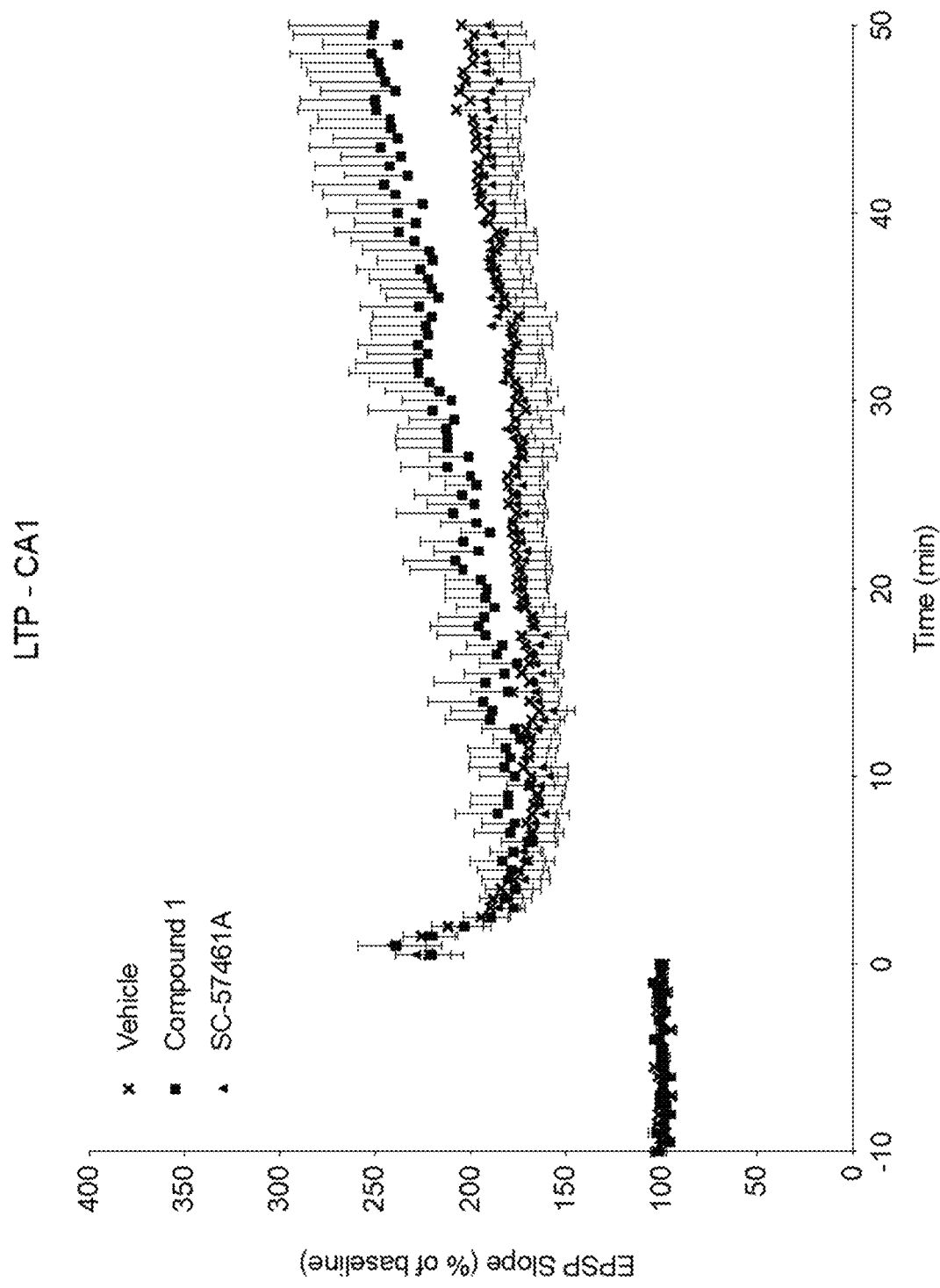

FIG. 96 shows the increase in long term potentiation from CA1 neurons in the hippocampus of aged mice treated with Vehicle (x), Compound 1 (square), or SC57461A (triangle) for 1 month. Mice treated with Compound 1 show an increase in long term potentiation compared to Vehicle or SC57461A mice.

Figure 97:
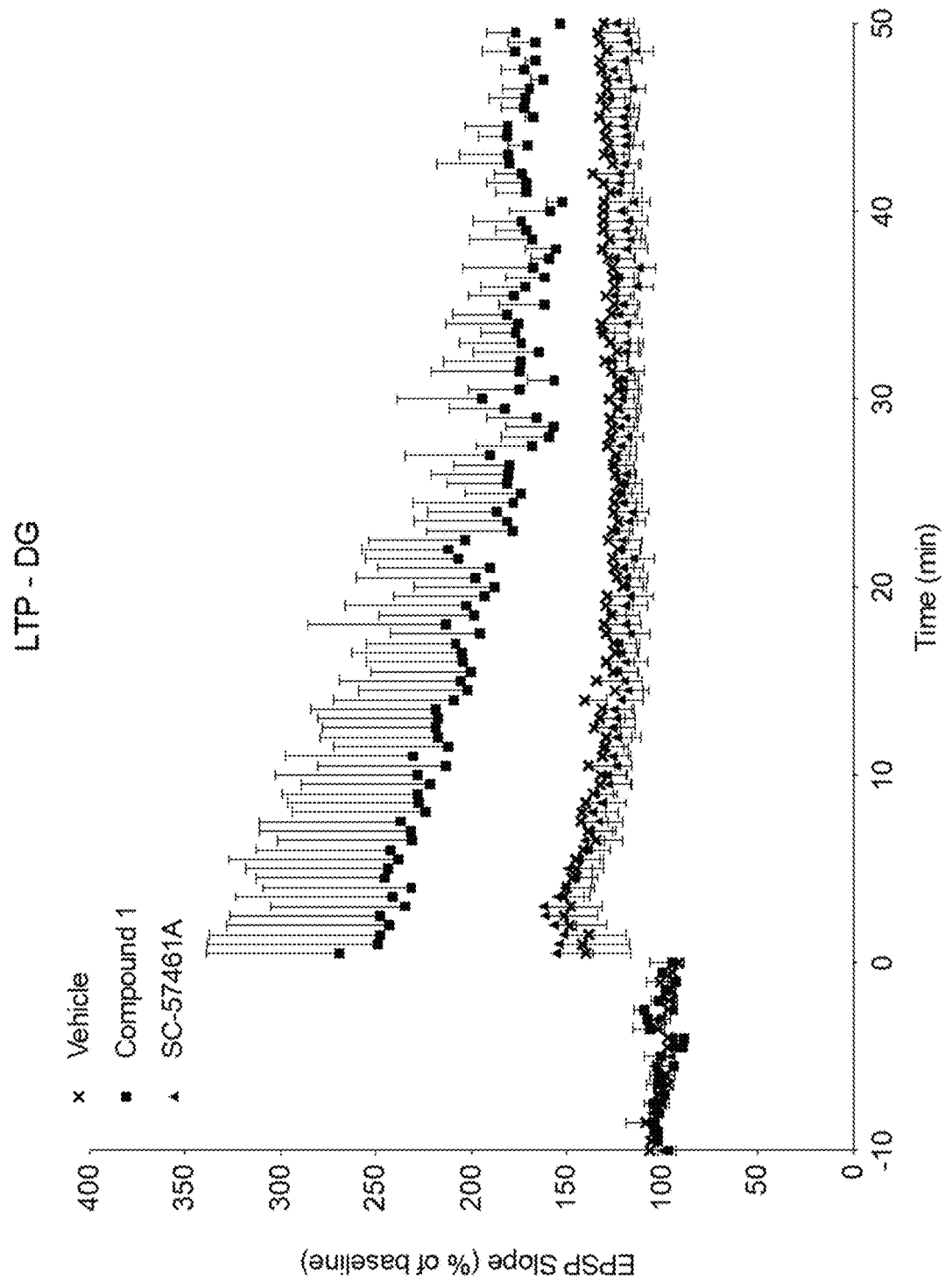

FIG. 97 shows the increase in long term potentiation from DG neurons in the hippocampus of aged mice treated with Vehicle (x), Compound 1 (square), or SC57461A (triangle) for 1 month. Mice treated with Compound 1 show an increase in long term potentiation compared to Vehicle or SC57461A mice.

Figure 98:
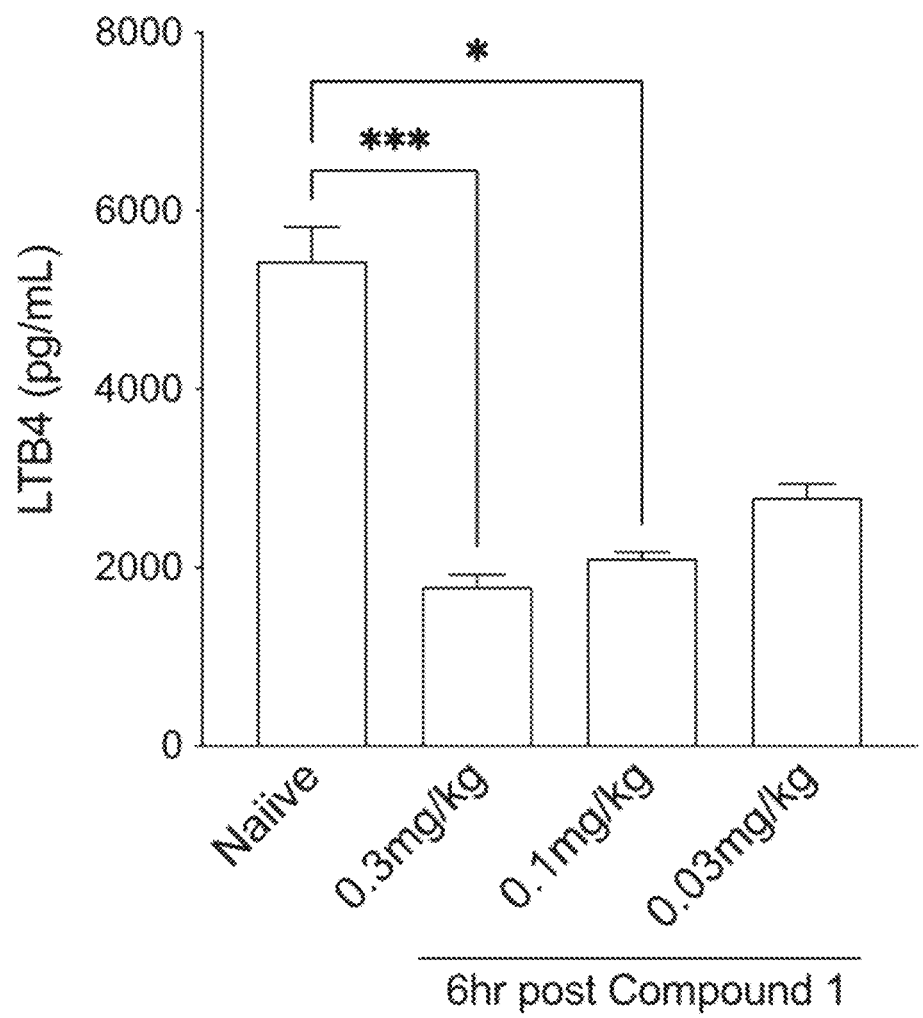

FIG. 98 reports pharmacodynamic dose response of Compound 1 in the form of LTB4 plasma levels in C57BL/6 mice treated with a single oral gavage dose of Compound 1 at 0.3, 0.1, and 0.03 mg/kg 6 hours post dosing.

Figure 99:
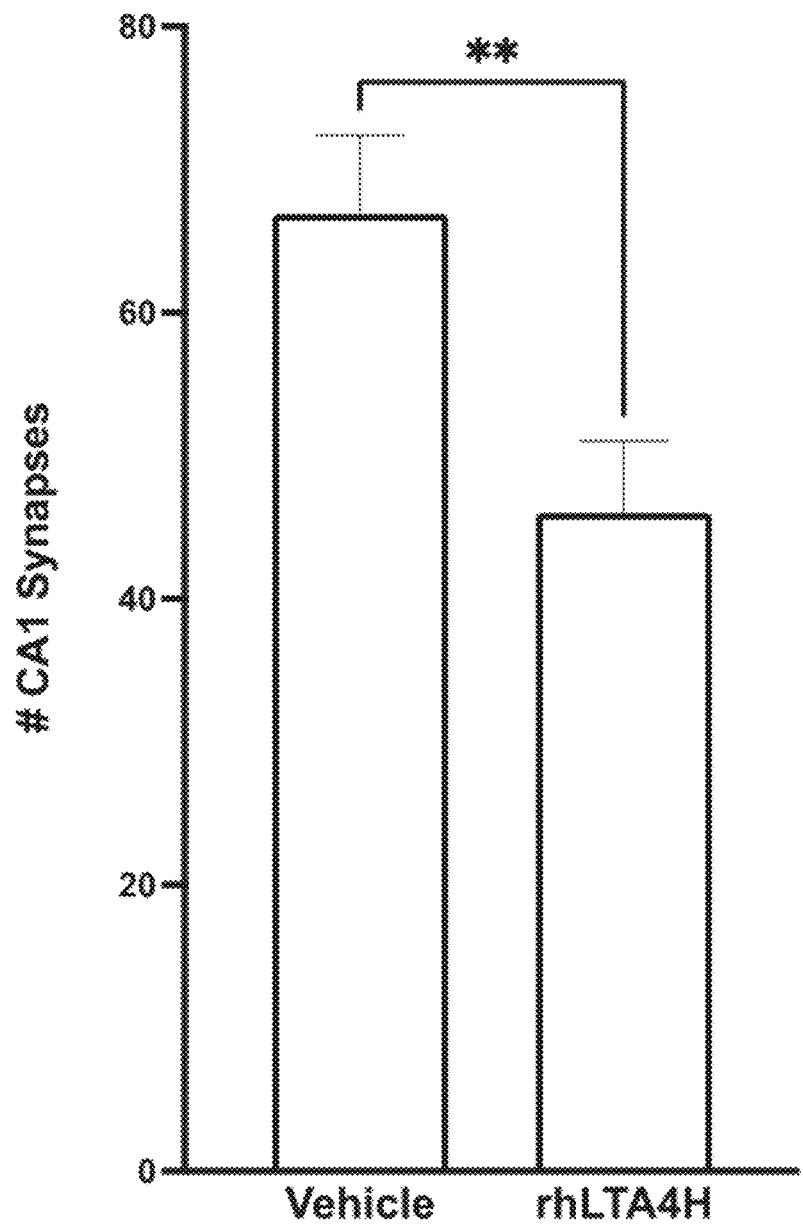

FIG. 99 shows a decrease in CA1 hippocampal synapse density in young mice treated with recombinant human LTA4H protein for 1 week.

Figure 100:
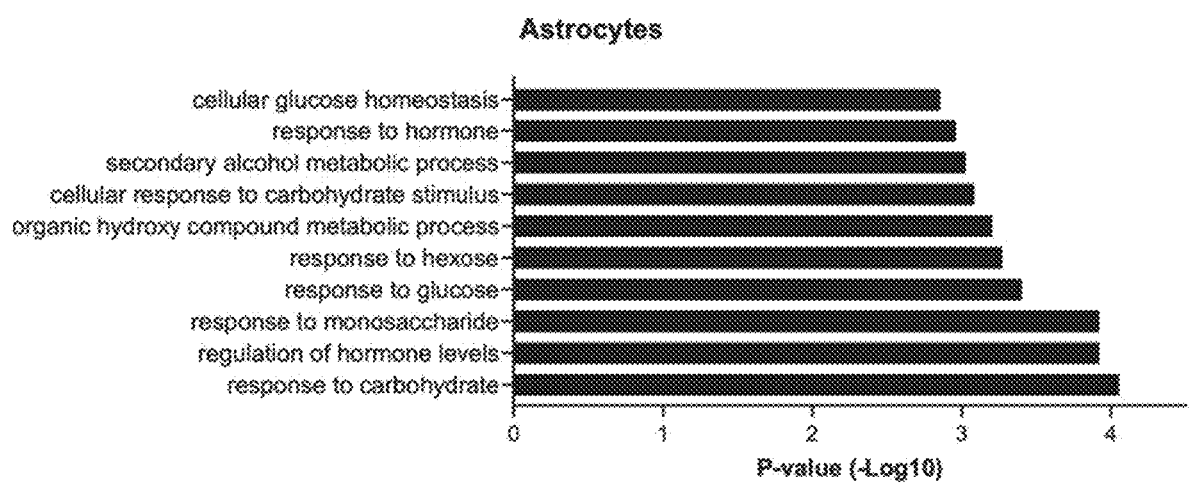

FIG. 100 details the Top 10 significant Biological Process GO terms identified comparing single cell sequencing results from astrocytes from aged mice treated with vehicle or the LTA4H inhibitor SC-57461A. The g:Profiler Web server (https://bitt.cs.ut.ee/gprofiler).

Figure 101:
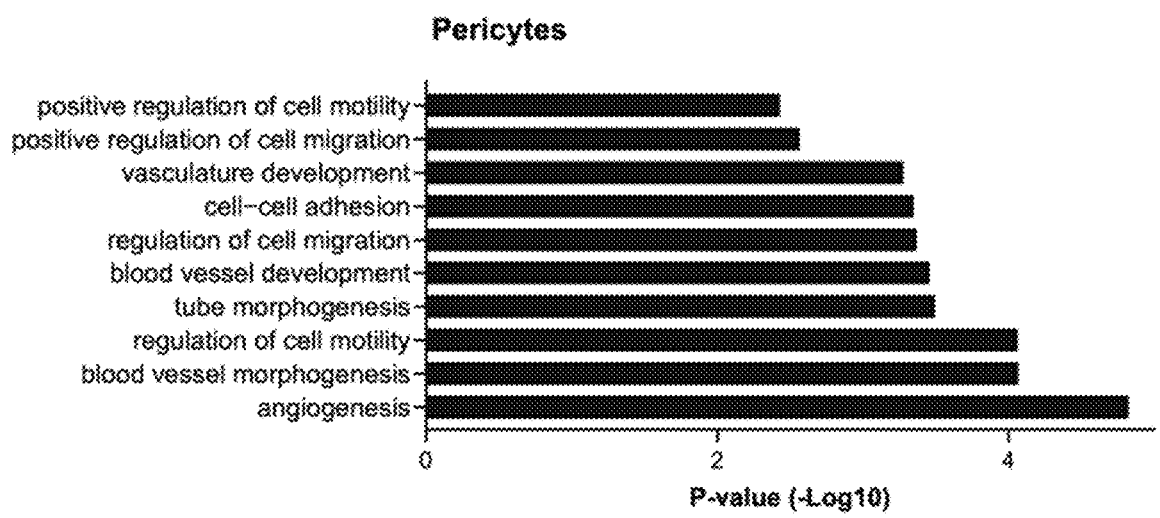

FIG. 101 details the Top 10 significant Biological Process GO terms identified comparing single cell sequencing results from pericytes from aged mice treated with vehicle or the LTA4H inhibitor SC-57461A. The g:Profiler Web server (https://bitt.cs.ut.ee/gprofiler).

Figure 102:
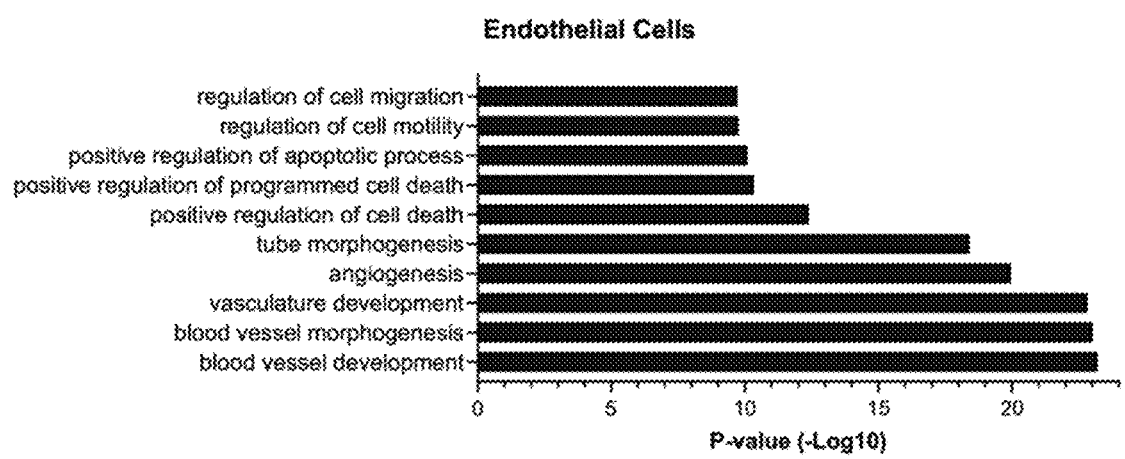
Figure 43:
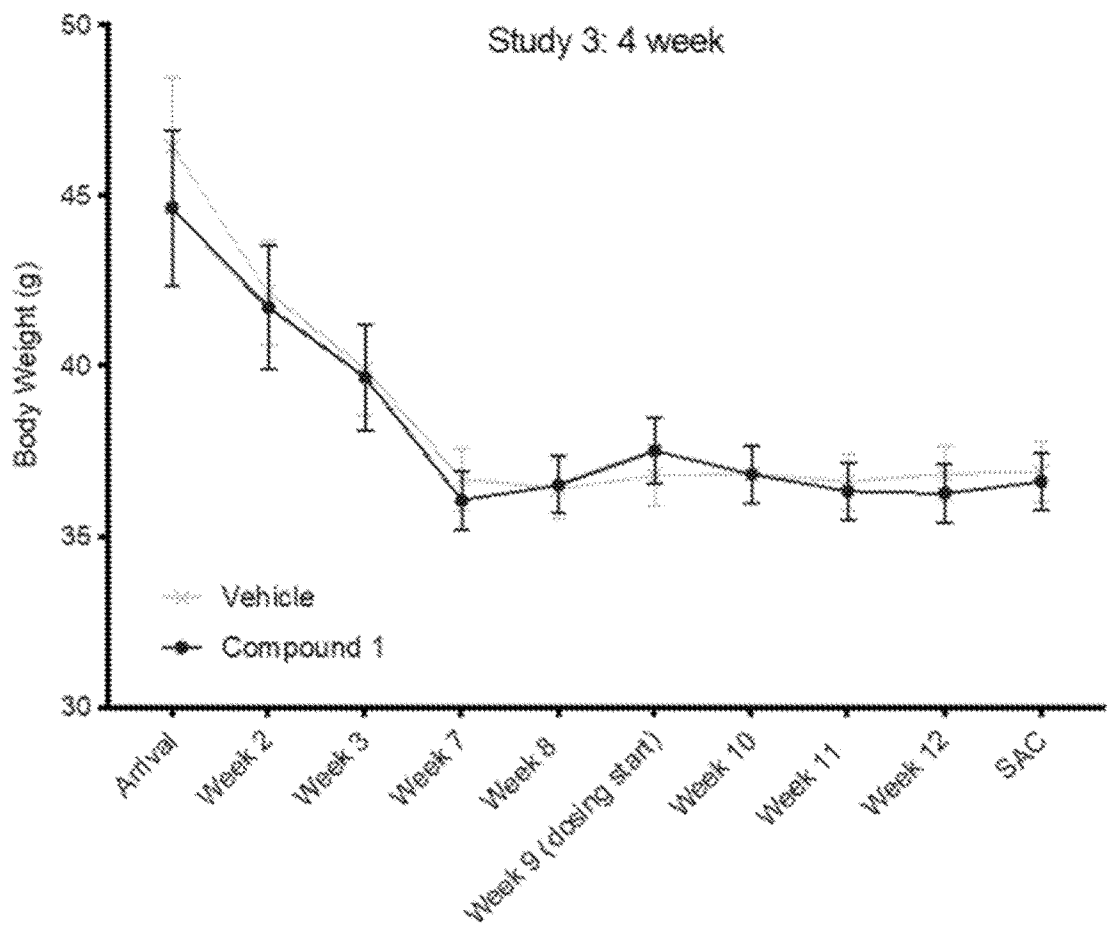

FIG. 102 details the Top 10 significant Biological Process GO terms identified comparing single cell sequencing results from endothelial from aged mice treated with vehicle or the LTA4H inhibitor SC-57461A. The g:Profiler Web server (https://bitt.cs.ut.ee/gprofiler).

VI. DETAILED DESCRIPTION

A. Introduction

The present invention relates to the identification and discovery of methods and compositions for the treatment and/or prevention of cognitive and motor impairment, including age-associated dementia, decline in motor skills, neuroinflammation, and neurodegenerative disease. Described herein are methods and compositions for the treatment of subjects suffering from such disorders, which are aspects of the present invention. The methods and compositions described herein are useful in: preventing or treating cognitive or motor impairment, age-associated dementia or motor impairment, neuroinflammation, and neurodegenerative disease; ameliorating the symptoms of cognitive or motor impairment, age-associated dementia or motor impairment, neuroinflammation, and neurodegenerative disease; slowing progression of aging-associated cognitive or motor impairment, age-associated dementia or motor impairment, neuroinflammation, and neurodegenerative disease; and/or reversing the progression of aging-associated cognitive or motor impairment, age-associated dementia or motor impairment, neuroinflammation, and neurodegenerative disease. An implementation of the invention includes using the LTA4H modulatory agent(s) as treatment. An embodiment of the invention includes the LTA4H modulatory agent(s). Another embodiment of the invention includes using an LTA4H modulating agent which selectively inhibits the epoxide hydrolase activity of the LTA4H enzyme. Another embodiment of the invention includes using an LTA4H modulating agent which inhibits both the epoxide hydrolase activity and the aminopeptidase activity of the LTA4H enzyme. Another embodiment of the invention includes one or more LTA4H modulating agent(s) that bind to the epoxide hydrolase and/or aminopeptidase active site(s).

Before describing the present invention in detail, it is to be understood that this invention is not limited to a particular method or composition described, as such may, of course, vary. It is also understood that the terminology used herein is for the purpose of describing particular embodiments only, and is not intended to be limiting, since the scope of the present invention will be limited only by the appended claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

It is noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein have discrete components and features which may be readily separated from or combined with the features of any of the other several embodiments without departing from the scope or the spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

B. Definitions

Unless otherwise defined, all technical and scientific terms used herein have the same meaning as commonly understood by one having ordinary skill in the art to which the invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those having skill in the art, and so forth.

In describing methods of the present invention, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). As such, subjects of the invention, include but are not limited to mammals, e.g., humans and other primates, such as chimpanzees and other apes and monkey species; and the like, where in certain embodiments the subject are humans. The term subject is also meant to include a person or organism of any age, weight or other physical characteristic, where the subjects may be an adult, a child, an infant or a newborn.

By a "young" or "young individual" it is meant an individual that is of chronological age of 40 years old or younger, e.g., 35 years old or younger, including 30 years old or younger, e.g., 25 years old or younger or 22 years old or younger. As such, "young" and "young individual" may refer to a subject that is between the ages of 0 and 40, e.g., 0, 1, 5, 10, 15, 20, 25, 30, 35, or 40 years old. In other instances, "young" and "young individual" may refer to a biological (as opposed to chronological) age such as an individual who has not exhibited the levels of inflammatory cytokines in the plasma exhibited in comparatively older individuals. Conversely, these "young" and "young individual" may refer to a biological (as opposed to chronological) age such as an individual who exhibits greater levels of anti-inflammatory cytokines in the plasma compared to levels in comparatively older individuals. By way of example, and not limitation, the inflammatory cytokine is Eotaxin, and the fold difference between a young subject or young individual and older individuals is at least 1.5-fold. Similarly, the fold difference between older and younger individuals in other inflammatory cytokines may be used to refer to a biological age. (See U.S. patent application Ser. No. 13/575,437 which is herein incorporated by reference). Usually, the individual is healthy, e.g., the individual has no hematological malignancy or autoimmune disease at the time of harvest.

By "an individual suffering from or at risk of suffering from an aging-associated impairment" is meant an individual that is about more than 50% through its expected lifespan, such as more than 60%, e.g., more than 70%, such as more than 75%, 80%, 85%, 90%, 95% or even 99% through its expected lifespan. The age of the individual will depend on the species in question. Thus, this percentage is based on the predicted life-expectancy of the species in question. For example, in humans, such an individual is 50 year old or older, e.g., 60 years old or older, 70 years old or older, 80 years old or older, 90 years old or older, and usually no older than 100 years old, such as 90 years old, i.e., between the ages of about 50 and 100, e.g., 50 . . . 55 . . . 60 . . . 65 . . . 70 . . . 75 . . . 80 . . . 85 . . . 90 . . . 95 . . . 100 years old or older, or any age between 50-1000, that suffers from an aging-associated condition as further described below, e.g., cognitive or motor impairment associated with the natural aging process; an individual that is about 50 years old or older, e.g., 60 years old or older, 70 years old or older, 80 years old or older, 90 years old or older, and usually no older than 100 years old, i.e., between the ages of about 50 and 100, e.g., 50 . . . 55 . . . 60 . . . 65 . . . 70 . . . 0.75 . . . 80 . . . 85 . . . 90 . . . 95 . . . 100 years old, that has not yet begun to show symptoms of an aging-associated condition e.g., cognitive or motor impairment; an individual of any age that is suffering from a cognitive or motor impairment due to an aging-associated disease, as described further below, and an individual of any age that has been diagnosed with an aging-associated disease that is typically accompanied by cognitive or motor impairment, where the individual has not yet begun to show symptoms of cognitive or motor impairment. The corresponding ages for non-human subjects are known and are intended to apply herein.

As used herein, "treatment" refers to any of (i) the prevention of the disease or disorder, or (ii) the reduction or elimination of symptoms of the disease or disorder. Treatment may be effected prophylactically (prior to the onset of disease) or therapeutically (following the onset of the disease). The effect may be prophylactic in terms of completely or partially preventing a disease or symptom thereof and/or may be therapeutic in terms of a partial or complete cure for a disease and/or adverse effect attributable to the disease. Thus, the term "treatment" as used herein covers any treatment of an aging-related disease or disorder in a mammal and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, rejuvenation of tissue or organs, etc.

The therapeutic agent may be administered before, during or after the onset of disease. The treatment of ongoing disease, where the treatment stabilizes or reduces the undesirable clinical symptoms of the patient, is of particular interest. Such treatment may be performed prior to complete loss of function in the affected tissues. The subject therapy may be administered during the symptomatic stage of the disease, and in some cases after the symptomatic stage of the disease. In another embodiment of the invention, "treatment" refers to reducing local tissue or blood levels of neutrophils to a more homeostatic state, i.e. to levels observed in a healthy individual of the same or similar age.

Chemical Abbreviations

DCE=dichloroethane
DCM=dichloromethane
DEA=diethylamine
DIBAL-H=diisobutylaluminum hydride
DIPEA=diisopropylethylamine
DMA=dimethylacetamide
DMAP=4-dimethylaminopyridine
DME=dimethyl ether
DMF=dimethylformamide
DMSO=dimethylsulfoxide
Et2O=ethylether
EtOAc=ethyl acetate
EtOH=ethanol
IPA=isopropyl alcohol
KHMDS=potassium bis(trimethylsilyl)amide
MeCN=acetonitrile MeOH=methanol
TBTU=2-(1H-benzotriazole-1-yl)-1,1,3,3-tetramethyl-uronium tetrafluoroborate
TEA=triethylamine
TFA=trifluoroacetic acid
THF=tetrahydrofuran
TMSCF3=(trifluoromethyl)trimethylsilane It will be understood that the terms "compounds of formula (I)" and "compounds of the invention" have the same meaning unless indicated otherwise.

In some embodiments, the aging-associated condition that is treated is an aging-associated impairment in cognitive ability in an individual. By cognitive ability, or "cognition," it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "cognitive decline", it is meant a progressive decrease in one or more of these abilities, e.g., a decline in memory, language, thinking, judgment, etc. By "an impairment in cognitive ability" and "cognitive impairment", it is meant a reduction in cognitive ability relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. By "aging-associated cognitive impairment," it is meant an impairment in cognitive ability that is typically associated with aging, including, for example, cognitive impairment associated with the natural aging process, e.g., mild cognitive impairment (M.C.I.); and cognitive impairment associated with an aging-associated disorder, that is, a disorder that is seen with increasing frequency with increasing senescence, e.g., a neurodegenerative condition such as Alzheimer's disease, Parkinson's disease, frontotemporal dementia, Huntington disease, amyotrophic lateral sclerosis, multiple sclerosis, glaucoma, myotonic dystrophy, vascular dementia, and the like.

In some embodiments, the aging-associated condition that is treated is an aging-associated impairment in motor ability in an individual. By motor ability, it is meant the motor processes that include the ability to perform complex muscle-and-nerve actions that produce movement such as fine motor skills producing small or precise movements (e.g., writing, tying shoes) and gross motor skills for large movements (e.g. walking, running, kicking). By "motor decline", it is meant a progressive decrease in one or more of these abilities, e.g., a decline in find movement or gross motor skills, etc. By "motor impaired" and "motor impairment", it is meant a reduction in motor ability/skills relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. By "aging-associated motor impairment," it is meant an impairment or decline in motor ability that is typically associated with aging, including, for example, motor impairment associated with the natural aging process and motor impairment, or decline associated with an aging-associated disorder, that is, a disorder that is seen with increasing frequency with increasing senescence, e.g., a neurodegenerative condition such as Parkinson's disease, amyotrophic lateral sclerosis, and the like.

In some embodiments, the aging-associated condition that is treated is an aging-associated increase in neuroinflammation in an individual. By "neuroinflammation" it is meant biochemical and cellular responses of the nervous system to injury, infection, or neurodegenerative diseases. Such responses are directed at decreasing the triggering factors by involving central nervous system immunity to defend against potential harm. Neurodegeneration occurs in the central nervous system and exhibits hallmarks of loss of neuronal structure and function. Neuroinflammatory diseases or neuroinflammatory-associated conditions or diseases, includes by way of example and not limitation, neurodegenerative diseases such as Alzheimer's disease, Parkinson's disease, multiple sclerosis and the like.

C. Compounds

Formula I

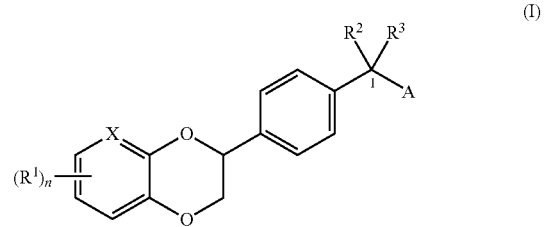

In one embodiment, the invention relates to compounds of formula (I) as described above (the "first embodiment"), and pharmaceutically acceptable salts thereof, as described above. In another embodiment the invention relates to a compound of formula (I) as described in the immediately preceding embodiment of the invention (the "second embodiment"), or a pharmaceutically acceptable salt thereof, wherein group A is a group of formula —NR$^4$R$^5$. In another embodiment the invention relates to a compound of formula (I) as described in the first embodiment, or a pharmaceutically acceptable salt thereof, wherein group A is a (4- to 11-membered)N-heterocyclic ring of formula B:

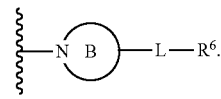

In another embodiment, the invention relates to a compound of formula (I) as described in the second embodiment, or a pharmaceutically acceptable salt thereof, wherein R$^4$ is —H or —(C$_1$-C$_6$)alkyl, and R$^5$ is —(C$_1$-C$_6$)alkyl; wherein each —(C$_1$-C$_6$)alkyl of said R$^4$ and R$^5$ groups, when present, is optionally independently substituted by one to three R$^6$ groups.

In another embodiment, the invention relates to a compound of formula (I) as described in the embodiment immediately above, or a pharmaceutically acceptable salt thereof, wherein R$^4$ is —H or —(C$_1$-C$_6$)alkyl, and R$^5$ is —(C$_1$-C$_6$)alkyl; wherein said —(C$_1$-C$_6$)alkyl of said R$^5$ group is substituted by —(C$_3$-C$_6$)cycloalkyl, -(4- to 11-membered)heterocycloalkyl, —(C$_6$-C$_{10}$)aryl, or —(5- to 11-membered)heteroaryl; wherein each of said, —(C$_3$-C$_6$)cycloalkyl, -(4- to 11-membered)heterocycloalkyl, —($C_6$-$C_{10}$)aryl, and -(5- to 11-membered)heteroaryl is optionally substituted with one to three groups independently selected from —($C_1$-$C_6$) alkyl, —$CF_3$, and —C(O)$OR^8$.

In another embodiment, the invention relates to a compound of formula (I) as described in the second embodiment of the invention, or a pharmaceutically acceptable salt thereof, wherein $R^4$ is —H or —($C_1$-$C_6$)alkyl, and $R^5$ is —($C_1$-$C_6$)alkyl; wherein said —($C_1$-$C_6$)alkyl of said $R^5$ group is independently substituted by one to three groups selected from —($C_1$-$C_6$)alkyl, —O($C_1$-$C_6$)alkyl, —C(O)$R^8$, —C(O)$OR^5$, —S(O)$_2R^8$, and —NHC(O)$R^8$.

In another embodiment, the invention relates to a compound of formula (I) as described in the second embodiment of the invention, or a pharmaceutically acceptable salt thereof, wherein $R^4$ and $R^5$ are each independently selected from —H or —($C_1$-$C_6$)alkyl.

In another embodiment, the invention relates to a compound of formula (I) as described in the second embodiment of the invention, or a pharmaceutically acceptable salt thereof, wherein $R^4$ is —H or —($C_1$-$C_6$)alkyl, and $R^5$ is —($C_3$-$C_6$)cycloalkyl, -(4- to 11-membered)heterocycloalkyl, —($C_6$-$C_{10}$)aryl, and -(5- to 11-membered)heteroaryl; wherein each of the foregoing —($C_3$-$C_6$)cycloalkyl, -(4- to 11-membered)heterocycloalkyl, —($C_6$-$C_{10}$)aryl, and -(5- to 11-membered)heteroaryl groups of said $R^5$ is optionally independently substituted by one to three groups selected from —($C_1$-$C_6$)alkyl, —O($C_1$-$C_6$)alkyl, —C(O)$R^8$, —C(O)$OR^5$, —S(O)$_2R^8$, and —NHC(O)$R^8$.

In another embodiment, the invention relates to a compound of formula (I) as described in the third embodiment of the invention, or a pharmaceutically acceptable salt thereof, wherein said ring B is 4 to 8-membered monocyclic radical.

In another embodiment, the invention relates to a compound of formula (I) as described in the embodiment immediately above, or a pharmaceutically acceptable salt thereof, wherein said 4 to 8-membered monocyclic radical is selected from the group consisting of azetidine, tetrahydropyrrole, piperidine, hexamethyleneimine, 1,2-diazetidine, pyrazolidine, imidazolidine, piperazine, hexahydrodiazepine, isoxazolidine, oxazolidine, tetrahydro-2H-1,3-oxazine, morpholine, and hexahydro-1,4-oxazepine; wherein said monocyclic ring may be further optionally substituted by one to three groups selected from halo, —OH, (=O), —C(O)OH, —C(O)O—($C_1$-$C_6$)alkyl, and —($C_1$-$C_6$) alkyl.

In another embodiment, the invention relates to a compound of formula (I) as described in the third embodiment of the invention, or a pharmaceutically acceptable salt thereof, wherein said ring B is a spirocyclic heterocyclic radical.

In another embodiment, the invention relates to a compound of formula (I) as described in the embodiment immediately above, or a pharmaceutically acceptable salt thereof, wherein said spirocyclic heterocyclic radical is selected from:

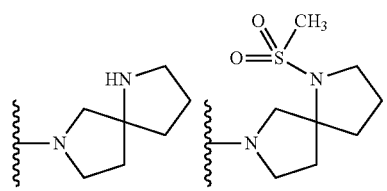

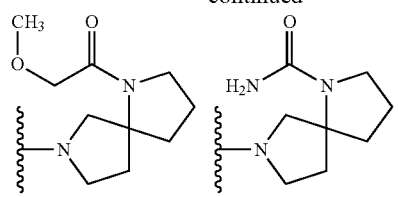

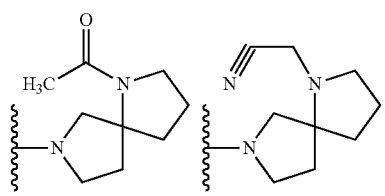

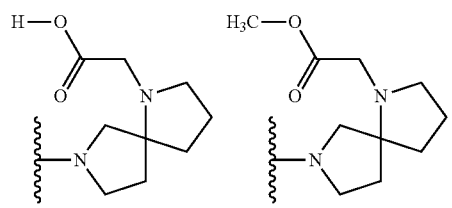

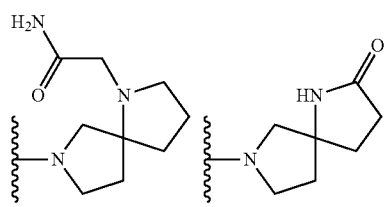

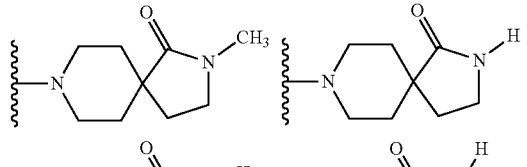

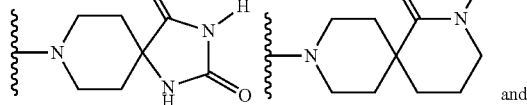

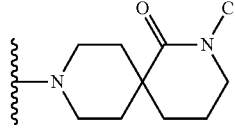

and

In another embodiment, the invention relates to a compound of formula (I) as described in the third embodiment of the invention, or a pharmaceutically acceptable salt thereof, wherein said ring B is a bridged bicyclic radical; or a 6 to 11-membered fused bicyclic radical which may be non-aromatic or have one aromatic ring provided that the aromatic ring of the bicyclic radical, when present, is not attached to methylene carbon atom 1 of the compound of formula (I).

In another embodiment, the invention relates to a compound of formula (I) as described in the embodiment immediately above, or a pharmaceutically acceptable salt thereof, wherein said 6 to 11-membered fused bicyclic radical or bridged bicyclic radical is selected from:

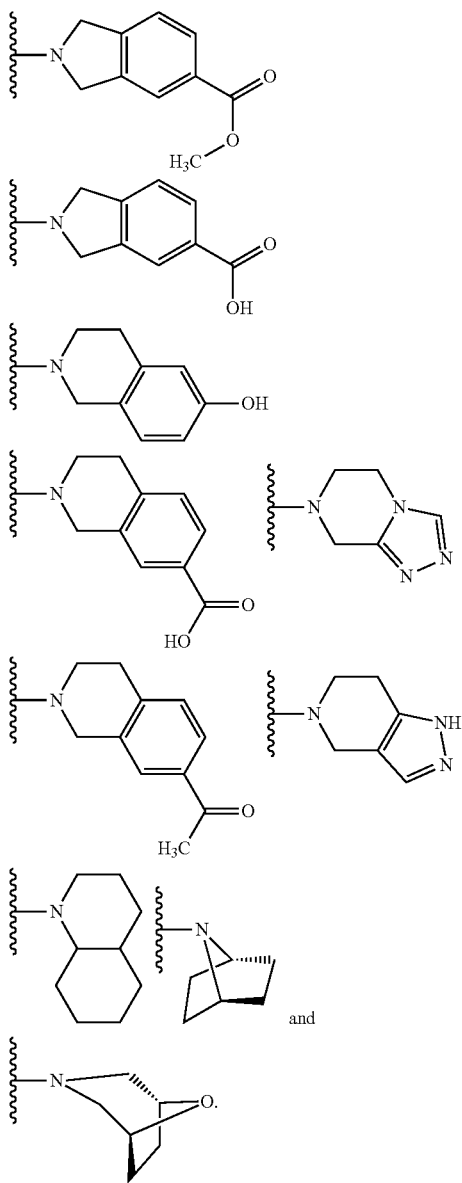

and

In another embodiment, the invention relates to a compound of formula (I) as described in the third embodiment of the invention, or a pharmaceutically acceptable salt thereof, wherein L is —CH$_2$—.

In another embodiment, the invention relates to a compound of formula (I) as described in the third embodiment of the invention, or a pharmaceutically acceptable salt thereof, wherein L is absent.

In another embodiment, the invention relates to a compound of formula (I) as described in the third embodiment of the invention, or a pharmaceutically acceptable salt thereof, wherein said 4 to 8-membered heterocyclic ring B is a selected from azetidinyl, pyrrolidinyl, piperidinyl and azepanyl; wherein each of the foregoing azetidinyl, pyrrolidinyl, piperidinyl and azepanyl rings is optionally substituted by one to three groups selected from halo, —OH, (=O), —C(O)OH, C(O)O—(C$_1$-C$_6$)alkyl, and —(C$_1$-C$_6$)alkyl; and wherein L is absent or a linker selected from —(C1-C6)alkylene; and wherein R$^6$ is elected from halo, —OR$^7$, —CF$_3$, —CN, —(C$_1$-C$_6$)alkyl, —C(O)R$^7$, —C(O)$_2$R$^7$, —C(O)N(R$^7$)$_2$, —N(R$^7$)$_2$, —NHC(O)R$^7$, —NHC(O)N(R$^7$)$_2$, —S(O)$_2$R$^7$, —NH—S(O)$_2$—R$^7$, —(C$_3$-C$_6$)cycloalkyl, -(4- to 11-membered)heterocycloalkyl, —(C$_6$-C$_{10}$)aryl, and -(5- to 11-membered)heteroaryl; wherein each of said, —(C$_1$-C$_6$)alkyl, —O(C$_1$-C$_6$)alkyl, —(C$_3$-C$_6$)cycloalkyl, -(4- to 11-membered)heterocycloalkyl, —(C$_6$-C$_{10}$)aryl, and -(5- to 11-membered)heteroaryl of said R$^6$ group is optionally substituted where possible with one to three groups selected from halo, —OH, —CF$_3$, —CN, (=O), —(C$_1$-C$_6$)alkyl, —C(O)OH, —C(O)O—(C$_1$-C$_6$)alkyl, —NH$_2$, —NH(C$_1$-C$_6$)alkyl, —N((C$_1$-C$_6$)alkyl)$_2$, —S(O)$_2$(C$_1$-C$_6$)alkyl, —(C$_3$-C$_6$)cycloalkyl, -(4- to 11-membered)heterocycloalkyl, —(C$_6$-C$_{10}$)aryl, and -(5- to 11-membered)heteroaryl.

In another embodiment, the invention relates to a compound of formula (I) as described in any of the embodiments above, or a pharmaceutically acceptable salt thereof, wherein X is N.

In another embodiment, the invention relates to a compound of formula (I) as described in any of the embodiments above except the embodiment immediately above, or a pharmaceutically acceptable salt thereof, wherein X is CH.

The following are representative compounds of the invention which were made by the general synthetic schemes, the examples, and known methods in the art.

TABLE 1

Exemplary compounds of the invention.

| Compound No. | Structure | Name |
|---|---|---|
| 1 | 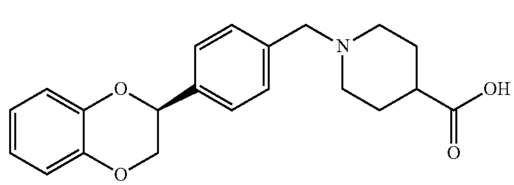 [SMILES: O=C(O)C1CCN(Cc2ccc([C@H]3COc4ccccc4O3)cc2)CC1] | 1-{4-[(2S)-2,3-dihydro-1,4-benzodioxin-2-yl]benzyl}piperidine-4-carboxylic acid |

TABLE 1-continued

Exemplary compounds of the invention.

| Compound No. | Structure | Name |
|---|---|---|
| 2 | 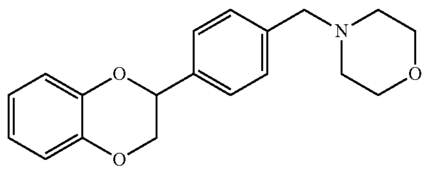 [SMILES: c1ccc2c(c1)OCC(c1ccc(CN3CCOCC3)cc1)O2] | 4-[4-(2,3-dihydro-1,4-benzodioxin-2-yl)benzyl]morpholine |
| 3 | 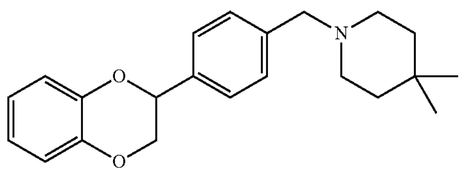 [SMILES: CC1(C)CCN(Cc2ccc(C3COc4ccccc4O3)cc2)CC1] | 1-[4-(2,3-dihydro-1,4-benzodioxin-2-yl)benzyl]-4,4-dimethylpiperidine |
| 4 | 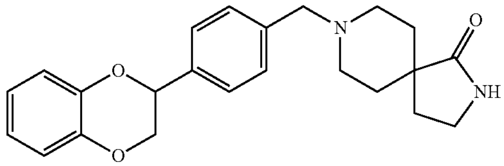 [SMILES: O=C1NCCC12CCN(Cc1ccc(C3COc4ccccc4O3)cc1)CC2] | 8-[4-(2,3-dihydro-1,4-benzodioxin-2-yl)benzyl]-2,8-diazaspiro[4.5]decan-1-one |
| 5 | 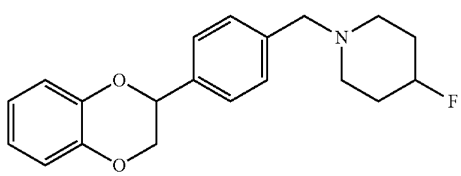 [SMILES: FC1CCN(Cc2ccc(C3COc4ccccc4O3)cc2)CC1] | 1-[4-(2,3-dihydro-1,4-benzodioxin-2-yl)benzyl]-4-fluoropiperidine |
| 6 | 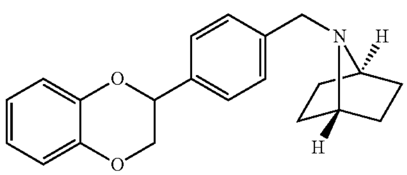 [SMILES: c1ccc2c(c1)OCC(c1ccc(CN3[C@H]4CC[C@@H]3CC4)cc1)O2] | (1s,4s)-7-[4-(2,3-dihydro-1,4-benzodioxin-2-yl)benzyl]-7-azabicyclo[2.2.1]heptane |
| 7 | 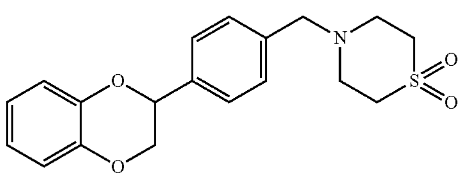 [SMILES: O=S1(=O)CCN(Cc2ccc(C3COc4ccccc4O3)cc2)CC1] | 4-[4-(2,3-dihydro-1,4-benzodioxin-2-yl)benzyl]thiomorpholine 1,1-dioxide |
| 8 | 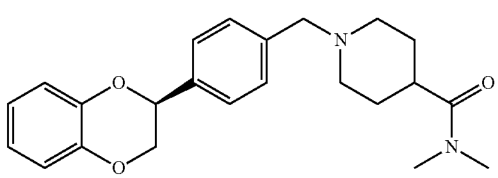 [SMILES: CN(C)C(=O)C1CCN(Cc2ccc([C@H]3COc4ccccc4O3)cc2)CC1] | 1-{4-[(2S)-2,3-dihydro-1,4-benzodioxin-2-yl]benzyl}-N,N-dimethylpiperidine-4-carboxamide |
| 9 | 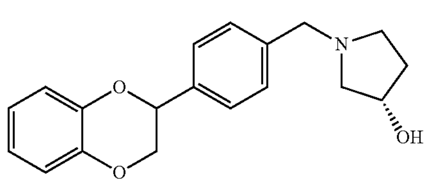 [SMILES: O[C@H]1CCN(Cc2ccc(C3COc4ccccc4O3)cc2)C1] | (3S)-1-[4-(2,3-dihydro-1,4-benzodioxin-2-yl)benzyl]pyrrolidin-3-ol |

TABLE 1-continued

Exemplary compounds of the invention.

| Compound No. | Structure | Name |
|---|---|---|
| 10 | 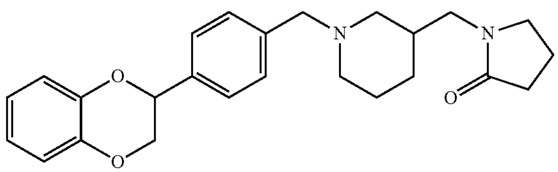 [SMILES: O=C1CCCN1CC1CCCN(Cc2ccc(C3COc4ccccc4O3)cc2)C1] | 1-({1-[4-(2,3-dihydro-1,4-benzodioxin-2-yl)benzyl]piperidin-3-yl}methyl)pyrrolidin-2-one |
| 11 | 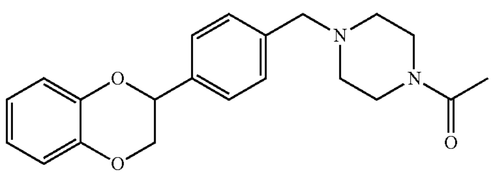 [SMILES: CC(=O)N1CCN(Cc2ccc(C3COc4ccccc4O3)cc2)CC1] | 1-{4-[4-(2,3-dihydro-1,4-benzodioxin-2-yl)benzyl]piperazin-1-yl}ethanone |
| 12 | 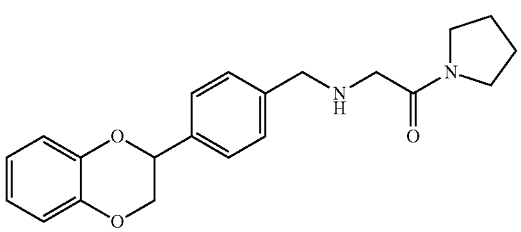 [SMILES: O=C(CNCc1ccc(C2COc3ccccc3O2)cc1)N1CCCC1] | 2-{[4-(2,3-dihydro-1,4-benzodioxin-2-yl)benzyl]amino}-1-(pyrrolidin-1-yl)ethanone |
| 13 | 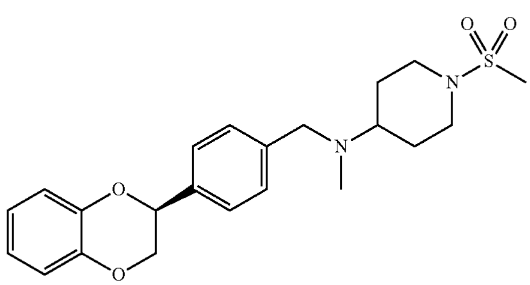 [SMILES: CN(Cc1ccc([C@H]2COc3ccccc3O2)cc1)C1CCN(S(C)(=O)=O)CC1] | N-{4-[(2S)-2,3-dihydro-1,4-benzodioxin-2-yl]benzyl}-N-methyl-1-(methylsulfonyl)piperidin-4-amine |
| 14 | 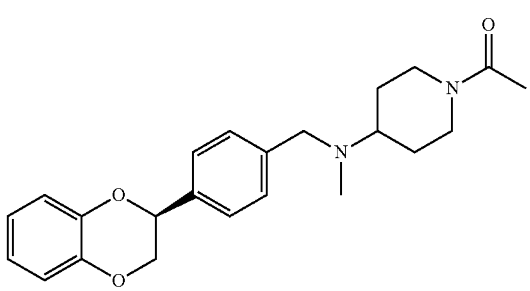 [SMILES: CC(=O)N1CCC(N(C)Cc2ccc([C@H]3COc4ccccc4O3)cc2)CC1] | 1-{4-{4-[(2S)-2,3-dihydro-1,4-benzodioxin-2-yl]benzyl}(methyl)amino]piperidin-1-yl}ethanone |
| 15 | 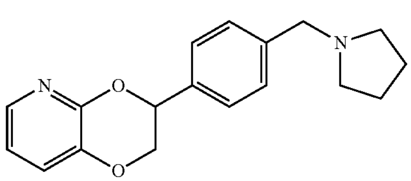 [SMILES: c1cnc2c(c1)OCC(c1ccc(CN3CCCC3)cc1)O2] | 3-[4-(pyrrolidin-1-ylmethyl)phenyl]-2,3-dihydro[1,4]dioxin[2,3-b]pyridine |

TABLE 1-continued

Exemplary compounds of the invention.

| Compound No. | Structure | Name |
| --- | --- | --- |
| 16 | 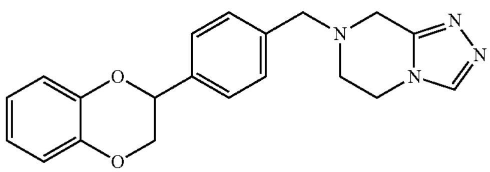 [SMILES: c1ccc2c(c1)OCC(c1ccc(CN3CCn4cnnc4C3)cc1)O2] | 7-[4-(2,3-dihydro-1,4-benzodioxin-2-yl)benzyl]-5,6,7,8-tetrahydro[1,2,4,]triazolo[4,3-a]pyrazine |
| 17 | 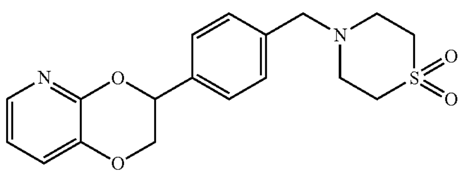 [SMILES: O=S1(=O)CCN(Cc2ccc(C3COc4cccnc4O3)cc2)CC1] | 3-{4-[(1,1-dioxidothiomorpholin-4-yl)methyl]phenyl}-2,3-dihydro[1,4]dioxino[2,3-b]pyridine |
| 18 | 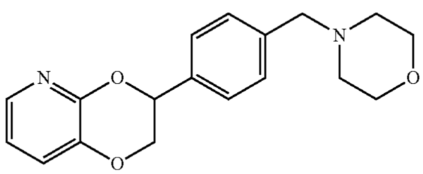 [SMILES: c1cnc2c(c1)OCC(c1ccc(CN3CCOCC3)cc1)O2] | 3-[4-(morpholin-4-ylmethyl)phenyl]-2,3-dihydro[1,4]dioxino[2,3-b]pyridine |
| 19 | 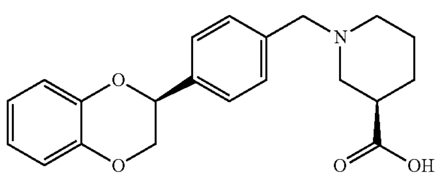 [SMILES: O=C(O)[C@@H]1CCCN(Cc2ccc([C@H]3COc4ccccc4O3)cc2)C1] | (3R)-1-{4-[(2S)-2,3-dihydro-1,4-benzodioxin-2-yl]benzyl}piperidine-3-carboxylic acid |
| 20 | 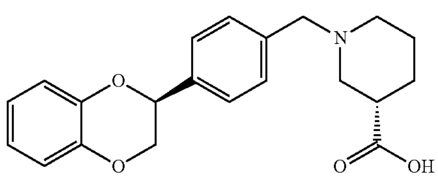 [SMILES: O=C(O)[C@H]1CCCN(Cc2ccc([C@H]3COc4ccccc4O3)cc2)C1] | (3S)-1-{4-[(2S)-2,3-dihydro-1,4-benzodioxin-2-yl]benzyl}piperidine-3-carboxylic acid |
| 21 | 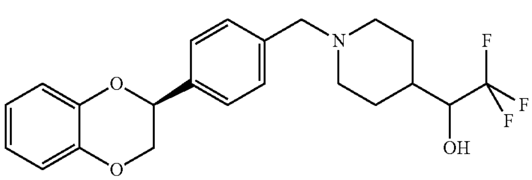 [SMILES: OC(C1CCN(Cc2ccc([C@H]3COc4ccccc4O3)cc2)CC1)C(F)(F)F] | 1-(1-{4-[(2S)-2,3-dihydro-1,4-benzodioxin-2-yl]benzyl}piperidin-4-yl)-2,2,2-trifluoroethanol |
| 22 | 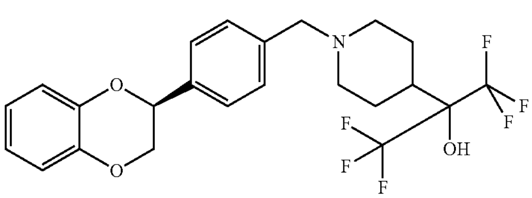 [SMILES: OC(C1CCN(Cc2ccc([C@H]3COc4ccccc4O3)cc2)CC1)(C(F)(F)F)C(F)(F)F] | 2-(1-{4-[(2S)-2,3-dihydro-1,4-benzodioxin-2-yl]benzyl}piperidin-4-yl)-1,1,1,3,3,3-hexafluoropropan-2-ol |
| 23 | 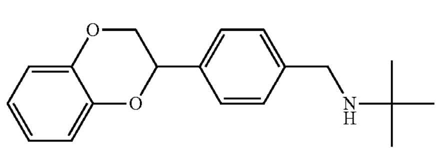 [SMILES: CC(C)(C)NCc1ccc(C2COc3ccccc3O2)cc1] | N-[4-(2,3-dihydro-1,4-benzodioxin-2-yl)benzyl]-2-methylpropan-2-amine |

TABLE 1-continued

Exemplary compounds of the invention.

| Compound No. | Structure | Name |
|---|---|---|
| 24 | 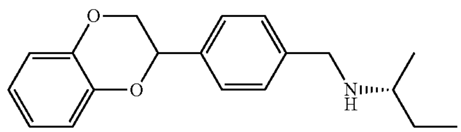 | (2R)-N-[4-(2,3-dihydro-1,4-benzodioxin-2-yl)benzyl]butan-2-amine |
| 25 | 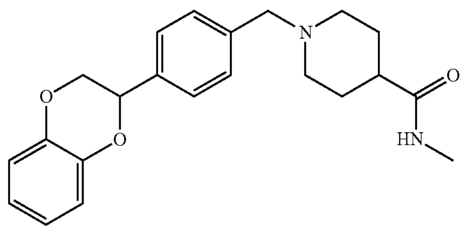 [SMILES: CNC(=O)C1CCN(Cc2ccc(C3COc4ccccc4O3)cc2)CC1] | 1-[4-(2,3-dihydro-1,4-benzodioxin-2-yl)benzyl]-N-methylpiperidine-4-carboxamide |
| 26 | 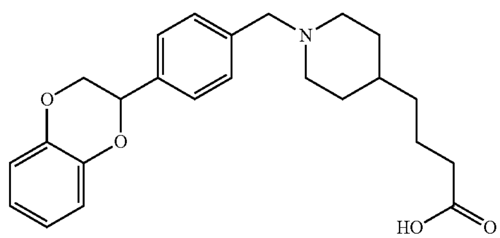 [SMILES: O=C(O)CCCC1CCN(Cc2ccc(C3COc4ccccc4O3)cc2)CC1] | 4-{1-[4-(2,3-dihydro-1,4-benzodioxin-2-yl)benzyl]piperidin-4-yl}butanoic acid |
| 27 | 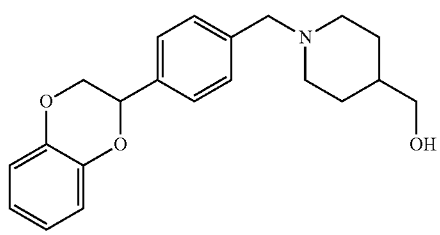 | {1-[4-(2,3-dihydro-1,4-benzodioxin-2-yl)benzyl]piperidin-4-yl}methanol |
| 28 | 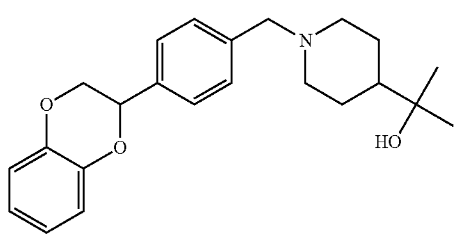 [SMILES: CC(C)(O)C1CCN(Cc2ccc(C3COc4ccccc4O3)cc2)CC1] | 2-{1-[4-(2,3-dihydro-1,4-benzodioxin-2-yl)benzyl]piperidin-4-yl}propan-2-ol |
| 29 | 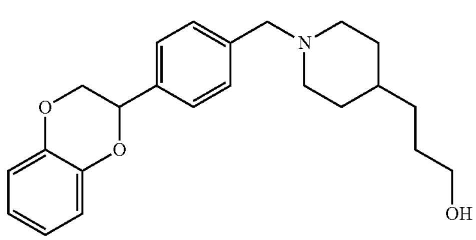 [SMILES: OCCCC1CCN(Cc2ccc(C3COc4ccccc4O3)cc2)CC1] | 3-{1-[4-(2,3-dihydro-1,4-benzodioxin-2-yl)benzyl]piperidin-4-yl}propan-1-ol |

TABLE 1-continued

Exemplary compounds of the invention.

| Compound No. | Structure | Name |
|---|---|---|
| 30 | 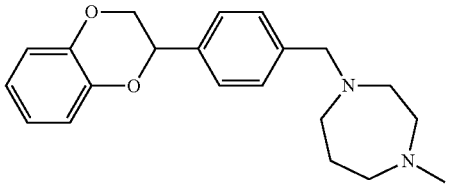 [SMILES: CN1CCCN(Cc2ccc(C3COc4ccccc4O3)cc2)CC1] | 1-[4-(2,3-dihydro-1,4-benzodioxin-2-yl)benzyl]-4-methyl-1,4-diazepane |
| 31 | 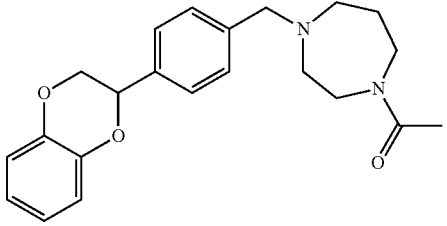 [SMILES: CC(=O)N1CCCN(Cc2ccc(C3COc4ccccc4O3)cc2)CC1] | 1-{4-[4-(2,3-dihydro-1,4-benzodioxin-2-yl)benzyl]-1,4-diazepan-1-yl}ethanone |
| 32 | 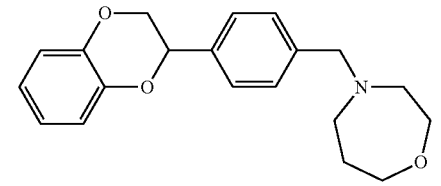 [SMILES: c1ccc2c(c1)OCC(c1ccc(CN3CCCOCC3)cc1)O2] | 4-[4-(2,3-dihydro-1,4-benzodioxin-2-yl)benzyl]-1,4-oxazepane |
| 33 | 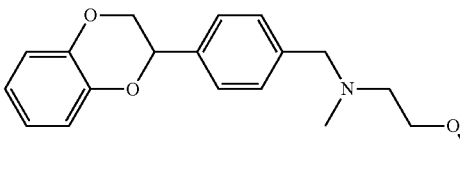 | N-[4-(2,3-dihydro-1,4-benzodioxin-2-yl)benzyl]-2-methoxy-N-methylethanamine |
| 34 | 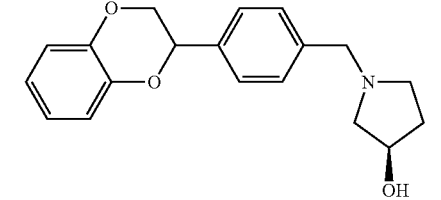 [SMILES: O[C@@H]1CCN(Cc2ccc(C3COc4ccccc4O3)cc2)C1] | (3R)-1-[4-(2,3-dihydro-1,4-benzodioxin-2-yl)benzyl]pyrrolidin-3-ol |
| 35 | 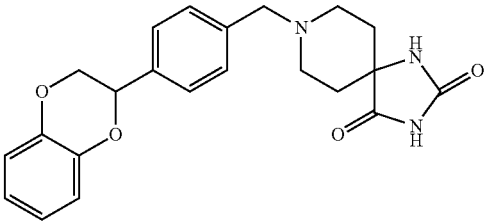 [SMILES: O=C1NC(=O)C2(CCN(Cc3ccc(C4COc5ccccc5O4)cc3)CC2)N1] | 8-[4-(2,3-dihydro-1,4-benzodioxin-2-yl)benzyl]-1,3,8-triazaspiro[4.5]decane-2,4-dione |
| 36 | 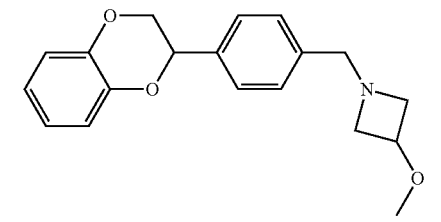 [SMILES: COC1CN(Cc2ccc(C3COc4ccccc4O3)cc2)C1] | 1-[4-(2,3-dihydro-1,4-benzodioxin-2-yl)benzyl]-3-methoxyazetidine |

TABLE 1-continued

Exemplary compounds of the invention.

| Compound No. | Structure | Name |
|---|---|---|
| 37 | 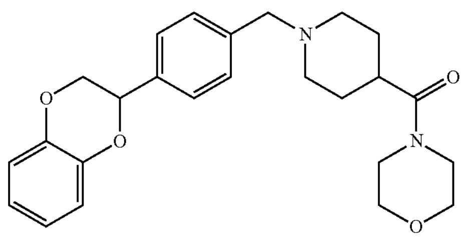 [SMILES: O=C(C1CCN(Cc2ccc(C3COc4ccccc4O3)cc2)CC1)N1CCOCC1] | {1-[4-(2,3-dihydro-1,4-benzodioxin-2-yl)benzyl]piperidin-4-yl}(morpholin-4-yl)methanone |
| 38 | 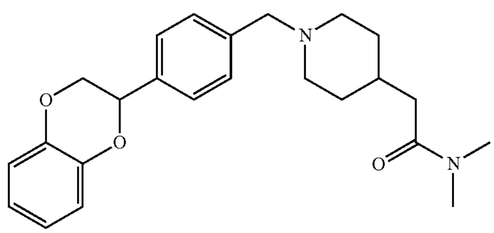 [SMILES: CN(C)C(=O)CC1CCN(Cc2ccc(C3COc4ccccc4O3)cc2)CC1] | 2-{1-[4-(2,3-dihydro-1,4-benzodioxin-2-yl)benzyl]piperidin-4-yl}-N,N-dimethylacetamide |
| 39 | 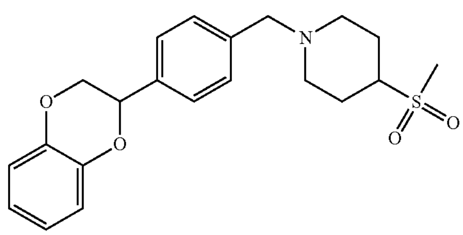 [SMILES: CS(=O)(=O)C1CCN(Cc2ccc(C3COc4ccccc4O3)cc2)CC1] | 1-[4-(2,3-dihydro-1,4-benzodioxin-2-yl)benzyl]-4-(methylsulfonyl)piperidine |
| 40 | 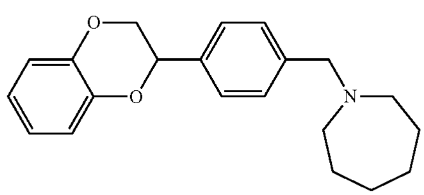 [SMILES: c1ccc2c(c1)OCC(c1ccc(CN3CCCCCC3)cc1)O2] | 1-[4-(2,3-dihydro-1,4-benzodioxin-2-yl)benzyl]azepane |
| 41 | 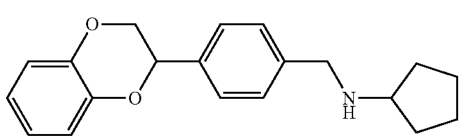 [SMILES: c1ccc2c(c1)OCC(c1ccc(CNC3CCCC3)cc1)O2] | N-[4-(2,3-dihydro-1,4-benzodioxin-2-yl)benzyl]cyclopentanamine |
| 42 | 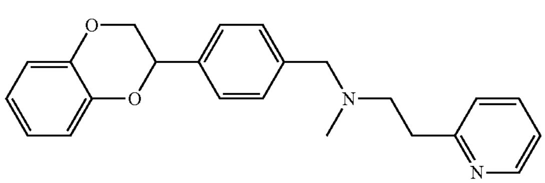 | N-[4-(2,3-dihydro-1,4-benzodioxin-2-yl)benzyl]-N-methyl-2-(pyridin-2-yl)ethanamine |
| 43 | 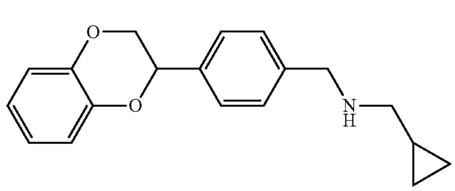 [SMILES: c1ccc2c(c1)OCC(c1ccc(CNCC3CC3)cc1)O2] | 1-cyclopropyl-N-[4-(2,3-dihydro-1,4-benzodioxin-2-yl)benzyl]methanamine |

TABLE 1-continued

Exemplary compounds of the invention.

| Compound No. | Structure | Name |
|---|---|---|
| 44 | 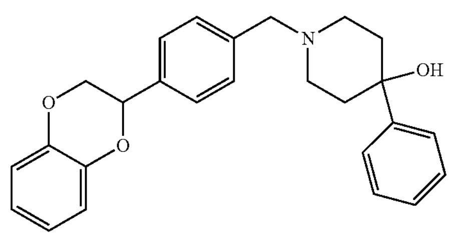 [SMILES: OC1(c2ccccc2)CCN(Cc2ccc(C3COc4ccccc4O3)cc2)CC1] | 1-[4-(2,3-dihydro-1,4-benzodioxin-2-yl)benzyl]-4-phenylpiperidin-4-ol |
| 45 | 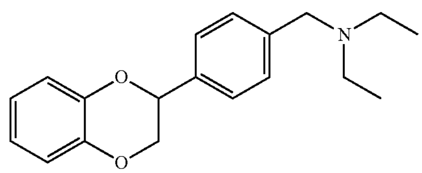 [SMILES: CCN(CC)Cc1ccc(C2COc3ccccc3O2)cc1] | N-[4-(2,3-dihydro-1,4-benzodioxin-2-yl)benzyl]-N-ethylethanamine |
| 46 | 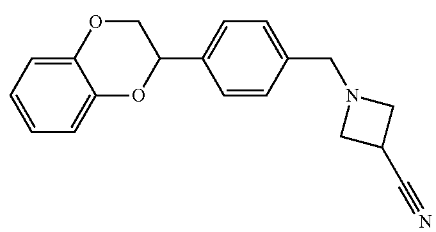 [SMILES: N#CC1CN(Cc2ccc(C3COc4ccccc4O3)cc2)C1] | 1-[4-(2,3-dihydro-1,4-benzodioxin-2-yl)benzyl]azetidine-3-carbonitrile |
| 47 | 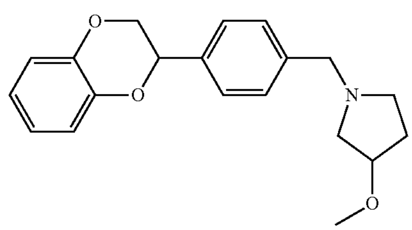 [SMILES: COC1CCN(Cc2ccc(C3COc4ccccc4O3)cc2)C1] | 1-[4-(2,3-dihydro-1,4-benzodioxin-2-yl)benzyl]-3-methoxypyrrolidine |
| 48 | 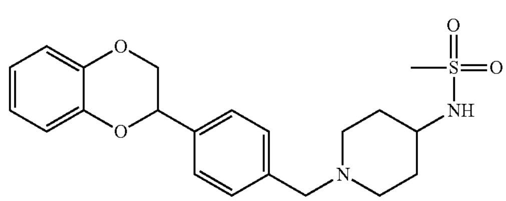 [SMILES: CS(=O)(=O)NC1CCN(Cc2ccc(C3COc4ccccc4O3)cc2)CC1] | N-{1-[4-(2,3-dihydro-1,4-benzodioxin-2-yl)benzyl]piperidin-4-yl}methanesulfonamide |
| 49 | 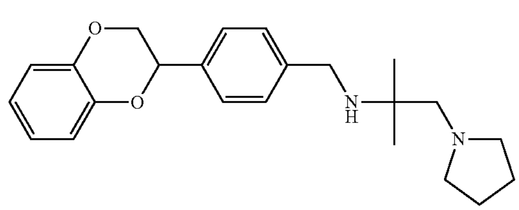 [SMILES: CC(C)(CN1CCCC1)NCc1ccc(C2COc3ccccc3O2)cc1] | N-[4-(2,3-dihydro-1,4-benzodioxin-2-yl)benzyl]-2-methyl-1-(pyrrolidin-1-yl)propan-2-amine |

TABLE 1-continued

Exemplary compounds of the invention.

| Compound No. | Structure | Name |
|---|---|---|
| 50 | 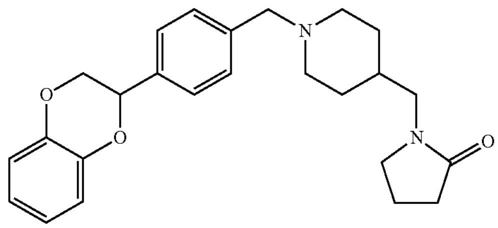 [SMILES: O=C1CCCN1CC1CCN(Cc2ccc(C3COc4ccccc4O3)cc2)CC1] | 1-({1-[4-(2,3-dihydro-1,4-benzodioxin-2-yl)benzyl]piperidin-4-yl}methyl)pyrrolidin-2-one |
| 51 | 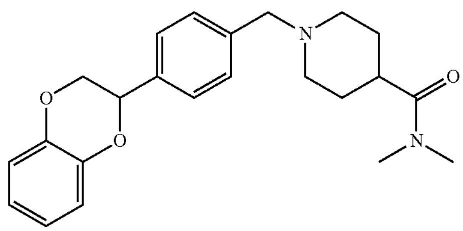 [SMILES: CN(C)C(=O)C1CCN(Cc2ccc(C3COc4ccccc4O3)cc2)CC1] | 1-[4-(2,3-dihydro-1,4-benzodioxin-2-yl)benzyl]-N,N-dimethylpiperidine-4-carboxamide |
| 52 | 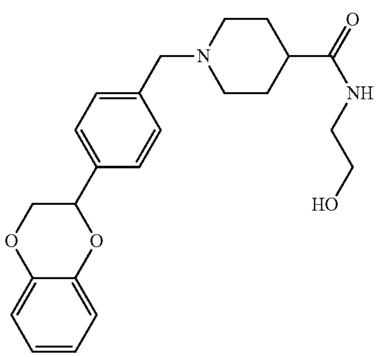 [SMILES: O=C(NCCO)C1CCN(Cc2ccc(C3COc4ccccc4O3)cc2)CC1] | 1-[4-(2,3-dihydro-1,4-benzodioxin-2-yl)benzyl]-N-(2-hydroxyethyl)piperidine-4-carboxamide |
| 53 | 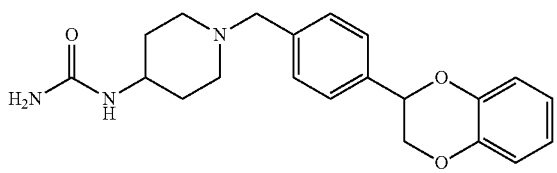 [SMILES: NC(=O)NC1CCN(Cc2ccc(C3COc4ccccc4O3)cc2)CC1] | 1-{1-[4-(2,3-dihydro-1,4-benzodioxin-2-yl)benzyl]piperidin-4-yl}urea |
| 54 | 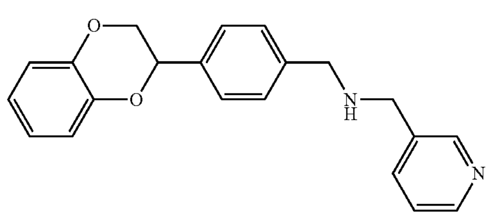 [SMILES: c1cncc(CNCc2ccc(C3COc4ccccc4O3)cc2)c1] | 1-[4-(2,3-dihydro-1,4-benzodioxin-2-yl)phenyl]-N-(pyridin-3-ylmethyl)methanamine |
| 55 | 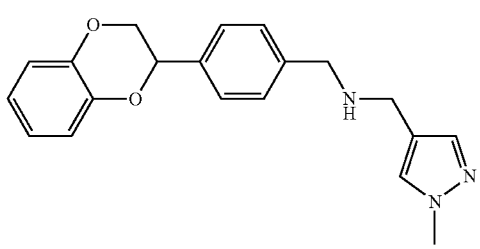 [SMILES: Cn1cc(CNCc2ccc(C3COc4ccccc4O3)cc2)cn1] | 1-[4-(2,3-dihydro-1,4-benzodioxin-2-yl)phenyl]-N-[(1-methyl-1H-imidazol-4-yl)methyl]methanamine |

TABLE 1-continued

Exemplary compounds of the invention.

| Compound No. | Structure | Name |
|---|---|---|
| 56 | 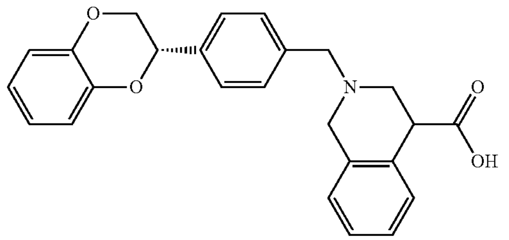 [SMILES: O=C(O)C1CN(Cc2ccc([C@H]3COc4ccccc4O3)cc2)Cc2ccccc21] | 2-{4-[(2S)-2,3-dihydro-1,4-benzodioxin-2-yl]benzyl}-1,2,3,4-tetrahydroisoquinoline-4-carboxylic acid |
| 57 | 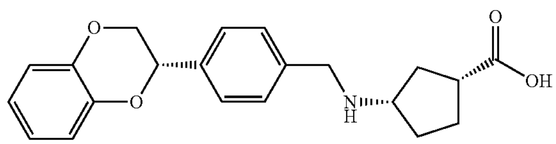 [SMILES: O=C(O)[C@@H]1CC[C@H](NCc2ccc([C@H]3COc4ccccc4O3)cc2)C1] | (1R,3S)-3-({4-[(2S)-2,3-dihydro-1,4-benzodioxin-2-yl]benzyl}amino)cyclopentanecarboxylic acid |
| 58 | 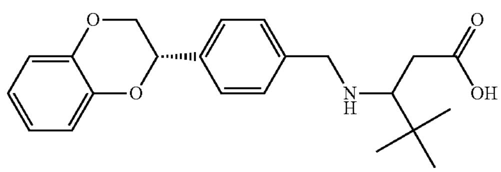 [SMILES: CC(C)(C)C(CC(=O)O)NCc1ccc([C@H]2COc3ccccc3O2)cc1] | 3-({4-[(2S)-2,3-dihydro-1,4-benzodioxin-2-yl]benzyl}amino)-4,4-dimethylpentanoic acid |
| 59 | 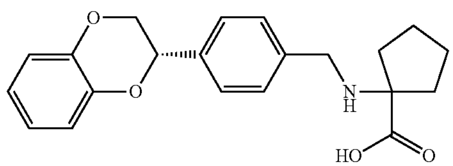 [SMILES: O=C(O)C1(NCc2ccc([C@H]3COc4ccccc4O3)cc2)CCCC1] | 1-({4-[(2S)-2,3-dihydro-1,4-benzodioxin-2-yl]benzyl}amino)cyclopentanecarboxylic acid |
| 60 | 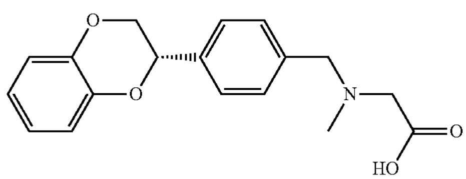 [SMILES: CN(CC(=O)O)Cc1ccc([C@H]2COc3ccccc3O2)cc1] | N-{4-[(2S)-2,3-dihydro-1,4-benzodioxin-2-yl]benzyl}-N-methylglycine |
| 61 | 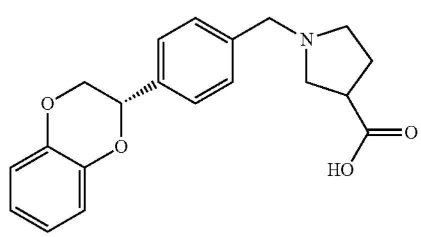 [SMILES: O=C(O)C1CCN(Cc2ccc([C@H]3COc4ccccc4O3)cc2)C1] | 1-{4-[(2S)-2,3-dihydro-1,4-benzodioxin-2-yl]benzyl}pyrrolidine-3-carboxylic acid |
| 62 | 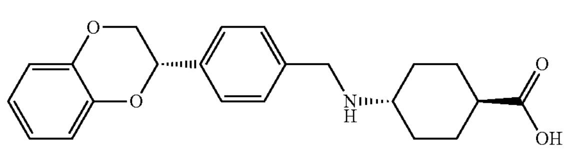 [SMILES: O=C(O)[C@H]1CC[C@H](NCc2ccc([C@H]3COc4ccccc4O3)cc2)CC1] | trans-4-({4-[(2S)-2,3-dihydro-1,4-benzodioxin-2-yl]benzyl}amino)cyclohexanecarboxylic acid |
| 63 | 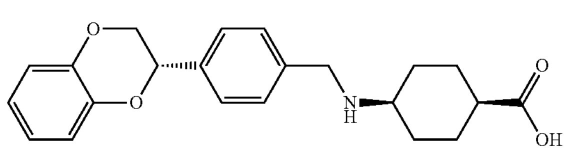 [SMILES: O=C(O)[C@H]1CC[C@@H](NCc2ccc([C@H]3COc4ccccc4O3)cc2)CC1] | cis-4-({4-[(2S)-2,3-dihydro-1,4-benzodioxin-2-yl]benzyl}amino)cyclohexanecarboxylic acid |

TABLE 1-continued

Exemplary compounds of the invention.

| Compound No. | Structure | Name |
|---|---|---|
| 64 | 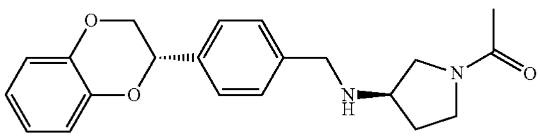 [SMILES: CC(=O)N1CC[C@@H](NCc2ccc([C@H]3COc4ccccc4O3)cc2)C1] | 1-[(3R)-3-({4-[(2S)-2,3-dihydro-1,4-benzodioxin-2-yl]benzyl}amino)pyrrolidin-1-yl]ethanone |
| 65 | 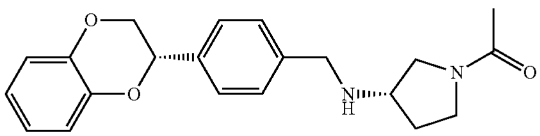 [SMILES: CC(=O)N1CC[C@H](NCc2ccc([C@H]3COc4ccccc4O3)cc2)C1] | 1-[(3S)-3-({4-[(2S)-2,3-dihydro-1,4-benzodioxin-2-yl]benzyl}amino)pyrrolidin-1-yl]ethanone |
| 66 | 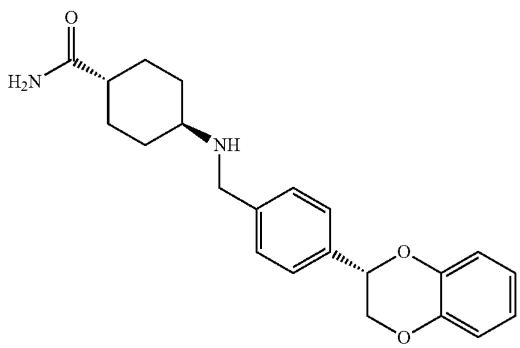 [SMILES: NC(=O)[C@H]1CC[C@H](NCc2ccc([C@H]3COc4ccccc4O3)cc2)CC1] | trans-4-({4-[(2S)-2,3-dihydro-1,4-benzodioxin-2-yl]benzyl}amino)cyclohexanecarboxamide |
| 67 | 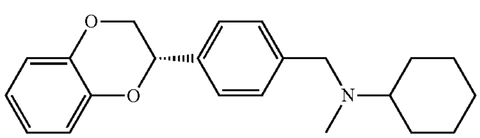 [SMILES: CN(Cc1ccc([C@H]2COc3ccccc3O2)cc1)C1CCCCC1] | N-{4-[(2S)-2,3-dihydro-1,4-benzodioxin-2-yl]benzyl}-N-methylcyclohexanamine |
| 68 | 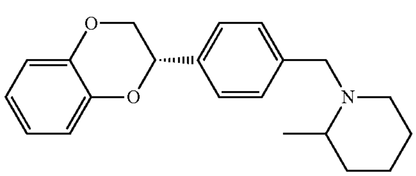 [SMILES: CC1CCCCN1Cc1ccc([C@H]2COc3ccccc3O2)cc1] | 1-{4-[(2S)-2,3-dihydro-1,4-benzodioxin-2-yl]benzyl}-2-methylpiperidine |
| 69 | 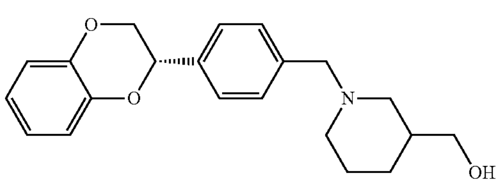 [SMILES: OCC1CCCN(Cc2ccc([C@H]3COc4ccccc4O3)cc2)C1] | (1-{4-[(2S)-2,3-dihydro-1,4-benzodioxin-2-yl]benzyl}piperidin-3-yl)methanol |
| 70 | 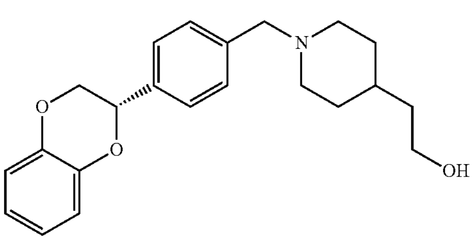 [SMILES: OCCC1CCN(Cc2ccc([C@H]3COc4ccccc4O3)cc2)CC1] | 2-(1-{4-[(2S)-2,3-dihydro-1,4-benzodioxin-2-yl]benzyl}piperidin-4-yl)ethanol |

TABLE 1-continued

Exemplary compounds of the invention.

| Compound No. | Structure | Name |
|---|---|---|
| 71 | 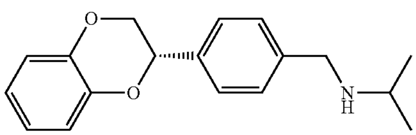 [SMILES: CC(C)NCc1ccc([C@H]2COc3ccccc3O2)cc1] | N-{4-[(2S)-2,3-dihydro-1,4-benzodioxin-2-yl]benzyl}propan-2-amine |
| 72 | 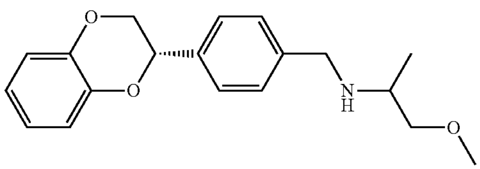 [SMILES: COCC(C)NCc1ccc([C@H]2COc3ccccc3O2)cc1] | N-{4-[(2S)-2,3-dihydro-1,4-benzodioxin-2-yl]benzyl}-1-methoxypropan-2-amine |
| 73 | 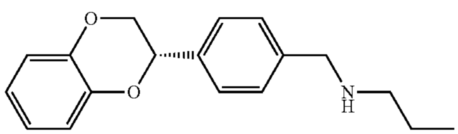 [SMILES: CCCNCc1ccc([C@H]2COc3ccccc3O2)cc1] | N-{4-[(2S)-2,3-dihydro-1,4-benzodioxin-2-yl]benzyl}propan-1-amine |
| 74 | 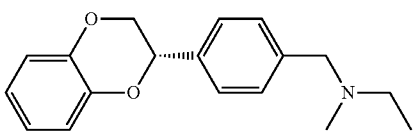 [SMILES: CCN(C)Cc1ccc([C@H]2COc3ccccc3O2)cc1] | N-{4-[(2S)-2,3-dihydro-1,4-benzodioixn-2-yl]benzyl)-N-methylethanamine |
| 75 | 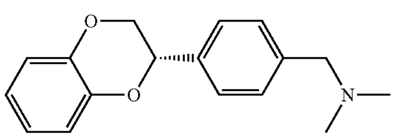 [SMILES: CN(C)Cc1ccc([C@H]2COc3ccccc3O2)cc1] | 1-{4-[(2S)-2,3-dihydro-1,4-benzodioxin-2-yl]phenyl}-N,N-dimethylmethanamine |
| 76 | 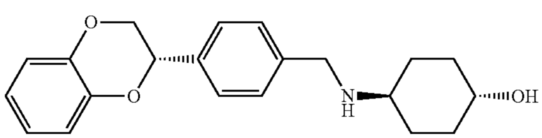 [SMILES: O[C@H]1CC[C@H](NCc2ccc([C@H]3COc4ccccc4O3)cc2)CC1] | trans-4-({4-[(2S)-2,3-dihydro-1,4-benzodioxin-2-yl]benzyl}amino)cyclohexan-ol |
| 77 | 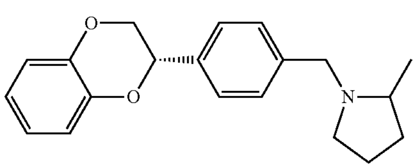 [SMILES: CC1CCCN1Cc1ccc([C@H]2COc3ccccc3O2)cc1] | 1-{4-[(2S)-2,3-dihydro-1,4-benzodioxin-2-yl]benzyl}-2-methylpyrrolidine |
| 78 | 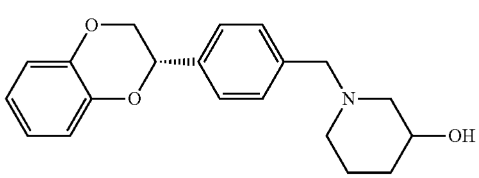 [SMILES: OC1CCCN(Cc2ccc([C@H]3COc4ccccc4O3)cc2)C1] | 1-{4-[(2S)-2,3-dihydro-1,4-benzodioxin-2-yl]benzyl}piperidin-3-ol |
| 79 | 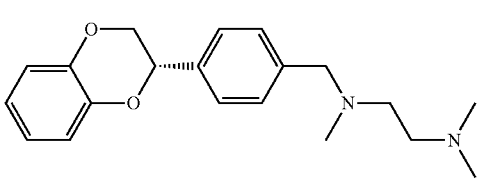 | N-{4-[(2S)-2,3-dihydro-1,4-benzodioxin-2-yl]benzyl}-N,N',N'-trimethylethane-1,2-diamine |

TABLE 1-continued

Exemplary compounds of the invention.

| Compound No. | Structure | Name |
|---|---|---|
| 80 | 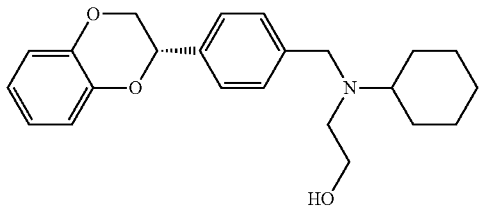 [SMILES: OCCN(Cc1ccc([C@H]2COc3ccccc3O2)cc1)C1CCCCC1] | 2-(cyclohexyl{4-[(2S)-2,3-dihydro-1,4-benzodioxin-2-yl]benzyl}amino)ethanol |
| 81 | 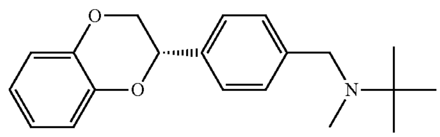 [SMILES: CN(Cc1ccc([C@H]2COc3ccccc3O2)cc1)C(C)(C)C] | N-{4-[(2S)-2,3-dihydro-1,4-benzodioxin-2-yl]benzyl}-N,2-dimethylpropan-2-amine |
| 82 | 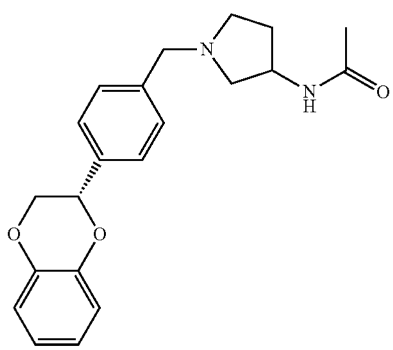 [SMILES: CC(=O)NC1CCN(Cc2ccc([C@H]3COc4ccccc4O3)cc2)C1] | N-(1-{4-[(2S)-2,3-dihydro-1,4-benzodioxin-2-yl]benzyl}pyrrolidin-3-yl)acetamide |
| 83 | 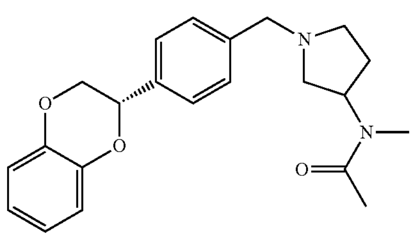 [SMILES: CC(=O)N(C)C1CCN(Cc2ccc([C@H]3COc4ccccc4O3)cc2)C1] | N-(1-{4-[(2S)-2,3-dihydro-1,4-benzodioxin-2-yl]benzyl}pyrrolidin-3-yl)-N-methylacetamide |
| 84 | 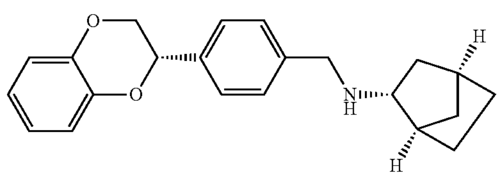 [SMILES: c1ccc2c(c1)OC[C@H](c1ccc(CN[C@@H]3C[C@H]4CC[C@@H]3C4)cc1)O2] | (1R,2R,4S)-N-{4-[(2S)-2,3-dihydro-1,4-benzodioxin-2-yl]benzyl}bicyclo[2.2.1]heptan-2-amine |
| 85 | 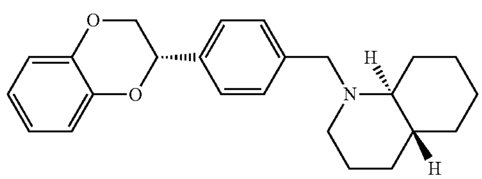 [SMILES: c1ccc2c(c1)OC[C@H](c1ccc(CN3CCC[C@H]4CCCC[C@@H]43)cc1)O2] | (4aR,8aS)-1-{4-[(2S)-2,3-dihydro-1,4-benzodioxin-2-yl]benzyl}decahydroquinoline |
| 86 | 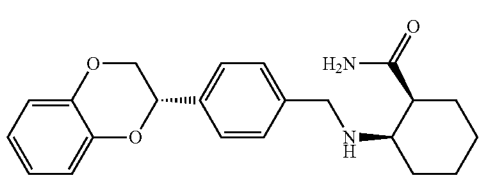 [SMILES: NC(=O)[C@H]1CCCC[C@H]1NCc1ccc([C@H]2COc3ccccc3O2)cc1] | (1S,2R)-2-({4-[(2S)-2,3-dihydro-1,4-benzodioxin-2-yl]benzyl}amino)cyclohexanecarboxamide |

TABLE 1-continued

Exemplary compounds of the invention.

| Compound No. | Structure | Name |
| --- | --- | --- |
| 87 | 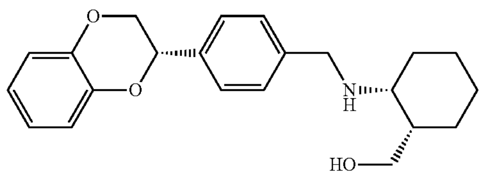 [SMILES: OC[C@H]1CCCC[C@H]1NCc1ccc([C@H]2COc3ccccc3O2)cc1] | [(1S,2R)-2-({4-[(2S)-2,3-dihydro-1,4-benzodioxin-2-yl]benzyl}amino)cyclohexyl]methanol |
| 88 | 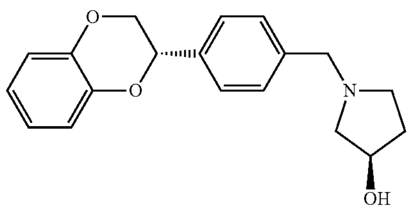 [SMILES: O[C@@H]1CCN(Cc2ccc([C@H]3COc4ccccc4O3)cc2)C1] | (3R)-1-{4-[(2S)-2,3-dihydro-1,4-benzodioxin-2-yl]benzyl}pyrrolidin-3-ol |
| 89 | 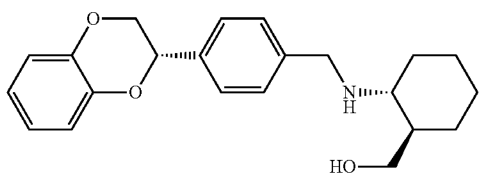 [SMILES: OC[C@@H]1CCCC[C@H]1NCc1ccc([C@H]2COc3ccccc3O2)cc1] | [(1R,2R)-2-({4-[(2S)-2,3-dihydro-1,4-benzodioxin-2-yl]benzyl}amino)cylcohexyl]methanol |
| 90 | 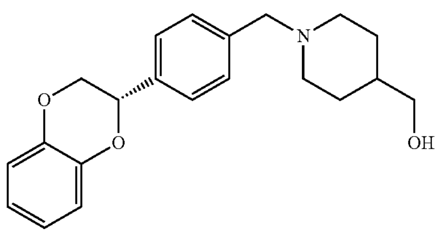 [SMILES: OCC1CCN(Cc2ccc([C@H]3COc4ccccc4O3)cc2)CC1] | (1-{4-[(2S)-2,3-dihydro-1,4-benzodioxin-2-yl]benzyl}piperidin-4-yl)methanol |
| 91 | 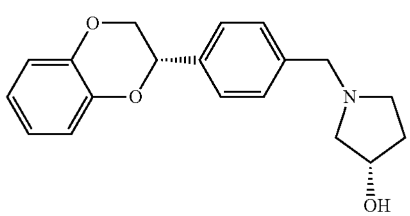 [SMILES: O[C@H]1CCN(Cc2ccc([C@H]3COc4ccccc4O3)cc2)C1] | (3S)-1-{4-[(2S)-2,3-dihydro-1,4-benzodioxin-2-yl]benzyl}pyrrolidin-3-ol |
| 92 | 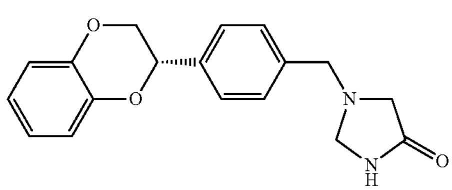 [SMILES: O=C1CN(Cc2ccc([C@H]3COc4ccccc4O3)cc2)CN1] | 1-{4-[(2S)-2,3-dihydro-1,4-benzodioxin-2-yl]benzyl}imidazolidin-4-one |
| 93 | 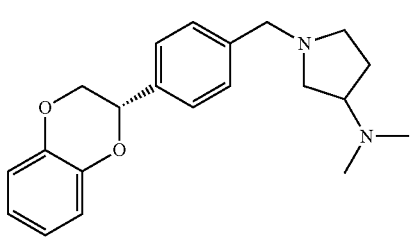 [SMILES: CN(C)C1CCN(Cc2ccc([C@H]3COc4ccccc4O3)cc2)C1] | 1-{4-[(2S)-2,3-dihydro-1,4-benzodioxoin-2-yl]benzyl}-N,N-dimethylpyrrolidin-3-amine |

TABLE 1-continued

Exemplary compounds of the invention.

| Compound No. | Structure | Name |
|---|---|---|
| 94 | 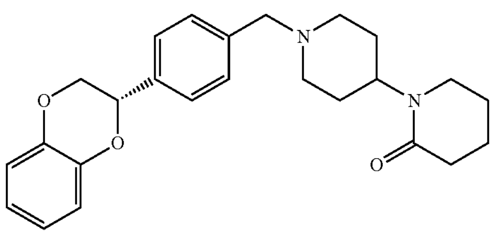 [SMILES: O=C1CCCCN1C1CCN(Cc2ccc([C@H]3COc4ccccc4O3)cc2)CC1] | 1'-{4-[(2S)-2,3-dihydro-1,4-benzodioxin-2-yl]benzyl}-1,4'-bipiperidin-2-one |
| 95 | 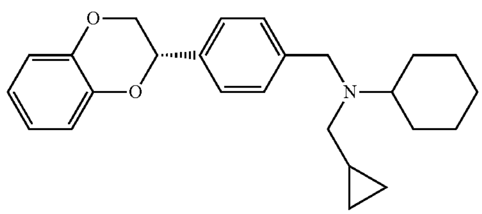 [SMILES: c1ccc2c(c1)OC[C@H](c1ccc(CN(CC3CC3)C3CCCCC3)cc1)O2] | N-(cyclopropylmethyl)-N-{4-[(2S)-2,3-dihydro-1,4-benzodioxin-2-yl]benzyl}cyclohexanamine |
| 96 | 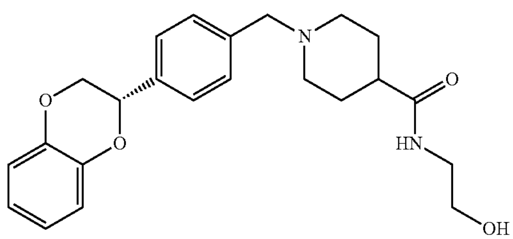 [SMILES: O=C(NCCO)C1CCN(Cc2ccc([C@H]3COc4ccccc4O3)cc2)CC1] | 1-{4-[(2S)-2,3-dihydro-1,4-benzodioxin-2-yl]benzyl}-N-(2-hydroxyethyl)piperidine-4-carboxamide |
| 97 | 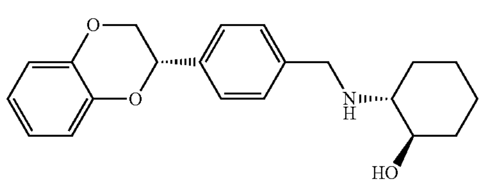 [SMILES: O[C@@H]1CCCC[C@H]1NCc1ccc([C@H]2COc3ccccc3O2)cc1] | (1R,2R)-2-({4-[(2S)-2,3-dihydro-1,4-benzodioxin-2-yl]benzyl}amino)cylcohexan-ol |
| 98 | 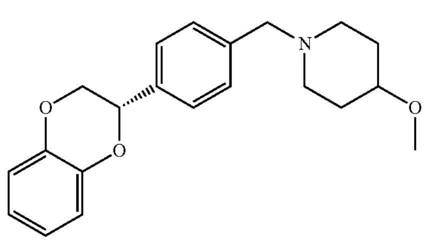 [SMILES: COC1CCN(Cc2ccc([C@H]3COc4ccccc4O3)cc2)CC1] | 1-{4-[(2S)-2,3-dihydro-1,4-benzodioxin-2-yl]benzyl}-4-methoxypiperidine |
| 99 | 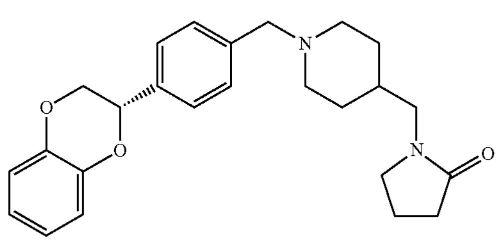 [SMILES: O=C1CCCN1CC1CCN(Cc2ccc([C@H]3COc4ccccc4O3)cc2)CC1] | 1-[(1-{4-[(2S)-2,3-dihydro-1,4-benzodioxin-2-yl]benzyl}piperidin-4-yl)methyl]pyrrolidin-2-one |

TABLE 1-continued

Exemplary compounds of the invention.

| Compound No. | Structure | Name |
|---|---|---|
| 100 | 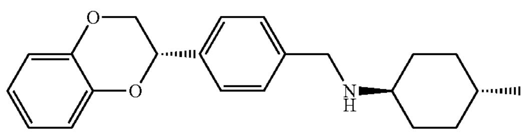 [SMILES: C[C@H]1CC[C@H](NCc2ccc([C@H]3COc4ccccc4O3)cc2)CC1] | trans-N-{4-[(2S)-2,3-dihydro-1,4-benzodioxin-2-yl]benzyl}-4-methylcyclohexanamine |
| 101 | 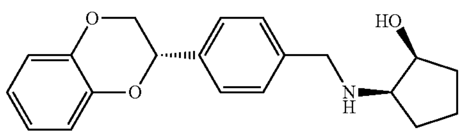 [SMILES: O[C@H]1CCC[C@H]1NCc1ccc([C@H]2COc3ccccc3O2)cc1] | (1S,2R)-2-({4-[(2S)-2,3-dihydro-1,4-benzodioxin-2-yl]benzyl}amino)cyclopentanol |
| 102 | 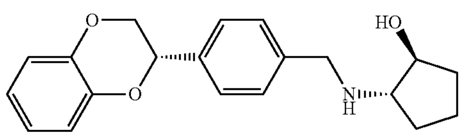 [SMILES: O[C@H]1CCC[C@@H]1NCc1ccc([C@H]2COc3ccccc3O2)cc1] | (1S,2S)-2-({4-[(2S)-2,3-dihydro-1,4-benzodioxin-2-yl]benzyl}amino)cyclopentanol |
| 103 | 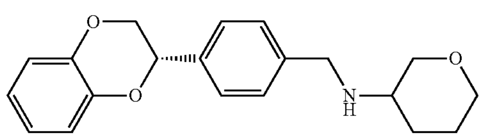 [SMILES: c1ccc2c(c1)OC[C@H](c1ccc(CNC3CCCOC3)cc1)O2] | N-{4-[(2S)-2,3-dihydro-1,4-benzodioxin-2-yl]benzyl}tetrahydro-2H-pyran-3-amine |
| 104 | 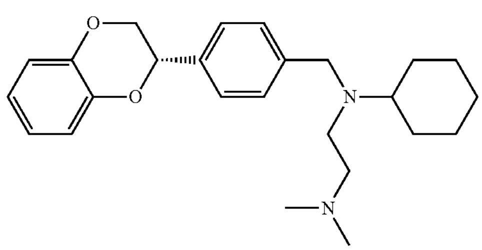 [SMILES: CN(C)CCN(Cc1ccc([C@H]2COc3ccccc3O2)cc1)C1CCCCC1] | N-cyclohexyl-N-{4-[(2S)-2,3-dihydro-1,4-benzodioxin-2-yl]benzyl}-N',N'-dimethylethane-1,2-diamine |
| 105 | 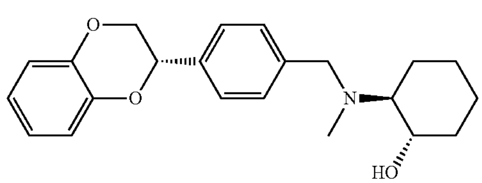 [SMILES: CN(Cc1ccc([C@H]2COc3ccccc3O2)cc1)[C@H]1CCCC[C@@H]1O] | (1S,2S)-2-[{4-[(2S)-2,3-dihydro-1,4-benzodioxin-2-yl]benzyl}(methyl)amino]cyclohexanol |
| 106 | 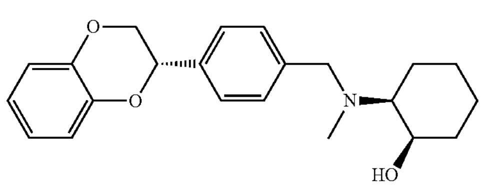 [SMILES: CN(Cc1ccc([C@H]2COc3ccccc3O2)cc1)[C@H]1CCCC[C@H]1O] | (1R,2S)-2-[{4-[(2S)-2,3-dihydro-1,4-benzodioxin-2-yl]benzyl}(methyl)amino]cyclohexanol |
| 107 | 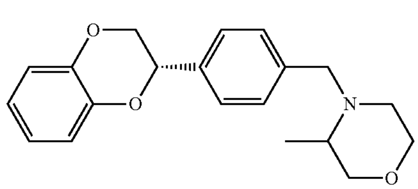 [SMILES: CC1COCCN1Cc1ccc([C@H]2COc3ccccc3O2)cc1] | 4-{4-[(2S)-2,3-dihydro-1,4-benzodioxin-2-yl]benzyl}-3-methylmorpholine |

TABLE 1-continued

Exemplary compounds of the invention.

| Compound No. | Structure | Name |
| --- | --- | --- |
| 108 | 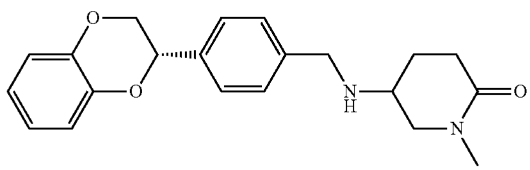 [SMILES: CN1CC(NCc2ccc([C@H]3COc4ccccc4O3)cc2)CCC1=O] | 5-({4-[(2S)-2,3-dihydro-1,4-benzodioxin-2-yl]benzyl}amino)-1-methylpiperidin-2-one |
| 109 | 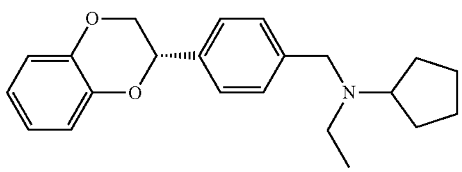 [SMILES: CCN(Cc1ccc([C@H]2COc3ccccc3O2)cc1)C1CCCC1] | N-{4-[(2S)-2,3-dihydro-1,4-benzodioxin-2-yl]benzyl}-N-ethylcyclopentanamine |
| 110 | 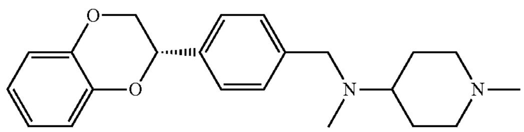 | N-{4-[(2S)-2,3-dihydro-1,4-benzodioxin-2-yl]benzyl}-N,1-dimethylpiperidin-4-amine |
| 111 | 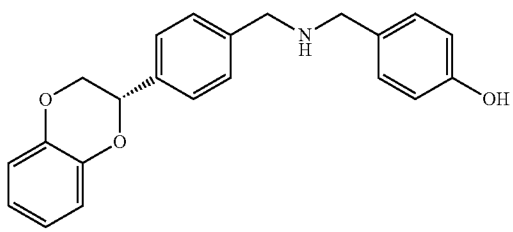 [SMILES: Oc1ccc(CNCc2ccc([C@H]3COc4ccccc4O3)cc2)cc1] | 4-[({4-[(2S)-2,3-dihydro-1,4-benzodioxin-2-yl]benzyl}amino)methyl]phenol |
| 112 | 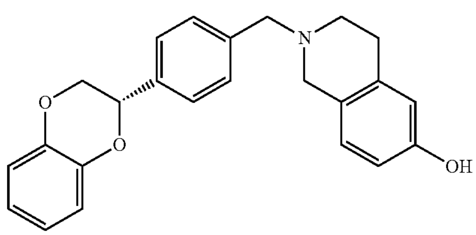 [SMILES: Oc1ccc2c(c1)CCN(Cc1ccc([C@H]3COc4ccccc4O3)cc1)C2] | 2-{4-[(2S)-2,3-dihydro-1,4-benzodioxin-2-yl]benzyl}-1,2,3,4-tetrahydroisoquinolin-6-ol |
| 113 | 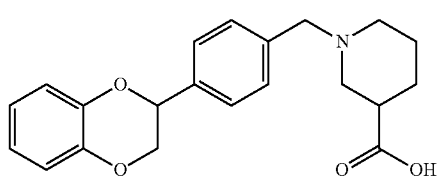 [SMILES: O=C(O)C1CCCN(Cc2ccc(C3COc4ccccc4O3)cc2)C1] | 1-[4-(2,3-dihydro-1,4-benzodioxin-2-yl)benzyl]piperidine-3-carboxylic acid |
| 114 | 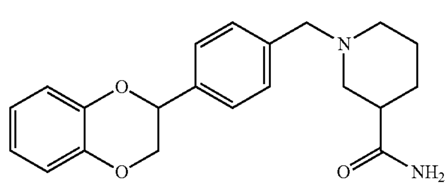 [SMILES: NC(=O)C1CCCN(Cc2ccc(C3COc4ccccc4O3)cc2)C1] | 1-{4-(2,3-dihydro-1,4-benzodioxin-2-yl)benzyl]piperidine-3-carboxamide |

TABLE 1-continued

Exemplary compounds of the invention.

| Compound No. | Structure | Name |
|---|---|---|
| 115 | 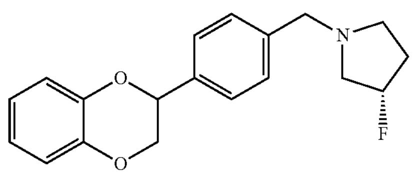 [SMILES: F[C@H]1CCN(Cc2ccc(C3COc4ccccc4O3)cc2)C1] | (3S)-1-[4-(2,3-dihydro-1,4-benzodioxin-2-yl)benzyl]-3-fluoropyrrolidine |
| 116 | 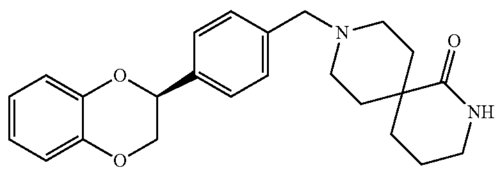 [SMILES: O=C1NCCCC12CCN(Cc1ccc([C@H]3COc4ccccc4O3)cc1)CC2] | 9-{4-[(2S)-2,3-dihydro-1,4-benzodioxin-2-yl]benzyl}-2,9-diazaspiro[5.5]undecan-1-one |
| 117 | 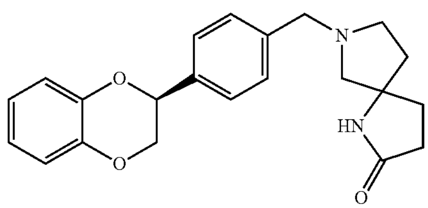 [SMILES: O=C1CCC2(CCN(Cc3ccc([C@H]4COc5ccccc5O4)cc3)C2)N1] | 7-{4-[(2S)-2,3-dihydro-1,4-benzodioxin-2-yl]benzyl}-1,7-diazaspiro[4.4]nonan-2-one |
| 118 | 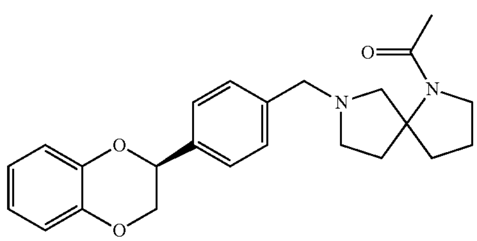 [SMILES: CC(=O)N1CCCC12CCN(Cc1ccc([C@H]3COc4ccccc4O3)cc1)C2] | 1-(7-{4-[(2S)-2,3-dihydro-1,4-benzodioxin-2-yl]benzyl}-1,7-diazaspiro[4.4]non-1-yl)ethanone |
| 119 | 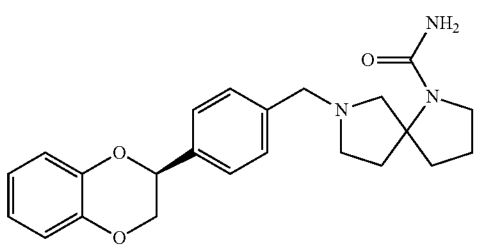 [SMILES: NC(=O)N1CCCC12CCN(Cc1ccc([C@H]3COc4ccccc4O3)cc1)C2] | 7-{4-[(2S)-2,3-dihydro-1,4-benzodioxin-2-yl]benzyl}-1,7-diazaspiro[4.4]nonane-1-carboxamide |
| 120 | 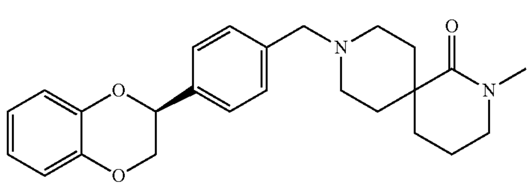 [SMILES: CN1CCCC2(CCN(Cc3ccc([C@H]4COc5ccccc5O4)cc3)CC2)C1=O] | 9-{4-[(2S)-2,3-dihydro-1,4-benzodioxin-2-yl]benzyl)-2-methyl-2,9-diazaspiro[5.5]undecan-1-one |
| 121 | 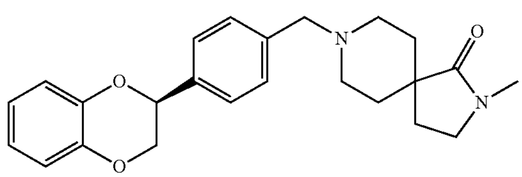 [SMILES: CN1CCC2(CCN(Cc3ccc([C@H]4COc5ccccc5O4)cc3)CC2)C1=O] | 8-{4-[(2S)-2,3-dihydro-1,4-benzodioxin-2-yl]benzyl}-2-methyl-2,8-diazaspiro[4.5]decan-1-one |

TABLE 1-continued

Exemplary compounds of the invention.

| Compound No. | Structure | Name |
|---|---|---|
| 122 | 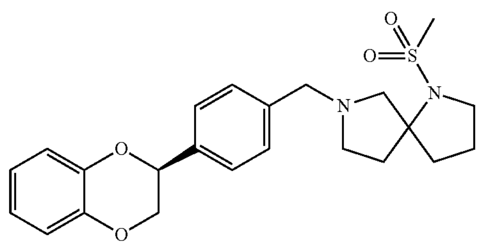 [SMILES: CS(=O)(=O)N1CCCC12CCN(Cc1ccc([C@H]3COc4ccccc4O3)cc1)C2] | 7-{4-[(2S)-2,3-dihydro-1,4-benzodioxin-2-yl]benzyl}-1-(methylsulfonyl)-1,7-diazaspiro[4.4]nonane |
| 123 | 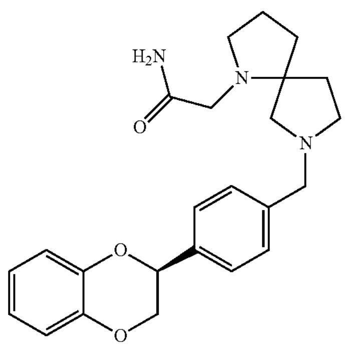 [SMILES: NC(=O)CN1CCCC12CCN(Cc1ccc([C@H]3COc4ccccc4O3)cc1)C2] | 2-(7-{4-[(2S)-2,3-dihydro-1,4-benzodioxin-2-yl]benzyl}-1,7-diazaspiro[4.4]non-1-yl)acetamide |
| 124 | 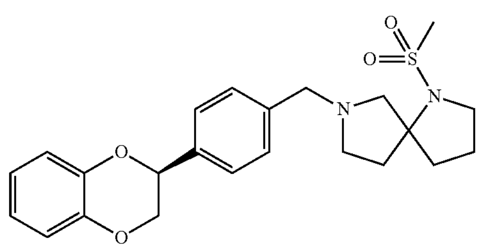 [SMILES: CS(=O)(=O)N1CCCC12CCN(Cc1ccc([C@H]3COc4ccccc4O3)cc1)C2] | (7-{4-[(2S)-2,3-dihydro-1,4-benzodioxin-2-yl]benzyl}-1,7-diazaspiro[4.4]non-1-yl)acetonitrile |
| 125 | 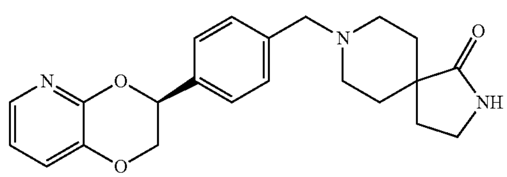 [SMILES: O=C1NCCC12CCN(Cc1ccc([C@H]3COc4cccnc4O3)cc1)CC2] | 8-{4-[(3S)-2,3-dihydro[1,4]dioxino[2,3-b]pyridin-3-yl]benzyl}-2,8-diazaspiro[4.5]decan-1-one |
| 126 | Chiral | (3S)-3-[4-(pyrrolidin-1-ylmethyl)phenyl]-2,3-dihydro[1,4]dioxino[2,3-b]pyridine |
| 127 | 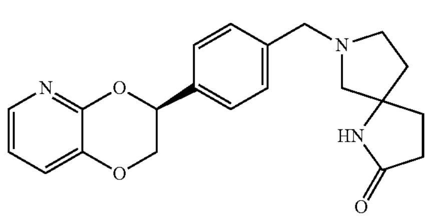 [SMILES: O=C1CCC2(CCN(Cc3ccc([C@H]4COc5cccnc5O4)cc3)C2)N1] | 7-{4-[(3S)-2,3-dihydro[1,4]dioxino[2,3-b]pyridin-3-yl]benzyl}-1,7-diazaspiro[4.4]nonan-2-one |

TABLE 1-continued

Exemplary compounds of the invention.

| Compound No. | Structure | Name |
| --- | --- | --- |
| 128 | 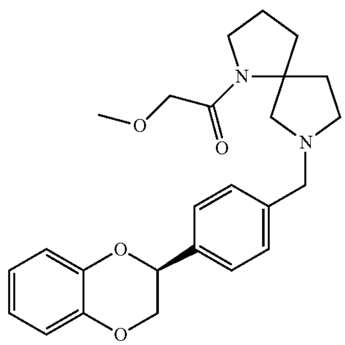 [SMILES: COCC(=O)N1CCCC12CCN(Cc1ccc([C@H]3COc4ccccc4O3)cc1)C2] | 1-(7-{4-[(2S)-2,3-dihydro-1,4-benzodioxin-2-yl]benzyl]-1,7-diazaspiro[4.4]non-1-yl)-2-methoxyethanone |
| 129 | 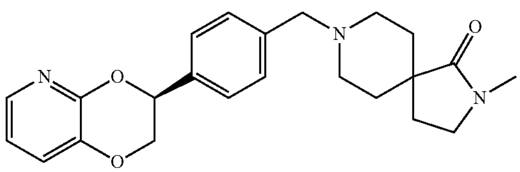 [SMILES: CN1CCC2(CCN(Cc3ccc([C@H]4COc5cccnc5O4)cc3)CC2)C1=O] | 8-{4-[(3S)-2,3-dihydro[1,4]dioxino[2,3-b]pyridin-3-yl]benzyl}-2-methyl-2,8-diazaspiro[4.5]decan-1-one |
| 130 | 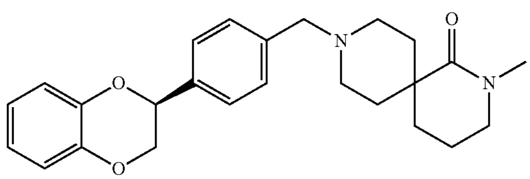 [SMILES: CN1CCCC2(CCN(Cc3ccc([C@H]4COc5ccccc5O4)cc3)CC2)C1=O] | 9-[(S)-4-(2,3-Dihydro-benzo[1,4]dioxin-2-yl)-benzyl]-2-methyl-2,9-diaza-spiro[5.5]undecan-1-one |
| 131 | 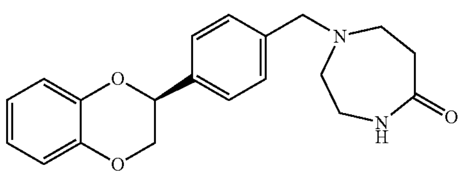 [SMILES: O=C1CCN(Cc2ccc([C@H]3COc4ccccc4O3)cc2)CCN1] | 1-{4-[(2S)-2,3-dihydro-1,4-benzodioxin-2-yl]benzyl}-1,4-diazepan-5-one |
| 132 | 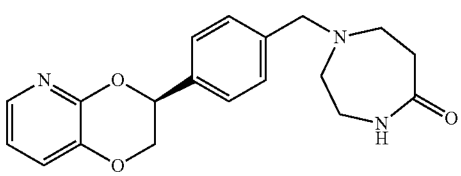 [SMILES: O=C1CCN(Cc2ccc([C@H]3COc4cccnc4O3)cc2)CCN1] | 1-{4-[(3S)-2,3-dihydro[1,4]dioxino[2,3-b]pyridin-3-yl]benzyl}-1,4-diazepan-5-one |
| 133 | 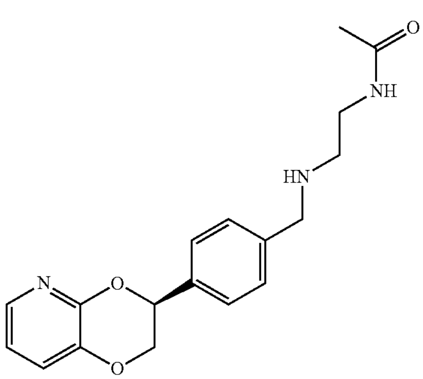 [SMILES: CC(=O)NCCNCc1ccc([C@H]2COc3cccnc3O2)cc1] | N-[2-({4-[(3S)-2,3-dihydro[1,4]dioxino[2,3-b]pyridin-3-yl]benzyl}amino)ethyl]acetamide |

TABLE 1-continued

Exemplary compounds of the invention.

| Compound No. | Structure | Name |
|---|---|---|
| 134 | 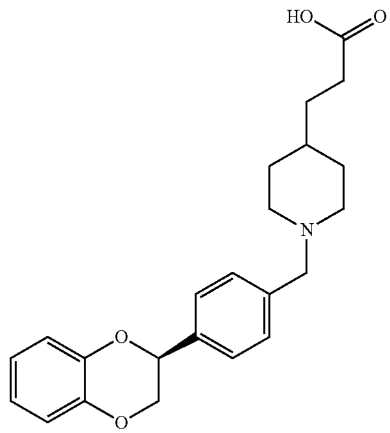 [SMILES: O=C(O)CCC1CCN(Cc2ccc([C@H]3COc4ccccc4O3)cc2)CC1] | 3-(1-{4-[(2S)-2,3-dihydro-1,4-benzodioxin-2-yl]benzyl}piperidin-4-yl)propanoic acid |
| 135 | 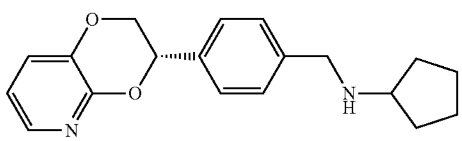 [SMILES: c1cnc2c(c1)OC[C@H](c1ccc(CNC3CCCC3)cc1)O2] | N-{4-[(3S)-2,3-dihydro[1,4]dioxino[2,3-b]pyridin-3-yl]benzyl]cyclopentanamine |
| 136 | 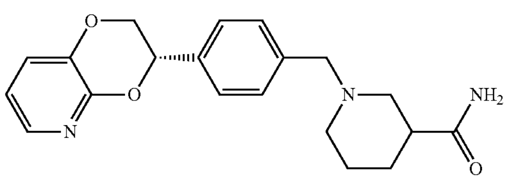 [SMILES: NC(=O)C1CCCN(Cc2ccc([C@H]3COc4cccnc4O3)cc2)C1] | 1-{4-[(3S)-2,3-dihydro[1,4]dioxino[2,3-b]pyridin-3-yl]benzyl}piperidine-3-carboxamide |
| 137 | 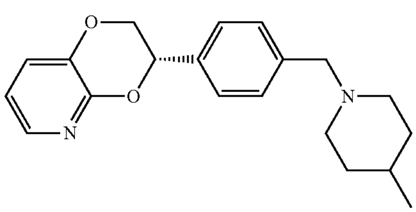 [SMILES: CC1CCN(Cc2ccc([C@H]3COc4cccnc4O3)cc2)CC1] | (3S)-3-{4-[(4-methylpiperidin-1-yl)methyl]phenyl}-2,3-dihydro[1,4]dioxino[2,3-b]pyridine |
| 138 | 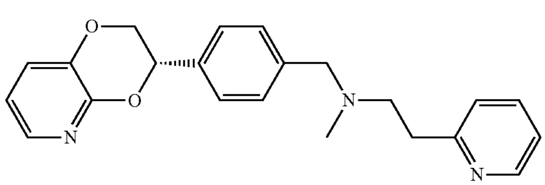 [SMILES: CN(CCc1ccccn1)Cc1ccc([C@H]2COc3cccnc3O2)cc1] | N-{4-[(3S)-2,3-dihydro[1,4]dioxino[2,3-b]pyridin-3-yl]benzyl}-N-methyl-2-(pyridin-2-yl)ethanamine |
| 139 | 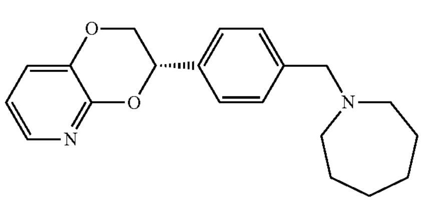 | (3S)-3-[4-(azepan-1-ylmethyl)phenyl]-2,3-dihydro[1,4]dioxino[2,3-b]pyridine |

TABLE 1-continued

Exemplary compounds of the invention.

| Compound No. | Structure | Name |
|---|---|---|
| 140 | 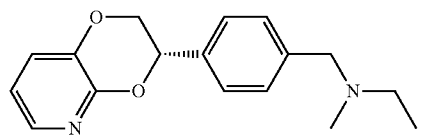 [SMILES: CCN(C)Cc1ccc([C@H]2COc3cccnc3O2)cc1] | N-{4-[(3S)-2,3-dihydro[1,4]dioxino[2,3-b]pyridin-3-yl]benzyl}-N-methylethanamine |
| 141 | 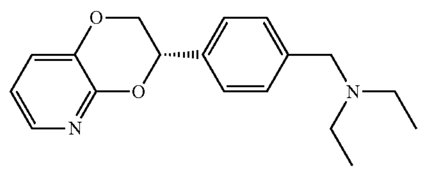 [SMILES: CCN(CC)Cc1ccc([C@H]2COc3cccnc3O2)cc1] | N-{4-[(3S)-2,3-dihydro[1,4]dioxino[2,3-b]pyridin-3-yl]benzyl}-N-ethylanamine |
| 142 | 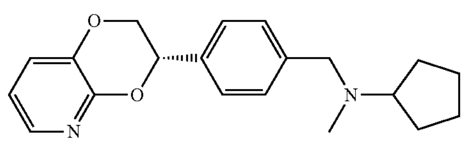 [SMILES: CN(Cc1ccc([C@H]2COc3cccnc3O2)cc1)C1CCCC1] | N-{4-[(3S)-2,3-dihydro[1,4]dioxino[2,3-b]pyridin-3-yl]benzyl}-N-methylcyclopentanamine |
| 143 | 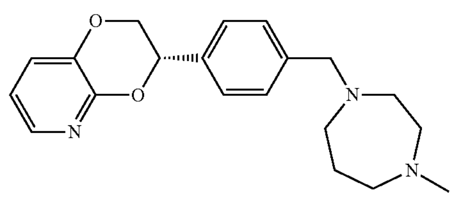 | (3S)-3-{4-[(4-methyl-1,4-diazepan-1-yl)methyl]phenyl}-2,3-dihydro[1,4]dioxino[2,3-b]pyridine |
| 144 | 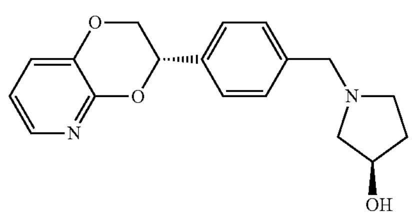 [SMILES: O[C@@H]1CCN(Cc2ccc([C@H]3COc4cccnc4O3)cc2)C1] | (3R)-1-{4-[(3S)-2,3-dihydro[1,4]dioxino[2,3-b]pyridin-3-yl]benzyl}pyrrolidin-3-ol |
| 145 | 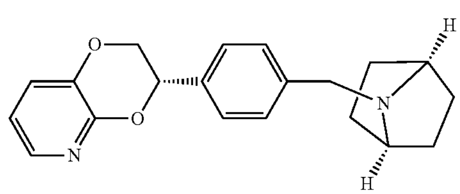 [SMILES: c1cnc2c(c1)OC[C@H](c1ccc(CN3[C@H]4CC[C@@H]3CC4)cc1)O2] | (3S)-3-{4-[(1s,4s)-7-azabicyclo[2.2.1]hept-7-ylmethyl]phenyl}-2,3-dihydro[1,4]dioxino[2,3-b]pyridine |
| 146 | 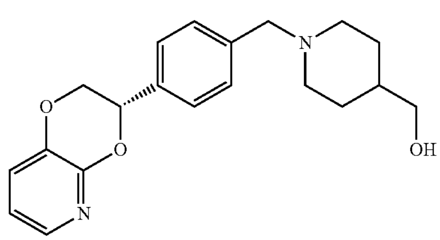 [SMILES: OCC1CCN(Cc2ccc([C@H]3COc4cccnc4O3)cc2)CC1] | (1-{4-[(3S)-2,3-dihydro[1,4]dioxino[2,3-b]pyridin-3-yl]benzyl}piperidin-4-yl)methanol |

TABLE 1-continued

Exemplary compounds of the invention.

| Compound No. | Structure | Name |
|---|---|---|
| 147 | 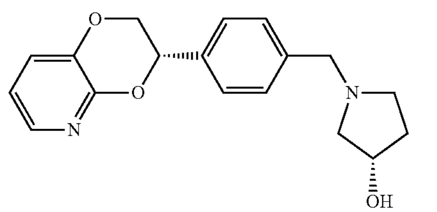 [SMILES: O[C@H]1CCN(Cc2ccc([C@H]3COc4cccnc4O3)cc2)C1] | (3S)-1-{4-[(3S)-2,3-dihydro[1,4]dioxino[2,3-b]pyridin-3-yl]benzyl}pyrrolidin-3-ol |
| 148 | 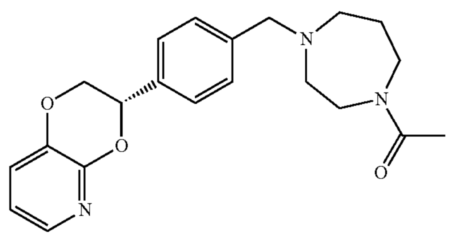 [SMILES: CC(=O)N1CCCN(Cc2ccc([C@H]3COc4cccnc4O3)cc2)CC1] | 1-(4-{4-[(3S)-2,3-dihydro[1,4]dioxino[2,3-b]pyridin-3-yl]benzyl}-1,4-diazepan-1-yl)ethanone |
| 149 | 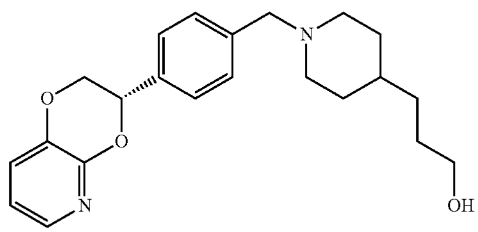 [SMILES: OCCCC1CCN(Cc2ccc([C@H]3COc4cccnc4O3)cc2)CC1] | 3-(1-{4-[(3S)-2,3-dihydro[1,4]dioxino[2,3-b]pyridin-3-yl]benzyl}piperidin-4-yl)propan-1-ol |
| 150 | 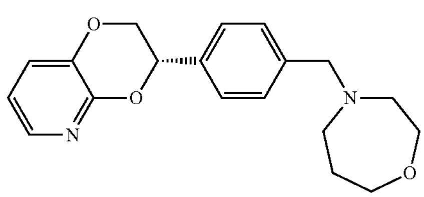 | (3S)-3-[4-(1,4-oxazepan-4-ylmethyl)phenyl]-2,3-dihydro[1,4]dioxino[2,3-b]pyridine |
| 151 | 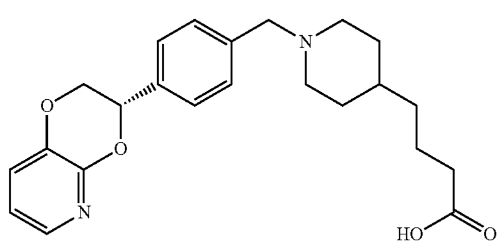 [SMILES: O=C(O)CCCC1CCN(Cc2ccc([C@H]3COc4cccnc4O3)cc2)CC1] | 4-(1-{4-[(3S)-2,3-dihydro[1,4]dioxino[2,3-b]pyridin-3-yl]benzyl}piperidin-4-yl)butanoic acid |
| 152 | 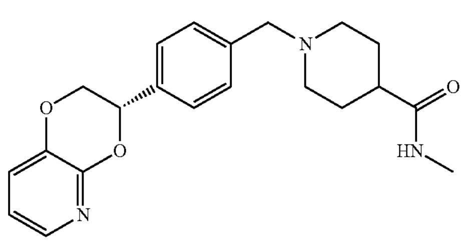 [SMILES: CNC(=O)C1CCN(Cc2ccc([C@H]3COc4cccnc4O3)cc2)CC1] | 1-{4-[(3S)-2,3-dihydro[1,4]dioxino[2,3-b]pyridin-3-yl]benzyl}-N-methylpiperidine-4-carboxamide |

TABLE 1-continued

Exemplary compounds of the invention.

| Compound No. | Structure | Name |
|---|---|---|
| 153 | 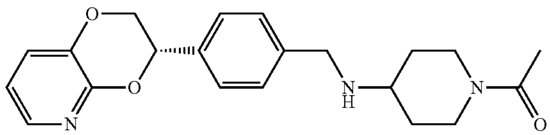 [SMILES: CC(=O)N1CCC(NCc2ccc([C@H]3COc4cccnc4O3)cc2)CC1] | 1-[4-({4-[(3S)-2,3-dihydro[1,4]dioxino[2,3-b]pyridin-3-yl]benzyl}amino)piperidin-1-yl]ethanone |
| 154 | 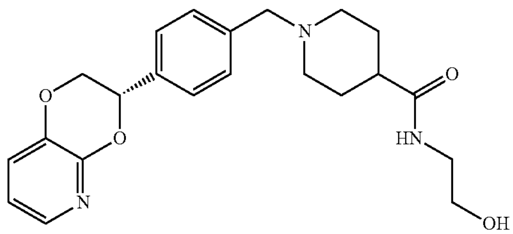 [SMILES: O=C(NCCO)C1CCN(Cc2ccc([C@H]3COc4cccnc4O3)cc2)CC1] | 1-{4-[(3S)-2,3-dihydro[1,4]dioxino[2,3-b]pyridin-3-yl]benzyl}-N-(2-hydroxyethyl)piperidine-4-carboxamide |
| 155 | 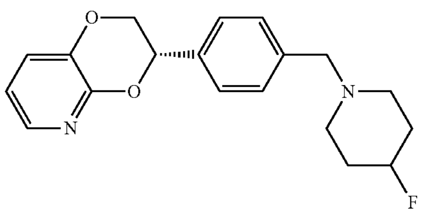 [SMILES: FC1CCN(Cc2ccc([C@H]3COc4cccnc4O3)cc2)CC1] | (3S)-3-{4-[(4-fluoropiperidin-1-yl)methyl]phenyl}-2,3-dihydro[1,4]dioxino[2,3-b]pyridine |
| 156 | 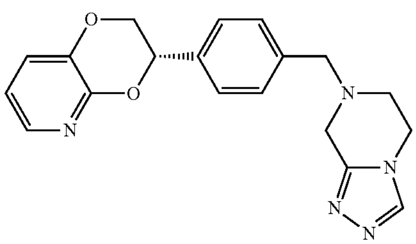 [SMILES: c1cnc2c(c1)OC[C@H](c1ccc(CN3CCn4cnnc4C3)cc1)O2] | (3S)-3-[4-(5,6-dihydro[1,2,4]triazolo[4,3-a]pyrazin-7(8H)-ylmethyl)phenyl]-2,3-dihydro[1,4]dioxino[2,3-b]pyridine |
| 157 | 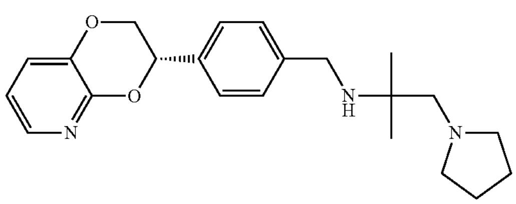 [SMILES: CC(C)(CN1CCCC1)NCc1ccc([C@H]2COc3cccnc3O2)cc1] | N-{4-[(3S)-2,3-dihydro[1,4]dioxino[2,3-b]pyridin-3-yl]benzyl}-2-methyl-1-(pyrrolidin-1-yl)propan-2-amine |
| 158 | 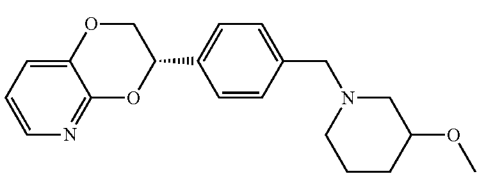 [SMILES: COC1CCCN(Cc2ccc([C@H]3COc4cccnc4O3)cc2)C1] | (3S)-3-{4-[(3-methoxypiperidin-1-yl)methyl]phenyl}-2,3-dihydro[1,4]dioxino[2,3-b]pyridine |
| 159 | 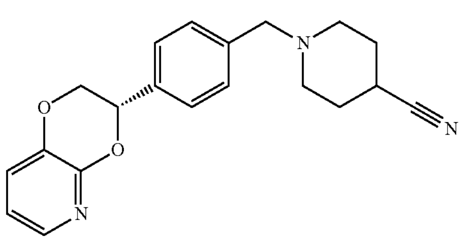 [SMILES: N#CC1CCN(Cc2ccc([C@H]3COc4cccnc4O3)cc2)CC1] | 1-{4-[(3S)-2,3-dihydro[1,4]dioxino[2,3-b]pyridin-3-yl]benzyl}piperidine-4-carbonitrile |

TABLE 1-continued

Exemplary compounds of the invention.

| Compound No. | Structure | Name |
|---|---|---|
| 160 | 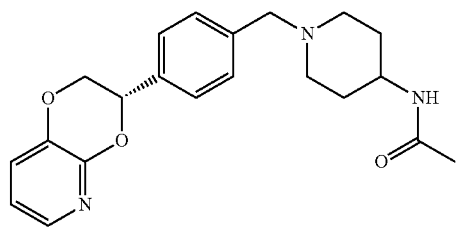 [SMILES: CC(=O)NC1CCN(Cc2ccc([C@H]3COc4cccnc4O3)cc2)CC1] | N-(1-{4-[(3S)-2,3-dihydro[1,4]dioxino[2,3-b]pyridin-3-yl)benzyl}piperidin-4-yl)acetamide |
| 161 | 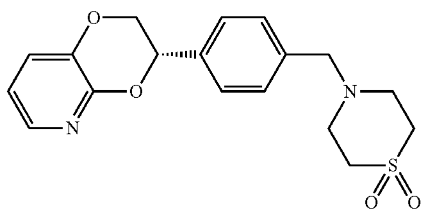 [SMILES: O=S1(=O)CCN(Cc2ccc([C@H]3COc4cccnc4O3)cc2)CC1] | (3S)-3-{4-[(1,1-dioxidothiomorpholin-4-yl)methyl]phenyl}-2,3-dihydro[1,4]dioxino[2,3-b]pyridine |
| 162 | 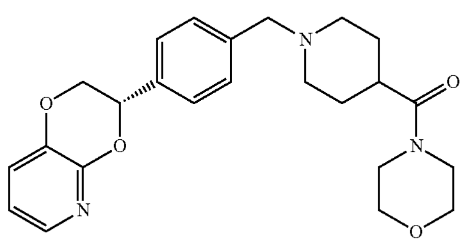 [SMILES: O=C(C1CCN(Cc2ccc([C@H]3COc4cccnc4O3)cc2)CC1)N1CCOCC1] | (1-{4-[(3S)-2,3-dihydro[1,4]dioxino[2,3-b]pyridin-3-yl]benzyl}piperidin-4-yl)(morpholin-4-yl)methanone |
| 163 | 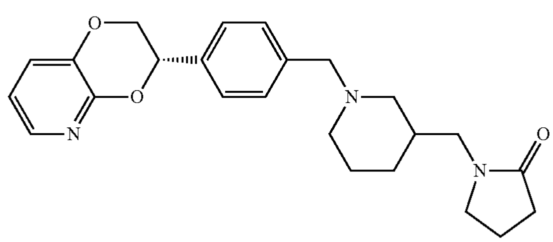 [SMILES: O=C1CCCN1CC1CCCN(Cc2ccc([C@H]3COc4cccnc4O3)cc2)C1] | 1-[(1-{4-[(3S)-2,3-dihydro[1,4]dioxino[2,3-b]pyridin-3-yl]benzyl}piperidin-3-yl)methyl]pyrrolidin-2-one |
| 164 | 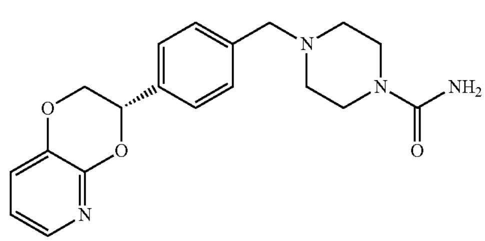 [SMILES: NC(=O)N1CCN(Cc2ccc([C@H]3COc4cccnc4O3)cc2)CC1] | 4-{4-[(3S)-2,3-dihydro[1,4]dioxino[2,3-b]pyridin-3-yl]benzyl}piperazine-1-carboxamide |
| 165 | 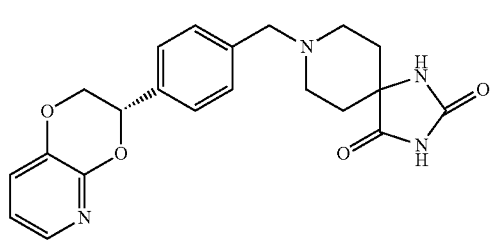 [SMILES: O=C1NC(=O)C2(CCN(Cc3ccc([C@H]4COc5cccnc5O4)cc3)CC2)N1] | 8-{4-[(3S)-2,3-dihydro[1,4]dioxino[2,3-b]pyridin-3-yl]benzyl}-1,3,8-triazaspiro[4.5]decane-2,4-dione |

TABLE 1-continued

Exemplary compounds of the invention.

| Compound No. | Structure | Name |
|---|---|---|
| 166 | 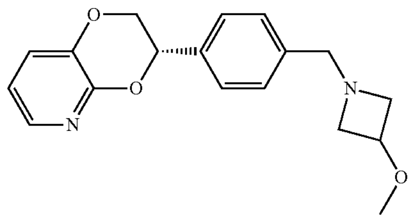 [SMILES: COC1CN(Cc2ccc([C@H]3COc4cccnc4O3)cc2)C1] | (3S)-3-{4-[(3-methoxyazetidin-1-yl)methyl]phenyl}-2,3-dihydro[1,4]dioxino[2,3-b]pyridine |
| 167 | 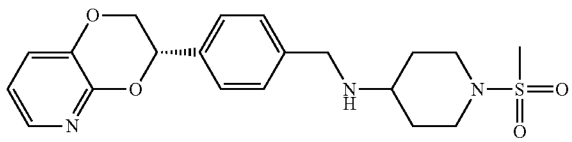 [SMILES: CS(=O)(=O)N1CCC(NCc2ccc([C@H]3COc4cccnc4O3)cc2)CC1] | N-{4-[(3S)-2,3-dihydro[1,4]dioxino[2,3-b]pyridin-3-yl]benzyl}-1-(methylsulfonyl)piperidin-4-amine |
| 168 | 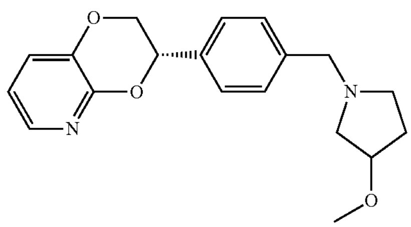 | (3S)-3-{4-[(3-methoxypyrrolidin-1-yl)methyl]phenyl}-2,3-dihydro[1,4]dioxino[2,3-b]pyridine |
| 169 | 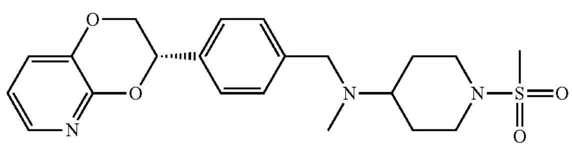 [SMILES: CN(Cc1ccc([C@H]2COc3cccnc3O2)cc1)C1CCN(S(C)(=O)=O)CC1] | N-{4-[(3S)-2,3-dihydro[1,4]dioxino[2,3-b]pyridin-3-yl]benzyl}-N-methyl-1-(methylsulfonyl)piperidin-4-amine |
| 170 | 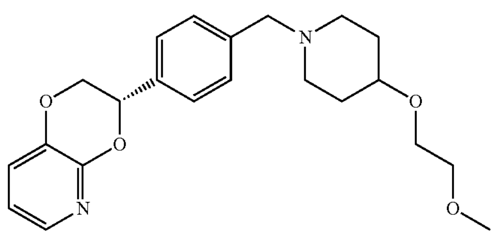 [SMILES: COCCOC1CCN(Cc2ccc([C@H]3COc4cccnc4O3)cc2)CC1] | (3S)-3-(4-{[4-(2-methoxyethoxy)piperidin-1-yl]methyl}phenyl)-2,3-dihydro[1,4]dioxino[2,3-b]pyridine |
| 171 | 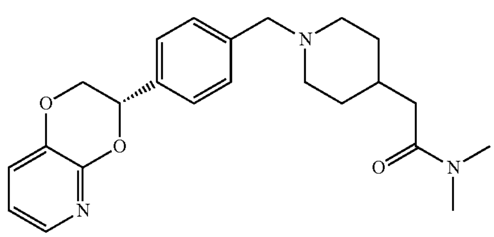 [SMILES: CN(C)C(=O)CC1CCN(Cc2ccc([C@H]3COc4cccnc4O3)cc2)CC1] | 2-(1-{4-[(3S)-2,3-dihydro[1,4]dioxino[2,3-b]pyridin-3-yl]benzyl}piperidin-4-yl)-N,N-dimethylacetamide |
| 172 | 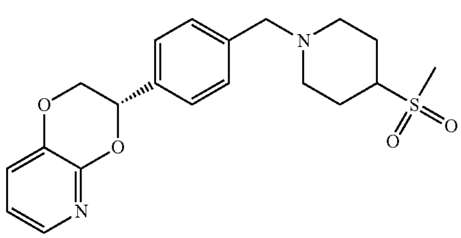 [SMILES: CS(=O)(=O)C1CCN(Cc2ccc([C@H]3COc4cccnc4O3)cc2)CC1] | (3S)-3-(4-{[4-(methylsulfonyl)piperidin-1-yl]methyl}phenyl)-2,3-dihydro[1,4]dioxino[2,3-b]pyridine |

TABLE 1-continued

Exemplary compounds of the invention.

| Compound No. | Structure | Name |
|---|---|---|
| 173 | 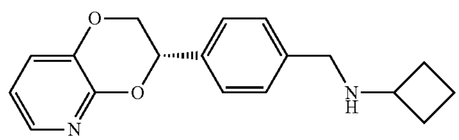 [SMILES: c1cnc2c(c1)OC[C@H](c1ccc(CNC3CCC3)cc1)O2] | N-{4-[(3S)-2,3-dihydro[1,4]dioxino[2,3-b]pyridin-3-yl]benzyl}cyclobutanamine |
| 174 | 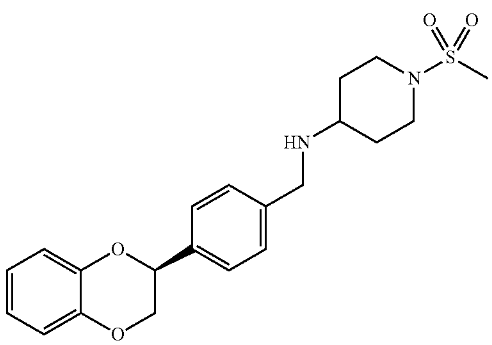 [SMILES: CS(=O)(=O)N1CCC(NCc2ccc([C@H]3COc4ccccc4O3)cc2)CC1] | N-{4-[(2S)-2,3-dihydro-1,4-benzodioxin-2-yl]benzyl}-1-(methylsulfonyl)piperidin-4-amide |
| 175 | 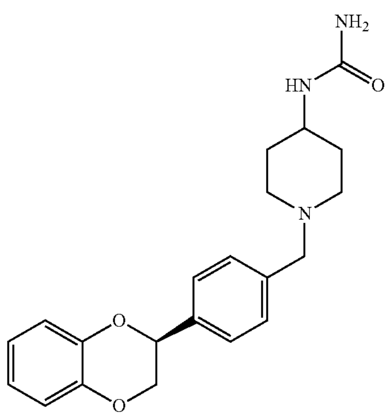 [SMILES: NC(=O)NC1CCN(Cc2ccc([C@H]3COc4ccccc4O3)cc2)CC1] | 1-(1-{4-[(2S)-2,3-dihydro-1,4-benzodioxin-2-yl]benzyl}piperidin-4-yl)urea |
| 176 | 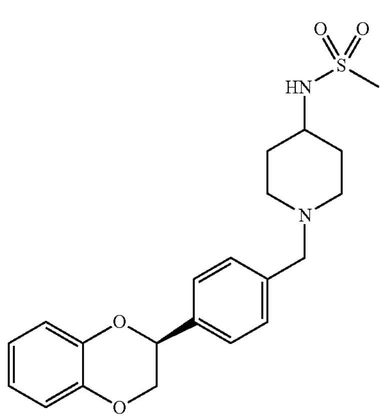 [SMILES: CS(=O)(=O)NC1CCN(Cc2ccc([C@H]3COc4ccccc4O3)cc2)CC1] | N-(1-{4-[(2S)-2,3-dihydro-1,4-benzodioxin-2-yl]benzyl}piperidin-4-yl)methanesulfonamide |

TABLE 1-continued

Exemplary compounds of the invention.

| Compound No. | Structure | Name |
|---|---|---|
| 177 | 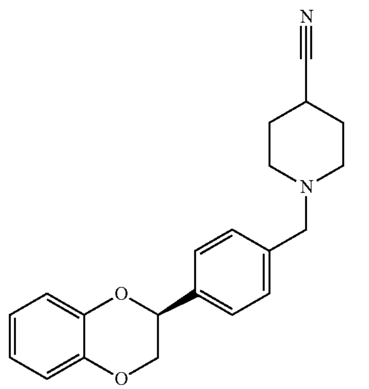 [SMILES: N#CC1CCN(Cc2ccc([C@H]3COc4ccccc4O3)cc2)CC1] | 1-{4-[(2S)-2,3-dihydro-1,4-benzodioxin-2-yl]benzyl}piperidine-4-carbonitrile |
| 178 | 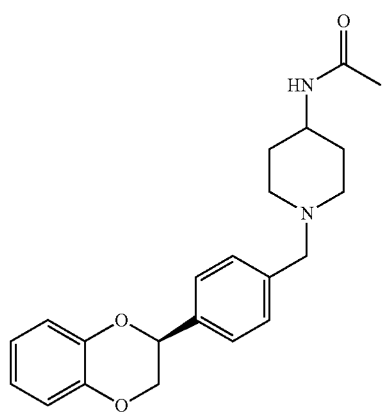 [SMILES: CC(=O)NC1CCN(Cc2ccc([C@H]3COc4ccccc4O3)cc2)CC1] | N-(1-(4-[(2S)-2,3-dihydro-1,4-benzodioxin-2-yl]benzyl}piperidin-4-yl)acetamide |
| 179 | 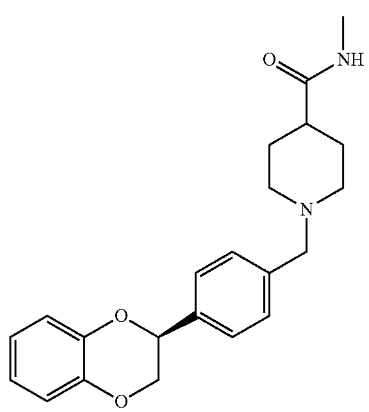 [SMILES: CNC(=O)C1CCN(Cc2ccc([C@H]3COc4ccccc4O3)cc2)CC1] | 1-{4-[(2S)-2,3-dihydro-1,4-benzodioxin-2-yl]benzyl}-N-methylpiperidine-4-carboxamide |

TABLE 1-continued
Exemplary compounds of the invention.
| Compound No. | Structure | Name |
|---|---|---|
| 180 | 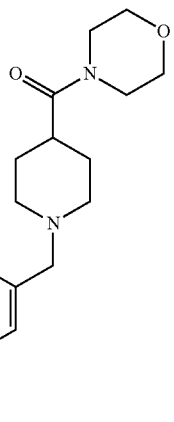 | (1-{4-[(2S)-2,3-dihydro-1,4-benzodioxin-2-yl]benzyl}piperidin-4-yl)(morpholin-4-yl)methanone |
| 181 | 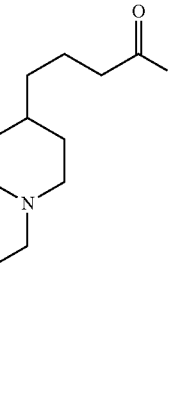 | 4-(1-{4-[(2S)-2,3-dihydro-1,4-benzodioxin-2-yl]benzyl}piperidin-4-yl)butanoic acid |
| 182 | 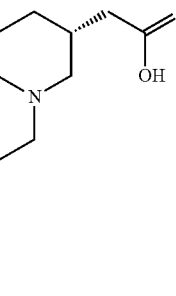 | [(3R)-1-{4-[(2S)-2,3-dihydro-1,4-benzodioxin-2-yl]benzyl}piperidin-3-yl]acetic acid |
| 183 | 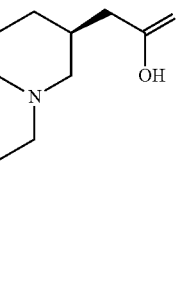 | [(3S)-1-{4-[(2S)-2,3-dihydro-1,4-benzodioxin-2-yl]benzyl)piperidin-3-yl]acetic acid |

TABLE 1-continued

Exemplary compounds of the invention.

| Compound No. | Structure | Name |
|---|---|---|
| 184 | 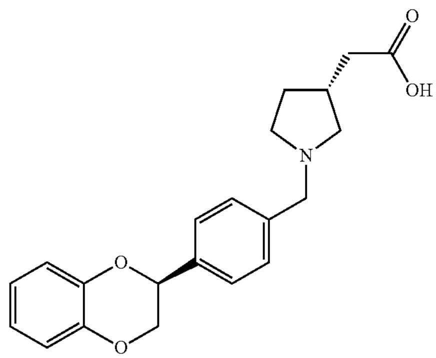 [SMILES: O=C(O)C[C@H]1CCN(Cc2ccc([C@H]3COc4ccccc4O3)cc2)C1] | [(3R)-1-{4-[(2S)-2,3-dihydro-1,4-benzodioxin-2-yl]benzyl}pyrrolidin-3-yl]acetic acid |
| 185 | 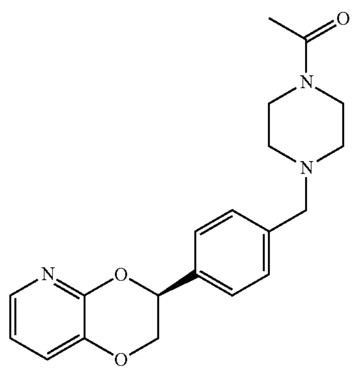 [SMILES: CC(=O)N1CCN(Cc2ccc([C@H]3COc4cccnc4O3)cc2)CC1] | 1-(4-{4-[(3S)-2,3-dihydro[1,4]dioxino[2,3-b]pyridin-3-yl]benzyl}piperazin-1-yl)ethanone |
| 186 | 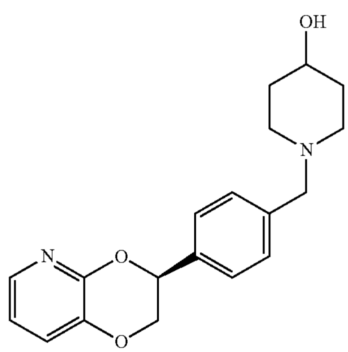 [SMILES: OC1CCN(Cc2ccc([C@H]3COc4cccnc4O3)cc2)CC1] | 1-{4-[(3S)-2,3-dihydro[1,4]dioxino[2,3-b]pyridin-3-yl]benzyl}piperidin-4-ol |
| 187 | 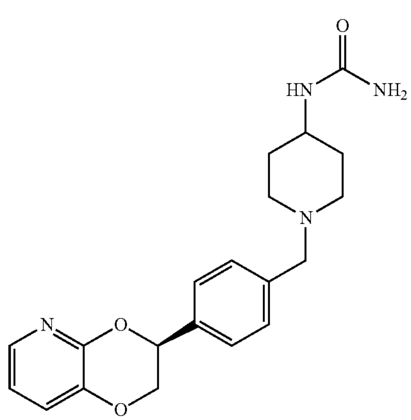 [SMILES: NC(=O)NC1CCN(Cc2ccc([C@H]3COc4cccnc4O3)cc2)CC1] | 1-(1-{4-[(3S)-2,3-dihydro[1,4]dioxino[2,3-b]pyridin-3-yl]benzyl}piperidin-4-yl)urea |

TABLE 1-continued

Exemplary compounds of the invention.

| Compound No. | Structure | Name |
|---|---|---|
| 188 | 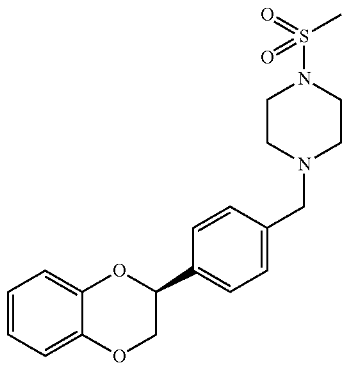 [SMILES: CS(=O)(=O)N1CCN(Cc2ccc([C@H]3COc4ccccc4O3)cc2)CC1] | (3S)-3-(4-{[4-(methylsulfonyl)piperazin-1-yl]methyl}phenyl)-2,3-dihydro[1,4]dioxino[2,3-b]pyridine |
| 189 | 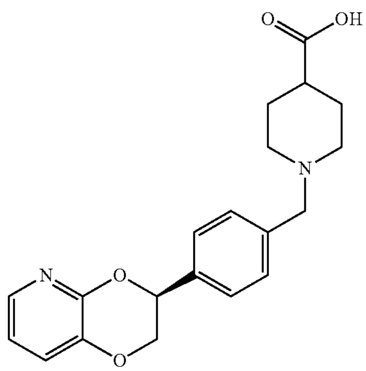 [SMILES: O=C(O)C1CCN(Cc2ccc([C@H]3COc4cccnc4O3)cc2)CC1] | 1-{4-[(3S)-2,3-dihydro[1,4]dioxino[2,3-b]pyridin-3-yl]benzyl}piperidine-4-carboxylic acid |
| 190 | 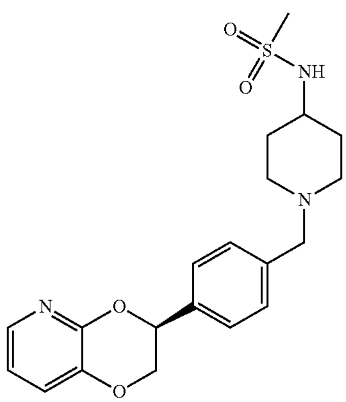 [SMILES: CS(=O)(=O)NC1CCN(Cc2ccc([C@H]3COc4cccnc4O3)cc2)CC1] | N-(1-{4-[(3S)-2,3-dihydro[1,4]dioxino[2,3-b]pyridin-3-yl]benzyl}piperidin-4-yl)methanesulfonamide |
| 191 | 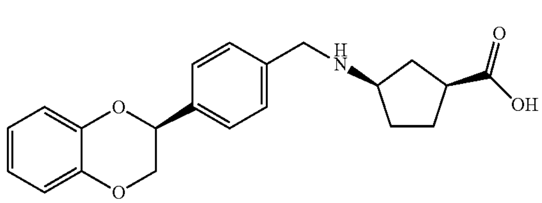 [SMILES: O=C(O)[C@H]1CC[C@@H](NCc2ccc([C@H]3COc4ccccc4O3)cc2)C1] | (1S,3R)-3-({4-[(2S)-2,3-dihydro-1,4-benzodioxin-2-yl]benzyl}amino)cyclopentanecarboxylic acid |
| 192 | 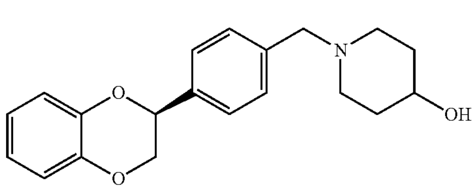 [SMILES: OC1CCN(Cc2ccc([C@H]3COc4ccccc4O3)cc2)CC1] | 1-{4-[(2S)-2,3-dihydro)-1,4-benzodioxin-2-yl]benzyl}piperidin-4-ol |

TABLE 1-continued

Exemplary compounds of the invention.

| Compound No. | Structure | Name |
|---|---|---|
| 193 | 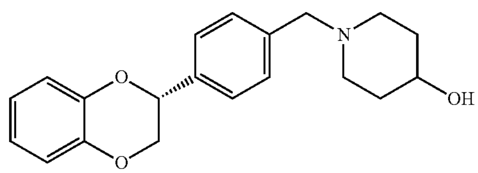 [SMILES: OC1CCN(Cc2ccc([C@@H]3COc4ccccc4O3)cc2)CC1] | 1-{4-[(2R)-2,3-dihydro-1,4-benzodioxin-2-yl]benzyl}piperidin-4-ol |
| 194 | 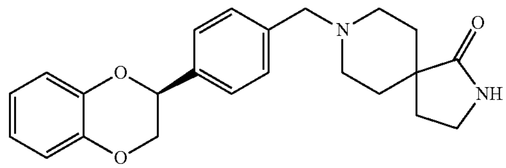 [SMILES: O=C1NCCC12CCN(Cc1ccc([C@H]3COc4ccccc4O3)cc1)CC2] | 8-{4-[(2S)-2,3-dihydro-1,4-benzodioxin-2-yl]benzyl}-2,8-diazaspiro[4.5]decan-1-one |
| 195 | 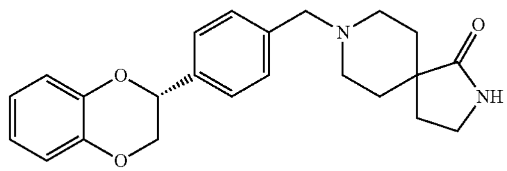 | 8-{4-[(2R)-2,3-dihydro-1,4-benzodioxin-2-yl]benzyl}-2,8-diazaspiro[4.5]decan-1-one |
| 196 | 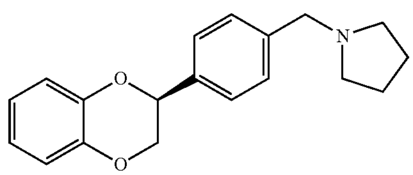 [SMILES: c1ccc2c(c1)OC[C@H](c1ccc(CN3CCCC3)cc1)O2] | 1-{4-[(2S)-2,3-dihydro-1,4-benzodioxin-2-yl]benzyl}pyrrolidine |
| 197 | 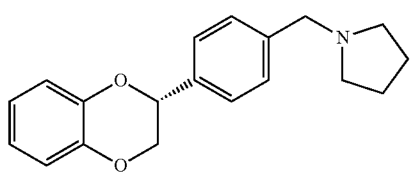 [SMILES: c1ccc2c(c1)OC[C@@H](c1ccc(CN3CCCC3)cc1)O2] | 1-{4-[(2R)-2,3-dihydro-1,4-benzodioxin-2-yl]benzyl}pyrrolidine |
| 198 | 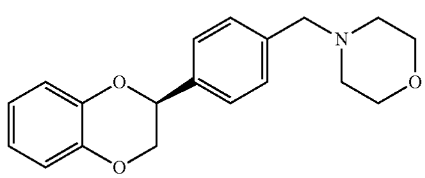 [SMILES: c1ccc2c(c1)OC[C@H](c1ccc(CN3CCOCC3)cc1)O2] | 4-{4-[(2S)-2,3-dihydro-1,4-benzodioxin-2-yl]benzyl}morpholine |
| 199 | 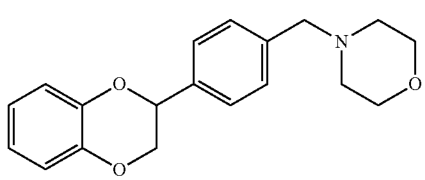 [SMILES: c1ccc2c(c1)OCC(c1ccc(CN3CCOCC3)cc1)O2] | 4-{4-[(2R)-2,3-dihydro-1,4-benzodioxin-2-yl]benzyl}morpholine |
| 200 | 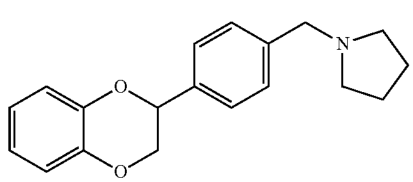 [SMILES: c1ccc2c(c1)OCC(c1ccc(CN3CCCC3)cc1)O2] | 1-[4-(2,3-dihydro-1,4-benzodioxin-2-yl)benzyl]pyrrolidine |

TABLE 1-continued

Exemplary compounds of the invention.

| Compound No. | Structure | Name |
|---|---|---|
| 201 | 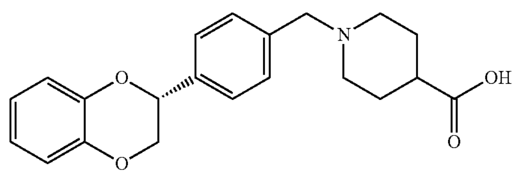 | 1-{4-[(2R)-2,3-dihydro-1,4-benzodioxin-2-yl]benzyl}piperidine-4-carboxylic acid |
| 202 | 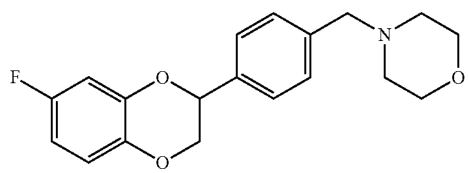 [SMILES: Fc1ccc2c(c1)OC(c1ccc(CN3CCOCC3)cc1)CO2] | 4-[4-(7-fluoro-2,3-dihydro-1,4-benzodioxin-2-yl)benzyl]morpholine |
| 203 | 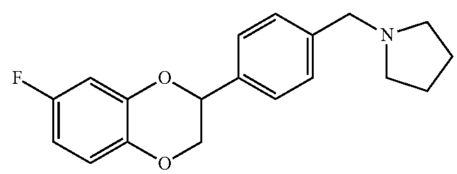 [SMILES: Fc1ccc2c(c1)OC(c1ccc(CN3CCCC3)cc1)CO2] | 1-[4-(7-fluoro-2,3-dihydro-1,4-benzodioxin-2-yl)benzyl)pyrrolidine |
| 204 | 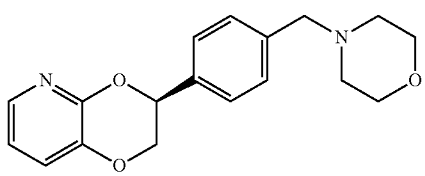 [SMILES: c1cnc2c(c1)OC[C@H](c1ccc(CN3CCOCC3)cc1)O2] | (3S)-3-[4-(morpholin-4-ylmethyl)phenyl]-2,3-dihydro[1,4]dioxino[2,3-b]pyridine |
| 205 | 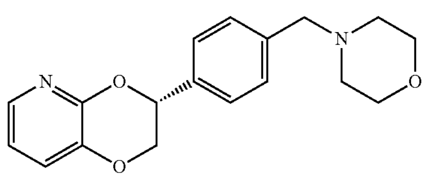 [SMILES: c1cnc2c(c1)OC[C@@H](c1ccc(CN3CCOCC3)cc1)O2] | (3R)-3-[4-(morpholin-4-ylmethyl)phenyl]-2,3-dihydro[1,4]dioxino[2,3-b]pyridine |
| 206 | 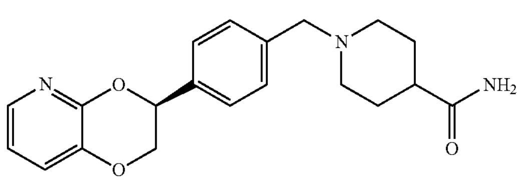 [SMILES: NC(=O)C1CCN(Cc2ccc([C@H]3COc4cccnc4O3)cc2)CC1] | 1-{4-[(3S)-2,3-dihydro[1,4]dioxino[2,3-b]pyridin-3-yl]benzyl}piperidine-4-carboxamide |
| 207 | 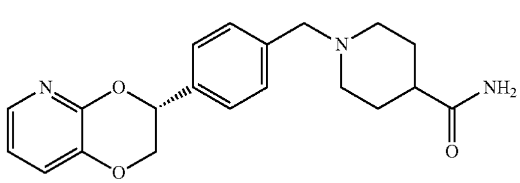 [SMILES: NC(=O)C1CCN(Cc2ccc([C@@H]3COc4cccnc4O3)cc2)CC1] | 1-{4-[(3R)-2,3-dihydro[1,4]dioxino[2,3-b]pyridin-3-yl]benzyl}piperidine-4-carboxamide |

TABLE 1-continued

Exemplary compounds of the invention.

| Compound No. | Structure | Name |
|---|---|---|
| 208 | 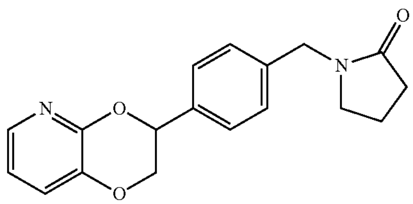 [SMILES: O=C1CCCN1Cc1ccc(C2COc3cccnc3O2)cc1] | 1-[4-(2,3-dihydro[1,4]dioxino[2,3-b]pyridin-3-yl)benzyl]pyrrolidine-2-one |
| 209 | 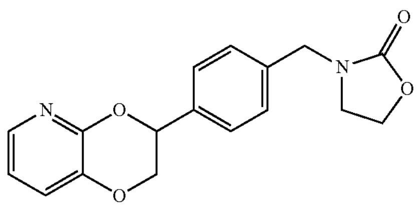 [SMILES: O=C1OCCN1Cc1ccc(C2COc3cccnc3O2)cc1] | 3-[4-(2,3-dihydro[1,4]dioxino[2,3-b]pyridin-3-yl)benzyl]-1,3-oxazolidin-2-one |
| 210 | 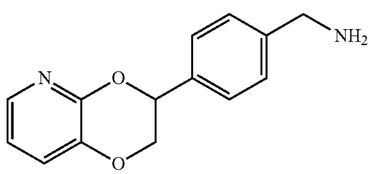 [SMILES: NCc1ccc(C2COc3cccnc3O2)cc1] | 1-[4-(2,3-dihydro[1,4]dioxino[2,3-b]pyridin-3-yl)phenyl]methanamine |
| 211 | 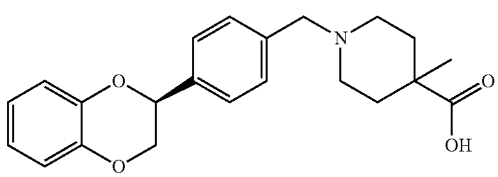 [SMILES: CC1(C(=O)O)CCN(Cc2ccc([C@H]3COc4ccccc4O3)cc2)CC1] | 1-{4-[(2S)-2,3-dihydro-1,4-benzodioxin-2-yl]benzyl}-4-methylpiperidine-4-carboxylic acid |
| 212 | 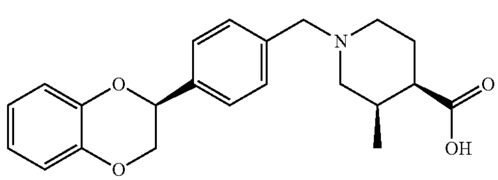 [SMILES: C[C@H]1CN(Cc2ccc([C@H]3COc4ccccc4O3)cc2)CC[C@H]1C(=O)O] | (3R,4R)-1-{4-[(2S)-2,3-dihydro-1,4-benzodioxin-2-yl]benzyl}-3-methylpiperidine-4-carboxylic acid |
| 213 | 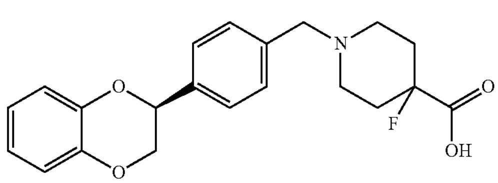 [SMILES: O=C(O)C1(F)CCN(Cc2ccc([C@H]3COc4ccccc4O3)cc2)CC1] | 1-{4-[(2S)-2,3-dihydro-1,4-benzodioxin-2-yl]benzyl}-4-fluoropiperidine-4-carboxylic acid |

TABLE 1-continued
Exemplary compounds of the invention.
| Compound No. | Structure | Name |
|---|---|---|
| 214 | 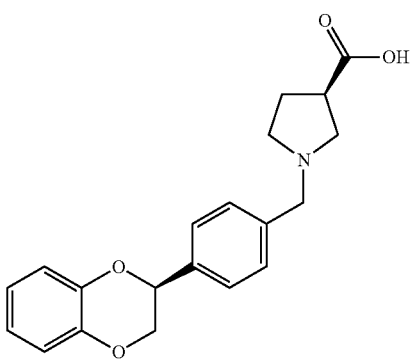 [SMILES: O=C(O)[C@@H]1CCN(Cc2ccc([C@H]3COc4ccccc4O3)cc2)C1] | (3R)-1-{4-[(2S)-2,3-dihydro-1,4-benzodioxin-2-yl]benzyl}pyrrolidine-3-carboxylic acid |
| 215 | 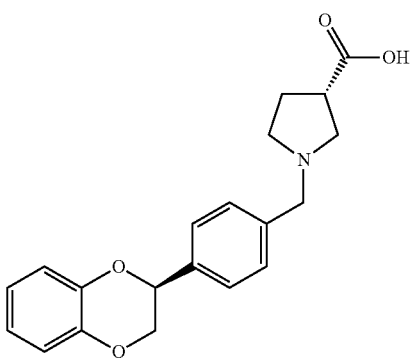 [SMILES: O=C(O)[C@H]1CCN(Cc2ccc([C@H]3COc4ccccc4O3)cc2)C1] | (3S)-1-{4-[(2S)-2,3-dihydro-1,4-benzodioxin-2-yl]benzyl}pyrrolidine-3-carboxylic acid |
| 216 | 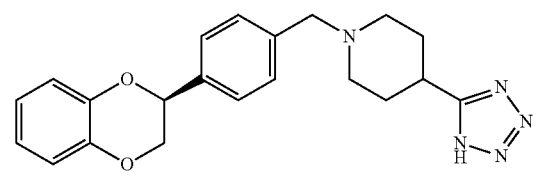 [SMILES: c1ccc2c(c1)OC[C@H](c1ccc(CN3CCC(c4nnn[nH]4)CC3)cc1)O2] | 1-{4-[(2S)-2,3-dihydro-1,4-benzodioxin-2-yl]benzyl)-4-(1H-tetrazol-5-yl)piperidine |
| 217 | 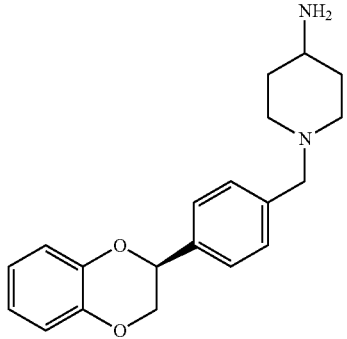 [SMILES: NC1CCN(Cc2ccc([C@H]3COc4ccccc4O3)cc2)CC1] | 1-{4-[(2S)-2,3-dihydro-1,4-benzodioxin-2-yl]benzyl}piperidin-4-amine |

TABLE 1-continued

Exemplary compounds of the invention.

| Compound No. | Structure | Name |
|---|---|---|
| 218 | 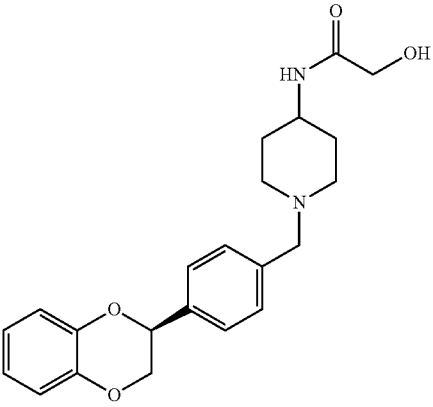 [SMILES: O=C(CO)NC1CCN(Cc2ccc([C@H]3COc4ccccc4O3)cc2)CC1] | N-(1-{4-[(2S)-2,3-dihydro-1,4-benzodioxin-2-yl]benzyl}piperidin-4-yl)-2-hydroxyacetamide |
| 219 | 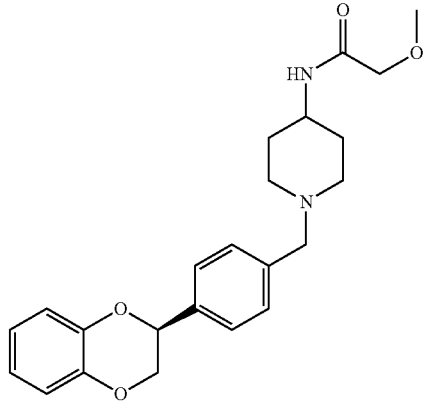 [SMILES: COCC(=O)NC1CCN(Cc2ccc([C@H]3COc4ccccc4O3)cc2)CC1] | N-(1-{4-[(2S)-2,3-dihydro-1,4-benzodioxin-2-yl]benzyl}piperidin-4-yl)-2-methoxyacetamide |
| 220 | 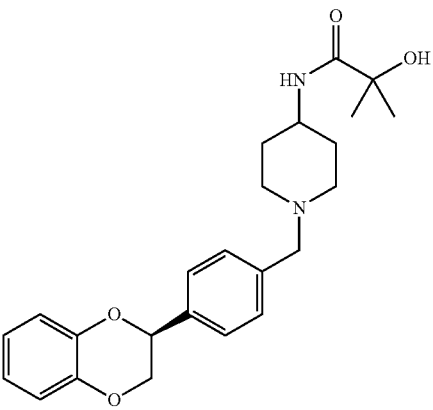 [SMILES: CC(C)(O)C(=O)NC1CCN(Cc2ccc([C@H]3COc4ccccc4O3)cc2)CC1] | N-(1-{4-[(2S)-2,3-dihydro-1,4-benzodioxin-2-yl]benzyl}piperidin-4-yl)-2-hydroxy-2-methylpropanamide |
| 221 | 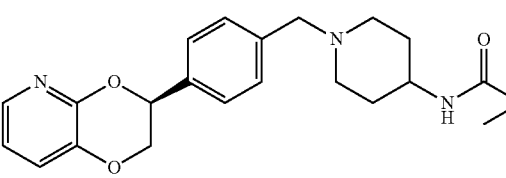 | N-(1-{4-[(3S)-2,3-dihydro[1,4]dioxino[2,3-b]pyridin-3-yl]benzyl}piperidin-4-yl)-2-hydroxy-2-methylpropanamide |

TABLE 1-continued

Exemplary compounds of the invention.

| Compound No. | Structure | Name |
|---|---|---|
| 222 | 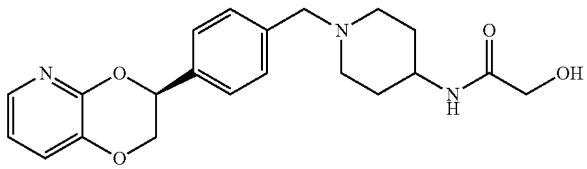 [SMILES: O=C(CO)NC1CCN(Cc2ccc([C@H]3COc4cccnc4O3)cc2)CC1] | N-(1-{4-[(3S)-2,3-dihydro[1,4]dioxino[2,3-b]pyridin-3-yl]benzyl}piperidin-4-yl)-2-hydroxyacetamide |
| 223 | 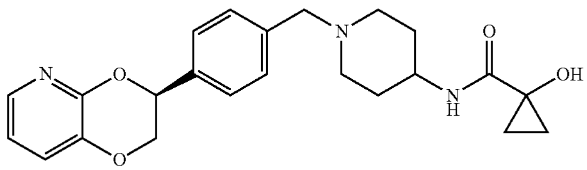 [SMILES: O=C(NC1CCN(Cc2ccc([C@H]3COc4cccnc4O3)cc2)CC1)C1(O)CC1] | N-(1-{4-[(3S)-2,3-dihydro[1,4]dioxino[2,3-b]pyridin-3-yl]benzyl}piperidin-4-yl)-1-hydroxycyclopropanecarboxamide |
| 224 | 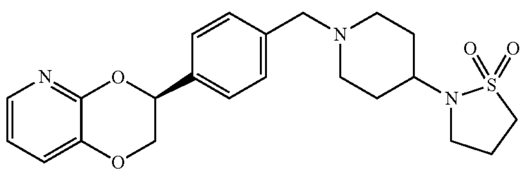 [SMILES: O=S1(=O)CCCN1C1CCN(Cc2ccc([C@H]3COc4cccnc4O3)cc2)CC1] | 1-{4-[(2S)-2,3-dihydro-1,4-benzodioxin-2-yl]benzyl}-4-(1,1-dioxido-1,2-thiazolidine-2-yl)piperidine |
| 225 | 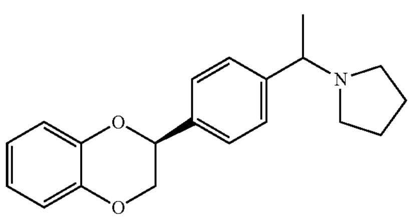 [SMILES: CC(c1ccc([C@H]2COc3ccccc3O2)cc1)N1CCCC1] | 1-(1-{4-[(2S)-2,3-dihydro-1,4-benzodioxin-2-yl]phenyl}ethyl)pyrrolidine |
| 226 | 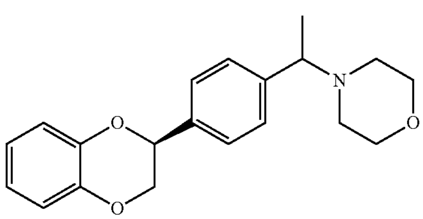 [SMILES: CC(c1ccc([C@H]2COc3ccccc3O2)cc1)N1CCOCC1] | 4-(1-{4-[(2S)-2,3-dihydro-1,4-benzodioxin-2-yl]phenyl}ethyl)morpholine |
| 227 | 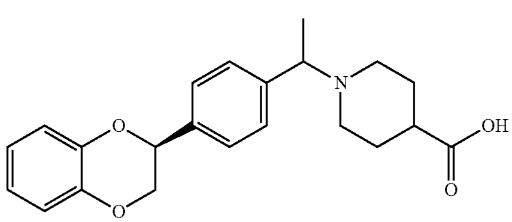 [SMILES: CC(c1ccc([C@H]2COc3ccccc3O2)cc1)N1CCC(C(=O)O)CC1] | 1-(1-{4-[(2S)-2,3-dihydro-1,4-benzodioxin-2-yl]phenyl}ethyl)piperidine-4-carboxylic acid |
| 228 | 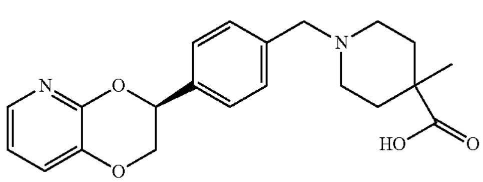 [SMILES: CC1(C(=O)O)CCN(Cc2ccc([C@H]3COc4cccnc4O3)cc2)CC1] | 1-{4-[(3S)-2,3-dihydro[1,4]dioxino[2,3-b]pyridin-3-yl]benzyl}-4-methylpiperidine-4-carboxylic acid |

TABLE 1-continued

Exemplary compounds of the invention.

| Compound No. | Structure | Name |
|---|---|---|
| 229 | 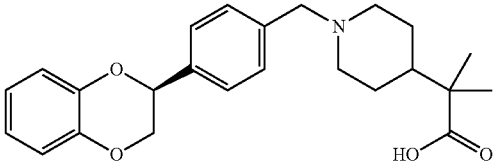 [SMILES: CC(C)(C(=O)O)C1CCN(Cc2ccc([C@H]3COc4ccccc4O3)cc2)CC1] | 2-(1-{4-[(2S)-2,3-dihydro-1,4-benzodioxin-2-yl]benzyl}piperidin-4-yl)-2-methylpropanoic acid |
| 230 | 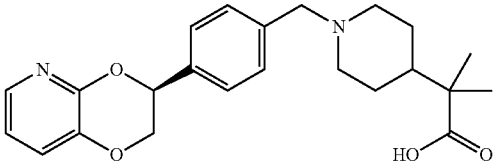 [SMILES: CC(C)(C(=O)O)C1CCN(Cc2ccc([C@H]3COc4cccnc4O3)cc2)CC1] | 2-(1-{4-[(3S)-2,3-dihydro[1,4]dioxino[2,3-b]pyridin-3-yl]benzyl}piperidin-4-yl)-2-methylpropanoic acid |
| 231 | 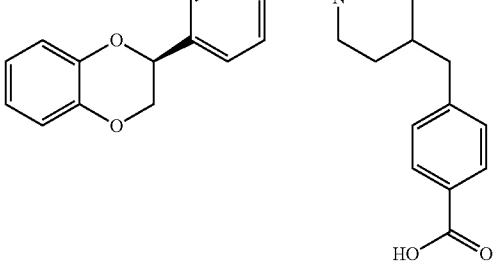 | 4-[(1-{4-[(2S)-2,3-dihydro-1,4-benzodioxin-2-yl]benzyl}piperidin-4-yl)methyl]benzoic acid |
| 232 | 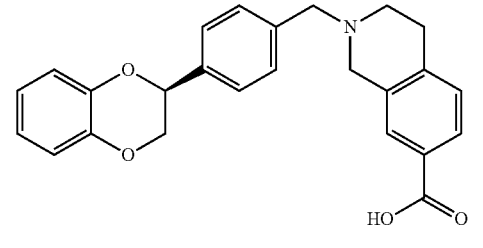 [SMILES: O=C(O)c1ccc2c(c1)CN(Cc1ccc([C@H]3COc4ccccc4O3)cc1)CC2] | 2-{4-[(2S)-2,3-dihydro-1,4-benzodioxin-2-yl]benzyl}-1,2,3,4-tetrahydroisoquinoline-7-carboxylic acid |
| 233 | 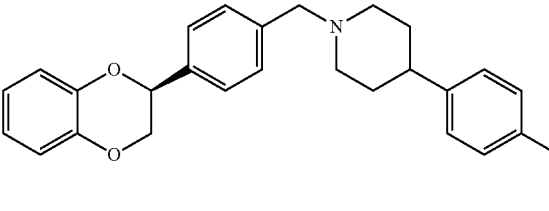 | 4-(1-(4-[(2S)-2,3-dihydro-1,4-benzodioxin-2-yl]benzyl}piperidin-4-yl)benzoic acid |
| 234 | 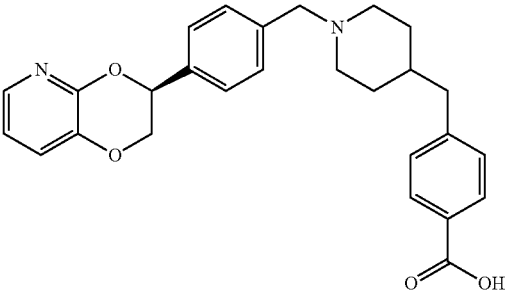 [SMILES: O=C(O)c1ccc(CC2CCN(Cc3ccc([C@H]4COc5cccnc5O4)cc3)CC2)cc1] | 4-[(1-{4-[(3S)-2,3-dihydro[1,4]dioxino[2,3-b]pyridin-3-yl]benzyl}piperidin-4-yl)methyl]benzoic acid |

TABLE 1-continued

Exemplary compounds of the invention.

| Compound No. | Structure | Name |
|---|---|---|
| 235 | 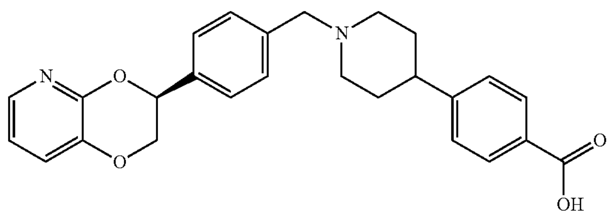 [SMILES: O=C(O)c1ccc(C2CCN(Cc3ccc([C@H]4COc5cccnc5O4)cc3)CC2)cc1] | 4-(1-{4-[(3S)-2,3-dihydro[1,4]dioxino[2,3-b]pyridin-3-yl]benzyl}piperidin-4-yl)benzoic acid |
| 236 | 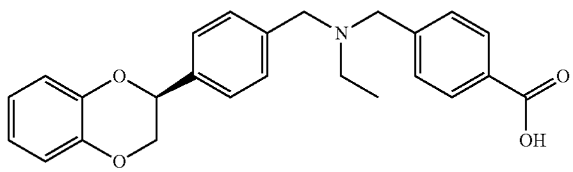 [SMILES: CCN(Cc1ccc(C(=O)O)cc1)Cc1ccc([C@H]2COc3ccccc3O2)cc1] | 4-{[{4-[(2S)-2,3-dihydro-1,4-benzodioxin-2-yl]benzyl}(ethyl)amino]methyl}benzoic acid |
| 237 | 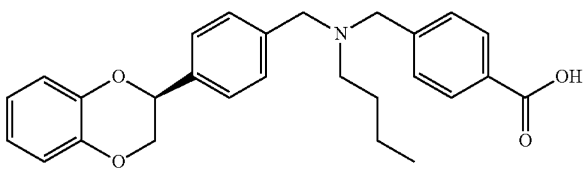 [SMILES: CCCCN(Cc1ccc(C(=O)O)cc1)Cc1ccc([C@H]2COc3ccccc3O2)cc1] | 4-[(butyl{4-[(2S)-2,3-dihydro-1,4-benzodioxin-2-yl]benzyl]amino)methyl[benzoic acid |
| 238 | 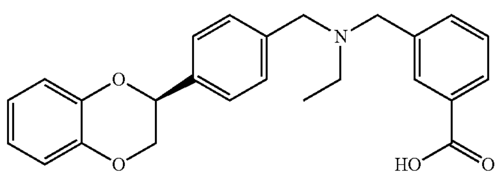 [SMILES: CCN(Cc1ccc([C@H]2COc3ccccc3O2)cc1)Cc1cccc(C(=O)O)c1] | 3-{[{4-[(2S)-2,3-dihydro-1,4-benzodioxin-2-yl]benzyl}(ethyl)amino]methyl}benzoic acid |
| 239 | 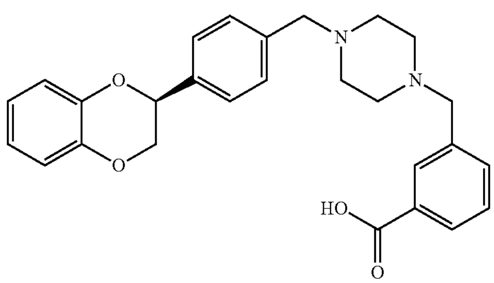 [SMILES: O=C(O)c1cccc(CN2CCN(Cc3ccc([C@H]4COc5ccccc5O4)cc3)CC2)c1] | 3-[(4-(4-[(2S)-2,3-dihydro-1,4-benzodioxin-2-yl]benzyl)piperazin-1-yl)methyl]benzoic acid |

In one embodiment, the invention relates to any of the compounds depicted in Table 1, and pharmaceutically acceptable salts thereof.

In another embodiment, the invention relates to a compound selected from the group consisting of:
4-(1-{4-[(2S)-2,3-dihydro-1,4-benzodioxin-2-yl]benzyl}piperidin-4-yl)butanoic acid;
4-(1-{4-[(3S)-2,3-dihydro[1,4]dioxino[2,3-b]pyridin-3-yl]benzyl}piperidin-4-yl)benzoic acid;
(3S)-3-{4-[(1s,4s)-7-azabicyclo[2.2.1]hept-7-ylmethyl]phenyl}-2,3-dihydro[1,4]dioxino[2,3-b]pyridine;
N-(1-{4-[(3S)-2,3-dihydro[1,4]dioxino[2,3-b]pyridin-3-yl]benzyl}piperidin-4-yl)methanesulfonamide;
(3S)-3-[4-(azepan-1-ylmethyl)phenyl]-2,3-dihydro[1,4]dioxino[2,3-b]pyridine;
1-{4-[(2S)-2,3-dihydro-1,4-benzodioxin-2-yl]benzyl}-2-methylpiperidine;
7-{4-[(2S)-2,3-dihydro-1,4-benzodioxin-2-yl]benzyl}-1,7-diazaspiro[4.4]nonane-1-carboxamide;
7-{4-[(3S)-2,3-dihydro[1,4]dioxino[2,3-b]pyridin-3-yl]benzyl}-1,7-diazaspiro[4.4]nonan-2-one;
1-{4-[(2S)-2,3-dihydro-1,4-benzodioxin-2-yl]benzyl}piperidine-4-carboxylic acid;
(1-{4-[(2S)-2,3-dihydro-1,4-benzodioxin-2-yl]benzyl}piperidin-4-yl)(morpholin-4-yl)methanone;
8-{4-[(3S)-2,3-dihydro[1,4]dioxino[2,3-b]pyridin-3-yl]benzyl}-1,3,8-triazaspiro[4.5]decane-2,4-dione;
(3S)-3-{4-[(3-methoxypiperidin-1-yl)methyl]phenyl}-2,3-dihydro[1,4]dioxino{2,3-b}pyridine;
N-(1-{4-[(2S)-2,3-dihydro-1,4-benzodioxin-2-yl]benzyl}pyrrolidin-3-yl)-N-methylacetamide;
1-{4-[(2S)-2,3-dihydro-1,4-benzodioxin-2-yl]benzyl}-4-(1,1-dioxido-1,2-thiazolidin-2-yl)piperidine;
(3R)-1-{4-[(3S)-2,3-dihydro[1,4]dioxino[2,3-b]pyridin-3-yl]benzyl}pyrrolidin-3-ol;

N-(1-{4-[(3S)-2,3-dihydro[1,4]dioxino[2,3-b]pyridin-3-yl]benzyl}piperidin-4-yl)-2-hydroxyacetamide;
4-{(1-{4-[(3S)-2,3-dihydro[1,4]dioxino[2,3-b]pyridin-3-yl]benzyl}piperidin-4-yl)methyl}benzoic acid;
(1-{4-[(3S)-2,3-dihydro[1,4]dioxino[2,3-b]pyridin-3-yl]benzyl}piperidin-4-yl)(morpholin-4-yl)methanone;
(3S)-3-[4-(morpholin-4-ylmethyl)phenyl]-2,3-dihydro[1,4]dioxino[2,3-b]pyridine;
8-{4-[(2S)-2,3-dihydro-1,4-benzodioxin-2-yl]benzyl}-2,8-diazaspiro[4.5]decan-1-one;
1-{4-[(3S)-2,3-dihydro[1,4]dioxino[2,3-b]pyridin-3-yl]benzyl}piperidine-4-carbonitrile;
1-{4-[(2S)-2,3-dihydro-1,4-benzodioxin-2-yl]benzyl}-N-methylpiperidine-4-carboxamide;
8-{4-[(3S)-2,3-dihydro[1,4]dioxino[2,3-b]pyridin-3-yl]benzyl}-2,8-diazaspiro[4.5]decan-1-one;
N-(1-{4-[(3S)-2,3-dihydro[1,4]dioxino[2,3-b]pyridin-3-yl]benzyl}piperidin-4-yl)-2-hydroxy-2-methylpropanamide;
N-(1-{4-[(3S)-2,3-dihydro[1,4]dioxino[2,3-b]pyridin-3-yl]benzyl}piperidin-4-yl)-1-hydroxycyclopropanecarboxamide;
N-{4-[(2S)-2,3-dihydro-1,4-benzodioxin-2-yl]benzyl}-N-ethylcyclopentanamine;
1-{4-[(3S)-2,3-dihydro[1,4]dioxino[2,3-b]pyridin-3-yl]benzyl}-N-methylpiperidine-4-carboxamide;
N-{4-[(3S)-2,3-dihydro[1,4]dioxino[2,3-b]pyridin-3-yl]benzyl}-N-methylcyclopentanamine;
1-{(1-{4-[(3S)-2,3-dihydro[1,4]dioxino[2,3-b]pyridin-3-yl]benzyl}piperidin-3-yl)methyl}pyrrolidin-2-one;
1-{4-[(2S)-2,3-dihydro-1,4-benzodioxin-2-yl]benzyl}-2-methylpyrrolidine;
N-{4-[(3S)-2,3-dihydro[1,4]dioxino[2,3-b]pyridin-3-yl]benzyl}-2-methyl-1-(pyrrolidin-1-yl)propan-2-amine;
N-cyclohexyl-N-{4-[(2S)-2,3-dihydro-1,4-benzodioxin-2-yl]benzyl}-N',N'-dimethylethane-1,2-diamine;
N-(1-{4-[(3S)-2,3-dihydro[1,4]dioxino[2,3-b]pyridin-3-yl]benzyl}piperidin-4-yl)acetamide;
N-{4-[(3S)-2,3-dihydro[1,4]dioxino[2,3-b]pyridin-3-yl]benzyl}-N-methyl-2-(pyridin-2-yl)ethanamine;
(3S)-3-[4-(pyrrolidin-1-ylmethyl)phenyl]-2,3-dihydro[1,4]dioxino[2,3-b]pyridine;
1-{4-[(3S)-2,3-dihydro[1,4]dioxino[2,3-b]pyridin-3-yl]benzyl}piperidine-3-carboxamide;
1-{4-[(3S)-2,3-dihydro[1,4]dioxino[2,3-b]pyridin-3-yl]benzyl}piperidine-4-carboxamide;
N-(1-{4-[(2S)-2,3-dihydro-1,4-benzodioxin-2-yl]benzyl}pyrrolidin-3-yl)acetamide;
1-{4-[(3S)-2,3-dihydro[1,4]dioxino[2,3-b]pyridin-3-yl]benzyl}-N-(2-hydroxyethyl)piperidine-4-carboxamide;
(3S)-3-[4-(1,4-oxazepan-4-ylmethyl)phenyl]-2,3-dihydro[1,4]dioxino[2,3-b]pyridine;
1-{4-[(2S)-2,3-dihydro-1,4-benzodioxin-2-yl]benzyl}-N-(2-hydroxyethyl)piperidine-4-carboxamide;
4-(1-{4-[(2S)-2,3-dihydro-1,4-benzodioxin-2-yl]benzyl}piperidin-4-yl)benzoic acid;
1-(1-{4-[(2S)-2,3-dihydro-1,4-benzodioxin-2-yl]benzyl}piperidin-4-yl)urea;
7-{4-[(2S)-2,3-dihydro-1,4-benzodioxin-2-yl]benzyl}-1,7-diazaspiro[4.4]nonan-2-one;
8-{4-[(3S)-2,3-dihydro[1,4]dioxino[2,3-b]pyridin-3-yl]benzyl}-2-methyl-2,8-diazaspiro[4.5]decan-1-one;
1-{4-[(3S)-2,3-dihydro[1,4]dioxino[2,3-b]pyridin-3-yl]benzyl}piperidin-4-ol;
N-(1-{4-[(2S)-2,3-dihydro-1,4-benzodioxin-2-yl]benzyl}piperidin-4-yl)methanesulfonamide;
3-(1-[4-{(3S)-2,3-dihydro[1,4]dioxino[2,3-b]pyridin-3-yl]benzyl}piperidin-4-yl)propan-1-ol;
(3S)-3-{4-[(4-methylpiperidin-1-yl)methyl]phenyl}-2,3-dihydro[1,4]dioxino{2,3-b}pyridine;
N-{4-[(3S)-2,3-dihydro[1,4]dioxino[2,3-b]pyridin-3-yl]benzyl}-N-ethylethanamine;
N-{4-[(3S)-2,3-dihydro[1,4]dioxino[2,3-b]pyridin-3-yl]benzyl}-1-(methylsulfonyl)piperidin-4-amine;
(3S)-3-{4-[(4-fluoropiperidin-1-yl)methyl]phenyl}-2,3-dihydro[1,4]dioxino {2,3-b}pyridine;
1-(4-{4-[(3S)-2,3-dihydro[1,4]dioxino[2,3-b]pyridin-3-yl]benzyl}-1,4-diazepan-1-yl)ethanone;
[(3R)-1-{4-[(2S)-2,3-dihydro-1,4-benzodioxin-2-yl]benzyl}piperidin-3-yl]acetic acid;
(1-{4-[(3S)-2,3-dihydro[1,4]dioxino[2,3-b]pyridin-3-yl]benzyl}piperidin-4-yl)-methanol;
4-[(1-{4-[(2S)-2,3-dihydro-1,4-benzodioxin-2-yl]benzyl}piperidin-4-yl)methyl]benzoic acid;
(3S)-3-{4-[(4-methyl-1,4-diazepan-1-yl)methyl]phenyl}-2,3-dihydro[1,4]dioxino {2,3-b}pyridine;
(3S)-3-{4-[(3-methoxypyrrolidin-1-yl)methyl]phenyl}-2,3-dihydro[1,4]dioxino {2,3-b}pyridine; and
N-{4-[(2S)-2,3-dihydro-1,4-benzodioxin-2-yl]benzyl}-N,2-dimethylpropan-2-amine; or a pharmaceutically salt thereof of each of the foregoing.

In another embodiment, the invention relates to a compound selected from the group consisting of:
(3S)-3-[4-(azepan-1-ylmethyl)phenyl]-2,3-dihydro[1,4]dioxino[2,3-b]pyridine;
N-{4-[(3S)-2,3-dihydro[1,4]dioxino[2,3-b]pyridin-3-yl]benzyl}-N-methylcyclopentanamine;
N-(1-{4-[(3S)-2,3-dihydro[1,4]dioxino[2,3-b]pyridin-3-yl]benzyl}-piperidin-4-yl)methanesulfonamide;
(3S)-3-{4-[(3-methoxypiperidin-1-yl)methyl]phenyl}-2,3-dihydro[1,4]dioxino{2,3-b}pyridine;
(3S)-3-{4-[(4-methylpiperidin-1-yl)methyl]phenyl}-2,3-dihydro[1,4]dioxino{2,3-b}pyridine;
N-(1-{4-[(3S)-2,3-dihydro[1,4]dioxino[2,3-b]pyridin-3-yl]benzyl}piperidin-4-yl)acetamide;
(3S)-3-{4-[(1s,4s)-7-azabicyclo[2.2.1]hept-7-ylmethyl]phenyl}-2,3-dihydro[1,4]dioxino[2,3-b]pyridine;
(3S)-3-[4-(pyrrolidin-1-ylmethyl)phenyl]-2,3-dihydro[1,4]dioxino[2,3-b]pyridine;
N-{4-[(3S)-2,3-dihydro[1,4]dioxino[2,3-b]pyridin-3-yl]benzyl}-N-ethylethanamine;
N-(1-{4-[(2S)-2,3-dihydro-1,4-benzodioxin-2-yl]benzyl}pyrrolidin-3-yl)-N-methylacetamide;
N-{4-[(3S)-2,3-dihydro[1,4]dioxino[2,3-b]pyridin-3-yl]benzyl}-2-methyl-1-(pyrrolidin-1-yl)propan-2-amine;
1-{4-[(3S)-2,3-dihydro[1,4]dioxino[2,3-b]pyridin-3-yl]benzyl}piperidin-4-ol;
8-{4-[(3S)-2,3-dihydro[1,4]dioxino[2,3-b]pyridin-3-yl]benzyl}-2,8-diazaspiro[4.5]decan-1-one;
(1-{4-[(3S)-2,3-dihydro[1,4]dioxino[2,3-b]pyridin-3-yl]benzyl}piperidin-4-yl)(morpholin-4-yl)methanone;
N-(1-{4-[(2S)-2,3-dihydro-1,4-benzodioxin-2-yl]benzyl}pyrrolidin-3-yl)acetamide;
1-{4-[(3S)-2,3-dihydro[1,4]dioxino[2,3-b]pyridin-3-yl]benzyl}-N-methylpiperidine-4-carboxamide;
7-{4-[(3S)-2,3-dihydro[1,4]dioxino[2,3-b]pyridin-3-yl]benzyl}-1,7-diazaspiro[4.4]nonan-2-one;
(3S)-3-[4-(1,4-oxazepan-4-ylmethyl)phenyl]-2,3-dihydro[1,4]dioxino[2,3-b]pyridine;
3-(1-{4-[(3S)-2,3-dihydro[1,4]dioxino[2,3-b]pyridin-3-yl]benzyl}piperidin-4-yl)propan-1-ol;
8-{4-[(3S)-2,3-dihydro[1,4]dioxino[2,3-b]pyridin-3-yl]benzyl}-2-methyl-2,8-diazaspiro[4.5]decan-1-one;
(3S)-3-{4-[(4-methyl-1,4-diazepan-1-yl)-methyl]phenyl}-2,3-dihydro[1,4]dioxino {2,3-b}pyridine;

4-(1-{4-[(2S)-2,3-dihydro-1,4-benzodioxin-2-yl]
    benzyl}piperidin-4-yl)benzoic acid;
(3R)-1-{4-[(3S)-2,3-dihydro[1,4]dioxino[2,3-b]pyridin-3-
    yl]benzyl}pyrrolidin-3-ol;
1-(4-{4-[(3S)-2,3-dihydro[1,4]dioxino[2,3-b]pyridin-3-yl]
    benzyl}-1,4-diazepan-1-yl)ethanone;
1-{4-[(3S)-2,3-dihydro[1,4]dioxino[2,3-b]pyridin-3-yl]
    benzyl}piperidine-4-carbonitrile;
N-(1-{4-[(3S)-2,3-dihydro[1,4]dioxino[2,3-b]pyridin-3-yl]
    benzyl}piperidin-4-yl)-2-hydroxy-2-methylpropanamide;
1-{4-[(3S)-2,3-dihydro[1,4]dioxino[2,3-b]pyridin-3-yl]
    benzyl}piperidine-3-carboxamide;
(1-{4-[(3S)-2,3-dihydro[1,4]dioxino[2,3-b]pyridin-3-yl]
    benzyl}piperidin-4-yl)methanol;
8-{4-[(3S)-2,3-dihydro[1,4]dioxino[2,3-b]pyridin-3-yl]benzyl}-1,3,8-triazaspiro[4.5]decane-2,4-dione;
N-(1-{4-[(3S)-2,3-dihydro[1,4]dioxino[2,3-b]pyridin-3-yl]
    benzyl}piperidin-4-yl)-1-hydroxycyclopropanecarboxamide;
1-{4-[(2S)-2,3-dihydro-1,4-benzodioxin-2-yl]benzyl}-N-
    (2-hydroxyethyl)piperidine-4-carboxamide;
N-{4-[(3S)-2,3-dihydro[1,4]dioxino[2,3-b]pyridin-3-yl]
    benzyl}-1-(methylsulfonyl)piperidin-4-amine;
1-{4-[(3S)-2,3-dihydro[1,4]dioxino[2,3-b]pyridin-3-yl]
    benzyl}piperidine-4-carboxamide;
4-(1-{4-[(3S)-2,3-dihydro[1,4]dioxino[2,3-b]pyridin-3-yl]
    benzyl}piperidin-4-yl)benzoic acid;
1-{4-[(2S)-2,3-dihydro-1,4-benzodioxin-2-yl]benzyl}-2-
    methylpyrrolidine;
1-{(1-{4-[(3S)-2,3-dihydro[1,4]dioxino[2,3-b]pyridin-3-yl]
    benzyl}piperidin-3-yl)methyl}pyrrolidin-2-one;
7-{4-[(2S)-2,3-dihydro-1,4-benzodioxin-2-yl]benzyl}-1,7-
    diazaspiro[4.4]nonan-2-one;
1-(1-{4-[(2S)-2,3-dihydro-1,4-benzodioxin-2-yl]
    benzyl}piperidin-4-yl)urea;
N-{4-[(2S)-2,3-dihydro-1,4-benzodioxin-2-yl]benzyl}-N-
    ethylcyclopentanamine;
N-{4-[(3S)-2,3-dihydro[1,4]dioxino[2,3-b]pyridin-3-yl]
    benzyl}-N-methyl-2-(pyridin-2-yl)ethanamine;
1-{4-[(2S)-2,3-dihydro-1,4-benzodioxin-2-yl]benzyl}-2-
    methylpiperidine;
1-{4-[(2S)-2,3-dihydro-1,4-benzodioxin-2-yl]
    benzyl}piperidine-4-carboxylic acid;
4-{(1-{4-[(3S)-2,3-dihydro[1,4]dioxino[2,3-b]pyridin-3-yl]
    benzyl}piperidin-4-yl)methyl}benzoic acid;
(3S)-3-[4-(morpholin-4-ylmethyl)phenyl]-2,3-dihydro[1,4]
    dioxino[2,3-b]pyridine;
(3S)-3-{4-[(4-fluoropiperidin-1-yl)methyl]phenyl}-2,3-dihydro[1,4]dioxino{2,3-b}pyridine;
(1-{4-[(2S)-2,3-dihydro-1,4-benzodioxin-2-yl]
    benzyl}piperidin-4-yl)(morpholin-4-yl)methanone;
8-{4-[(2S)-2,3-dihydro-1,4-benzodioxin-2-yl]benzyl}-2,8-
    diazaspiro[4.5]decan-1-one;
N-(1-{4-[(3S)-2,3-dihydro[1,4]dioxino[2,3-b]pyridin-3-yl]
    benzyl}piperidin-4-yl)-2-hydroxyacetamide;
4-[(1-{4-[(2S)-2,3-dihydro-1,4-benzodioxin-2-yl]
    benzyl}piperidin-4-yl)methyl]benzoic acid;
N-(1-{4-[(2S)-2,3-dihydro-1,4-benzodioxin-2-yl]
    benzyl}piperidin-4-yl)methanesulfonamide;
1-{4-[(2S)-2,3-dihydro-1,4-benzodioxin-2-yl]benzyl}-N-
    methylpiperidine-4-carboxamide;
4-(1-{4-[(2S)-2,3-dihydro-1,4-benzodioxin-2-yl]
    benzyl}piperidin-4-yl)butanoic acid;
7-{4-[(2S)-2,3-dihydro-1,4-benzodioxin-2-yl]benzyl}-1,7-
    diazaspiro[4.4]nonane-1-carboxamide;
N-cyclohexyl-N-{4-[(2S)-2,3-dihydro-1,4-benzodioxin-2-
    yl]benzyl}-N',N'-dimethylethane-1,2-diamine;
[(3R)-1-{4-[(2S)-2,3-dihydro-1,4-benzodioxin-2-yl]
    benzyl}piperidin-3-yl]acetic acid;
1-{4-[(2S)-2,3-dihydro-1,4-benzodioxin-2-yl]benzyl}-4-(1,
    1-dioxido-1,2-thiazolidin-2-yl)piperidine; and
1-{4-[(3S)-2,3-dihydro[1,4]dioxino[2,3-b]pyridin-3-yl]benzyl}-N-(2-hydroxyethyl)piperidine-4-carboxamide; or
a pharmaceutically acceptable salt thereof of each of the foregoing.

In another embodiment, the invention relates a pharmaceutical composition comprising one or more compounds of formula (I) as defined in any of the embodiments above, or a pharmaceutically acceptable salt thereof, and a pharmaceutically acceptable carrier or excipient.

All terms as used herein in this specification, unless otherwise stated, shall be understood in their ordinary meaning as known in the art. Other more specific definitions are as follows:

The term "$(C_1-C_6)$alkyl" refers to branched and unbranched alkyl groups having from 1 to 6 carbon atoms. Examples of —$(C_1-C_6)$alkyls include methyl, ethyl, n-propyl, isopropyl, n-butyl, sec-butyl, isobutyl, tert-butyl, n-pentane, iso-pentyl, neopentyl, n-hexane, iso-hexanes (e.g., 2-methylpentyl, 3-methylpentyl, 2,3-dimethylbutyl, and 2,2-dimethylbutyl). It will be understood that any chemically feasible carbon atom of the $(C_1-C_6)$alkyl group can be the point of attachment to another group or moiety.

The term "$(C_3-C_6)$cycloalkyl" refers to a nonaromatic 3- to 6-membered monocyclic carbocyclic radical. Examples of "$(C_3-C_6)$cycloalkyls" include cyclopropyl, cyclobutyl, cyclohexyl, cyclopentyl and cyclohexyl.

As used herein, the term "$(C_6-C_{10})$aryl" refers to an aromatic hydrocarbon rings containing from six to ten carbon ring and includes monocyclic rings and bicyclic rings where at least one of the rings is aromatic. Non-limiting examples of $C_6$-10 aryls include phenyl, indanyl, indenyl, benzocyclobutanyl, dihydronaphthyl, tetrahydronaphthyl, naphthyl, benzocycloheptanyl and benzocycloheptenyl.

As used herein, the term "4 to 11-membered heterocycle" includes stable nonaromatic 4 to 8-membered monocyclic heterocyclic radical or a stable nonaromatic 6 to 11-membered fused bicyclic, bridged bicyclic or spirocyclic heterocyclic radical. The 4 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4- to 8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

As used herein, the term "5 to 11-membered heteroaryl" includes aromatic 5 to 6-membered monocyclic heteroaryls and aromatic 7 to 11-membered heteroaryl bicyclic rings where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic rings include benzimidazolyl, 1,3-dihydrobenzoimidazol-2-one, quinolinyl, dihydro-2H-quinolinyl, isoquinolinyl, quinazolinyl, indazolyl, thieno[2,3-d]pyrimidinyl, indolyl, isoindolyl, indazolyl, benzotriazolyl, benzofuranyl, benzopyranyl, benzodioxolyl, benzoxazolyl, benzothiazolyl, pyrrolo[2,3-b]pyridinyl, and imidazo[4,5-b]pyridinyl.

It will be understood that when a heterocyclyl or heteroaryl contains a S ring atom, such S ring atom can be present in the ring in its divalent, tetravalent, or hexavalent form, i.e., —S—, S(O)— or —S(O)$_2$—.

Each aryl or heteroaryl unless otherwise specified includes it's partially or fully hydrogenated derivatives. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

The term "heteroatom" as used herein shall be understood to mean atoms other than carbon such as O, N, and S The term "halo" or "halogen" refers to fluoro, chloro, bromo or iodo.

The symbol

means point of attachment of a group R to a moiety.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms to or internal carbon atoms within a branched or unbranched carbon chain. Such groups can be substituted as herein above described by groups such as oxo to result in definitions such as but not limited to: alkoxycarbonyl, acyl, amido and thioxo.

For all compounds disclosed in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g. $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

The compounds of the invention are only those which are contemplated to be 'chemically stable' as will be appreciated by those skilled in the art. For example, a compound which would have a 'dangling valency', or a 'carbanion' is not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C$_1$-C$_4$)alkyl)$^{4+}$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect

D. Assessment of Biological Properties

The compounds of the invention are assessed for the ability to interact with human LTA4 hydrolase in an enzymatic assay that measures the ability of the enzyme to cleave the peptide bond of arginyl-aminomethylcoumarin (Arg-AMC). LTA4H Enzyme (1 nM final), Arg-AMC substrate (50 µM final), and compound are combined in a reaction buffer (50 mM Tris-HCl (pH 7.5), 100 mM KCl, 0.5% bovine serum albumin) at room temperature for 1 h. The formation of product is assessed by measuring the fluorescence of aminomethylcoumarin product (excitation wavelength 380 nm/emission wavelength 460 nm). In general, the preferred potency range (IC50) of compounds in the $LTA_4H$ Enzyme assay is between 0.1 nM to 10 μM, the more preferred potency range is 0.1 nM to 0.1 μM, and the most preferred potency range is 0.1 nM to 10 nM.

TABLE 2

$IC_{50}$ values of LTA4H Enzyme assay.

| Example | $IC_{50}$ (nM) |
| --- | --- |
| 1 | 0.12 |
| 2 | 2.45 |
| 3 | 2.57 |
| 4 | 0.74 |
| 5 | 2.96 |
| 6 | 0.46 |
| 7 | 2.79 |
| 8 | 0.32 |
| 9 | 1.49 |
| 10 | 0.75 |
| 11 | 2.95 |
| 12 | 10.19 |
| 13 | 0.36 |
| 14 | 2.32 |
| 15 | 0.77 |
| 16 | 1.14 |
| 17 | 0.73 |
| 18 | 1.14 |
| 19 | 0.73 |
| 20 | 1.30 |
| 21 | 4.43 |
| 22 | 200.00 |
| 23 | 5.20 |
| 24 | 5.90 |
| 25 | 0.76 |
| 26 | 0.43 |
| 27 | 1.20 |
| 28 | 3.40 |
| 29 | 2.04 |
| 30 | 1.77 |
| 31 | 1.54 |
| 32 | 1.80 |
| 33 | 3.19 |
| 34 | 1.89 |
| 35 | 0.26 |
| 36 | 4.45 |
| 37 | 1.05 |
| 38 | 1.14 |
| 39 | 2.14 |
| 40 | 0.82 |
| 41 | 3.71 |
| 42 | 0.69 |
| 43 | 4.42 |
| 44 | 0.69 |
| 45 | 0.90 |
| 46 | 24.82 |
| 47 | 1.73 |
| 48 | 0.16 |
| 49 | 0.32 |
| 50 | 0.60 |
| 51 | 0.82 |
| 52 | 0.75 |
| 53 | 0.42 |
| 54 | 5.93 |
| 55 | 3.63 |
| 56 | 6.08 |
| 57 | 13.66 |
| 58 | 1.36 |
| 59 | 89.24 |
| 60 | 31.02 |
| 61 | 0.60 |
| 62 | 1.79 |
| 63 | 7.90 |
| 64 | 0.83 |
| 65 | 1.15 |
| 66 | 1.79 |
| 67 | 0.61 |
| 68 | 0.10 |
| 69 | 0.60 |
| 70 | 0.57 |
| 71 | 1.88 |
| 72 | 1.80 |
| 73 | 3.65 |
| 74 | 1.00 |
| 75 | 4.51 |
| 76 | 1.90 |
| 77 | 0.18 |
| 78 | 1.40 |
| 79 | 0.51 |
| 80 | 0.71 |
| 81 | 0.31 |
| 82 | 0.20 |
| 83 | 0.13 |
| 84 | 2.69 |
| 85 | 0.45 |
| 86 | 0.92 |
| 87 | 0.69 |
| 88 | 0.54 |
| 89 | 1.40 |
| 90 | 0.77 |
| 91 | 0.54 |
| 92 | 35.99 |
| 93 | 1.98 |
| 94 | 0.45 |
| 95 | 0.49 |
| 96 | 0.22 |
| 97 | 2.87 |
| 98 | 0.61 |
| 99 | 0.37 |
| 100 | 2.36 |
| 101 | 1.90 |
| 102 | 2.68 |
| 103 | 2.40 |
| 104 | 0.18 |
| 105 | 0.51 |
| 106 | 0.46 |
| 107 | 1.35 |
| 108 | 0.87 |
| 109 | 0.17 |
| 110 | 2.15 |
| 111 | 2.25 |
| 112 | 1.07 |
| 113 | 2.49 |
| 114 | 0.77 |
| 115 | 3.03 |
| 116 | 0.82 |
| 117 | 0.23 |
| 118 | 0.45 |
| 119 | 0.10 |
| 120 | 0.51 |
| 121 | 0.37 |
| 122 | 0.91 |
| 123 | 0.73 |
| 124 | 2.45 |
| 125 | 0.16 |
| 126 | 0.18 |
| 127 | 0.12 |
| 128 | 0.65 |
| 129 | 0.23 |
| 130 | 0.51 |
| 131 | 1.73 |
| 132 | 0.91 |
| 133 | 1.75 |
| 134 | 0.47 |
| 135 | 0.47 |
| 136 | 0.19 |
| 137 | 0.26 |
| 138 | 0.18 |
| 139 | 0.10 |
| 140 | 0.38 |
| 141 | 0.26 |

TABLE 2-continued

IC$_{50}$ values of LTA4H Enzyme assay.

| Example | IC$_{50}$ (nM) |
|---|---|
| 142 | 0.17 |
| 143 | 0.30 |
| 144 | 0.14 |
| 145 | 0.09 |
| 146 | 0.29 |
| 147 | 0.35 |
| 148 | 0.28 |
| 149 | 0.24 |
| 150 | 0.21 |
| 151 | 0.10 |
| 152 | 0.17 |
| 153 | 0.82 |
| 154 | 0.20 |
| 155 | 0.28 |
| 156 | 0.91 |
| 157 | 0.18 |
| 158 | 0.13 |
| 159 | 0.16 |
| 160 | 0.18 |
| 161 | 0.41 |
| 162 | 0.14 |
| 163 | 0.17 |
| 164 | 0.84 |
| 165 | 0.13 |
| 166 | 0.68 |
| 167 | 0.27 |
| 168 | 0.31 |
| 169 | 0.33 |
| 170 | 0.47 |
| 171 | 0.45 |
| 172 | 0.53 |
| 173 | 0.73 |
| 174 | 0.60 |
| 175 | 0.22 |
| 176 | 0.24 |
| 177 | 1.45 |
| 178 | 0.35 |
| 179 | 0.16 |
| 180 | 0.12 |
| 181 | 0.042 |
| 182 | 0.29 |
| 183 | 0.48 |
| 184 | 0.11 |
| 185 | 0.59 |
| 186 | 0.24 |
| 187 | 0.07 |
| 188 | 0.87 |
| 189 | 0.16 |
| 190 | 0.09 |
| 191 | 1.62 |
| 192 | 0.43 |
| 193 | 5.35 |
| 194 | 0.15 |
| 195 | 1.59 |
| 196 | 0.39 |
| 197 | 2.69 |
| 198 | 2.28 |
| 199 | 40.12 |
| 200 | 0.38 |
| 201 | 1.59 |
| 202 | 23.37 |
| 203 | 2.94 |
| 204 | 0.15 |
| 205 | 27.50 |
| 206 | 0.19 |
| 207 | 0.86 |
| 208 | 21.45 |
| 209 | 12.41 |
| 210 | 19.00 |
| 211 | 0.69 |
| 212 | 0.49 |
| 213 | 0.81 |
| 214 | 0.47 |
| 215 | 0.70 |
| 216 | 0.13 |
| 217 | 2.28 |
| 218 | 0.37 |
| 219 | 0.49 |
| 220 | 0.47 |
| 221 | 0.16 |
| 222 | 0.14 |
| 223 | 0.16 |
| 224 | 0.13 |
| 225 | 5.30 |
| 226 | 42.95 |
| 227 | 1.40 |
| 228 | 0.61 |
| 229 | 3.85 |
| 230 | 1.24 |
| 231 | 0.29 |
| 232 | 2.75 |
| 233 | 0.22 |
| 234 | 0.14 |
| 235 | 0.08 |
| 236 | 6.04 |
| 237 | 0.81 |
| 238 | 0.55 |
| 239 | 0.15 |

The compounds of the invention are additionally tested in a human whole blood (HWB) assay to determine their ability to inhibit the synthesis of LTB$_4$ in a cellular system. Compounds are combined with heparinized human whole blood and incubated for 15 minutes at 37° C. Calcimycin (20 µM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma LTB$_4$ concentrations are then measured using an antibody-based homogenous time-resolved fluorescence method (CisBio, Bedford, Mass.). In general, the preferred potency range (IC50) of compounds in the HWB assay is between 10 nM to 10 µM, the more preferred potency range is 10 nM to 1 µM, and the most preferred potency range is 10 nM to 100 nM. The potencies of representative compounds of the invention in the WHB assays are shown in Table 3.

TABLE 3

IC$_{50}$ values of LTB$_4$ production inhibition assay in human whole blood.

| Example | IC$_{50}$ (nM) |
|---|---|
| 139 | 13.18 |
| 142 | 24.37 |
| 190 | 26.03 |
| 158 | 27.50 |
| 137 | 27.64 |
| 160 | 27.98 |
| 145 | 28.39 |
| 126 | 32.30 |
| 141 | 32.81 |
| 140 | 33.44 |
| 83 | 33.49 |
| 157 | 35.00 |
| 186 | 36.46 |
| 168 | 38.99 |
| 125 | 39.18 |
| 175 | 72.56 |
| 173 | 72.75 |
| 109 | 75.52 |
| 138 | 76.03 |
| 68 | 80.65 |
| 81 | 80.74 |

TABLE 3-continued

IC$_{50}$ values of LTB$_4$ production inhibition assay in human whole blood.

| Example | IC$_{50}$ (nM) |
| --- | --- |
| 200 | 82.95 |
| 220 | 91.31 |
| 185 | 92.28 |
| 237 | 94.53 |
| 134 | 94.60 |
| 234 | 94.77 |
| 204 | 94.98 |
| 155 | 95.39 |
| 99 | 95.39 |
| 52 | 145.12 |
| 219 | 148.90 |
| 183 | 151.13 |
| 14 | 154.92 |
| 53 | 154.92 |
| 64 | 157.95 |
| 156 | 158.75 |
| 121 | 159.37 |
| 178 | 159.61 |
| 69 | 164.89 |
| 214 | 168.70 |
| 18 | 176.14 |
| 187 | 176.77 |
| 1 | 179.33 |
| 98 | 180.00 |
| 61 | 250.398 |
| 118 | 255.61 |
| 174 | 268.33 |
| 87 | 268.33 |
| 9 | 284.85 |
| 229 | 289.83 |
| 25 | 294.12 |
| 85 | 304.96 |
| 227 | 307.44 |
| 26 | 308.47 |
| 116 | 310.32 |
| 123 | 312.41 |
| 37 | 323.66 |
| 67 | 345.74 |
| 10 | 352.40 |

E. Treatment

Aspects of the methods of the inventions described herein include treatment of a subject with a benzodioxane compound of the invention described herein. An embodiment includes treatment of a human subject with one or more of the benzodioxane compounds of the invention described herein. One of skill in the art would recognize that methods of treatment of subjects with benzodioxane compounds of the invention are recognized in the art. By way of example, and not limitation, one embodiment of the methods of the inventions described herein is comprised of administering one or more of the benzodioxane compounds of the invention described herein to a subject for treatment and/or prevention of cognitive impairment and/or age-related dementia. The one or more benzodioxane compounds of the invention may be administered through one or more routes such as IP, IV, PO, and the like. Additionally, the benzodioxane compounds of the invention described herein may be administered one or more times per day, such as once per day, twice per day, thrice per day, four time per day, etc., and such doses may be administered chronically (e.g. greater that one month, greater than two months, greater than 3 to five months, greater than six months, greater than one year, etc.), or acutely for a shorter time span (e.g. shorter than one month).

For treatment of the above-described diseases and conditions, a therapeutically effective dose will generally be in the range from about 0.01 mg to about 100 mg/kg of body weight per dosage of a benzodioxane compound of the invention; preferably, from about 0.1 mg to about 20 mg/kg of body weight per dosage. For example, for administration to a 70 kg person, the dosage range would be from about 0.7 mg to about 7000 mg per dosage of a benzodioxane compound of the invention, preferably from about 7.0 mg to about 1400 mg per dosage. Some degree of routine dose optimization may be required to determine an optimal dosing level and pattern. The active ingredient may be administered from 1 to 6 times a day.

F. Administration

Aspects of the methods of the inventions described herein include treatment of a subject with a benzodioxane compound of the invention described herein. One of skill in the art would recognize that methods of treatment of subjects with small molecule inhibitors such as the benzodioxane compound of the invention described herein, are recognized in the art.

An embodiment of the invention includes treating a subject diagnosed with a cognitive or motor impairment, or neuroinflammation by administering to the subject an effective amount of one or more of the benzodioxane compounds of the invention described herein. Another embodiment of the invention includes administering the effective amount of one or more of the benzodioxane compounds of the invention described herein and subsequently monitoring the subject for improved cognitive or motor function, or a reduction in neuroinflammation or increase in neurogenesis. Another embodiment of the invention includes administering an effective amount of one or more of the benzodioxane compounds of the invention described herein and subsequently monitoring the subject for reduced blood levels of leukotriene B4 (LTB4) after one or more administrations of said one or more benzodioxane compounds of the invention. Another embodiment of the invention involves monitoring the subject for changes in blood levels of other chemical byproducts downstream of the LTA4H enzymatic pathway.

Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances, reverse the progression of the cognitive impairment, age-associated dementia, motor disfunction, or neuroinflammation.

When used as pharmaceuticals, the benzodioxane compounds of the invention are typically administered in the form of a pharmaceutical composition. Such compositions can be prepared using procedures well known in the pharmaceutical art and comprise at least one benzodioxane compound of the invention. The compounds of the invention may also be administered alone or in combination with adjuvants that enhance stability of the benzodioxane compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount but may be administered in lower amounts for diagnostic or other purposes.

Administration of the benzodioxane compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art.

As one of skill in the art would expect the forms of the benzodioxane compounds of the invention utilized in a particular pharmaceutical formulation will be selected (e.g., salts) that possess suitable physical characteristics (e.g., water solubility) that are required for the formulation to be efficacious.

G. Indications

The subject methods and compounds find use in treating, including preventing, aging-associated conditions, such as impairments in the cognitive ability of individuals, e.g., cognitive disorders, including (but not limited to) age-associated dementia, immunological conditions, cancer, and physical and functional decline. Individuals suffering from or at risk of developing an aging-associated cognitive impairment that will benefit from treatment with the subject compounds, e.g., by the methods disclosed herein, include individuals that are about 50 years old or older, e.g., 60 years old or older, 70 years old or older, 80 years old or older, 90 years old or older, and 100 years old or older, i.e., between the age of about 50 and 100, e.g., 50, 55, 60, 65, 70, 75, 80, 85, 90, 95 or about 100 years old, and are suffering from cognitive impairment associated with natural aging process, e.g., mild cognitive impairment (M.C.I.); and individuals that are about 50 years old or older, e.g., 60 years old or older, 70 years old or older, 80 years old or older, 90 years old or older, and usually no older than 100 years old, i.e., between the ages of about 50 and 90, e.g., 50, 55, 60, 65, 70, 75, 80, 85, 90, 95 or about 100 years old, that have not yet begun to show symptoms of cognitive impairment. Examples of cognitive impairments/indications that may be due to natural aging include the following:

1. Mild Cognitive Impairment (M.C.I.)

Mild cognitive impairment is a modest disruption of cognition that manifests as problems with memory or other mental functions such as planning, following instructions, or making decisions that have worsened over time while overall mental function and daily activities are not impaired. Thus, although significant neuronal death does not typically occur, neurons in the aging brain are vulnerable to sub-lethal age-related alterations in structure, synaptic integrity, and molecular processing at the synapse, all of which impair cognitive function. Individuals suffering from or at risk of developing an aging-associated cognitive impairment that will benefit from treatment with the subject compounds, e.g., by the methods disclosed herein, also include individuals of any age that are suffering from a cognitive impairment due to an aging-associated disorder; and individuals of any age that have been diagnosed with an aging-associated disorder that is typically accompanied by cognitive impairment, where the individual has not yet begun to present with symptoms of cognitive impairment. Examples of such aging-associated disorders include the following:

2. Alzheimer's Disease

Alzheimer's disease is a progressive, inexorable loss of cognitive function associated with an excessive number of senile plaques in the cerebral cortex and subcortical gray matter, which also contains b-amyloid and neurofibrillary tangles consisting of tau protein. The common form affects persons>60 yrs. old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus coeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

3. Parkinson's Disease

Parkinson's Disease (PD) is an idiopathic, slowly progressive, degenerative CNS disorder characterized by slow and decreased movement (bradykinesia), muscular rigidity, resting tremor (dystonia), muscle freezing, and postural instability. Originally considered primarily a motor disorder, PD is now recognized to also cause depression and emotional changes. PD also can affect cognition, behavior, sleep, autonomic function, and sensory function. The most common cognitive impairments include an impairment in attention and concentration, working memory, executive function, producing language, and visuospatial function. A characteristic of PD is symptoms related to reduced motor function usually precede those related to cognitive impairment, which aids in diagnosis of the disease.

In primary Parkinson's disease, the pigmented neurons of the substantia nigra, locus coeruleus, and other brain stem dopaminergic cell groups degenerate. The cause is not known. The loss of substantia nigra neurons, which project to the caudate nucleus and putamen, results in depletion of the neurotransmitter dopamine in these areas. Onset is generally after age 40, with increasing incidence in older age groups.

Parkinson's disease is newly diagnosed in about 60,000 Americans each year and currently affects approximately one million Americans. Even though PD is not fatal in itself, its complications are the fourteenth leading cause of death in the United States. At present, PD cannot be cured, and treatment is generally prescribed to control symptoms, with surgery prescribed in later, severe cases.

Treatment options for PD include administration of pharmaceuticals to help manage motor deficits. These options increase or substitute for the neurotransmitter, dopamine, of which PD patients have low brain concentrations. Such medications include: carbidopa/levodopa (which create more dopamine in the brain); apomorphine, pramipexolole, ropinirole, and rotingotine (dopamine agonists); selegiline and rasagiline (MAO-B inhibitors which prevent breakdown of dopamine); entacapone and tolcapone (Catechol-O-methyltransferase [COMT] inhibitors which make more levodopa available in the brain); benztropine and trihexyphenidyl (anticholinergics); and amantadine (controls tremor and stiffness). Exercise/physical therapy is also commonly prescribed to help maintain physical and mental function.

Current treatment options, however, treat the symptoms of PD, are not curative, and fail to prevent disease progression. Additionally, current medications tend to lose efficacy in late-stage PD. The most prescribed drug, levodopa, commonly results in adverse effects within 5 to 10 years after commencing the medication. These adverse effects can be severe and can result in motor fluctuations and unpredictable swings in motor control between doses as well as jerking/twitching (dyskinesia) which are difficult to manage and are even as disabling as PD's own symptoms. Thus, there remains a need for new therapies with new mechanisms of action which can either be administrated along or in combination with current PD medications.

4. Parkinsonism

Secondary parkinsonism (also referred to as atypical Parkinson's disease or Parkinson's plus) results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including nigrostriatal degeneration. Certain disorders like Progressive Supranuclear Palsy (PSP), Multiple System Atrophy (MSA), Corticobasal degeneration (CBD) and Dementia with Lewy Bodies (DLB) can exhibit Parkinsonism symptoms before the cardinal symptoms necessary to the specific diagnosis can be made, and thus may be labeled as "Parkinsonism."

5. Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. Symptoms are classified into three groups based on the functions of the frontal and temporal lobes affected:

Behavioral variant FTD (bvFTD), with symptoms include lethargy and aspontaneity on the one hand, and disinhibition on the other; progressive nonfluent aphasia (PNFA), in which a breakdown in speech fluency due to articulation difficulty, phonological and/or syntactic errors is observed but word comprehension is preserved; and semantic dementia (SD), in which patients remain fluent with normal phonology and syntax but have increasing difficulty with naming and word comprehension. Other cognitive symptoms common to all FTD patients include an impairment in executive function and ability to focus. Other cognitive abilities, including perception, spatial skills, memory and praxis typically remain intact. FTD can be diagnosed by observation of reveal frontal lobe and/or anterior temporal lobe atrophy in structural MRI scans.

A number of forms of FTD exist, any of which may be treated or prevented using the subject methods and compositions. For example, one form of frontotemporal dementia is Semantic Dementia (SD). SD is characterized by a loss of semantic memory in both the verbal and non verbal domains. SD patients often present with the complaint of word-finding difficulties. Clinical signs include fluent aphasia, anomia, impaired comprehension of word meaning, and associative visual agnosia (the inability to match semantically related pictures or objects). As the disease progresses, behavioral and personality changes are often seen similar to those seen in frontotemporal dementia although cases have been described of 'pure' semantic dementia with few late behavioral symptoms. Structural MRI imaging shows a characteristic pattern of atrophy in the temporal lobes (predominantly on the left), with inferior greater than superior involvement and anterior temporal lobe atrophy greater than posterior.

As another example, another form of frontotemporal dementia is Pick's disease (PiD, also PcD). A defining characteristic of the disease is build-up of tau proteins in neurons, accumulating into silver-staining, spherical aggregations known as "Pick bodies." Symptoms include loss of speech (aphasia) and dementia. Patients with orbitofrontal dysfunction can become aggressive and socially inappropriate. They may steal or demonstrate obsessive or repetitive stereotyped behaviors. Patients with dorsomedial or dorsolateral frontal dysfunction may demonstrate a lack of concern, apathy, or decreased spontaneity. Patients can demonstrate an absence of self-monitoring, abnormal self-awareness, and an inability to appreciate meaning. Patients with gray matter loss in the bilateral posterolateral orbitofrontal cortex and right anterior insula may demonstrate changes in eating behaviors, such as a pathologic sweet tooth. Patients with more focal gray matter loss in the anterolateral orbitofrontal cortex may develop hyperphagia. While some of the symptoms can initially be alleviated, the disease progresses, and patients often die within two to ten years.

6. Huntington's Disease

Huntington's disease (HD) is a hereditary progressive neurodegenerative disorder characterized by the development of emotional, behavioral, and psychiatric abnormalities; loss of intellectual or cognitive functioning; and movement abnormalities (motor disturbances). The classic signs of HD include the development of chorea—involuntary, rapid, irregular, jerky movements that may affect the face, arms, legs, or trunk—as well as cognitive decline including the gradual loss of thought processing and acquired intellectual abilities. There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

7. Amyotrophic Lateral Sclerosis

Amyotrophic lateral sclerosis (ALS) is a rapidly progressive, invariably fatal, neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 years; 50% die within 3 years of onset, 20% live 5 years, and 10% live 10 years.

Diagnostic features include onset during middle or late adult life and progressive, generalized motor involvement without sensory abnormalities. Nerve conduction velocities are normal until late in the disease. Recent studies have documented the presentation of cognitive impairments as well, particularly a reduction in immediate verbal memory, visual memory, language, and executive function.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Promoting the formation or new synapses or preventing synapse loss may maintain neuron function in these patients.

8. Multiple Sclerosis

Multiple Sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Common cognitive impairments include impairments in memory (acquiring, retaining, and retrieving new information), attention and concentration (particularly divided attention), information processing, executive functions, visuospatial functions, and verbal fluency. Common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

9. Glaucoma

Glaucoma is a common neurodegenerative disease that affects retinal ganglion cells (RGCs). Evidence supports the existence of compartmentalized degeneration programs in synapses and dendrites, including in RGCs. Recent evidence also indicates a correlation between cognitive impairment in older adults and glaucoma (Yochim B P, et al. Prevalence of cognitive impairment, depression, and anxiety symptoms among older adults with glaucoma. J Glaucoma. 2012; 21(4):250-254).

10. Myotonic Dystrophy

Myotonic dystrophy (DM) is an autosomal dominant multisystem disorder characterized by dystrophic muscle weakness and myotonia. The molecular defect is an expanded trinucleotide (CTG) repeat in the 3' untranslated region of the myotonin protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (e.g., diabetes mellitus). Mental retardation is common in severe congenital forms, while an aging-related decline of frontal and temporal cognitive functions, particularly language and executive functions, is observed in milder adult forms of the disorder. Severely affected persons die by their early 50s.

11. Dementia

Dementia describes a class of disorders having symptoms affecting thinking and social abilities severely enough to interfere with daily functioning. Other instances of dementia in addition to the dementia observed in later stages of the aging-associated disorders discussed above include vascular dementia, and dementia with Lewy bodies, described below.

In vascular dementia, or "multi-infarct dementia," cognitive impairment is caused by problems in supply of blood to the brain, typically by a series of minor strokes, or sometimes, one large stroke preceded or followed by other smaller strokes. Vascular lesions can be the result of diffuse cerebrovascular disease, such as small vessel disease, or focal lesions, or both. Patients suffering from vascular dementia present with cognitive impairment, acutely or subacutely, after an acute cerebrovascular event, after which progressive cognitive decline is observed. Cognitive impairments are similar to those observed in Alzheimer's disease, including impairments in language, memory, complex visual processing, or executive function, although the related changes in the brain are not due to AD pathology but to chronic reduced blood flow in the brain, eventually resulting in dementia. Single photon emission computed tomography (SPECT) and positron emission tomography (PET) neuroimaging may be used to confirm a diagnosis of multi-infarct dementia in conjunction with evaluations involving mental status examination.

Dementia with Lewy bodies (DLB, also known under a variety of other names including Lewy body dementia, diffuse Lewy body disease, cortical Lewy body disease, and senile dementia of Lewy type) is a type of dementia characterized anatomically by the presence of Lewy bodies (clumps of alpha-synuclein and ubiquitin protein) in neurons, detectable in postmortem brain histology. Its primary feature is cognitive decline, particularly of executive functioning. Alertness and short-term memory will rise and fall.

Persistent or recurring visual hallucinations with vivid and detailed pictures are often an early diagnostic symptom. DLB it is often confused in its early stages with Alzheimer's disease and/or vascular dementia, although, where Alzheimer's disease usually begins quite gradually, DLB often has a rapid or acute onset. DLB symptoms also include motor symptoms similar to those of Parkinson's. DLB is distinguished from the dementia that sometimes occurs in Parkinson's disease by the time frame in which dementia symptoms appear relative to Parkinson symptoms. Parkinson's disease with dementia (POD) would be the diagnosis when dementia onset is more than a year after the onset of Parkinson's. DLB is diagnosed when cognitive symptoms begin at the same time or within a year of Parkinson symptoms.

12. CADASIL

Cerebral autosomal dominant arteriopathy with subcortical infarcts and leukoencephalopathy (CADASIL), is a hereditary disorder associated with mutations in the NOTCH 3 gene. (Locatelli M, et al., Front. Pharmacol. 11:321 (2020)). It usually occurs in middle-aged adults, with manifestations including cognitive impairment leading to dementia and disability. (Id.) Other manifestations are mood disorders, migraine with aura, and recurring stroke. Effective treatment has been elusive because the manner in which the disease develops (pathogenesis) is still uncertain. (Id.) CADASIL is the most common hereditary subcortical type of vascular dementia. (Kalimo H, et al., Future Neurology, 3(6) (2008)).

CADASIL is characterized by four primary common symptoms: migraine with aura, recurrent ischemic stroke, psychiatric disturbances, and cognitive decline. The first is usually the presenting symptom, occurring in 20-40% of the affected. The second symptom occur in 60-85% of symptomatic individuals. The third, psychiatric disturbances occur in 25-30% of patients in the form of moderate/major depression, bipolar disease, panic disorders, schizophrenia, and apathy. Cognitive impairment occurs in 60% of patients, becoming clinically detectable between ages 35-50 and worsens progressively with aging. (Id.) In younger patients, attention, memory, and executive disturbances predominate. (Buffon F, et al., J Neurol Neurosurg Psychiatry 77(2):175-80 (2006)). Visuospatial abilities and reasoning deteriorate with age, mainly after 60 years of age. Dementia presents in 25% of patients, 75% of which are over the age of 60. But the number of ischemic attacks has not been associated with dementia. (Id.)

CADASIL is a progressive and fatal disease. There has been no disease modifying treatment made to date. (Locatelli et al., supra). Symptomatic treatment is the only recourse for clinicians, based on regular clinical practice such as: acetazolamide or sodium valproate for migraines; daily aspirin to reduce chance of heart attack or stroke; and supportive care for loss of cognitive function. Notably, there are still no drugs that have clearly shown benefit on the loss of cognitive function associated with CADASIL. (Id.) Interventions that have been studied but have failed include donepezil (used to improve Alzheimer's cognitive dysfunction), galantamine (acetylcholinesterase inhibitor used to treat cognitive dysfunction in Alzheimer's), and L-dopa (used in Alzheimer's and Parkinson's diseases).

13. Progressive Supranuclear Palsy

Progressive supranuclear palsy (PSP) is a brain disorder that causes serious and progressive problems with control of gait and balance, along with complex eye movement and thinking problems. One of the classic signs of the disease is an inability to aim the eyes properly, which occurs because of lesions in the area of the brain that coordinates eye movements. Some individuals describe this effect as a blurring. Affected individuals often show alterations of mood and behavior, including depression and apathy as well as progressive mild dementia. The disorder's long name indicates that the disease begins slowly and continues to get worse (progressive), and causes weakness (palsy) by damaging certain parts of the brain above pea-sized structures called nuclei that control eye movements (supranuclear). PSP was first described as a distinct disorder in 1964, when three scientists published a paper that distinguished the condition from Parkinson's disease. It is sometimes referred to as Steele-Richardson-Olszewski syndrome, reflecting the combined names of the scientists who defined the disorder. Although PSP gets progressively worse, no one dies from PSP itself.

14. Ataxia

People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias which are the National Ataxia Foundation's primary emphases.

15. Multiple-System Atrophy

Multiple-system atrophy (MSA) is a degenerative neurological disorder. MSA is associated with the degeneration of nerve cells in specific areas of the brain. This cell degeneration causes problems with movement, balance, and other autonomic functions of the body such as bladder control or blood-pressure regulation.

The cause of MSA is unknown and no specific risk factors have been identified. Around 55% of cases occur in men, with typical age of onset in the late 50s to early 60s. MSA often presents with some of the same symptoms as Parkinson's disease. However, MSA patients generally show minimal if any response to the dopamine medications used for Parkinson's.

16. Frailty

Frailty Syndrome ("Frailty") is a geriatric syndrome characterized by functional and physical decline including decreased mobility, muscle weakness, physical slowness, poor endurance, low physical activity, malnourishment, and involuntary weight loss. Such decline is often accompanied and a consequence of diseases such as cognitive dysfunction and cancer. However, Frailty can occur even without disease. Individuals suffering from Frailty have an increased risk of negative prognosis from fractures, accidental falls, disability, comorbidity, and premature mortality. (C. Buigues, et al. Effect of a Prebiotic Formulation on Frailty Syndrome: A Randomized, Double-Blind Clinical Trial, Int. J. Mol. Sci. 2016, 17, 932). Additionally, individuals suffering from Frailty have an increased incidence of higher health care expenditure. (Id.)

Common symptoms of Frailty can be determined by certain types of tests. For example, unintentional weight loss involves a loss of at least 10 lbs. or greater than 5% of body weight in the preceding year; muscle weakness can be determined by reduced grip strength in the lowest 20% at baseline (adjusted for gender and BMI); physical slowness can be based on the time needed to walk a distance of 15 feet; poor endurance can be determined by the individual's self-reporting of exhaustion; and low physical activity can be measured using a standardized questionnaire. (Z. Palace et al., The Frailty Syndrome, Today's Geriatric Medicine 7(1), at 18 (2014)).

In some embodiments, the subject methods and compositions find use in slowing the progression of aging-associated cognitive, motor, neuroinflammatory, neurodegenerative, or other age-related impairment or condition. In other words, cognitive, motor, neuroinflammatory, neurodegenerative, or other abilities or conditions in the individual will decline more slowly following treatment by the disclosed methods than prior to or in the absence of treatment by the disclosed methods. In some such instances, the subject methods of treatment include measuring the progression of cognitive, motor, neuroinflammation, or other age-related ability or symptom decline after treatment, and determining that the progression of decline is reduced. In some such instances, the determination is made by comparing to a reference, e.g., the rate of decline in the individual prior to treatment, e.g., as determined by measuring cognitive, motor, neuroinflammatory, or other age-related abilities or conditions prior at two or more time points prior to administration of the subject blood product.

The subject methods and compositions also find use in stabilizing the cognitive, motor, neuroinflammatory, or other abilities or conditions of an individual, e.g., an individual suffering from aging-associated cognitive decline or an individual at risk of suffering from aging-associated cognitive decline. For example, the individual may demonstrate some aging-associated cognitive impairment, and progression of cognitive impairment observed prior to treatment with the disclosed methods will be halted following treatment by the disclosed methods. As another example, the individual may be at risk for developing an aging-associated cognitive decline (e.g., the individual may be aged 50 years old or older or may have been diagnosed with an aging-associated disorder), and the cognitive abilities of the individual are substantially unchanged, i.e., no cognitive decline can be detected, following treatment by the disclosed methods as compared to prior to treatment with the disclosed methods.

The subject methods and compositions also find use in reducing cognitive, motor, neuroinflammatory, or other age-related impairment in an individual suffering from an aging-associated impairment. In other words, the affected ability is improved in the individual following treatment by the subject methods. For example, the cognitive or motor ability in the individual is increased, e.g., by 2-fold or more, 5-fold or more, 10-fold or more, 15-fold or more, 20-fold or more, 30-fold or more, or 40-fold or more, including 50-fold or more, 60-fold or more, 70-fold or more, 80-fold or more, 90-fold or more, or 100-old or more, following treatment by the subject methods relative to the cognitive or motor ability that is observed in the individual prior to treatment by the subject methods.

In some instances, treatment by the subject methods and compositions restores the cognitive, motor, or other ability in the individual suffering from aging-associated cognitive or motor decline, e.g., to their level when the individual was about 40 years old or less. In other words, cognitive or motor impairment is abrogated.

17. Neuromyelitis Optica Spectrum Disorder

Neuromyelitis Optica Spectrum Disorder (NMOSD), also known as Devic disease, is a rare, inflammatory disease of the central nervous system. It is characterized by optic neuritis (optic nerve inflammation) and myelitis (spinal cord inflammation). Typically, patients experience reoccurring bouts of inflammation separated by periods of remission. The disease is thought to be caused by auto-antibodies that often target myelin oligodendrocyte glycoprotein (MOG-IgG) or aquaporin 4 (AQP4-IgG), which leads to demyelination and axonal damage in the optic nerve and spinal cord.

18. Post-Operative Cognitive Dysfunction

Post-operative cognitive decline occurs following anesthesia and a surgical procedure. It is common in patients older than 60 and is diagnosed by pre- and post-surgery cognitive testing. Patients typically present with memory impairment, delirium, and impairment in performance on intellectual tasks.

19. Chronic Traumatic Encephalopathy

Chronic traumatic encephalopathy (CTE) is a neurodegenerative brain disorder most commonly found in athletes, veterans, or others with a history of repeated head trauma. It is one of many tauopathies that is characterized by the overabundance of Tau protein in the brain of patients that leads to neuron loss. Symptoms include memory loss, changes in mood or personality, confusion, impaired judgement, impulse control, aggression, and depression.

20. Traumatic Brain Injury

Traumatic brain injury (TBI) is caused by a violent hit to the head or body. It can also be caused by an object penetrating brain tissue during an injury. It results in bleeding, torn tissue, and physical damage to brain cells and cell death. The physical symptoms are varied, but include loss of consciousness, headaches, nausea, extreme fatigue, impaired speech, trouble sleeping, dizziness, blurred vision, sensitivity to light or sound, memory loss, and concentration problems.

H. Methods of Diagnosing and Monitoring for Improvement

In some instances, among the variety of methods to diagnose and monitor disease progression and improvement in cognitive disease, motor impairment, neuroinflammatory, or neurodegenerative disease the following types of assessments are used alone or in combination with subjects suffering from neurodegenerative disease, as desired. The following types of methods are presented as examples and are not limited to the recited methods. Any convenient methods to monitor disease may be used in practicing the invention, as desired. Those methods are also contemplated by the methods of the invention.

i. General Cognition

Embodiments of the methods of the invention further comprise methods of monitoring the effect of a medication or treatment on a subject for treating cognitive impairment and/or age-related dementia, the method comprising comparing cognitive function before and after treatment. Those having ordinary skill in the art recognize that there are well-known methods of evaluating cognitive function. For example, and not by way of limitation, the method may comprise evaluation of cognitive function based on medical history, family history, physical and neurological examinations by clinicians who specialize dementia and cognitive function, laboratory tests, and neuropsychological assessment. Additional embodiments which are contemplated by the invention include: the assessment of consciousness, such as using the Glasgow Coma Scale (EMV); mental status examination, including the abbreviated mental test score (AMTS) or mini-mental state examination (MMSE) (Folstein et al., J. Psychiatr. Res 1975; 12:1289-198); global assessment of higher functions; estimation of intracranial pressure such as by fundoscopy. In one embodiment, monitoring the effect on cognitive impairment and/or age-related dementia includes a 1, 2, 3, 4, 5, 6, 7, 8, 9, 10, 11, or 12-point improvement using the Alzheimer's Disease Assessment Scale-Cognitive Subscale (ADAS-COG).

In one embodiment, examinations of the peripheral nervous system may be used to evaluate cognitive function, including any one of the followings: sense of smell, visual fields and acuity, eye movements and pupils (sympathetic and parasympathetic), sensory function of face, strength of facial and shoulder girdle muscles, hearing, taste, pharyngeal movement and reflex, tongue movements, which can be tested individually (e.g. the visual acuity can be tested by a Snellen chart; a reflex hammer used testing reflexes including masseter, biceps and triceps tendon, knee tendon, ankle jerk and plantar (i.e. Babinski sign); Muscle strength often on the MRC scale 1 to 5; Muscle tone and signs of rigidity.

ii. CADASIL

Embodiments of the methods of the invention further comprise methods of monitoring the effect of a medication or treatment on a subject for treating cerebral autosomal dominant arteriopathy with subcortical infarcts and leukoencephalopathy (CADASIL), the method comprising comparing symptoms of CADASIL before and after treatment. Said symptoms include cognitive impairment, such as by way of example and not limitation, attention, memory, executive disturbance, visuospatial abilities, reasoning, and dementia. The symptoms can also be symptoms monitored in other types of cognitive impairment or dementia such as those described herein for general cognition, Alzheimer's Disease, Parkinson's Disease, Huntington's Disease, Lewy Body Dementia, and the like.

Embodiments of the methods of the invention further comprise methods of diagnosing CADASIL in a subject. Embodiments for diagnosing CADASIL in a subject include, by way of example and not limitation, magnetic resonance imaging (MRI) scans of subjects and detection of Notch 3 genetic mutations. An example of an MRI scan used to detect CADASIL is a T2-weighted MRI (diffusion tensor imaging) which detects one of the main characteristics of CADASIL, namely the presence of nonspecific white matter lesions (leukoaraiosis). This technique is based on measuring diffusion of water, which is due to the random motion of water molecules resulting from thermal energy. (Molko N, et al., Stroke, 33(12):2902-08 (2002)). It is a sensitive technique revealing tissue microstructure that in turn reveals subtle modifications in various cognitive-related diseases like Alzheimer's disease and schizophrenia. (Id.) CADASIL often features a large increase in water diffusion within the white matter and basal ganglia both inside and outside cerebral lesions detected by conventional MRI.

An additional method of diagnosing CADASIL in a subject is detection of Notch 3 genetic mutations. Most of the mutations in CADASIL involve one of the 34 epidermal growth factor-like repeats (EGFR) in the extracellular domain of Notch 3. (Locatelli et al., supra). In particular, 98% of Notch 3 mutations occur in exons 2-23 which encode the 34 EGFR on the extracellular domain. (Id.) Clinical/commercial embodiments include by way of example and not limitation, Athena Diagnostics' Notch3 CADASIL Sequencing Test (No. 1175).

iii. Parkinson's Disease

Embodiments of the methods of the invention further comprise methods of monitoring the effect of a medication or treatment on a subject for treating motor impairment, the method comprising comparing motor function before and after treatment. Those having ordinary skill in the art recognize that there are well-known methods of evaluating motor function. For example, and not by way of limitation, the method may comprise evaluation of motor function based on medical history, family history, physical and neurological examinations by clinicians who specialize neurodegeneration and motor impairment, laboratory tests, and neurodegenerative assessment. Additional embodiments which are contemplated by the invention include employment of the rating scales discussed below.

Several rating scales have been utilized for evaluating the progression of PD. The most widely-used scales include the Unified Parkinson's Disease Rating Scale (UPDRS, which was introduced in 1987) (J. Rehabil Res. Dev., 2012 49(8): 1269-76), and the Hoehn and Yahr scale (Neruology, 1967 17(5): 427-42). Additional scales include the Movement Disorder Society (MDS)'s updated UPDRS scale (MDS-UPDRS) as well as the Schwab and England Activities of Daily Living (ADL) Scale.

The UPDRS scale evaluates 31 items that contributed to three subscales: (1) mentation, behavior, and mood; (2) activities of daily living; and (3) motor examination. The Hoehn and Yahr scale classifies PD into five stages with discreet substages: 0—no signs of disease; 1—symptoms on one side only; 1.5—symptoms on one side but also involving neck and spine; 2—symptoms on both sides with no balance impairment; 2.5—mild symptoms on both sides, with recovery when the 'pull' test is given; 3—balance impairment with mild to moderate disease; 4—severe disability, but ability to walk or stand unassisted; and 5—need a wheelchair or bedridden without assistance. The Schwab and England scale classifies PD into several percentages (from 100%—complete independent to 10%—total dependent).

General motor function can be evaluated using widely-used scales including the General Motor Function Scale (GMF). This tests three components: dependence, pain, and insecurity. (Aberg A. C., et al. (2003) Disabil. Rehabil. 2003 May 6; 25(9):462-72). Motor function can also be assessed using home-monitoring or wearable sensors. For example: gait (speed of locomotion, variability, leg rigidity) can be sensed with an accelerometer; posture (trunk inclination) by a gyroscope; leg movement by an accelerometer; hand movement by an accelerometer and gyroscope; tremor (amplitude, frequency, duration, asymmetry) by an accelerometer; falling by an accelerometer; gait freezing by an accelerometer; dyskinesia by an accelerometer, gyroscope, and inertial sensors; bradykinesia (duration and frequency) by an accelerometer plus gyroscope, and aphasia (pitch) using a microphone. (Pastorino M, et al., Journal of Physics: Conference Series 450 (2013) 012055).

iv. Multiple Sclerosis

In addition to monitoring improvement for symptoms associated with cognition, the progression or improvement of neurodegeneration associated with multiple sclerosis (MS) can be monitored using techniques well-known to those having ordinary skill in the art. By way of example, and not limitation, monitoring can be performed through techniques such as: cerebrospinal fluid (CSF) monitoring; magnetic resonance imaging (MRI) to detect lesions and development of demyelinating plaques; evoked potential studies; and gait monitoring.

CSF analysis may be performed, for example, through lumbar puncture to obtain pressure, appearance, and CSF content. Normal values typically range as follows: pressure (70-180 mm H20); appearance is clear and colorless; total protein (15-60 mg/100 mL); IgG is 3-12% of the total protein; glucose is 50-80 mg/100 mL; cell count is 0-5 white blood cells and no red blood cells; chloride (110-125 mEq/L). Abnormal results may indicate the presence or progression of MS.

MRI is another technique that may be performed to monitor disease progression and improvement. Typical criteria for monitoring MS with MRI include the appearance of patchy areas of abnormal white matter in cerebral hemisphere and in paraventricular areas, lesions present in the cerebellum and/or brain stem as well as in the cervical or thoracic regions of the spinal cord.

Evoked potentials may be used to monitor the progression and improvement of MS in subjects. Evoked potentials measure slowing of electrical impulses such as in Visual Evoked Response (VER), Brain Stem Auditory Evoked Responses (BAER), and Somatosensory Evoked Responses (SSER). Abnormal responses help to indicate that there is a decrease in the speed of conduction in central sensory pathways.

Gait monitoring can also be used to monitor disease progression and improvement in MS subjects. MS is often accompanied by an impairment in mobility and an abnormal gait due in part to fatigue. Monitoring may be performed, for example, with the use of mobile monitoring devices worn by subjects. (Moon, Y., et al., Monitoring gait in multiple sclerosis with novel wearable motion sensors, PLOS One, 12(2):e0171346 (2017)).

v. Huntington's Disease

In addition to monitoring improvement for symptoms associated with cognition, the progression or improvement of neurodegeneration associated with Huntington's Disease (HD) can be monitored using techniques well-known to those having ordinary skill in the art. By way of example, and not limitation, monitoring can be performed through techniques such as: motor function; behavior; functional assessment; and imaging.

Examples of motor function that may be monitored as an indication of disease progression or improvement include chorea and dystonia, rigidity, bradykinesia, oculomotor dysfunction, and gait/balance changes. Techniques for performing the monitoring of these metrics are well-known to those having ordinary skill in the art. (See Tang C, et al., Monitoring Huntington's disease progression through preclinical and early stages, Neurodegener Dis Manag 2(4):421-35 (2012)).

The psychiatric effects of HD present opportunities to monitor disease progression and improvement. For example, psychiatric diagnoses may be performed in order to determine whether the subject suffers from depression, irritability, agitation, anxiety, apathy and psychosis with paranoia. (Id.)

Functional assessment may also be employed to monitor disease progression or improvement. Total functional score techniques have been reported (Id.), and often declines by one point per year in some HD groups.

MRI or PET may be employed also to monitor disease progression or improvement. For example, there is a loss of striatal projection neurons in HD and change in number of these neurons may be monitored in subjects. Techniques to determine neuronal change in HD subjects include imaging Dopamine D2 receptor binding. (Id.)

vi. Amyotrophic Lateral Sclerosis (ALS)

In addition to monitoring improvement for symptoms associated with cognition, the progression or improvement of neurodegeneration associated with Amyotrophic Lateral Sclerosis (ALS) can be monitored using techniques well-known to those having ordinary skill in the art. By way of example, and not limitation, monitoring can be performed through techniques such as: functional assessment; determining muscle strength; measuring respiratory function; measuring lower motor neuron (LMN) loss; and measuring upper motor neuron (UMN) dysfunction.

Functional assessment can be performed using a functional scale well-known to those having ordinary skill in the art, such as the ALS Functional Rating Scale (ALSFRS-R), which evaluates symptoms related to bulbar, limb, and respiratory function. The rate of change is useful in predicting survival as well as disease progression or improvement. Another measure includes the Combined Assessment of Function and Survival (CAFS), ranking subjects' clinical outcomes by combining survival time with change in ALSFRS-R. (Simon N G, et al., Quantifying Disease Progression in Amyotrophic Lateral Sclerosis, Ann Neurol 76:643-57 (2014)).

Muscle strength may be tested and quantified through use of composite Manual Muscle Testing (MMT) scoring. This entails averaging measures acquired from several muscle groups using the Medical Research Council (MRC) muscle strength grading scale. (Id.) Hand-held dynamometry (HHD) may also be used, among other techniques. (Id.)

Respiratory function can be performed using portable spirometry units, used to obtain Forced Vital Capacity (FVC) at baseline to predict the progression or improvement of the disease. Additionally, maximal inspiratory pressure, sniff nasal inspiratory pressure (SNIP), and supping FVC may be determined and used to monitor disease progression/improvement. (Id.)

Loss in lower motor neurons is another metric which can be utilized to monitor disease progression or improvement in ALS. The Neurophysiological Index may be determined by measuring compound muscle action potentials (CMAPs) on motor nerve conduction studies, of which parameters include CMAP amplitude and F-wave frequency. (Id. and de Carvalho M, et al., Nerve conduction studies in amyotrophic lateral sclerosis. Muscle Nerve 23:344-352, (2000)). Lower motor neuron unit numbers (MUNE) may be estimated as well. In MUNE, the number of residual motor axons supplying a muscle through estimation of the contribution of individual motor units to the maximal CMAP response is estimated and used to determine disease progression or improvement. (Simon N G, et al., supra). Additional techniques for determining loss of LMN include testing nerve excitability, electrical impedance myography, and using muscle ultrasound to detect changes in thickness in muscles. (Id.)

Dysfunction of upper motor neurons is another metric which can be utilized to monitor disease progression or improvement in ALS. Techniques for determining dysfunction include performing MRI or PET scans on the brain and spinal cord, transcranial magnetic stimulation; and determining levels of biomarkers in the cerebrospinal fluid (CSF).

vii. Glaucoma

In addition to monitoring improvement for symptoms associated with cognition, the progression or improvement of neurodegeneration associated with glaucoma can be monitored using techniques well-known to those having ordinary skill in the art. By way of example, and not limitation, monitoring can be performed through techniques such as: determining intraocular pressure; assessment of the optic disc or optic nerve head for damage; visual field testing for peripheral vision loss; and imaging of the optic disc and retina for topographic analysis.

viii. Progressive Supranuclear Palsy (PSP)

In addition to monitoring improvement for symptoms associated with cognition, the progression or improvement of neurodegeneration associated with Progressive Supranuclear Palsy (PSP) can be monitored using techniques well-known to those having ordinary skill in the art. By way of example, and not limitation, monitoring can be performed through techniques such as: functional assessment (activities of daily living, or ADL); motor assessment; determination of psychiatric symptoms; and volumetric and functional magnetic resonance imaging (MRI).

The level of function of a subject in terms of independence, partial dependence upon others, or complete dependence can be useful for determining the progression or improvement in the disease. (See Duff, K, et al., Functional impairment in progressive supranuclear palsy, Neurology 80:380-84, (2013)). The Progressive Supranuclear Palsy Rating Scale (PSPRS) is a rating scale that comprises twenty-eight metrics in six categories: daily activities (by history); behavior; bulbar, ocular motor, limb motor and gait/midline. The result is a score ranging from 0-100. Six items are graded 0-2 and twenty-two items graded 0-4 for a possible total of 100. The PSPRS scores are practical measures, and robust predictors of patient survival. They are also sensitive to disease progression and useful in monitoring disease progression or improvement. (Golbe L I, et al., A clinical rating scale for progressive supranuclear palsy, Brain 130:1552-65, (2007)).

The ADL section from the UPDRS (Unified Parkinson's Disease Rating Scale) can also be used to quantify functional activity in subjects with PSP. (Duff K, et al., supra). Similarly, the Schwab & England Activities Daily Living Score (SE-ADL) can be used for evaluate independence. (Id.) Additionally, the motor function sections of the UPDRS are useful as a reliable measure for assessing disease progression in PSP patients. The motor section may contain, for example, 27 different measures for quantifying motor function in PSP patients. Examples of these include resting tremor, rigidity, finger tapping, posture, and gait). A subject's disease progression or improvement may also be assessed by performing a baseline neuropsychological evaluation completed by trained medical personnel, the assessment using the Neuropsychiatric Inventory (NPI) to determine the frequency and severity of behavior abnormalities (e.g. delusions, hallucinations, agitation, depression, anxiety, euphoria, apathy, disinhibition, irritability, and aberrant motor behavior). (Id.)

Functional MRI (fMRI) can be employed to monitor disease progression and improvement as well. fMRI is a technique using MRI to measure changes in brain activity in certain regions of the brain, usually based on blood flow to those regions. Blood flow is considered to correlate with brain region activation. Patients with neurodegenerative disorders like PSP can be subjected to physical or mental tests before or during being scanned in an MRI scanner. By way of example, and not limitation, tests can be a well-established force control paradigm where patients as asked to produce force with the hand most affected by PSP and maximum voluntary contraction (MVC) is measured by fMRI immediately after the test takes place. Burciu, R G, et al., Distinct patterns of brain activity in progressive supranuclear palsy and Parkinson's disease, Mov. Disord. 30(9): 1248-58 (2015)).

Volumetric MRI is a technique where MRI scanners determine volume differences in regional brain volume. This may be done, for example, by contrasting different disorders, or by determining differences in volume of a brain region in a patient over time. Volumetric MRI may be employed to determine disease progression or improvement in neurodegenerative disorders like PSP. The technique is well-known to those having ordinary skill in the art. (Messina D, et al., Patterns of brain atrophy in Parkinson's disease, progressive supranuclear palsy and multiple system atrophy, Parkinsonism and Related Disorders, 17(3):172-76 (2011)). Examples of cerebral regions which may be measured include, but are not limited to, intracranial volume, cerebral cortex, cerebellar cortex, thalamus, caudate, putamen, *pallidum*, hippocampus, amygdala, lateral ventricles, third ventricle, fourth ventricle, and brain stem.

ix. Neurogenesis

The invention also contemplates treating or improving neurogenesis in a subject with declining or impaired neurogenesis, which may manifest itself, for example, through reduced cognitive or motor function, or through association with neuroinflammation. An embodiment of the invention includes administering, by way of example and not limitation, an LTA4H modulatory agent to the subject with reduced or impaired neurogenesis using a Pulsed Dosing treatment regimen.

An embodiment of the invention also contemplates determining the level of neurogenesis before, during, and/or after administration of the LTA4H modulatory agent. Noninvasive techniques for evaluating neurogenesis have been reported. (Tamura Y. et al., J. Neurosci. (2016) 36(31):8123-31). Positron emission tomography (PET) used with the tracer, [18F]FLT, in combinations with the BBB transporter inhibitor probenecid, allows for accumulation of the tracer in neurogenic regions of the brain. Such imaging allows for an evaluation of neurogenesis in patients being treated for neurodegenerative disease.

x. Neuromyelitis Optica Spectrum Disorder (NMOSD)

Neuromyelitis Optica Spectrum Disorder (NMOSD) can be diagnosed with a blood test to detect AQP4-IgG or MOG-IgG antibodies. Disease monitoring uses blood tests, cerebrospinal fluid tests, spinal taps, and magnetic resonance imaging (MRI) or computed tomography (CT) scans.

I. Reagents, Devices, and Kits

Also provided are reagents, devices, and kits thereof for practicing one or more of the above-described methods. The subject reagents, devices, and kits thereof may vary greatly. Reagents and devices of interest include those mentioned above with respect to the methods of administering the compositions described herein (e.g., benzodioxane LTA4H inhibitors) to the subject.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a remote site. Any convenient means may be present in the kits.

J. Exercise

Exercise can be characterized by aerobic or anaerobic activity and can involve high calorie-burning activity and moderate calorie-burning activity. Exercise may involve strength training (e.g., weight training or isometric exercise). Exercise may also involve, for example, running, bicycling, walking, dancing, marching, swimming, yoga, Tai Chi, balance exercises, leg bends, jumping rope, surfing, rowing, rotating or flexing the arms or legs, gardening, cleaning, active games such as bowling, aerobics, Pilates, and martial arts.

An exercise regimen may include performing a single exercise at a certain frequency, or a combination of exercises at a certain frequency. The frequency may be one, two, three, four, five, six, or seven times per week. The frequency may vary from week-to-week. The exercise regimen may be at the same level of intensity and/or frequency as the subject practiced before administration of the compositions of the invention. The exercise regimen may also be at a higher level of intensity and/or frequency compared to the levels the subject practiced before administration of the compositions of the invention. The exercise regimen may have been suggested or prescribed by a health or fitness professional, or the exercise regimen may have been initiated by the subject himself or herself.

VII. EXPERIMENTAL EXAMPLES

A. Experimental Procedures

SomaScan Assay (SomaLogic)

Plasma samples and MMSE scores from an Alzheimer's disease population were acquired through FACEHBI as previously described (de Rojas I et al., Alzheimers Res Ther, 10:119 (2018) and Rodriguez-Gomez 0 et al., Prev Alzheimers Dis, 4(2):100-108 (2017). DTA plasma samples were shipped frozen to Alkahest, aliquoted and stored at −80 C until use. Aliquoting for proteomic analysis of all three sets of plasma samples were carried out as follows: original frozen plasma samples were thawed on ice, centrifuged at 3,200×g for 30 min at OC, and filtered through 0.22 um Millex GV filter (MilliporeSigma, Burlington, MA) to remove cryoprecipitate. Filtrate was aliquoted into cryotubes and stored at −80 C until use. Plasma samples were analyzed by the SomaScan multiplex proteomic profiling platform measuring 1305 protein analystes at Somalogic, Inc. (Boulder, Colorado) as described (Gold L et al., PLoS ONE, 5(12):e15004 (2010)). Briefly, test samples were incubated with a mixture of proprietary aptamer-based affinity reagents called SOMAmers. Two sequential bead-based immobilization and washing steps eliminated unbound or non-specifically bound proteins and the unbound SOMAmers, leaving only protein target-bound SOMAmers. These remaining SOMAmers were isolated, and each reagent quantified simultaneously on a custom Agilent hybridization array.

Contextual Fear Conditioning (CFC)

Mice were brought into the testing room immediately before their trial to avoid exposure to sounds and scents from testing. Day 1: For training, mice were placed in the chambers, bright house light and fan on, for 2 minutes. Then an auditory cue (2000 Hz, 70 dB, conditioned stimulus (CS)) was presented for 30 seconds. A 2 second foot shock (0.6 mA; unconditioned stimulus (US)) was administered for the final 2 seconds of the CS. This procedure was repeated once, each after a 2-minute interval, and the mouse was removed from the chamber 30 seconds after the second shock. The pans, chamber walls and grid floors were cleaned with 70% ethanol between trials. Day 2: Seventy-two hours after the training, the mouse was returned to the same chamber in which the training occurred (memory for context), and freezing behavior was recorded for 3 min. The mouse was returned to its home cage. The pans, chamber walls, and grid floors were cleaned with 70% ethanol between trials. Day 3: 24 hours after context testing, the mouse was returned to the same chamber and freezing was recorded in a novel environment (altered context) and in response to the cue (memory for cue). The novel environment included different odors (Peppermint water), sounds, a chamber divider, and different floor material. The mouse was placed in the novel environment and freezing was recorded for 2 minutes. The auditory cue (2000 Hz, 70 dB, CS) was then presented for 30 seconds, and freezing was again recorded for 2 minutes. Mice were returned to their home cages, and the pans, chamber walls, and floors were cleaned with Ethanol and with Peppermint water between trials.

Y-Maze

A large Y-maze test assessed short-term memory of the familiarity of a specific context. Mice were brought to the experimental room for at least 30 min of acclimation to the experimental room conditions (dim lighting) prior to testing. For the initial training trial, the mouse was placed at the end of one arm of a large Y-maze designated "start arm" (arm length: 15 inches). The third arm of the maze was blocked off, allowing the mouse to explore two of the three arms freely ("start arm" and "familiar arm") for 5 min. Each arm contained spatial cues. Three hours later, the mouse was placed back into the maze in the "start arm," and allowed to explore all three arms with the third arm unblocked ("novel arm"). Movements in and out of each arm were tracked using automated tracking software (ANY-maze). Testing was performed under dim lighting, and the apparatus was cleaned with 70% ethanol between trials. The time spent and number of entireties into the "novel arm" and "familiar arm" were analyzed, as well as total distance travelled and velocity as measures of general locomotor activity.

Radial Arm Water Maze (RAWM)

The water maze (see, e.g. Alamed J, et al., *Two-day radial-arm water maze learning and memory tasks; robust resolution of amyloid-related memory deficits in transgenic mice*, Nat. Protoc., 1(4):1671-79 (2006)), was filled with water at least 24 hours prior to the test to equilibrate to 25° C. The water was dyed with white latex paint to make the animals visible for tracking and to allow for the use of a hidden platform. Eight distinct visual cues were placed at the end of each of eight arms of the RAWM inserts. On day 1 animals were subjected to 5 trials each with a visible platform and a 30-minute inter-trial interval. Animals had 60 seconds to reach the platform. If they did not reach the platform in that time they were guided to it and allowed to remain for 15 seconds before being removed from the tank. The goal arm remained constant, and a different start arm was randomly assigned for each of the 5 trials so that mouse started in every arm once except for the two arms directly across from the platform. The goal arm was switched after every two mice and balanced between all treatment groups. After each trial the mice were placed in an empty cage with blue pads and allowed to dry off under a heat lamp before being placed back into their home cage. Testing day was 48 hours after training, when animals were subjected to the same test of 5 trials each and a 30-minute inter-trial interval, but with a hidden platform. Animals were scored for the number of errors (entry into a non-goal arm) and for latency to reach the platform. All trials were recorded using ANY-maze software.

Tissue Collection and Histology

Brains were collected following saline perfusion and separated by mid-sagittal slice with one-half drop fixed in freshly prepared 4% PFA. PFA was changed to 30% sucrose 24-48 hours later. A second change to 30% sucrose occurred 24 hours later. Brain tissue was sectioned or lysed and analyzed for GFAP, AQP4, or IBA1 by standard histological methods. Images were acquired using a confocal microscope or Axioscan slide scanner.

Pharmacokinetic Measurement of Compound 1

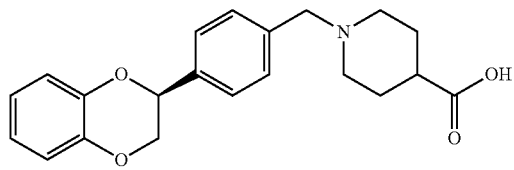 [SMILES: O=C(O)C1CCN(Cc2ccc([C@H]3COc4ccccc4O3)cc2)CC1]

Compound 1

The mice are subjected to cardiac puncture and blood samples were collected using syringes pre-filled with $K_2EDTA$ or heparin. Plasma and blood levels of Compound 1 were measured using LC-MS/MS following a single oral gavage dose to C57BL/6 mice at 10 mg/kg, 1 mg/kg and 0.3 mg/kg at multiple timepoints following dosing. Hemi-brain tissue was homogenized with 3× volumes of ice-cold water, then further diluted 2× with blank mouse plasma prior to analysis. Brain levels of Compound 1 were measured using LC-MS/MS following a single oral gavage dose to C57BL/6 mice at 10 mg/kg, 1 mg/kg and 0.3 mg/kg at multiple timepoints following dosing.

Ex Vivo LTB4 Assay

Whole blood was incubated with Compound 1 or vehicle and then a calcium ionophore (Calcimycin, A23187), or 10% DMSO. LTB4 levels in plasma were measured using ELISA.

Open Field

The open field test was used to evaluate general locomotor activity and exploratory behavior in a novel environment. It consisted of a square arena (16 in ×16 in). Mice were brought to the experimental room for at least 30 min of acclimation to the experimental room conditions (dim lighting) prior to testing. Mice were placed in the center of the arena, recorded, and tracked within a predefined peripheral and center space using the photobeam activity system automated software (ANY-maze) for 15 min. Total distance traveled, average velocity, and time spent in the peripheral and center zones were analyzed.

Nesting

All nesting material was removed from home cage and mice were given 2 fresh nestlets 12-18 hours prior to scoring. The nest was carefully scored on a scale of 0-5 by an experimenter blinded to treatment group: 0 undisturbed, 1 disturbed, 2 flat, 3 cup, 4 incomplete dome, 5 complete dome.

Inverted Wire Hang

Mice were brought into the experimental room for at least 20 minutes of acclimation to the experimental room conditions (bright lighting) prior to testing. Each mouse was placed in the center of the grid. Then swiftly in one continuous motion the grid was inverted 180 degrees to suspend the mouse upside down with their nose being the last part of the mouse to be suspended. The timer was started once the mouse was completely suspended and time to fall was recorded. Mice were tested 3 times with no rest period between each test with a maximum suspension time of 120 seconds. The maximum and average time to fall were scored for each animal.

Rotarod

Mice were trained by allowing to run on the rotarod at 5 RPM speed setting on the i-Therm CTR-44 Rotarod for 5 minutes, if the mouse fell off it was put back on until it was able to complete minutes without falling off. After 15 minutes, if the mouse is unable to stay on the rotarod for a continuous 5 minutes, the mouse is excluded from analysis. Mice were then given 3 trials where the speed was increased from 5 RPM to 40 RPM over 90 seconds; the time at which the mouse fell off was recorded for each trial. Inter-trial interval is at least 15 minutes to allow the mice adequate rest. The rotarod is cleaned with 70% ethanol between trials.

qPCR

Brains were collected following saline perfusion and separated by mid-sagittal slice with one-half dissected into hippocampus and cortex and then snap frozen on dry ice. RNA was isolated from brain tissue using the RNAeasy Qiagen Kit according to the manufacturer's instruction, briefly, tissue was homogenized using an Omni Bead Ruptor in RLT buffer, RNA was bound to RNA isolation column, washed and eluted. Contaminating DNA was removed by DNAse digestion and cDNA was generated using the Life Technologies SuperScript III Kit. A master mix for qPCR was made using the appropriate forward and reverse primers, and SYBR green reagent or TaqMan reagent. The reaction was run on a Life Technologies QuantStudio Real-Time PCR System and analyzed using the std ddCT protocol on the QuantStudio6 software.

LTB4 Target Engagement Assay

Whole blood was collected by cardiac puncture using heparin as an anti-coagulant. 160 µL of whole blood was collected in duplicate for each mouse and incubated for 15 minutes in 37° C./5% CO2. During this time a 0.1 mM calcimycin stock was made by diluting 10 mM calcimycin (Sigma C7522) formulated in DMSO into PBS. Control solution was made by diluting the same volume of DMSO in PBS. Both solutions were sonicated for 10 minutes in a 37° C. water bath. 40 µL of 0.1 mM calcimycin (stimulated) or control solution (unstimulated) was added to each well of whole blood and incubated at 37° C./5% CO2 for 30 minutes. Whole blood was spun for 10 minutes at 1000×g to separate out plasma. LTB4 levels were detected by running an ELISA on the collected stimulated and unstimulated plasma diluted 1:10 (Enzo Life Sciences, ADI-901-068). The ELISA plates were read on a BMG LABTECH CLARIOstar plate reader at 405 nm.

CADASIL Mouse Model

Transgenic Notch3$^{R169C}$ mice are obtained along with transgenic Notch3$^{WT}$ and/or wild type mice as described previously (Ghosh M, et al., Ann Neurol., 78(6):887-900 (2015); Rajani R M, et al., Acta Neuropathologica Comm., 7(187) (2019); and Joutel A, et al., J. Clin. Invest., 120(2): 433-45 (2010), herein incorporated by reference in their entirety). Twenty Notch3R169c mice and 10 littermate control 5-month-old wild type mice are dosed with Vehicle or Compound 1 at 1 mg/kg PO bid for four months. Mice are anesthetized and blood and tissues are collected for further analysis.

B. Example 1

The concentration of LTA4H protein was measured in plasma from a human Alzheimer's disease cohort acquired through FACEHBI. LTA4H levels were measured using the SomaScan multiplex proteomic profiling platform in subjects with subjective cognitive decline (SCD), mild cognitive impairment (MCI) and Alzheimer's disease (AD).

Figure 1:
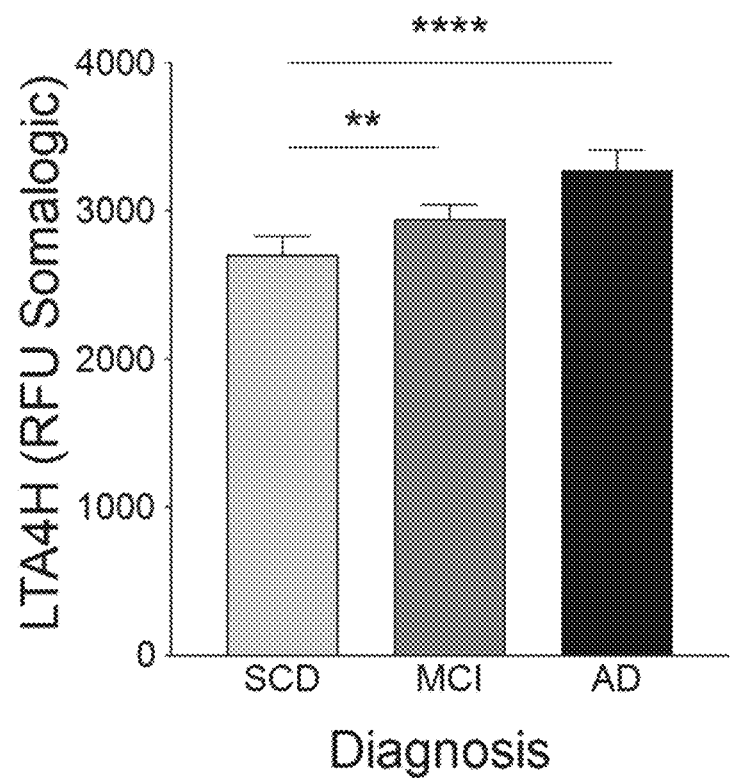
Figure 2:
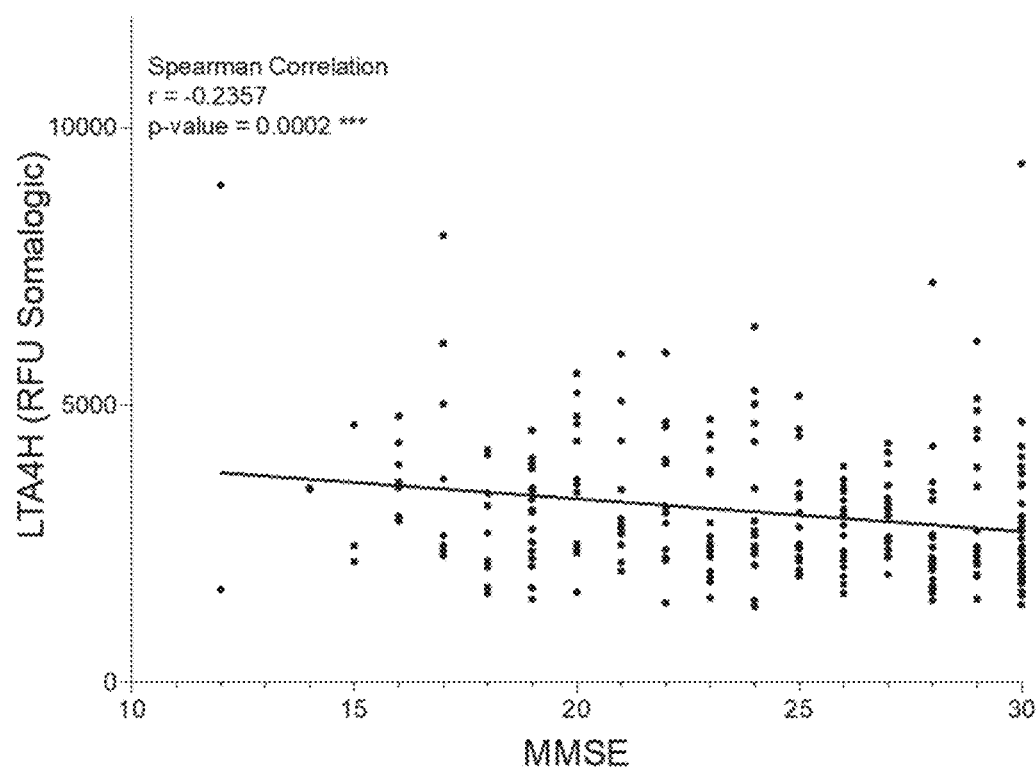

FIG. 1 reports a significant increase in human LTA4H plasma levels with worsening Alzheimer's disease diagnosis from SDC, to MCI. (Kruskal-Wallis test, p=0.0023 with Dunn's multiple comparisons: SCD vs. MCI p=0.0037, SCD vs. AD p<0.0001; n=122). FIG. 2 reports that human LTA4H plasma levels are significantly correlated with a worsening cognitive score on the mini-mental state exam (MMSE). (Spearmann R=−0.2357, p=0.0002; n=332.)

In summary, this example identifies that increased LTA4H plasma levels in humans is significantly correlated with worsening cognition and cognitive disease suggesting that LTA4H may be a driver and/or biomarker of age-related cognitive decline.

C. Example 2

Three independent cohorts of aged wild type (WT; C57BL/6) mice between twenty to twenty-two months of age (20-22 mo) were homogenized into two (2) groups by body weight, total distance travelled in the open field test, and average velocity in the open field test. Group 1 was administered vehicle control PO daily. Group 2 was administered 10 mg/kg of the LTA4H inhibitor Compound 1 PO daily. Both groups were dosed for either 10 days or 4 weeks daily. Behavioral assays were run during the last week of dosing and animals were sacrificed at the end of the study for histological and molecular assays.

Figure 3:
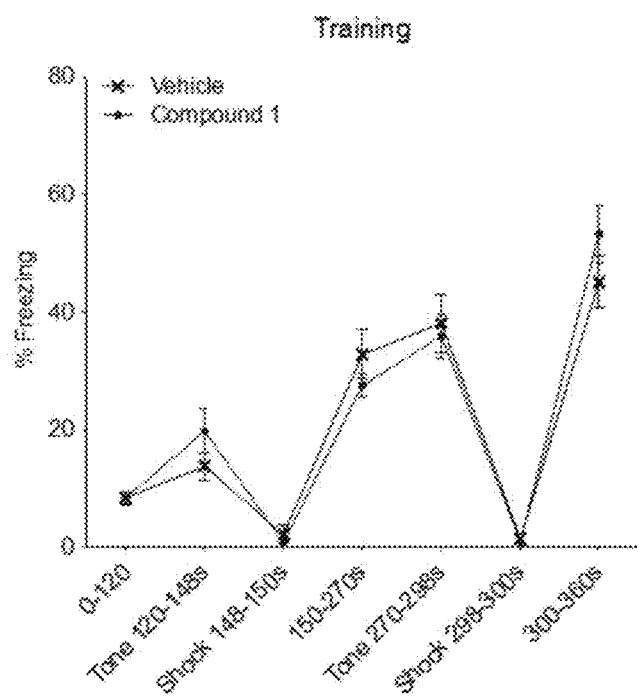
FIG. 3 shows the average percent freezing time in training bins (s, seconds) across training for a contextual fear conditioning test.
Figure 4:
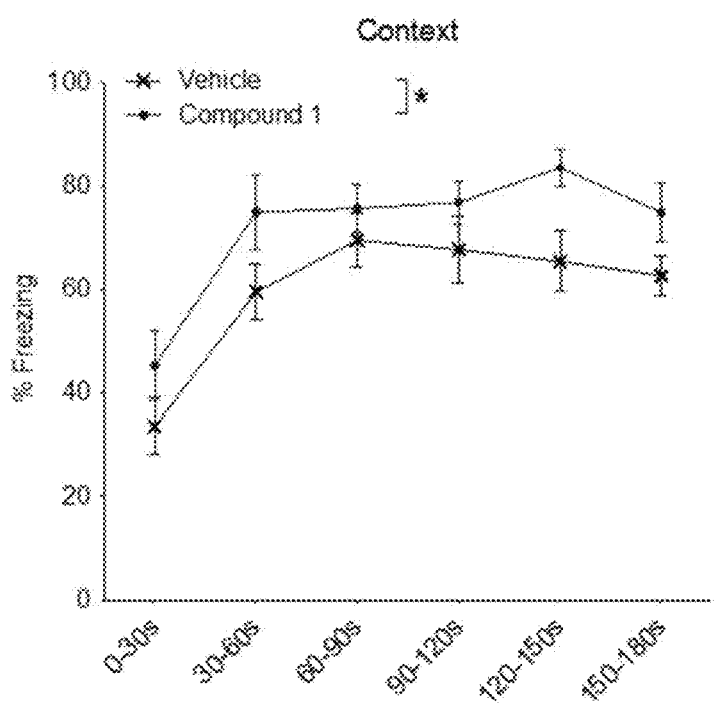
FIG. 4 shows the average percent freezing time in 30 second (s) bins across contextual fear conditioning testing.
Figure 5:
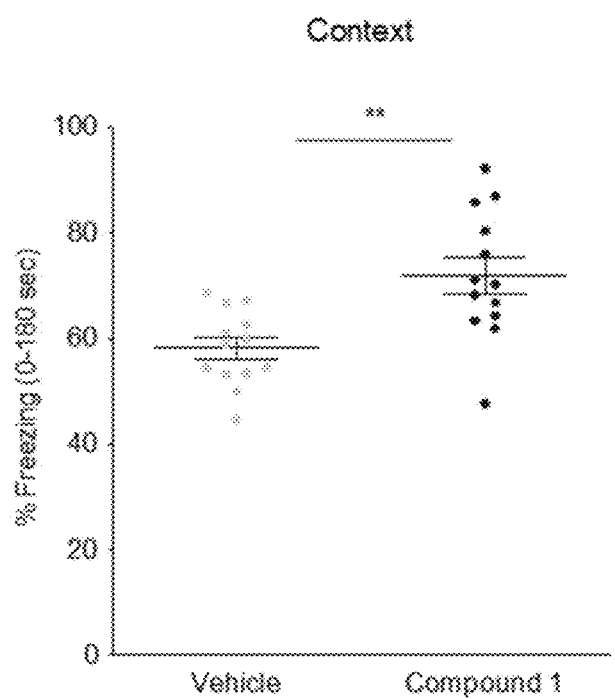
FIG. 5 shows the total percent freezing time averaged across the entire 180 second contextual fear conditioning test.

FIGS. 3-5 report the results of the CFC, which measures contextual memory in aged mice after 8 days of treatment. FIG. 3 reports the percent time freezing during training of the task indicating that mice treated with vehicle or Compound 1 were both able to learn the task. (Two-way ANOVA. (n=14, 13)). FIG. 4 and FIG. 5 report the percent time freezing during testing phase of CFC. (FIG. 4: Two-way ANOVA *p<0.05. (n=14, 13); FIG. 5: Mann-Whitney. **p<0.01. (n=13, 13)). Mice treated with Compound 1 have increased freezing time compared to mice treated with vehicle.

FIGS. 6-9 report the results of the Y-maze, which measures spatial memory in aged mice after 12 days of treatment. FIG. 6 reports the time (Unpaired t-test. (n=14, 14)) and FIG. 7 reports the number of entries (Unpaired t-test. (n=14, 14)) during the training phase of the experiment, indicating that both vehicle and Compound 1 treated mice can learn the task. FIG. 8 reports the percent time spent in the novel (N) or familiar (F) arms during the testing phase (Two-way ANOVA, paired t-test *p<0.05. (n=13, 13). Mice treated with the LTA4H inhibitor Compound 1 spend significantly more time in the novel arm, indicating an improvement in spatial memory with short term treatment. FIG. 9 reports that mice in both treatment groups enter the N and F arms equally (Two-way ANOVA, paired t-test *p<0.05. (n=13, 13)).

FIG. 10-13 report the results of the Y-maze, which measures spatial memory in aged mice after 26 days of treatment. FIG. 10 reports the number of entries into the training arm (Unpaired t-test. (n=14, 14)) and FIG. 11 reports the time (Unpaired t-test. (n=14, 14)) during the training phase of the experiment, indicating that both vehicle and Compound 1 treated mice can learn the task at this timepoint. FIG. 12 reports the percent time spent in the novel (N) or familiar (F) arms during the testing phase (Two-way ANOVA, paired t-test *p<0.05. (n=14, 14)). FIG. 13 reports the percentage of entries into the N and F arms (Two-way ANOVA, paired t-test *p<0.05. (n=14, 14)). Mice treated with the LTA4H inhibitor Compound 1 enter the novel arm significantly more than the familiar arm, indicating an improvement in spatial memory with longer term treatment.

FIGS. 14-17 report the results of the Radial Arm Water Maze (RAWM), which measures spatial memory in aged mice after 29 days of treatment. FIG. 14 reports the latency (Two-way ANOVA. (n=12, 12)) and FIG. 15 reports the number of errors during the training and testing phases of the experiment (Two-way ANOVA. (n=12, 12)), indicating that mice treated with the LTA4H inhibitor Compound 1 have a small, but significant improvement in number of errors during this task. FIG. 16 reports the latency to find the hidden platform during the last phase of the trial (Unpaired t-test. (n=12, 12; 12, 13)). Mice treated with the LTA4H inhibitor Compound 1 have a trend towards a reduction in time to find the platform during their last trial. FIG. 17 reports the average number of errors during the last trial to find the hidden platform (Unpaired t-test. (n=12, 12; 12, 13)). Mice treated with the LTA4H inhibitor Compound 1 have a significant decreased in number of errors to find the hidden platform during the last trial.

FIGS. 18-21 report the results of the Y-maze, which measures spatial memory in aged mice after 18 days of treatment. FIG. 18 reports the time spent in the training arm (Unpaired t-test. (n=15, 14)) and FIG. 19 reports the number of entries into the training arm, indicating that both vehicle and Compound 1 treated mice can learn the task at this timepoint (Unpaired t-test. (n=15, 14)). FIG. 20 reports the percent time spent in the novel (N) or familiar (F) arms during the testing phase was significantly improved with LTA4H inhibition with Compound 1 (Two-way ANOVA, paired t-test **p<0.0001. (n=14, 13)). FIG. 21 reports the percentage of entries into the N and F arms. Mice treated with the LTA4H inhibitor Compound 1 enter the novel arm significantly more than the familiar arm (Two-way ANOVA, paired t-test **p<0.0001. (n=14, 13)), indicating an improvement in spatial memory with 18 days of treatment.

In summary, this work identifies that inhibiting LTA4H with Compound 1 in mice improves contextual and spatial memory. These results using Compound 1 were surprising compared to previous work that identified cognitive improvement with the LTA4H inhibitor SC-57461A. It was discovered that cognitive improvements with Compound 1 were more robust. First, Compound 1 proved to improve cognition faster than previous results. For example, FIG. 4 and FIG. 5 identify improved cognition as early as after 8 days of dosing. Second, the cognitive improvement with Compound 1 was reproducible across 3 independent cohorts of mice with robust statistical significance. And third, it was determined that inhibition with Compound 1 can improve both contextual and spatial memory domains, while previous studies with SC-57461A only improved spatial memory.

D. Example 3

FIGS. 22-30 report the results of the histology of astrocytes. GFAP is a pan astrocytic marker that was used to measure total number and size of astrocytes as a readout for astrocyte reactivity. AQP4 is a water channel expressed in astrocyte endfeet that line the blood-brain barrier. GFAP and AQP4 are increased with age and diseases with cognitive decline and BBB impairment (Kress B T et al., Ann Neurol, 76(6):845-61 (2014), Owasil R et al., Int J Mol Sci, 21(4) (2020), and Qi L et al., Life Sci, 88(1-2):50-56)). FIG. 22 reports GFAP percent area (Mann-Whitney test. (n=10, 10)), FIG. 23 reports the number of GFAP+ cells (Mann-Whitney test. (n=10, 10)), and FIG. 24 reports the average size of GFAP+ cells (Mann-Whitney test. (n=10, 10)) in the CA1 region of the hippocampus following 10 days of dosing. FIG. 25 reports the AQP4 intensity across a 60 micron (um) long line drawn across the large descending vessels of the CA1 hippocampus after 10 days of dosing with vehicle or Compound 1. There was a trending reduction in AQP4 intensity with 10 days of Compound 1 treatment (Mixed effects analysis with repeated measures. p=0.1918. (n=40, 40).

FIG. 26 reports GFAP percent area (Unpaired t-test. (n=15, 15)), FIG. 27 reports the number of GFAP+ cells (Unpaired t-test. (n=15, 15)), and FIG. 28 reports the average size of GFAP+ cells (Unpaired t-test. (n=15, 15)) in the CA1 region of the hippocampus. There was a significant reduction GFAP percent thresholded area following 4 weeks of treatment, while total GFAP+ cell number did not change. FIG. 29 reports a reduction in the AQP4 intensity across a 60 micron (um) long line drawn across the large descending vessels of the CA1 hippocampus (Mixed effects analysis with repeated measures. **$p<0.0001$. (n=60, 60)). FIG. 30 shows representative images of the data graphed in FIG. 7. FIG. 31 shows that perivascular (Pearson r=0.4628. p=0.0026 n=40) and FIG. 32 shows vascular AQP4 fluorescence intensity is significantly correlated with plasma levels of LTB4 (Pearson r=0.4346, *p=0.0164 n=30).

In summary, this example identifies that inhibition of LTA4H in aged mice for 4 weeks reduces astrocyte reactivity, but not total astrocyte number as measured using GFAP. Additionally, inhibition with the LTA4H inhibitor Compound 1 reduced AQP4 levels at the BBB after 4 weeks of dosing and this trend was observed as early as 10 days after dosing Compound 1 in aged mice. These results using Compound 1 were surprising compared to previous work that identified changes to astrocytes with the LTA4H inhibitor SC-57461A. It was discovered that the reduction in AQP4 at the BBB with Compound 1 occurred faster than previous results. FIG. 25 identify a trend towards reduced AQP4 as early as 10 days after dosing. And FIG. 29 identify a significant reduction in AQP4 after 4 weeks of dosing.

E. Example 4

FIGS. 33-35 report the results of pharmacokinetics of Compound 1 in plasma, brain, and blood at multiple timepoints following a single oral gavage dose to C57BL/6 mice at 10 mg/kg, 1 mg/kg, 0.3 mg/kg, and 0.1 mg/kg and measured using LC-MS/MS. FIG. 33 and FIG. 34 report that Compound 1 levels were sustained and detectable in plasma and blood for up to 24 hours following a single dose. FIG. 35 reports the detection and kinetics of Compound 1 in the brains of mice following a single oral dose was sustained and detectable for up to 24 hours following a single dose.

In summary, this example identifies the pharmacokinetic profile of Compound 1 in plasma, blood, and brain. This novel result indicates that Compound 1 is brain penetrant, even at low doses, which has not been identified for other LTA4H inhibitors and may explain the robustness of Compound 1's effects described in Example 2 compared to another, chemically structurally dissimilar LTA4H inhibitor (SC-57461A).

F. Example 5

FIGS. 36-37 report the results of ex vivo target engagement assays with Compound 1 in human and mouse plasma. Whole blood from human or mouse was incubated with vehicle or Compound 1, following by a calcium ionophore stimulation. Plasma was generated and LTB4 levels were measured using ELISA. LTB4 is the product of LTA4H hydrolysis so this assay reports on LTA4H enzymatic activity. FIG. 36 reports the human results and FIG. 37 reports the mouse results identifying that calcium ionophore stimulation increases LTB4 plasma levels and Compound 1 treatment reduces LTB4 plasma levels to unstimulated levels.

In summary, this example indicates that Compound 1 inhibits LTA4H hydrolysis activity ex vivo in both human and mouse blood.

G. Example 6

FIGS. 38-52 report the results of general overall health of aged C57BL6 mice treated with vehicle or Compound 1. FIG. 38 reports no change in body weight after 10 days of dosing Compound 1 compared to vehicle in the first cohort of mice (Two-way ANOVA. (n=14, 14)). FIG. 39 reports no change in body weight after 4 weeks of dosing Compound 1 compared to vehicle in the first cohort of mice (Two-way ANOVA. (n=14, 14)). FIG. 40 reports no change in body weight after 10 days of dosing Compound 1 compared to vehicle in the second cohort of mice (Two-way ANOVA. (n=15, 13)). FIG. 41 reports no change in body weight after 4 weeks of dosing Compound 1 compared to vehicle in the second cohort of mice (Two-way ANOVA. (n=14, 14)). FIG. 42 reports no change in body weight after 10 days of dosing Compound 1 compared to vehicle in the third cohort of mice (Two-way ANOVA. (n=15, 15)). FIG. 43 reports no change in body weight after 4 weeks of dosing Compound 1 compared to vehicle in the third cohort of mice (Two-way ANOVA. (n=15, 14)).

FIG. 44 reports no change in total distance traveled in an open field test after 10 days of dosing Compound 1 compared to vehicle. (Mann-Whitney. (n=13, 13). FIG. 45 reports no change in velocity in an open field test after 10 days of dosing Compound 1 compared to vehicle. (Mann-Whitney. (n=13, 13). FIG. 46 reports no difference between time spent in the periphery (P) or center (C) in an open field test after 10 days of dosing Compound 1 compared to vehicle. Both groups spent more time in the P. (Two-way ANOVA. Paired t-tests **$p<0.0001$. (n=14, 14)). FIG. 47 reports no change in total distance traveled in an open field test after 4 weeks of dosing Compound 1 compared to vehicle. (Mann-Whitney. (n=14, 14). FIG. 48 reports no change in velocity in an open field test after 4 weeks of dosing Compound 1 compared to vehicle. (Mann-Whitney. (n=14, 14). FIG. 49 reports no difference between time spent in the periphery (P) or center (C) in an open field test after 4 weeks of dosing Compound 1 compared to vehicle. Both groups spent more time in the P. (Two-way ANOVA. Paired t-tests **$p<0.0001$. (n=13, 14)).

FIG. 50 reports no change in nesting building score after 10 days of dosing with Compound 1 or vehicle (Unpaired t-test. (n=14, 14). FIG. 51 reports no change in maximum hang time in the wire hang test building score after 12 days of dosing with Compound 1 or vehicle (Unpaired t-test. (n=15, 14). FIG. 52 reports no change in average time before falling on the rotarod task the wire hang test building score after 19 days of dosing with Compound 1 or vehicle (Unpaired t-test. (n=15, 14).

In summary, this example indicates that Compound 1 does not impact general readouts for mouse health, including body weight, locomotion and anxiety measured using an open field, activities of daily living measured using nesting score, and motor function measured using wire hang and rotarod.

H. Example 7

FIG. 53 reports trends towards reduced il1b hippocampal gene expression following 10 days of dosing Compound 1 compared to vehicle (One-way ANOVA, Tukey's multiple comparisons test p=0.07. (n=13, 13, 11, 12). FIG. 54 reports trends towards reduced iba1 hippocampal gene expression following 10 days of dosing Compound 1 compared to vehicle (One-way ANOVA, Tukey's multiple comparisons test p=0.07. (n=13, 13, 12, 11). FIG. 55 reports trends towards reduced h2d1 hippocampal gene expression following 10 days and 4 weeks of dosing Compound 1 compared to vehicle (One-way ANOVA, Tukey's multiple comparisons test p=0.054, p=0.08. (n=14, 13, 12, 12). FIG. 56 reports increased dcx hippocampal gene expression following 4 weeks of dosing Compound 1 compared to vehicle (One-way ANOVA, Tukey's multiple comparisons test *p<0.05. (n=14, 13, 12, 12). FIG. 57 reports increased egr1 hippocampal gene expression following 10 days of dosing Compound 1 compared to vehicle (One-way ANOVA, Tukey's multiple comparisons test *p<0.05. (n=14, 13, 12, 12). FIG. 58 reports increased creb1 hippocampal gene expression following 10 days of dosing Compound 1 compared to vehicle (One-way ANOVA, Tukey's multiple comparisons test *p<0.05. (n=14, 13, 12, 12).

FIG. 59 reports a reduction in Iba-1 percent thresholded area in the hippocampal as measured by histology following 4 weeks of dosing Compound 1 compared to vehicle. (Unpaired t-test *p<0.05. (n=14, 13)).

In summary, this example indicates that treatment of aged mice with Compound 1 reduced inflammatory genes and proteins in the brain, including FIG. 53 il1b gene expression, FIG. 54 iba1 gene expression, FIG. 55 h2d1 gene expression, and FIG. 59 IBA1 protein expression. Compound 1 treatment also increased gene expression of the neurogenesis marker dcx FIG. 56. Additionally, Compound 1 treatment increased gene expression of immediate early genes important for neuronal activity including FIG. 57 egr1 and FIG. 58 creb1.

I. Example 8

FIGS. 60-62 report the results of in vivo target engagement assays with Compound 1 in mouse plasma. Whole blood from mice dosed with Compound 1 for 10-day FIG. 60 or 4 weeks FIG. 61 was incubated with a calcium ionophore to stimulate LTB4 release. Plasma was generated and LTB4 levels were measured using ELISA. LTB4 is the product of LTA4H hydrolysis so this assay reports on LTA4H enzymatic activity. FIG. 60 reports the inhibition of LTA4H with Compound 1 following 10 days of dosing in aged mice (One-way ANOVA, Tukey's multiple comparisons test **p<0.0001. (n=15, 15, 15, 15) and FIG. 61 reports the inhibition of LTA4H with Compound 1 following 4 weeks of dosing in aged mice (One-way ANOVA, Tukey's multiple comparisons test **p<0.0001. (n=15, 14, 15, 14)). FIG. 62 reports the comparison of mice dosed with Compound 1 made for 3 independent studies in young mice. (One-way ANOVA, Tukey's multiple comparisons test *p<0.05. (n=3, 3, 3, 3)).

In summary, this example indicates that treatment of aged mice with Compound 1 for 10 days or 4 weeks inhibits LTA4H hydrolysis activity and that there was no difference in the amount of inhibition across the 3 independent studies.

J. Example 9

FIGS. 63-66 report the results of an in vivo model of blood-brain-barrier (BBB) leakiness. Aged mice were treated for 4 weeks with vehicle or Compound 1 followed by an acute high dose of LPS was used to induce BBB breakdown. Sodium fluorescein was injected by tail vein and leakiness of sodium fluorescein into the brain was measured using a fluorescent plate reader. FIG. 63 reports that LPS induced BBB breakdown in young and aged mice. Treatment of aged mice with Compound 1 leads to a trend towards reduced BBB leakiness following LPS (Kruskal-Wallis test with Dunn's multiple comparisons with post-hoc Mann-Whitney test. *p<0.001, p<0.005, *p<0.05. (n=10, 10, 8, 9, 5, 7). FIG. 64 reports the AQP4 intensity across a 60 micron (μm) long line drawn across the large descending vessels of the CA1 hippocampus after 4 weeks of dosing with vehicle or Compound 1 followed by a high dose LPS to induced BBB breakdown. There was a trending reduction in AQP4 intensity with Compound 1 treatment (Mixed effects analysis with repeated measures. p=0.0912. (n=69, 57)). FIG. 65 reports the GFAP intensity across a 60 micron (μm) long line drawn across the large descending vessels of the CA1 hippocampus after 4 weeks of dosing with vehicle or Compound 1 followed by a high dose LPS to induced BBB breakdown. (Mixed effects analysis with repeated measures. (n=69, 57)). FIG. 66 reports the results of in vivo target engagement assays with Compound 1 in mouse plasma. Whole blood from mice dosed with Compound 1 for 4 weeks followed by high dose LPS was incubated with a calcium ionophore to stimulate LTB4 release. Plasma was generated and LTB4 levels were measured using ELISA. LTB4 is the product of LTA4H hydrolysis so this assay reports on LTA4H enzymatic activity. FIG. 66 reports the significant reduction in LTB4 levels following dosing Compound 1 and the trending reduction in mice treated Compound 1 followed by LPS. (Kruskal-Wallis test with Dunn's multiple comparisons with post-hoc Mann-Whitney test. ****p<0.0001 (n=8, 9, 8, 9)).

In summary, this example indicates that treatment of aged mice with Compound 1 improves response to a high dose LPS blood-brain barrier breakdown model. This model was used to mimic the breakdown that occurs in CADASIL. Together these data suggest that LTA4H inhibition with Compound 1 may be beneficial to improve BBB leakiness that occurs in these and similar diseases.

K. Example 10

Transgenic Notch3$^{R169C}$ mice treated with Vehicle or Compound as described previously in section A (Experimental Procedures supra) have blood collected via cardiac puncture in syringes pre-filled with Heparin. Brains are collected following saline and Heparin infusion and separated by mid-sagittal slice. One half of the brain is drop fixed in 4% PFA and 24 hours later, the brain is changed into a solution of 15% sucrose. A secondary change to 30% sucrose is performed 48 hours after initial fixation in PFA.

Pericytes

Brains are then sectioned to 50 micrometers in thickness using a vibratome and placed on a slide for immunostaining and stained with PDGFRβ and LECTIN antibodies as described previously (Ghosh supra) to show pericyte coverage. The number of PDGFRβ positive pericytes per square millimeter of selected field area in the cortex is analyzed by randomly selecting four fields in nonadjacent sections at approximately 100 μm intervals.

Resulting pericyte coverage and number in Transgenic Notch3R169C mice treated with Compound 1 are compared to Transgenic Notch3R169C mice treated with Vehicle or wild-type control mice treated with Vehicle. Transgenic mice treated with Vehicle show reduced pericyte coverage and number compared to wild-type control mice treated with Vehicle. And transgenic mice treated with Compound 1 show an increase in pericyte coverage and number compared to transgenic mice treated with vehicle. Pericytes play an essential role in the neurovascular unit and loss of pericytes in this CADASIL transgenic mouse model Notch3R169C is correlated with blood-brain barrier dysfunction (Ghosh supra). An increase in pericyte coverage and number with Compound 1 indicates that treatment with this inhibitor improves the function of the neurovascular unit and restores the loss of pericytes that occurs due to the CADASIL mutation R169C. These data suggest that Compound 1 treatment may be beneficial in CADASIL patients to improve the function of their neurovascular unit.

Blood-Brain Barrier Integrity

Albumin and fibrinogen presence is measured as a positive signal in the brain parenchyma. The signals are quantified as described previously (Ghosh supra). Transgenic mice treated with Vehicle has increased albumin and fibrinogen leakiness into the brain parenchyma compared to Vehicle treated wild-type controls. Transgenic mice treated with Compound 1 exhibit reduced albumin and fibrinogen compared to Vehicle-treated mice indicating improved blood-brain barrier (BBB) integrity. CADASIL patients also display increased BBB leakiness, and these data suggest that Compound 1 treatment may be beneficial in humans to improve BBB integrity.

GFAP and AQP4 Markers

GFAP and AQP4 markers for astrocytes are measured to determine the presence of astrocyte end-feet. Transgenic mice treated with Vehicle is reduced GFAP and AQP4 compared with Vehicle treated wild-type controls. And increased positive signal at Lectin-positive vessels in the cortex are observed in Compound 1-treated mice compared to Vehicle-treated mice. AQP4 and GFAP are markers for astrocyte, which make up an important part of the neurovascular unit and are lost in CADASIL mouse models and human patients. The increase in astrocyte coverage with Compound 1 suggests this treatment may be beneficial to improve neurovascular function in CADASIL human patients.

Additional Blood-Brain Barrier Markers Markers for blood-brain barrier improvement such as endothelial cells, plasma proteins, cell-adhesion proteins, basement membrane proteins, gap-junction proteins, and tight-junction proteins all show significant levels of improvement in the cortices of Compound 1-treated mice compared to Vehicle-treated mice.

LTB4 Levels

Plasma levels of LTB4 are measured using plasma collected from Transgenic Notch3R169C mice treated with Compound 1 or Vehicle control. A reduction in plasma levels of LTB4 is observed in Compound 1-treated mice compared to mice treated with Vehicle control. This indicates target engagement of Compound 1 in the CADASIL transgenic mouse model.

L. Example 11

LTB4 and LTA4H Plasma Levels in Transgenic Notch3$^{R169C}$ Mice Versus Wild Type Plasma levels of LTB4 and LTA4H are determined using plasma collected from wild type mice and Transgenic Notch3R169C mice. Measurement of LTB4 and LTA4H demonstrates that concentrations of both are increased in Transgenic Notch3$^{R169C}$ mice compared to wild type. This indicates that LTA4H and LTB4 is changed in CADASIL transgenic mice and that inhibition of LTA4H enzymatic activity may be beneficial to treat CADASIL.

M. Example 12

Male C57BL/6 mice aged 20-21 months were treated with Vehicle or SC-57461A commercially available LTA4H inhibitor. The mice were dosed with SC-57461A at 2.5 mg/kg PO bid for one month. Mice were anesthetized and blood and tissues were collected for further analysis. Blood was collected via cardiac puncture in syringes pre-filled with Heparin. Brains were collected following ACSF perfusion and processed for single cell RNA sequencing of labeled endothelial cells.

Brain endothelial cells (BECs) were sorted, sequenced, and analyzed based on techniques known to those having ordinary skill in the art. (See Chen M B, et al., Cell Rep, 30(13):4418-32e4 (2020) which is herein incorporated by reference in its entirety). Briefly, after dissection of the meninges, cortical caps, defined as the hippocampi and cortex, were microdissected, minced and enzymatically dissociated using the instructions for a Miltenyi, 130-092-628 Neural Dissociation Kit. The cell suspension was stained for endothelial cells with anti-CD31 and for microglia with anti-CD11b and sorted using flow cytometry using a Sony Multi-Application Cell Sorter MA900. Gates were determined to separate CD31-positive, CD11b-negative endothelial cells from CD11b-positive, CD31-negative microglia. Dead cells were excluded. Single cells were sorted directly into lysis buffer and processed for cDNA synthesis. Libraries were prepared and sequenced on the Illumina platform. Data was returned to Alkahest and processed to determine differential gene expression across treatment groups.

Gene Ontology (GO) Enrichment from Single Cell RNA Sequencing of BECs from Aged Mice Treated with Vehicle or the LTA4H Inhibitor SC-4651A Table 4 details the Top 5 significant Biological Process GO terms identified comparing single cell sequencing results from BECs isolated from aged mice treated with vehicle or the LTA4H inhibitor SC-57461A. The g:Profiler Web server (https://bitt.cs.ut.ee/gprofiler).

TABLE 4

| id | source | term_id | term_size | term_name | p_value |
|---|---|---|---|---|---|
| 1 | GO:BP | GO:0001944 | 755 | vasculature development | 3.97E−11 |
| 2 | GO:BP | GO:0072358 | 767 | cardiovascular system development | 6.39E−11 |
| 3 | GO:BP | GO:0001568 | 725 | blood vessel development | 6.66E−11 |
| 4 | GO:BP | GO:0048514 | 628 | blood vessel morphogenesis | 1.27E−09 |
| 5 | GO:BP | GO:0034097 | 940 | response to cytokine | 5.50E−09 |

The data from Table 4 highlight the broad, beneficial impact of LTA4H inhibition on brain endothelial cells gene expression. For example, long term LTA4H inhibition with SC-57461A in aged mice results in changes to the endothelial milieu, impacting GO terms such as "blood vessel development" and "response to cytokines" (FIG. 1).

N. Example 13

Microbulk qPCR of Endothelial Genes from Aged Mice Treated with LTA4H Inhibitors Downregulation of the detrimental genes Bsg, Gbp4, and CXCL12 in purified endothelial cells from the brains of mice treated with LTA4H inhibitors Compound 1 or SC57461A were compared to those of vehicle treated mice. Gene expression was measured by qPCR from 500 sorted endothelial cells and was normalized to GAPDH control.

Aged C57BL/6 mice (21 months of age) were treated for 1 month bid P.O. with vehicle, 1 mg/kg Compound 1, or 2.5 mg/kg SC57461A (n=3 mice per treatment group). One cortical cap (cortex and hippocampus) from each mouse was isolated and cells were dissociated using Miltenyi Neutral Dissociation Kit (#130-092-628). Cells were sorted using Sony Multi-Application Cell Sorter MA900 into clean, RNAase free 200 uL PCR strip tube with 5 uL RNAlater at a concentration of 500 cells per tube. RNA was isolated follow kit protocol for Qiagen RNeasy Micro Kit (#74004). cDNA was synthesized using SuperScript III Kit Protocol and qPCR assays were run using TaqMan or SYBR green primers.

FIG. 67 compares the down regulation of B sg gene in vehicle, Compound 1 LTA4H small molecule inhibitor, and SC-47561A commercially available small molecule LTA4H inhibitor. Treatment of either Compound 1 or SC-47561A resulted in down regulation of Bsg gene expression. Bsg encodes for Basigin/EMMPRIN/CD147, which is cell surface maker that is increased in brain endothelial following damage, such as stroke or inflammation (Patrizz A et al., Aging, 12(6):5121-39 (2020) which is herein incorporated by reference in its entirety).

FIG. 68 compares the down regulation of Gpb4 gene in vehicle, Compound 1 LTA4H small molecule inhibitor, and SC-47561A commercially available small molecule LTA4H inhibitor. Treatment of either Compound 1 or SC-47561A resulted in down regulation of Gpb4 gene expression. Gpb4 encodes for guanylate binding protein 4, which is upregulated in response to interferon or TNF alpha, suggesting its role as a detrimental, proinflammatory factor (Nair S R et al., J Neurovirol., 23(6):886-902 (2017) and Intlekofer K A et al., PLoS One, 14(4):e0215389 (2019) which are herein incorporated by reference in their entirety).

FIG. 69 compares the down regulation of pro-inflammatory gene CXCL12 (C—X—C Motif Chemokine Ligand 12 also known as stromal cell-derived factor 1 or SDF-1) in vehicle, Compound 1 LTA4H small molecule inhibitor, and SC-47561A commercially available small molecule LTA4H inhibitor. Treatment of either Compound 1 or SC-47561A resulted in down regulation of CXCL12 gene expression. Cxcl12 is a detrimental, proinflammatory chemokine that mediates blood-brain barrier impairment and neuroinflammation Mai C-L et al., Theranostics, 11(3):1059-78 (2021) and Stumm R K et al., J Neurosci., 22(14):5865-78 (2002) which are herein incorporated by reference in their entirety).

O. Example 14

Single Cell RNA Sequencing of Brain Tissue from Aged Mice Treated with LTA4H Inhibitor Aged C57BL/6 mice (21 months of age) were treated for 1 month bid P.O. with vehicle or 2.5 mg/kg SC57461A (n=3 mice per treatment group). One cortical cap (cortex and hippocampus) from each mouse was isolated and cells were dissociated and sorted using Sony Multi-Application Cell Sorter MA900. Unbiased RNA sequencing from single brain cells were analyzed according to techniques described previously (Yousf H, et al., Bio Protoc., 8(22):e3091 (2018), which is herein incorporated by reference in its entirety).

FIG. 70 shows a volcano plot of endothelial cell gene changes from unbiased single cell RNA sequencing of brain tissue from aged mice treated with the LTA4H inhibitor SC-57461A. Gene expression that is decreased is represented by gray dots while gene expression that is increased is represented by black dots. Genes with non-significant changes are not shown. Genes that were considered significant with a −log 10 Benjamini-Hochberg (BH) adjusted p-value>2 (p<0.01) and log 10 fold change>1.3 (P<0.05). Endothelial cells in the central nervous system, together with astrocytes and pericytes maintain a highly selective permeability barrier between the blood and the brain compartments that is critical for normal brain physiology. (Herland A et al., PLoS One. 11(3): e0150360 (2016)) which is herein incorporated by reference in its entirety.) These data therefore indicate that LTA4H inhibition results in many significant gene changes to brain endothelial cells suggesting improvement in neurovascular function.

FIG. 71 shows a volcano plot of astrocyte gene changes from unbiased single cell RNA sequencing of brain tissue from aged mice treated with the LTA4H inhibitor SC-57461A. Gene expression that is decreased is represented by gray dots while gene expression that is increased is represented by black dots. Genes with non-significant changes are not shown. Astrocytes are required for maintenance of the normal physiology of the neurovasculature and maintenance of the integrity of the blood brain barrier, extending their cell processes towards the endothelium and insert on the basement membrane (Herland supra). Genes that were considered significant with a −log 10 Benjamini-Hochberg (BH) adjusted p-value>2 (p<0.01) and log 10 fold change>1.3 (P<0.05). These data indicate that LTA4H inhibition results in many significant gene changes to astrocytes suggesting improvement in neurovascular function.

FIG. 72 shows a volcano plot of pericyte gene changes from unbiased single cell RNA sequencing of brain tissue from aged mice treated with the LTA4H inhibitor SC-57461A. Gene expression that is decreased is represented by blue dots while gene expression that is increased is represented by red dots. Gene expression with insignificant change is represented by black dots. Genes that were considered significant with a −log 10 Benjamini-Hochberg (BH) adjusted p-value>2 (p<0.01) and log 10 fold change>1.3 (P<0.05).

Embedded in the basement membrane of blood microvessels, pericytes are vascular mural cells that tightly encircle the endothelium. They extend their processes along precapillary arterioles, capillaries, and post-capillary venules. Pericytes in the central nervous system are uniquely positioned in the neurovascular unit between endothelial cells, astrocytes, and neurons. (Sweeney M D, et al., Nature Neuroscience, 19(771-83) (2016), which is herein incorporated by referenced in its entirety). Like astrocytes, pericytes convey cues that are required for normal function and differentiation of the brain microvascular endothelium and all three cell types—endothelial cells, pericytes, and astrocytes—are required for maintenance of the normal physiology of the neurovasculature and maintenance of the integrity of the blood brain barrier (Herland supra). These data therefore indicate that LTA4H inhibition results in many significant gene changes to pericytes suggesting improvement in neurovascular function.

P. Example 15

Male C57BL/6 mice aged 20-21 months are treated with Vehicle, Compound 1, or SC-57461A commercially available LTA4H inhibitor. The mice are dosed with Compound 1 at 1 mg/kg or SC-57461A at 2.5 mg/kg PO bid for one month. Mice are anesthetized and blood and tissues are collected for further analysis. Blood is collected via cardiac puncture in syringes pre-filled with Heparin. Brains are collected following ACSF perfusion and processed for single cell RNA sequencing of either labeled endothelial cells (experiment 1) or NeuN-positive neuronal nuclei (experiment 2). In a+ separate cohort of mice, brains are collected following 4% PFA perfusion for histological endpoints (experiment 3).

In experiment 1, endothelial gene expression in the brains of these aged mice are determined by single cell RNA Sequencing techniques, which are well-known to those having ordinary skill in the art. (See, e.g., Chen M B, et al., Cell Rep, 30(13):4418-32e4 (2020) which is herein incorporated by reference in its entirety). It is observed that Compound 1 produces a more robust change in endothelial gene expression in the brains of aged mice compared to SC-57461A compound, such as a decrease in detrimental genes including Vcam1 and Alp1, and an increase in beneficial genes including Selenop and Plat.

In experiment 2, neuronal gene expression in the brains of these aged mice are also determined by single cell RNA Sequencing techniques (See, e.g., Lacar B, et al., Nature Comm., 7(11022) (2016), herein incorporated by reference in its entirety). It is observed that Compound 1 produces a more robust change in neuronal gene expression in the brains of aged mice compared to SC-57461A compound, such as a decrease in detrimental genes including Cox6a2 and Sox11 and an increase in beneficial genes including, Grin1 and Grin2b.

In experiment 3, brain histology of endothelial cells and neurons in the brains of these aged mice are also observed. It is observed that Compound 1 produces a more robust changes in histology in endothelial cells and neurons in the brains of aged mice compared to SC-57461A compound.

Q. Example 16

Beneficial Gene Regulation Associated with LTA4H Inhibitors

Aged C57BL/6 mice (21 months of age) were treated for 1 month bid po with vehicle, 1 mg/kg Compound 1, or 2.5 mg/kg SC57461A (n=3 mice per treatment group). NucSeq For Mouse Brain Tissue protocol from 10× Genomics was used to isolate mouse hippocampus nuclei. Approximately 65 mg of brain tissue were used per treatment. Nonidet P40 was used to lyse cell walls and isolated nuclei were stained with Draq5 and NeuN antibodies for FACS sorting. Approximately 5,000 nuclei were collected for each sample. Eight samples were collected for each treatment for a total of 40,000 nuclei per treatment. These samples were prepped for sequencing using the 10× Genomics Chromium Next GEM kit.

FIG. 73 compares the regulation of Spock3 gene in Compound 1 LTA4H small molecule inhibitor and SC-47561A commercially available small molecule LTA4H inhibitor both relative to vehicle treated aged mice using single cell RNA sequencing of neurons in the dentate gryus of the hippocampus. Treatment of with Compound 1 resulted in the upregulation of Spock3 gene expression in the dentate gyrus. This gene was not significantly impacted by SC-47561A treatment. Spock3 encodes for secreted protein acidic and rich in cysteine (SPARC), which a secreted protein important for the development of synapses. In adulthood, SPARC expression is reduced, but is upregulated in response to injury or disease. This upregulation is considered to play a protective, beneficial role by increasing the number GluA1-containing AMPA receptors and improving synaptic function. Furthermore, SPARC treatment improves neuronal health and recovery following the middle cerebral artery occlusion (MCAO) model, which models that brain damage occurring following stroke and ischemia in diseases such as CADASIL (Jones E V, et al., Front Cell Neurosci, 12(22): 1-3 (2018)).

FIG. 74 compares the regulation of Dcc gene in vehicle, Compound 1 LTA4H small molecule inhibitor, and SC-47561A commercially available small molecule LTA4H inhibitor treated aged mice using single cell RNA sequencing of neurons. Treatment with Compound 1 resulted in the upregulation of Dcc gene expression in the dentate gyrus in the hippocampus. This gene was not significantly impacted by SC-57461A treatment. Dcc encodes for "deleted in colorectal cancer," which is a cell adhesion protein important for synaptic plasticity and learning and memory in the adult brain (Horn K E, et al., Cell Rep, 3:173-85 (2013)).

Microbulk qPCR Plat Beneficial Gene from Aged Mice Treated with LTA4H Inhibitors Downregulation of the beneficial gene, Plat, in purified endothelial cells from the brains of mice treated with LTA4H inhibitors Compound 1 or SC57461A were compared to those of vehicle treated mice. Gene expression was measured by qPCR from 500 sorted endothelial cells and was normalized to GAPDH control.

Aged C57BL/6 mice (21 months of age) were treated for 1 month bid P.O. with vehicle, 1 mg/kg Compound 1, or 2.5 mg/kg SC57461A (n=3 mice per treatment group). One cortical cap (cortex and hippocampus) from each mouse was isolated and cells were dissociated using Miltenyi Neutral Dissociation Kit (#130-092-628). Cells were sorted using Sony Multi-Application Cell Sorter MA900 into clean, RNAase free 200 uL PCR strip tube with 5 uL RNAlater at a concentration of 500 cells per tube. RNA was isolated follow kit protocol for Qiagen RNeasy Micro Kit (#74004). cDNA was synthesized using SuperScript III Kit Protocol and qPCR assays were run using TaqMan or SYBR green primers.

FIG. 75 compares the up regulation of Plat gene in vehicle, Compound 1 LTA4H small molecule inhibitor, and SC-47561A commercially available small molecule LTA4H inhibitor. Treatment of either Compound 1 or SC-47561A resulted in up regulation of Plat gene expression. Plat encodes for tissue plasminogen activator, which is an endothelial protein essential for the breakdown of blood clots and is commonly used as a therapeutic to treat stroke indications (Wardlaw J M, et al., Lancet, 379(9834):2364-72 (2012)).

R. Example 17

Colocalization of LTB4 Receptor (BLTR1) with Beta-Tubulin in Hippocampal Dendritic Neurons and LTA4H with NeuN in the Neurons of the Hippocampus Brain sections from C57BL/6 aged mice were washed in PBS and 0.5% PBST (Triton-X 100) prior to staining. Blocking with done for one hour with 10% serum before addition of primary antibodies. Primary antibodies to BLTR1, and beta-tubulin were incubated overnight at 4° C. and secondary antibodies were subsequently incubated for one hour at room temperature. Images were acquired at 40× magnification via confocal microscopy.

FIG. 76 shows the colocalization of the LTB4 receptor BLTR1 with the dendrite marker beta-tubulin in the CA1 region of the hippocampus. This result indicates that BLTR1 is expressed in the dendrites of neurons.

FIG. 77 shows the colocalization of the LTA4H with the neuronal nuclei marker NeuN in the CA1 region of the hippocampus. This result indicates that LTA4H is expressed in the neurons.

S. Example 18

Single Cell RNA Sequencing in Brain Endothelial Cells, CA1 Neurons, DG Neurons in Aged Mice Treated with LTA4H Inhibitors Brain Endothelial Cells Aged C57BL/6 mice (21 months of age) were treated for 1 month bid P.O. with vehicle, 1 mg/kg Compound 1, or 2.5 mg/kg SC57461A (n=3 mice per treatment group). Brain endothelial cells were sorted, sequenced and analyzed as described in Example 12 (See Chen M B, et al., Cell Rep, 30(13):4418-32e4 (2020) which is herein incorporated by reference in its entirety).

FIG. 78 shows a volcano plot of endothelial cell gene changes from single cell RNA sequencing performed on brain endothelial cells enriched from aged mice treated with SC-57461A LTA4H inhibitor. Gene expression that is decreased is represented by gray dots while gene expression that is increased is represented by black dots. Endothelial cells in the central nervous system, together with astrocytes and pericytes maintain a highly selective permeability barrier between the blood and the brain compartments that is critical for normal brain physiology. (Herland, supra.) These data therefore indicate that LTA4H inhibition results in many significant gene changes to brain endothelial cells suggesting improvement in neurovascular function.

CA1 Hippocampal Neurons, DG Hippocampal Neurons

Aged C57BL/6 mice (21 months of age) were treated for 1 month bid po with vehicle, 1 mg/kg Compound 1, or 2.5 mg/kg SC57461A (n=3 mice per treatment group). NucSeq For Mouse Brain Tissue protocol from 10× Genomics was used to isolate mouse hippocampus nuclei. Approximately 65 mg of brain tissue were used per treatment. Nonidet P40 was used to lyse cell walls and isolated nuclei were stained with Draq5 and NeuN antibodies for FACS sorting. Approximately 5,000 nuclei were collected for each sample. Eight samples were collected for each treatment for a total of 40,000 nuclei per treatment. These samples were prepped for sequencing using the 10× Genomics Chromium Next GEM kit.

FIG. 79 shows a volcano plot of CA1 neuronal gene changes from single cell RNA sequencing performed on NeuN+ nuclei enriched from aged mice treated with Compound 1 LTA4H inhibitor. Gene expression that is decreased is represented by gray dots while gene expression that is increased is represented by black dots. These data indicate that LTA4H inhibition results in many significant gene changes to neurons in the CA1 region of the hippocampus suggesting improvement in synaptic function and signaling FIG. 80 shows a volcano plot of DG neuronal gene changes from single cell RNA sequencing performed on NeuN+ nuclei enriched from aged mice treated with Compound 1 LTA4H inhibitor. Gene expression that is decreased is represented by gray dots while gene expression that is increased is represented by black dots. These data indicate that LTA4H inhibition results in many significant gene changes to neurons in the DG region of the hippocampus suggesting improvement in synaptic function and signaling.

FIG. 81 shows a volcano plot of CA1 neuronal gene changes from single cell RNA sequencing performed on NeuN+ nuclei enriched from aged mice treated with SC-57461A LTA4H inhibitor. Gene expression that is decreased is represented by gray dots while gene expression that is increased is represented by black dots. These data indicate that LTA4H inhibition results in many significant gene changes to neurons in the CA1 region of the hippocampus suggesting improvement in synaptic function and signaling.

FIG. 82 shows a volcano plot of DG neuronal gene changes from single cell RNA sequencing performed on NeuN+ nuclei enriched from aged mice treated with SC-57461A LTA4H inhibitor. Gene expression that is decreased is represented by gray dots while gene expression that is increased is represented by black dots. These data indicate that LTA4H inhibition results in many significant gene changes to neurons in the DG region of the hippocampus suggesting improvement in synaptic function and signaling.

T. Example 19

Reduction of Pecam-1 and MMP9 in Aged Mice Treated with LTA4H Inhibitors

Male C57BL/6 mice aged 20-21 months were treated with Vehicle or 10 mg/kg Compound 1 LTA4H inhibitor po for one month. Mice were anesthetized and perfused with saline. Brain tissue was collected, and sub dissected into cortex and hippocampus. Cortex samples were lysed in RIPA buffer and the soluble supernatant fraction was sent to Eve Technologies for analysis on the Cardiovascular Disease Panel using Luminex technology.

FIG. 83 shows a trending reduction in cortical Pecam-1 protein in aged mice treated with Compound 1 compared to vehicle. Pecam1 is increased in aging and disease where it contributes to neuroinflammation (Kalinowska A, et al., Eur J Neurol, 13(12):1284-90 (2006)). This result suggests that LTA4H inhibition by Compound 1 may contribute to reduced neuroinflammation by reducing in cortical Pecam-1 levels.

FIG. 84 shows a trending reduction in cortical MMP9 protein in aged mice treated with Compound 1 compared to vehicle. MMP9 is increased in aging and disease where it contributes to cognitive impairment (Bruno M A, et al., J Neuropathol Exp Neurol, 68(12):1309-18 (2009)). This result suggests that LTA4H inhibition by Compound 1 may contribute to improved cognition by reducing in cortical MMP9 levels.

U. Example 20

Pharmacodynamic Analysis of Plasma LTB4

Whole blood was collected by cardiac puncture using heparin as an anti-coagulant. 160 µL of whole blood was collected in duplicate for each mouse and incubated for 15 minutes in 37° C./5% CO2. During this time a 0.1 mM calcimycin stock was made by diluting 10 mM calcimycin (Sigma C7522) formulated in DMSO into PBS. Control solution was made by diluting the same volume of DMSO in PBS. Both solutions were sonicated for 10 minutes in a 37° C. water bath. 40 µL of 0.1 mM calcimycin (stimulated) or control solution (unstimulated) was added to each well of whole blood and incubated at 37° C./5% CO2 for 30 minutes. Whole blood was spun for 10 minutes at 1000×g to separate out plasma. LTB4 levels were detected by running an ELISA on the collected stimulated and unstimulated plasma diluted 1:10 (Enzo Life Sciences, ADI-901-068).

The ELISA plates were read on a BMG LABTECH CLARIOstar plate reader at 405 nm.

FIG. 85 shows a reduction in the pharmacodynamic readout of calcimycin stimulated plasma LTB4 levels following a single 1 mg/kg dose of Compound 1. This result shows positive target engagement with Compound 1 for LTA4H hydrolase activity.

V. Example 21

Plasma Levels of LTB4 Receptor in CADASIL Human Disease Population

Plasma samples from a CADASIL disease population and age/gender match healthy controls were obtained for analysis. EDTA plasma samples were analyzed by the SomaScan multiplex proteomic profiling platform measuring 7000 protein analytes at Somalogic, Inc. (Boulder, Colorado) as described (Gold L et al., PLoS ONE, 5(12):e15004 (2010)). Briefly, test samples were incubated with a mixture of proprietary aptamer-based affinity reagents called SOMAmers. Two sequential bead-based immobilization and washing steps eliminated unbound or non-specifically bound proteins and the unbound SOMAmers, leaving only protein target-bound SOMAmers. These remaining SOMAmers were isolated, and each reagent quantified simultaneously on a custom Agilent hybridization array.

FIG. 86 shows a trending increase in plasma level of the LTB4 receptor 1 (LTB4R) in the plasma of human CADASIL patients compared to healthy controls measured by SomaLogic (p value p=0.06 based on linear model adjusted for sex and age). This association between the LTB4 receptor 1 and CADASIL reveals that reducing LTB4 levels by inhibiting LTA4H activity may be a beneficial therapeutic strategy for CADASIL.

Plasma Levels of LTB4 in CADASIL Human Disease Population

Plasma samples from a CADASIL disease population and age/gender match healthy controls were obtained for analysis. EDTA plasma samples were analyzed for LTB4 using an ELISA on the collected plasma diluted 1:10 (Enzo Life Sciences, ADI-901-068). The ELISA plates were read on a BMG LABTECH CLARIOstar plate reader at 405 nm.

FIG. 87 shows a significant increase in plasma level of LTB4 in the plasma of human CADASIL patients compared to healthy controls measured by ELISA. This association between levels of LTB4 and CADASIL reveals that reducing LTB4 levels by inhibiting LTA4H activity may be a beneficial therapeutic strategy for CADASIL.

W. Example 22

Gene Ontology Analysis Using Single Cell Sequencing From Brain Endothelial Cells, CA1 Hippocampal Neurons, and Dentate Gyrus Hippocampal Neurons in Aged Mice Treated with LTA4H Inhibitors GO terms are generated using the g:Profiler Web server (https://bitt.cs.ut.ee/gprofiler) to analyze differential regulated gene lists. Reported are the top 20 gene ontology (GO terms) terms from the biological process category, sorted by significance as determined by P-value. This list was filtered to report significant GO terms that include less than 1000 genes.

FIG. 88A graphically represents as a bar graph the top 20 significant Biological Process GO terms from single cell sequencing of brain endothelial cells (BEC) isolated from aged mice treated long-term with vehicle or the SC-57461A LTA4H inhibitor. This treatment results in changes to the endothelial milieu, impacting GO terms such as "blood vessel development" and "response to cytokines" which are biological processes directly affected in CADASIL patients. FIG. 88B is a table listing additional information for the top 20 significant GO terms as described in FIG. 88A.

FIG. 89A graphically represents as a bar graph the top 20 significant Biological Process GO terms from single cell sequencing of CA1 hippocampal neurons isolated from aged mice treated long-term with vehicle or the Compound 1 LTA4H inhibitor. This treatment highlights the beneficial impact of LTA4H inhibition on CA1 gene expression associated with a broad array of biological processes. For example, long term LTA4H inhibition with Compound 1 in aged mice results in changes to "synaptic signaling" and "synaptic organization" which are processes directly related to cognition and neurogenesis and are detrimentally impacted in CADASIL patients. FIG. 89B is a table listing additional information for the top 20 significant GO terms as described in FIG. 89A.

FIG. 90A graphically represents as a bar graph the top 20 significant Biological Process GO terms from single cell sequencing of DG hippocampal neurons isolated from aged mice treated long-term with vehicle or the Compound 1 LTA4H inhibitor. This treatment highlights the beneficial impact of LTA4H inhibition on brain DC neuronal gene expression associated with a wide array of biological processes. For example, long term LTA4H inhibition with Compound 1 in aged mice results in changes to synapses, impacting GO terms such as "synaptic signaling" and "synapse organization" which are processes directly related to cognition and neurogenesis and are detrimentally impacted in CADASIL patients. FIG. 90B is a table listing additional information for the top 20 significant GO terms as described in FIG. 90A.

FIG. 91A graphically represents as a bar graph the top 20 significant Biological Process GO terms from single cell sequencing of CA1 hippocampal neurons isolated from aged mice treated long-term with vehicle or the SC-57461A LTA4H inhibitor. This treatment highlights the beneficial impact of LTA4H inhibition on brain CA1 neuronal gene expression associated with a broad array of biological processes. For example, long term LTA4H inhibition with SC-57461A in aged mice results in changes to synapses, impacting GO terms such as "synaptic signaling" and "synaptic organization" which are processes directly related to cognition and neurogenesis and are detrimentally impacted in CADASIL patients. FIG. 91B is a table listing additional information for the top 20 significant GO terms as described in FIG. 91A. Preliminary data also suggest that treatment with Compound 1 trends towards increasing synapse density in the CA1 region of the hippocampus when measured using histological techniques to stain for pre- and post-synaptic proteins and imaged using semi-high resolution confocal microscopy. This suggests that treatment with Compound 1 can increase synapse density, leading to the functional and cognitive improvements described in the examples disclosed herein. Notably, the SC-574661A LTA4H inhibitor, which is structurally dissimilar to Compound 1, exhibited no trend in increased CA1 synapse density.

FIG. 92A graphically represents as a bar graph the top 20 significant Biological Process GO terms from single cell sequencing of DG hippocampal neurons isolated from aged mice treated with vehicle or the LTA4H inhibitor SC-57461A. This treatment highlights the beneficial impact of LTA4H inhibition on brain DG neuronal gene expression associated with a broad array of biological processes. For example, longer term LTA4H inhibition with SC-57461A in aged mice results in changes to synapses, impacting GO germs such as "synaptic signaling" and "synaptic organization" which are processes directly related to cognition and neurogenesis and are detrimentally impacted in CADASIL patients. FIG. 92B is a table listing additional information for the top 20 significant GO terms as described in FIG. 92A.

X. Example 23

LTB4 Plasma Analysis from Human CADASIL Subjects Compared to Aged-Matched Controls.

Whole blood from 5 CADASIL subjects and 5 age-matched controls were acquired from Sunnybrook Research Institute. Whole blood was stimulated with calcimycin prior to generation of plasma. First, 100 µL of 10 mM calcimycin (Sigma #C7522) in DMSO was diluted into 10 mL of PBS and sonicated for 10 minutes at 37° C. In a 96 well polystyrene plate (Corning 354657), 160 µL of whole blood was incubated for 15 minutes in a 37° C./5% CO2 (Panasonic MCO-230AICUV-PA). Next, 40 µL of the 100 µM calcimycin working solution was added to each well and incubated again for 30 minutes at 37° C./5% CO2. After incubation, the plates were centrifuged for 10 minutes at 4° C. at 1500 rpm. Unstimulated plasma was diluted 1:10, and stimulated plasma was diluted 1:1000. Both were analyzed for LTB4 using LTB4 ELISA Kit (Enzo Life Sciences, ADI-901-068) in triplicate following the included kit protocol. The final readings were collected on a BMG LABTECH CLARIOstar plate reader at 405 nm.

FIG. 93A shows a significant increase in LTB4 levels in CADASIL subjects, measured in stimulated plasma, compared with age-matched controls. FIG. 93B shows unstimulated plasma LTB4 levels trend toward increase in CADASIL subjects.

Y. Example 24

Plasma and Brain Analysis from the CADASIL Transgenic Mouse Model Notch3$^{R169C}$ Compared to Littermate Controls Following Dosing with Compound 1 for 4 Months.

Notch3$^{R169C}$ mice (5-month-old) were treated PO BID with either vehicle or Compound 1 (1 mg/kg) for 4 months and littermate WT controls were treated with vehicle for 4 months. Prior to sacrifice, syringes were prepped with 7.5 µL of 1000 U/mL heparin. To increase LTB4 plasma levels, whole blood was stimulated with calcimycin prior to generation of plasma. First, 100 µL of 10 mM calcimycin (Sigma #C7522) in DMSO was diluted into 10 mL of PBS and sonicated for 10 minutes at 37° C. In a 96 well polystyrene plate (Corning 354657), 160 µL of mouse whole blood was collected for each animal and incubated for 15 minutes in a 37° C./5% CO2 (Panasonic MCO-230AICUV-PA). Next, 40 µL of the 100 µM calcimycin working solution was added to each well and incubated again for 30 minutes at 37° C./5% CO2. After incubation, the plates were centrifuged for 10 minutes at 4° C. at 1500 rpm. Plasma was diluted 1:10 and analyzed for LTB4 using LTB4 ELISA Kit (Enzo Life Sciences, ADI-901-068) in duplicate following the included kit protocol. The final readings were collected on a BMG LABTECH CLARIOstar plate reader at 405 nm. Brain tissue was dissected for cortex. One third of the cortex was homogenized in RIPA buffer (EMD Millipore 20-188) using an Omni BeadRuptor 24. Lysates were centrifuged for 10 mins at 10,000 g at 4° C. to collect the supernatant. Protein concentration was determined by BCA (Thermo Fisher 23225) and then diluted in PBS to approximately 10 mg/ml. Samples were sent to Eve Technologies for analysis.

FIG. 94A shows the significant increase in LTB4 levels in Notch3$^{R169C}$ transgenic mice (R169C), measured in stimulated plasma. LTB4 levels are significantly reduced in these mice following treatment with Compound 1. FIG. 94B shows there is no change in LTB4 levels detected between groups with unstimulated plasma.

FIG. 95A shows a trending increase in IL-2 in plasma in Notch3$^{R169C}$ transgenic mice (R169C) treated with vehicle. IL-2 levels in plasma are significantly reduced in Notch3R169c transgenic mice treated with Compound 1. FIG. 95B shows there is a trending increase in IL-7 levels in brain cortex lysate in Notch3R$^{169C}$ transgenic mice (R169C) treated with vehicle. IL-7 levels are significantly reduced in brain cortex lysate in Notch3$^{R169C}$ transgenic mice treated with Compound 1.

These results identify that Compound 1 can reduce LTB4 and brain inflammatory cytokines in the mouse model of CADASIL and may be a novel therapeutic strategy for this specific patient population.

Z. Example 25

Functional Synaptic Readout of Long-Term Potentiation in Aged Mice Treated with Vehicle, Compound 1, or SC-57461A for One Month.

Aged C57BL/6 mice (21 months of age) were treated for 1 month bid po with vehicle, 1 mg/kg Compound 1, or 2.5 mg/kg SC57461A (n=5 mice per treatment group). Electrophysical recordings were performed at AfaSci, Inc, as follows. Animals were deeply anesthetized with halothane and decapitated. The brain was quickly taken out and placed into ice-cold artificial cerebrospinal fluid (ACSF) that was continuously bubbled with 5% CO2/95% O$_2$. The ACSF was composed of (in mM) NaCl 130.0, KCl 2.5, KH$_2$PO$_4$ 1.2, CaCl$_2$ 2.4, MgSO$_4$ 1.3, NaHCO$_3$ 26.0 and glucose 10.0 (pH 7.4). Hippocampal slices (400 µm thick) were prepared using a tissue slicer (Stoelting Co., IL) and incubated at room temperature in continuously oxygenated ACSF for at least 1 h before being recorded with submerged mode in chamber (Harvard Apparatus) at room temperature. Data were collected with an Axopatch-2B amplifier and pClamp 10.4 program (Axon Instruments) through digidata 1320A. Slices were continuously perfused with ACSF bubbling with 5% CO2/95% O$_2$ at flow rate about 1.75 ml/min with peristaltic pump (Dynamax, Rainin).

Field population spike (PS) was recorded using glass microelectrode filled with ACSF (resistance: 1-3 MO). Biphasic current pulses (0.2 ms duration for one phase, 0.4 ms in total) were delivered in 10 s intervals through a concentric bipolar stimulating electrode (FHC, Inc.). No obvious synaptic depression or facilitation was observed at this frequency stimulation. To record field population spikes in dorsal dentate gyrus, the stimulating electrode was placed on the hippocampal fissure to stimulate the bypassing perforant pathway fibers and the recording electrode was placed on inner part of granular cell layer. To record field EPSPs in DG, the stimulating electrode was placed on the hippocampal fissure to stimulate the bypassing perforant pathway fibers and the recording electrode was placed on inner part of granular cell layer. Slices were recorded within 8 hours after dissection. Titanic stimulation consisted of 2 trains of 100 pulses (0.4 ms bipolar pulse duration, 100 Hz) lasting for 1 second with 5 seconds of interval. The slope of EPSP and amplitude of population spike were measured from the initial phase of negative wave with Clampfit10.4. Each data point was measured with average of 3 consecutive traces.

LTP was plotted as the percentage to baseline following high frequency stimulation (mean±SEM).

FIG. 96 compares the functional consequence on neuronal signaling in mice treated with vehicle, Compound 1 LTA4H small molecule inhibitor, and SC47561A commercially available small molecule LTA4H inhibitor treated aged mice using the electrophysiological technique long term potentiation (LTP). Treatment with Compound 1 resulted in the increase in LTP, which suggests an increase in neurons signaling in the CA1 region of the hippocampus following LTA4H inhibition with Compound 1. Surprisingly, treatment with the commercially available tool compound LTA4H inhibitor SC47561A did not show the same LTP increase.

FIG. 97 compares the functional consequence on neuronal signaling in mice treated with vehicle, Compound 1 LTA4H small molecule inhibitor, and SC47561A commercially available small molecule LTA4H inhibitor treated aged mice using the electrophysiological technique long term potentiation (LTP). Treatment with Compound 1 resulted in the increase in LTP, which suggests an increase in neurons signaling in the DG region of the hippocampus following LTA4H inhibition with Compound 1. Surprisingly, treatment with the commercially available tool compound LTA4H inhibitor SC47561A did not show the same LTP increase.

AA. Example 26

Pharmacodynamic Dose Response of Compound 1.

Whole blood was collected by cardiac puncture using heparin as an anti-coagulant. 160 µL of whole blood was collected in duplicate for each mouse and incubated for 15 minutes in 37° C./5% CO2. During this time a 0.1 mM calcimycin stock was made by diluting 10 mM calcimycin (Sigma C7522) formulated in DMSO into PBS. Control solution was made by diluting the same volume of DMSO in PBS. Both solutions were sonicated for 10 minutes in a 37° C. water bath. 40 µL of 0.1 mM calcimycin (stimulated) or control solution (unstimulated) was added to each well of whole blood and incubated at 37° C./5% CO2 for 30 minutes. Whole blood was spun for 10 minutes at 1000×g to separate out plasma. LTB4 levels were detected by running an ELISA on the collected stimulated and unstimulated plasma diluted 1:10 (Enzo Life Sciences, ADI-901-068). The ELISA plates were read on a BMG LABTECH CLARIOstar plate reader at 405 nm.

FIG. 98 shows a dose response in the pharmacodynamic readout of plasma LTB4 levels following a single dose of 0.3, 0.1, or 0.03 mg/kg dose of Compound 1. These results show positive target engagement with Compound 1 for LTA4H hydrolase activity and a pharmacodynamic dose response.

BB. Example 27

Reduced synaptic density in young mice treated with recombinant protein for 1 week compared to vehicle.

Young, 8-week-old wild-type (WT; C57BL/6) mice were homogenized between groups by body weight. Mice were dosed intravenously (IV) with PBS vehicle control or with recombinant human LTA4H protein daily for 7 consecutive days. Recombinant human LTA4H (Bio-techne, 4008-SN) was buffer-exchanged into sterile PBS prior to dosing at 4.6 ug/150 uL by tail vein i.v. injection. Brain tissue was collected 6 weeks after dosing and stained for synapses using Homer1 (post synaptic) and Synapsin (presynaptic) antibodies. Images were collecting using Airyscan on a confocal micrograph and synapse density was quantified as the juxtaposition of the pre and post synaptic markers in the CA1 region of the hippocampus.

FIG. 99 reports the number of synapses measured as juxtaposed Synapsin (presynaptic) and Homer1 (postsynaptic) markers in the CA1 region of the hippocampus in mice treated with either PBS control or human recombinant LTA4H protein. There is a significant decrease in the number of synapses in the LTA4H treated animals. All data shown are mean±s.e.m.; *p<0.05, unpaired t test, n=42 images from 5 mice per group. These results show that there is significant detrimental effect of peripherally administered human recombinant LTA4H protein on hippocampal synaptic density of 3 months old wild-type (C57BL/6) mice.

CC. Example 28

Single Cell RNA Sequencing of Brain Tissue from Aged Mice Treated with LTA4H Inhibitor Aged C57BL/6 mice (21 months of age) were treated for 1 month bid P.O. with vehicle or 2.5 mg/kg SC57461A (n=3 mice per treatment group). One cortical cap (cortex and hippocampus) from each mouse was isolated and cells were dissociated and sorted using Sony Multi-Application Cell Sorter MA900. Unbiased RNA sequencing from single brain cells were analyzed according to techniques described previously (Yousf H, et al., Bio Protoc., 8(22):e3091 (2018), which is herein incorporated by reference in its entirety).

The data from FIG. 100 highlight the broad, beneficial impact of LTA4H inhibition on brain astrocyte gene expression. For example, long term LTA4H inhibition with SC-57461A in aged mice results in changes to astrocytes, impacting GO terms such as "response to carbohydrate" and "cellular glucose homeostasis."

The data from FIG. 101 highlight the broad, beneficial impact of LTA4H inhibition on brain pericyte gene expression. For example, long term LTA4H inhibition with SC-57461A in aged mice results in changes to pericyte, impacting GO terms such as "angiogenesis" and "blood vessel morphogenesis."

The data from FIG. 102 highlight the broad, beneficial impact of LTA4H inhibition on brain endothelial cell gene expression. For example, long term LTA4H inhibition with SC-57461A in aged mice results in changes to endothelial, impacting GO terms such as "vascular development" and "blood vessel morphogenesis."

What is claimed:

1. A method of improving cognitive function in a subject diagnosed with an age-related cognitive disease, the method comprising administering a therapeutically effective amount of a compound of formula (I):

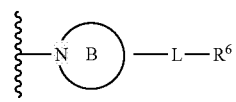

or a pharmaceutically acceptable salt thereof, wherein:
X is N or CH;
n is an integer from 0 to 3;
$R^1$ is selected from halo, —OH, —CN, —($C_1$-$C_6$)alkyl, —O($C_1$-$C_6$)alkyl, and —($C_3$-$C_6$)cycloalkyl;
$R^2$ and $R^3$ are each independently selected from —H and —($C_1$-$C_6$)alkyl,
wherein $R^2$ and $R^3$ may join to form a 3- to 6-membered ring optionally having from one to three heteroatoms, and further optionally substituted with one to three groups selected from halo, —OH, (=O), —(C$_1$-C$_6$)alkyl, —O(C$_1$-C$_6$)alkyl, —C(O)O—H, —C(O)(C$_1$-C$_6$)alkyl, and —C(O)NH$_2$;

A is a (4- to 14-membered)N-heterocyclic ring of the following formula:

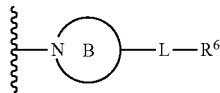

wherein said ring B is: (a) a non-aromatic 4-8 membered monocyclic radical; or (b) a bridged bicyclic radical, a spirocyclic radical, or a 6 to 11-membered fused bicyclic radical,
wherein at least a nonaromatic N-heterocyclic ring of each of said bridged bicyclic radical, spirocyclic radical, or 6 to 11-membered fused bicyclic radical is attached to the carbon atom 1 of the compound of formula (I),
wherein each of said bridged bicyclic radical, spirocyclic radical, and 6 to 11-membered fused bicyclic radical may optionally have an aromatic ring,
wherein said ring B may additionally have from one to three additional ring heteroatoms independently selected from N, O and S; and
wherein said ring B may be further optionally substituted by one to three groups selected from halo, —OH, (=O), —C(O)O—H, —C(O)O—(C$_1$-C$_6$)alkyl, and —(C$_1$-C$_6$)alkyl;

L is absent or a linker selected from —(C$_1$-C$_6$)alkylene-;

each R$^6$ is independently selected from halo, —OR$^7$, —CF$_3$, —CN, —(C$_1$-C$_6$)alkyl, —O(C$_1$-C$_6$)alkyl, —C(O)R$^7$, —C(O)$_2$R$^7$, —C(O)N(R$^7$)$_2$, —N(R$^7$)$_2$, —NHC(O)R$^7$, —NHC(O)N(R$^7$)$_2$, —S(O)$_2$R$^7$, —NH—S(O)$_2$-R$^7$, —(C$_3$-C$_6$)cycloalkyl, -(4- to 14-membered)heterocycloalkyl, —(C$_6$-C$_{10}$)aryl, and -(5- to 11-membered)heteroaryl,
wherein each of said —(C$_1$-C$_6$)alkyl, —O(C$_1$-C$_6$)alkyl, —(C$_3$-C$_6$)cycloalkyl, -(4- to 14-membered)heterocycloalkyl, —(C$_6$-C$_{10}$)aryl, and -(5- to 11-membered)heteroaryl of said R$^6$ group is optionally substituted where possible with one to three groups selected from halo, —OH, —CF$_3$, —CN, (=O), —(C$_1$-C$_6$)alkyl, —C(O)O—H, —C(O)O—(C$_1$-C$_6$)alkyl, —NH$_2$, —NH(C$_1$-C$_6$)alkyl, —N((C$_1$-C$_6$)alkyl)$_2$, —S(O)$_2$(C$_1$-C$_6$)alkyl, —(C$_3$-C$_6$)cycloalkyl, -(4- to 14-membered)heterocycloalkyl, —(C$_6$-C$_{10}$)aryl, and -(5- to 11-membered)heteroaryl; and each R$^7$ is independently selected from —H, —(C$_1$-C$_6$)alkyl, —(C$_1$-C$_6$)alkyl-OH, —(C$_1$-C$_6$)alkyl-O—(C$_1$-C$_6$)alkyl, —O(C$_1$-C$_6$)alkyl, —(C$_3$-C$_6$)cycloalkyl, —(C$_3$-C$_6$)cycloalkyl-OH, -(4- to 14-membered)heterocycloalkyl, —(C$_6$-C$_{10}$)aryl, and -(5- to 11-membered)heteroaryl,
wherein each of said R$^7$ groups is optionally substituted where possible with a group selected from —OH, —NH(C$_1$-C$_6$)alkyl, —NHC(O)(C$_1$-C$_6$)alkyl, —C(O)NH$_2$, —S(O)$_2$(C$_1$-C$_6$)alkyl, and -(4- to 14-membered)heterocycloalkyl,
wherein said -(4- to 14-membered)heterocycloalkyl group is optionally substituted where possible with a (=O) group;
and one or more additional active agents.

2. The method of claim 1, wherein the compound of formula (I) is selected from the group consisting of: 1-[4-(2,3-dihydro-1,4-benzodioxin-2-yl)benzyl]pyrrolidine, 4-[4-(2,3-dihydro-1,4-benzodioxin-2-yl)benzyl]morpholine, 1-[4-(2,3-dihydro-1,4-benzodioxin-2-yl)benzyl]-4,4-dimethylpiperidine, 8-[4(2,3-dihydro-1,4-benzodioxin-2-yl)benzyl]-2,8-diazaspiro[4.5]decan-1-one, 1-[4(2,3-dihydro-1,4-benzodioxin-2-yl)benzyl]-4-fluoropiperidine, (1s,4s)-7-[4(2,3-dihydro-1,4-benzodioxin-2-yl)benzyl]-7-azabicyclo[2.2.1]heptane, 4-[4(2,3-dihydro-1,4-benzodioxin-2-yl)benzyl]thiomorpholine 1,1-dioxide, 1-{4-[(2S)-2,3-dihydro-1,4-benzodioxin-2-yl]benzyl}-N,N-dimethylpiperidine-4-carboxamide, (3S)-1-[4-(2,3-dihydro-1,4-benzodioxin-2-yl)benzyl]pyrrolidin-3-ol, 1-({1-[4-(2,3-dihydro-1,4-benzodioxin-2-yl)benzyl]piperidin-3-yl}methyl)pyrrolidin-2-one, 1-{4-[4-(2,3-dihydro-1,4-benzodioxin-2-yl)benzyl]piperazin-1-yl}ethanone, 3-[4-(pyrrolidin-1-ylmethyl)phenyl]-2,3-dihydro[1,4]dioxino[2,3-b]pyridine, 7-[4-(2,3-dihydro-1,4-benzodioxin-2-yl)benzyl]-5,6,7,8-tetrahydro[1,2,4]triazolo[4,3-a]pyrazine, 3-{4-[(1,1-dioxidothiomorpholin-4-yl)methyl]phenyl}-2,3-dihydro[1,4]dioxino[2,3-b]pyridine, 3-[4-(morpholin-4-ylmethyl)phenyl]-2,3-dihydro[1,4]dioxino[2,3-b]pyridine, (3R)-1-{4-[(2S)-2,3-dihydro-1,4-benzodioxin-2-yl]benzyl}piperidine-3-carboxylic acid, (3S)-1-{4-[(2S)-2,3-dihydro-1,4-benzodioxin-2-yl]benzyl}piperidine-3-carboxylic acid, 1-(1-{4-[(2S)-2,3-dihydro-1,4-benzodioxin-2-yl]benzyl}piperidin-4-yl)-2,2,2-trifluoroethanol, 2-(1-{4-[(2S)-2,3-dihydro-1,4-benzodioxin-2-yl]benzyl}piperidin-4-yl)-1,1,1,3,3,3-hexafluoropropan-2-ol, 1-[4-(2,3-dihydro-1,4-benzodioxin-2-yl)benzyl]-N-methylpiperidine-4-carboxamide, 4-{1-[4-(2,3-dihydro-1,4-benzodioxin-2-yl)benzyl]piperidin-4-yl}butanoic acid, {1-[4-(2,3-dihydro-1,4-benzodioxin-2-yl)benzyl]piperidin-4-yl}methanol, 2-{1-[4-(2,3-dihydro-1,4-benzodioxin-2-yl)benzyl]piperidin-4-yl}propan-2-ol, 3-{1-[4-(2,3-dihydro-1,4-benzodioxin-2-yl)benzyl]piperidin-4-yl}propan-1-ol, 1-[4-(2,3-dihydro-1,4-benzodioxin-2-yl)benzyl]-4-methyl-1,4-diazepane, 1-{4-[(2,3-dihydro-1,4-benzodioxin-2-yl)benzyl]-1,4-diazepan-1-yl}ethanone, 4-[4-(2,3-dihydro-1,4-benzodioxin-2-yl)benzyl]-1,4-oxazepane, (3R)-1-[4-(2,3-dihydro-1,4-benzodioxin-2-yl)benzyl]pyrrolidin-3-ol, 8-[4-(2,3-dihydro-1,4benzodioxin-2-yl)benzyl]-1,3,8-triazaspiro[4.5]decane-2,4-dione, 1-[4-(2,3-dihydro-1,4-benzodioxin-2-yl)benzyl]-3-methoxyazetidine, {1-[4-(2,3-dihydro-1,4-benzodioxin-2-yl)benzyl]piperidin-4-yl}(morpholin-4-yl)methanone, 2-{1-[4-(2,3-dihydro-1,4-benzodioxin-2-yl)benzyl]piperidin-4-yl}-N,N-dimethylacetamide, 1-[4-(2,3-dihydro-1,4-benzodioxin-2-yl)benzyl]-4-(methylsulfonyl)piperidine, 1-[4-(2,3-dihydro-1,4-benzodioxin-2-yl)benzyl]azepane, 1-[4-(2,3-dihydro-1,4-benzodioxin-2-yl)benzyl]-4-phenylpiperidin-4-ol, 1-[4-(2,3-dihydro-1,4-benzodioxin-2-yl)benzyl]azetidine-3-carbonitrile, 1-[4-(2,3-dihydro-1,4-benzodioxin-2-yl)benzyl]-3-methoxypyrrolidine, N-{1-[4-(2,3-dihydro-1,4-benzodioxin-2-yl)benzyl]piperidin-4-yl}methanesulfonamide, 1-({1-[4-(2,3-dihydro-1,4-benzodioxin-2-yl)benzyl]piperidin-4-yl}methyl)pyrrolidin-2-one, 1-[4-(2,3-dihydro-1,4-benzodioxin-2-yl)benzyl]-N,N-dimethylpiperidine-4-carboxamide, 1-[4-(2,3-dihydro-1,4-benzodioxin-2-yl)benzyl]-N-(2-hydroxyethyl)piperidine-4-carboxamide, 1-{1-[4-(2,3-dihydro-1,4-benzodioxin-2-yl)benzyl]piperidin-4-yl}urea, 2-{4-[(2S)-2,3-dihydro-1,4-benzodioxin-2-yl]benzyl}-1,2,3,4-tetrahydroisoquinoline-4-carboxylic acid, 1-{4-[(2S)-2,3-dihydro-1,4-benzodioxin-2-yl]benzyl}pyrrolidine-3-carboxylic acid, 1-{4-[(2S)-2,3-dihydro-1,4-benzodioxin-2-yl]benzyl}-2-methylpiperidine, (1-{4-[(2S)-2,3-dihydro-1,4-benzodioxin-2-yl]

benzyl}piperidin-3-yl)methanol, 2-(1-{4-[(2S)-2,3-dihydro-1,4-benzodioxin-2-yl]benzyl}piperidin-4-yl)ethanol, 1-{4-[(2S)-2,3-dihydro-1,4-benzodioxin-2-yl]benzyl}-2-methylpyrrolidine, 1-{4-[(2S)-2,3-dihydro-1,4-benzodioxin-2-yl]benzyl}piperidin-3-ol, N-(1-{4-[(2S)-2,3-dihydro-1,4-benzodioxin-2-yl]benzyl}pyrrolidin-3-yl)acetamide, N-(1-{4-[(2S)-2,3-dihydro-1,4-benzodioxin-2-yl]benzyl}pyrrolidin-3-yl)-N-methylacetamide, (4aR,8aS)-1-{4-[(2S)-2,3-dihydro-1,4-benzodioxin-2-yl]benzyl}decahydroquinoline, (3R)-1-{4-[(2S)-2,3-dihydro-1,4-benzodioxin-2-yl]benzyl}pyrrolidin-3-ol, (1-{4-[(2S)-2,3-dihydro-1,4-benzodioxin-2-yl]benzyl}piperidin-4-yl)methanol, (3S)-1-{4-[(2S)-2,3-dihydro-1,4-benzodioxin-2-yl]benzyl}pyrrolidin-3-ol, 1-{4-[(2S)-2,3-dihydro-1,4-benzodioxin-2-yl]benzyl}imidazolidin4-one, 1-{4-[(2S)-2,3-dihydro-1,4-benzodioxin-2-yl]benzyl}-N,N-dimethylpyrrolidin-3-amine, 1'-{4-[(2S)-2,3-dihydro-1,4-benzodioxin-2-yl]benzyl}-1,4'-bipiperidin-2-one, 1-{4-[(2S)-2,3-dihydro-1,4-benzodioxin-2-yl]benzyl}-N-(2-hydroxyethyl)piperidine-4-carboxamide, 1-{4-[(2S)-2,3-dihydro-1,4-benzodioxin-2-yl]benzyl}-4-methoxypiperidine, 1-[(1-{4-[(2S)-2,3-dihydro-1,4-benzodioxin-2-yl]benzyl}piperidin-4-yl)methyl]pyrrolidin-2-one, 4-{4-[(2S)-2,3-dihydro-1,4-benzodioxin-2-yl]benzyl}-3-methylmorpholine, 2-{4-[(2S)-2,3-dihydro-1,4-benzodioxin-2-yl]benzyl}-1,2,3,4-tetrahydroisoquinolin-6-ol, 1-[4-(2,3-dihydro-1,4-benzodioxin-2-yl)benzyl]piperidine-3-carboxylic acid, 1-[4-(2,3-dihydro-1,4-benzodioxin-2-yl)benzyl]piperidine-3-carboxamide, (3S)-1-[4-(2,3-dihydro-1,4-benzodioxin-2-yl)benzyl]-3-fluoropyrrolidine, 9-{4-[(2S)-2,3-dihydro-1,4-benzodioxin-2-yl]benzyl}-2,9-diazaspiro[5.5]undecan-1-one, 7-{4-[(2S)-2,3-dihydro-1,4-benzodioxin-2-yl]benzyl}-1,7-diazaspiro[4.4]nonan-2-one, 1-(7-{4-[(2S)-2,3-dihydro-1,4-benzodioxin-2-yl]benzyl}-1,7-diazaspiro[4.4]non-1-yl)ethanone, 7-{4-[(2S)-2,3-dihydro-1,4-benzodioxin-2-yl]benzyl}-1,7-diazaspiro[4.4]nonane-1-carboxamide, 9-{4-[(2S)-2,3-dihydro-1,4-benzodioxin-2-yl]benzyl}-2-methyl-2,9-diazaspiro[5.5]undecan-1-one, 8-{4-[(2S)-2,3-dihydro-1,4-benzodioxin-2-yl]benzyl}-2-methyl-2,8-diazaspiro[4.5]decan-1-one, 7-{4-[(2S)-2,3-dihydro-1,4-benzodioxin-2-yl]benzyl}-1-(methylsulfonyl)-1,7-diazaspiro[4.4]nonane, 2-(7-{4-[(2S)-2,3-dihydro-1,4-benzodioxin-2-yl]benzyl}-1,7-diazaspiro[4.4]non-1-yl)acetamide, (7-{4-[(2S)-2,3-dihydro-1,4-benzodioxin-2-yl]benzyl}-1,7-diazaspiro[4.4]non-1-yl)acetonitrile, 8-{4-[(3S)-2,3-dihydro[1,4]dioxino[2,3-b]pyridin-3-yl]benzyl}-2,8-diazaspiro[4.5]decan-1-one, (3S)-3-[4-(pyrrolidin-1-ylmethyl)phenyl]-2,3-dihydro[1,4]dioxino[2,3-b]pyridine, 7-{4-[(3S)-2,3-dihydro[1,4]dioxino[2,3-b]pyridin-3-yl]benzyl}-1,7-diazaspiro[4.4]nonan-2-one, 1-(7-{4-[(2S)-2,3-dihydro-1,4-benzodioxin-2-yl]benzyl}-1,7-diazaspiro[4.4]non-1-yl)-2-methoxyethanone, 8-{4-[(3S)-2,3-dihydro[1,4]dioxino[2,3-b]pyridin-3-yl]benzyl}-2-methyl-2,8-diazaspiro[4.5]decan-1-one, 9-[(S)-4-(2,3-Dihydro-benzo[1,4]dioxin-2-yl)-benzyl]-2-methyl-2,9-diaza-spiro[5.5]undecan-1-one, 1-{4-[(2S)-2,3-dihydro-1,4-benzodioxin-2-yl]benzyl}-1,4-diazepan-5-one, 1-{4-[(3S)-2,3-dihydro[1,4]dioxino[2,3-b]pyridin-3-yl]benzyl}-1,4-diazepan-5-one, 3-(1-{4-[(2S)-2,3-dihydro-1,4-benzodioxin-2-yl]benzyl}piperidin-4-yl)propanoic acid, 1-{4-[(3S)-2,3-dihydro[1,4]dioxino[2,3-b]pyridin-3-yl]benzyl}piperidine-3-carboxamide, (3S)-3-{4-[(4-methylpiperidin-1-yl)methyl]phenyl}-2,3-dihydro[1,4]dioxino[2,3-b]pyridine, (3S)-3-[4-(azepan-1-ylmethyl)phenyl]-2,3-dihydro[1,4]dioxino[2,3-b]pyridine, (3S)-3-{4-[(4-methyl-1,4-diazepan-1-yl)methyl]phenyl}-2,3-dihydro[1,4]dioxino[2,3-b]pyridine, (3R)-1-{4-[(3S)-2,3-dihydro[1,4]dioxino[2,3-b]pyridin-3-yl]benzyl}pyrrolidin-3-ol, (3S)-3-{4-[(1s,4s)-7-azabicyclo[2.2.1]hept-7-ylmethyl]phenyl}-2,3-dihydro[1,4]dioxino[2,3-b]pyridine, (1-{4-[(3S)-2,3-dihydro[1,4]dioxino[2,3-b]pyridin-3-yl]benzyl}piperidin-4-yl)methanol, (3S)-1-{4-[(3S)-2,3-dihydro[1,4]dioxino[2,3-b]pyridin-3-yl]benzyl}pyrrolidin-3-ol, 1-(4-{4-[(3S)-2,3-dihydro[1,4]dioxino[2,3-b]pyridin-3-yl]benzyl}-1,4-diazepan-1-yl)ethanone, 3-(1-{4-[(3S)-2,3-dihydro[1,4]dioxino[2,3-b]pyridin-3-yl]benzyl}piperidin-4-yl)propan-1-ol, (3S)-3-[4-(1,4-oxazepan-4-ylmethyl)phenyl]-2,3-dihydro[1,4]dioxino[2,3-b]pyridine, 4-(1-{4-[(3S)-2,3-dihydro[1,4]dioxino[2,3-b]pyridin-3-yl]benzyl}piperidin-4-yl)butanoic acid, 1-[4-({4-[(3S)-2,3-dihydro[1,4]dioxino[2,3-b]pyridin-3-yl]benzyl}amino)piperidin-1-yl]ethanone, 1-{4-[(3S)-2,3-dihydro[1,4]dioxino[2,3-b]pyridin-3-yl]benzyl}-N-(2-hydroxyethyl)piperidine-4-carboxamide, (3S)-3-{4-[(4-fluoropiperidin-1-yl)methyl]phenyl}-2,3-dihydro[1,4]dioxino[2,3-b]pyridine, (3S)-3-[4(5,6-dihydro[1,2,4]triazolo[4,3-a]pyrazin-7(8H)-ylmethyl]phenyl]-2,3-dihydro[1,4]dioxino[2,3-b]pyridine, (3S)-3-{4-[(3-methoxypiperidin-1-yl)methyl]phenyl}-2,3-dihydro[1,4]dioxino[2,3-b]pyridine, 1-{4-[(3S)-2,3-dihydro[1,4]dioxino[2,3-b]pyridin-3-yl]benzyl}piperidine-4-carbonitrile, N-(1-{4-[(3S)-2,3-dihydro[1,4]dioxino[2,3-b]pyridin-3-yl]benzyl}piperidin-4-yl)acetamide, (3S)-3-{4-[(1,1-dioxidothiomorpholin-4-yl)methyl]phenyl}-2,3-dihydro[1,4]dioxino[2,3-b]pyridine, (1-{4-[(3S)-2,3-dihydro[1,4]dioxino[2,3-b]pyridin-3-yl]benzyl}piperidin-4-yl)(morpholin-4-yl)methanone, 1-[(1-{4-[(3S)-2,3-dihydro[1,4]dioxino[2,3-b]pyridin-3-yl]benzyl}piperidin-3-yl)methyl]pyrrolidin-2-one, 4-{4-[(3S)-2,3-dihydro[1,4]dioxino[2,3-b]pyridin-3-yl]benzyl}piperazine-1-carboxamide, 8-{4-[(3S)-2,3-dihydro[1,4]dioxino[2,3-b]pyridin-3-yl]benzyl}-1,3,8-triazaspiro[4.5]decane-2,4-dione, (3S)-3-{4-[(3-methoxyazetidin-1-yl)methyl]phenyl}-2,3-dihydro[1,4]dioxino[2,3-b]pyridine, (3S)-3-{4-[(3-methoxypyrrolidin-1-yl)methyl]phenyl}-2,3-dihydro[1,4]dioxino[2,3-b]pyridine, (3S)-3-(4-{[4-(2-methoxyethoxy)piperidin-1-yl]methyl}phenyl)-2,3-dihydro[1,4]dioxino[2,3-b]pyridine, 2-(1-{4-[(3S)-2,3-dihydro[1,4]dioxino[2,3-b]pyridin-3-yl]benzyl}piperidin-4-yl)-N,N-dimethylacetamide, (3S)-3-(4-{[4-(methylsulfonyl)piperidin-1-yl]methyl}phenyl)-2,3-dihydro[1,4]dioxino[2,3-b]pyridine, 1-(1-{4-[(2S)-2,3-dihydro-1,4-benzodioxin-2-yl]benzyl}piperidin-4-yl)urea, N-(1-{4-[(2S)-2,3-dihydro-1,4-benzodioxin-2-yl]benzyl}piperidin-4-yl)methanesulfonamide, 1-{4-[(2S)-2,3-dihydro-1,4-benzodioxin-2-yl]benzyl}piperidine-4-carbonitrile, N-(1-{4-[(2S)-2,3-dihydro-1,4-benzodioxin-2-yl]benzyl}piperidin-4-yl)acetamide, 1-{4-[(2S)-2,3-dihydro-1,4-benzodioxin-2-yl]benzyl}-N-methylpiperidine-4-carboxamide, (1-{4-[(2S)-2,3-dihydro-1,4-benzodioxin-2-yl]benzyl}piperidin-4-yl)(morpholin-4-yl)methanone, 4-(1-{4-[(2S)-2,-dihydro-1,4-benzodioxin-2-yl]benzyl}piperidin-4-yl)butanoic acid, [(3R)-1-{4-[(2S)-2,3-dihydro-1,4-benzodioxin-2-yl]benzyl}piperidin-3-yl]acetic acid, [(3S)-1-{4-[(2S)-2,3-dihydro-1,4-benzodioxin-2-yl]benzyl}piperidin-3-yl]acetic acid, [(3R)-1-{4-[(2S)-2,3-dihydro-1,4-benzodioxin-2-yl]benzyl}pyrrolidin-3-yl]acetic acid, 1-(4-{4-[(3S)-2,3-dihydro[1,4]dioxino[2,3-b]pyridin-3-yl]benzyl}piperazin-1-yl)ethanone, 1-{4-[(3S)-2,3-dihydro[1,4]dioxino[2,3-b]pyridin-3-yl]benzyl}piperidin-4-ol, 1-(1-{4-[(3S)-2,3-dihydro[1,4]dioxino[2,3-b]pyridin-3-yl]benzyl}piperidin-4-yl)urea, (3S)-3-(4-{[4-(methylsulfonyl)piperazin-1-yl]methyl}phenyl)-2,3-dihydro[1,4]dioxino[2,3-b]pyridine, 1-{4-[(3S)-2,3-dihydro[1,4]dioxino[2,3-b]pyridin-3-yl]benzyl}piperidine-4-carboxylic acid, N-(1-{4-[(3S)-2,3-dihydro[1,4]dioxino[2, 3-b]pyridin-3-yl]benzyl}piperidin-4-yl)methanesulfonamide, 1-{4-[(2S)-2,3-dihydro-1,4-benzodioxin-2-yl]benzyl}piperidin-4-ol, 1-{4-[(2R)-2,3-dihydro-1,4-benzodioxin-2-yl]benzyl}piperidin-4-ol, 8-{4-[(2S)-2,3-dihydro-1,4-benzodioxin-2-yl]benzyl]-2,8-diazaspiro[4.5]decan-1-one, 8-{4-[(2R)-2,3-dihydro-1,4-benzodioxin-2-yl]benzyl}-2,8-diazaspiro[4.5]decan-1-one, 1-{4-[(2S)-2,3-dihydro-1,4-benzodioxin-2yl]benzyl}pyrrolidine, 1-{4-[(2R)-2,3-dihydro-1,4-benzodioxin-2-yl]benzyl}pyrrolidine, 4-{4-[(2S)-2,3-dihydro-1,4-benzodioxin-2-yl]benzyl}morpholine, 4-{4-[(2R)-2,3-dihydro-1,4-benzodioxin-2-yl]benzyl}morpholine, 1-{4-[(2S)-2,3-dihydro-1,4-benzodioxin-2-yl]benzyl}piperidine-4-carboxylic acid, 1-{4-[(2R)-2,3-dihydro-1,4-benzodioxin-2-yl]benzyl}piperidine-4-carboxylic acid, 4-[4-(7-fluoro-2,3-dihydro-1,4-benzodioxin-2-yl)benzyl]morpholine, 1-[4-(7-fluoro-2,3-dihydro-1,4-benzodioxin-2-yl)benzyl]pyrrolidine, (3S)-3-[4-(morpholin-4-ylmethyl)phenyl]-2,3-dihydro[1,4]dioxino[2,3-b]pyridine, (3R)-3-[4-(morpholin-4-ylmethyl)phenyl]-2,3-dihydro[1,4]dioxino[2,3-b]pyridine, 1-{4-[(3S)-2,3-dihydro[1,4]dioxino[2,3-b]pyridin-3-yl]benzyl}piperidine-4-carboxamide, 1-{4-[(3R)-2,3-dihydro[1,4]dioxino[2,3-b]pyridin-3-yl]benzyl}piperidine-4-carboxamide, 1-[4-(2,3-dihydro[1,4]dioxino[2,3-b]pyridin-3-yl)benzyl]pyrrolidin-2-one, 3-[4-(2,3-dihydro[1,4]dioxino[2,3-b]pyridin-3-yl)benzyl]-1,3-oxazolidin-2-one, 1-{4-[(2S)-2,3-dihydro-1,4-benzodioxin-2-yl]benzyl}-4-methylpiperidine-4-carboxylic acid, (3R,4R)-1-{4-[(2S)-2,3-dihydro-1,4-benzodioxin-2-yl]benzyl}-3-methylpiperidine-4-carboxylic acid, 1-{4-[(2S)-2,3-dihydro-1,4-benzodioxin-2-yl]benzyl}-4-fluoropiperidine-4-carboxylic acid, (3R)-1-{4-[(2S)-2,3-dihydro-1,4-benzodioxin-2-yl]benzyl}pyrrolidine-3-carboxylic acid, (3S)-1-{4-[(2S)-2,3-dihydro-1,4-benzodioxin-2-yl]benzyl}pyrrolidine-3-carboxylic acid, 1-{4-[(2S)-2,3-dihydro-1,4-benzodioxin-2-yl]benzyl}-4-(1H-tetrazol-5-yl)piperidine, 1-{4-[(2S)-2,3-dihydro-1,4-benzodioxin-2-yl]benzyl}piperidin-4-amine, N-(1-{4-[(2S)-2,3-dihydro-1,4-benzodioxin-2-yl]benzyl}piperidin-4-yl)-2-hydroxyacetamide, N-(1-{4-[(2S)-2,3-dihydro-1,4-benzodioxin-2-yl]benzyl}piperidin-4-yl)-2-methoxyacetamide, N-(1-{4-[(2S)-2,3-dihydro-1,4-benzodioxin-2-yl]benzyl}piperidin-4-yl)-2-hydroxy-2-methylpropanamide, N-(1-{4-[(3S)-2,3-dihydro[1,4]dioxino[2,3-b]pyridin-3-yl]benzyl}piperidin-4-yl)-2-hydroxy-2-methylpropanamide, N-(1-{4-[(3S)-2,3-dihydro[1,4]dioxino[2,3-b]pyridin-3-yl]benzyl}piperidin-4-yl)-2-hydroxyacetamide, N-(1-{4-[(3S)-2,3-dihydro[1,4]dioxino[2,3-b]pyridin-3-yl]benzyl}piperidin-4-yl)-1-hydroxycyclopropanecarboxamide, 1-{4-[(2S)-2,3-dihydro-1,4-benzodioxin-2-yl]benzyl}-4-(1,1-dioxido-1,2-thiazolidin-2-yl)piperidine, 1-(1-{4-[(2S)-2,3-dihydro-1,4-benzodioxin-2-yl]phenyl}ethyl)pyrrolidine, 4-(1-{4-[(2S)-2,3-dihydro-1,4-benzodioxin-2-yl]phenyl}ethyl)morpholine, 1-(1-{4-[(2S)-2,3-dihydro-1,4-benzodioxin-2-yl]phenyl}ethyl)piperidine-4-carboxylic acid, 1-{4-[(3S)-2,3-dihydro[1,4]dioxino[2,3-b]pyridin-3-yl]benzyl}-4-methylpiperidine-4-carboxylic acid, 2-(1-{4-[(2S)-2,3-dihydro-1,4-benzodioxin-2-yl]benzyl}piperidin-4-yl)-2-methylpropanoic acid, 2-(1-{4-[(3S)-2,3-dihydro[1,4]dioxino[2,3-b]pyridin-3-yl]benzyl}piperidin-4-yl)-2-methylpropanoic acid, 4-[(1-{4-[(2S)-2,3-dihydro-1,4-benzodioxin-2-yl]benzyl}piperidin-4-yl)methyl]benzoic acid, 2-{4-[(2S)-2,3-dihydro-1,4-benzodioxin-2-yl]benzyl}-1,2,3,4-tetrahydroisoquinoline-7-carboxylic acid, 4-(1-{4-[(2S)-2,3-dihydro-1,4-benzodioxin-2-yl]benzyl}piperidin-4-yl)benzoic acid, 4-[(1-{4-[(3S)-2,3-dihydro[1,4]dioxino[2,3-b]pyridin-3-yl]benzyl}piperidin-4-yl)methyl]benzoic acid, 4-(1-{4-[(3S)-2,3-dihydro[1,4]dioxino[2,3-b]pyridin-3-yl]benzyl}piperidin-4-yl)benzoic acid, 3-[(4-{4-[(2S)-2,3-dihydro-1,4-benzodioxin-2-yl]benzyl}piperazin-1-yl)methyl]benzoic acid, 7-[(S)-4-(2,3-dihydro[2,3-b]pyridin-3-yl)-benzyl]-5,6,7,8-tetrahydro-[1,2,4]triazolo[4,3-a]pyrazine-3-carboxylic acid ethyl ester, 7-[(S)-4-(2,3-Dihydro-[1,4]dioxino[2,3-b]pyridin-3-yl)-benzyl]-5,6,7,8-tetrahydro-[1,2,4]triazolo[4,3-a]pyrazine-3-carboxylic acid amide, 7-[(S)-4-(2,3-dihydro-[1,4]dioxino[2,3-b]pyridin-3-yl)-benzyl]-5,6,7,8-tetrahydro-[1,2,4]triazolo[4,3-a]pyrazine-3-carboxylic acid methylamide, 7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid amide, 7-[(S)-4-(2,3-dihydro-[1,4]dioxino[2,3-b]pyridin-3-yl)-benzyl]-5,6,7,8-tetrahydro-imidazo[1,2-a]pyrazine-2-carboxylic acid methylamide, 6-[(S)-4-(2,3-dihydro-[1,4]dioxino[2,3-b]pyridin-3-yl)-benzyl]-5,6,7,8-tetrahydro-4H-1,2,3a,6-tetraaza-azulene-3-carboxylic acid amide, 6-[(S)-4-(2,3-Dihydro-[1,4]dioxino[2,3-b]pyridin-3-yl)-benzyl]-5,6,7,8-tetrahydro-4H-1,2,3a,6-tetraaza-azulene-3-carboxylic acid methylamide, [(1α,5α,6α)-3-[(S)-4-(2,3-dihydro-[1,4]dioxino[2,3-b]pyridin-3-yl)-benzyl]-3-aza-bicyclo[3.1.0]hexane]-6-carboxylic acid ((S)-2-hydroxy-propyl)-amide, [(1α,5α,6α)-3-[(S)-4-(2,3-Dihydro-[1,4]dioxino[2,3-b]pyridin-3-yl)-3-aza-bicyclo[3.1.0]hexane]-6-carboxylic acid ((S)-2-hydroxy-1-methyl-ethyl)-amide, 7-[(S)-4-(2,3-Dihydro-[1,4]dioxino[2,3-b]pyridin-3-yl)-benzyl]-5,6,7,8-tetrahydro-imidazo[1,2-a]pyrazine-3carbonitrile, N-{(1α,5α,6α)-3-[(S)-4-(2,3-Dihydro-[1,4]dioxino[2,3-b]pyridin-3-yl)-benzyl]-3-aza-bicyclo[3.1.0]hex-6-yl}-acetamide, [(1α,5α,6α)-3-[(S)-4-(2,3-Dihydro-[1,4]dioxino[2,3-b]pyridin-3-yl)-benzyl]-3-aza-bicyclo[3.1.0]hexane-6-carboxylic acid (2-hydroxy-2-methyl-propyl)]-amide, N-{1-[(S)-4-(2,3-Dihydro-[1,4]dioxino[2,3-b]pyridin-3-yl)-benzyl]-piperidin-4-yl}-2-methoxy-acetamide, 1-{4-[(S)-4-(2,3-Dihydro-[1,4]dioxino[2,3-b]pyridin-3-yl)-benzyl]-piperazin-1-yl}-2-hydroxy-ethanone, 4-{1-[(S)-4-(2,3-Dihydro-benzo[1,4]dioxin-2-yl)-benzyl]-azetidin-3-yl}-benzoic acid, 1-[(S)-4-(2,3-Dihydro-[1,4]dioxino[2,3-b]pyridin-3-yl)-benzyl]-piperidine-4-carboxylic acid (2-hydroxy-2-methyl-propyl)-amide, 1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-methanesulfonyl-ethanone, 1-{4-[(S)-4-(2,3-Dihydro-[1,4]dioxino[2,3-b]pyridin-3-yl)-benzyl]-[1,4]diazepan-1-yl}-2-methoxy-ethanone, 5-[(S)-4-(2,3-Dihydro-[1,4]dioxino[2,3-b]pyridin-3-yl)-benzyl]-4,5,6,7-tetrahydro-thiazolo[5,4-c]pyridin-2-ylamine, {(endo)-8-[(S)-4-(2,3-Dihydro-[1,4]dioxino[2,3-b]pyridin-3-yl)-benzyl]-8-aza-bicyclo[3.2.1]oct-3-yl}-urea, 2-{1-[(S)-4-(2,3-Dihydro-[1,4]dioxino[2,3-b]pyridin-3-yl)-benzyl]-piperidin-4-yl}-N-methoxy-acetamide, (R)—N-{1-[(S)-4-(2,3-Dihydro-[1,4]dioxino[2,3-b]pyridin-3-yl)-benzyl]-piperidin-4-yl}-2-methylamino-propionamide, N-{1-[(S)-4-(2,3-Dihydro-[1,4]dioxino[2,3-b]pyridin-3-yl)-benzyl]-piperidin-4-ylmethyl}-2-hydroxy-2-methyl-propionamide, N—{(1α,5α,6α)-3-[(S)-4-(2,3-Dihydro-[1,4]dioxino[2,3-b]pyridin-3-yl)-benzyl]-3-aza-bicyclo[3.1.0]hex-6-ylmethyl}-methanesulfonamide, 1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-ethanone, 4-{1-[(S)-4-(2,3-Dihydro-[1,4]dioxino[2,3-b]pyridin-3-yl)-benzyl]-piperidin-4-yl}-cyclohexanecarboxylic acid, 1-[(S)-4-(2,3-Dihydro-benzo[1,4]dioxin-2-yl)-benzyl]-azepane-4-carboxylic acid, [(1α,5α,6α)-3-[(S)-4-(2,3-Dihydro-benzo[1,4]dioxin-2-yl)-benzyl]-3-aza-bicyclo[3.1.0]hexane]-6-carboxylic acid, (1S,4S)-5-[(S)-4-(2,3-Dihydro-[1,4]dioxino[2,3-b]pyridin-3-yl)-benzyl]-2,5-diaza-bicyclo[2.2.1]

heptane-2-carboxylic acid amide, 1-[(S)-4-(2,3-Dihydro-[1,4]dioxino[2,3-b]pyridin-3-yl)-benzyl]-4-phenyl-piperidin-4-ol, 1-{5-[(S)-4-(2,3-Dihydro-[1,4]dioxino[2,3-b]pyridin-3-yl)-benzyl]-hexahydro-pyrrolo[3,4-c]pyrrol-2-yl}-ethanone, 1-{8-[(S)-4-(2,3-Dihydro-[1,4]dioxino[2,3-b]pyridin-3-yl)-benzyl]-3,8-diaza-bicyclo[3.2.1]oct-3-yl}-ethanone, 5-[(S)-4-(2,3-Dihydro-[1,4]dioxino[2,3-b]pyridin-3-yl)-benzyl]-hexahydro-pyrrolo[3,4-c]pyrrole-2-carboxylic acid amide, {(exo)-8-[(S)-4-(2,3-Dihydro-[1,4]dioxino[2,3-b]pyridin-3-yl)-benzyl]-8-aza-bicyclo[3.2.1]oct-3-yl}-urea, 2-{1-[(S)-4-(2,3-Dihydro-[1,4]dioxino[2,3-b]pyridin-3-yl)-benzyl]-piperidin-4-yloxy}-acetamide, (S)-3-[4-(1,1-Dioxo-1lambda6-[1,4]thiazepan-4-ylmethyl)-phenyl]-2,3-dihydro-[1,4]dioxino[2,3-b]pyridine, 1-[(S)-4-(2,3-Dihydro-[1,4]dioxino[2,3-b]pyridin-3-yl)-benzyl]-4-methyl-piperidin-4-ol, 1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-2-hydroxy-ethanone, N-{(endo)-8-[(S)-4-(2,3-Dihydro-[1,4]dioxino[2,3-b]pyridin-3-yl)-benzyl]-8-aza-bicyclo[3.2.1]oct-3-yl}-acetamide, N-{1-[(S)-4-(2,3-Dihydro-[1,4]dioxino[2,3-b]pyridin-3-yl)-benzyl]-piperidin-4-ylmethyl}-acetamide, 1-{(1S,4S)-5-[(S)-4-(2,3-Dihydro-[1,4]dioxino[2,3-b]pyridin-3-yl)-benzyl]-2,5-diaza-bicyclo[2.2.2]oct-2-yl}-2-hydroxy-ethanone, {1-[(S)-4-(2,3-dihydro-[1,4]dioxino-[2,3-b]pyridin-3-yl)-benzyl]-spiro-[3H-indole-3,4'-piperidine]-1(2H)-urea, {1-[(S)-4-(2,3-Dihydro-[1,4]dioxino[2,3-b]pyridin-3-yl)-benzyl]-piperidin-4-ylmethyl}-urea, {4-[(S)-4-(2,3-Dihydro-[1,4]dioxino[2,3-b]pyridin-3-yl)-benzyl]-piperazin-1-yl}-acetonitrile, (R)-7-[(S)-4-(2,3-Dihydro-[1,4]dioxino[2,3-b]pyridin-3-yl)-benzyl]-hexahydro-oxazolo[3,4-a]pyrazin-3-one, {1-[(S)-4-(2,3-Dihydro-[1,4]dioxino[2,3-b]pyridin-3-yl)-benzyl]-piperidin-4-yl}-(3-hydroxy-azetidin-1-yl)-methanone, 1-[(S)-4-(2,3-Dihydro-[1,4]dioxino[2,3-b]pyridin-3-yl)-benzyl]-piperidine-4-carboxylic acid [(S)-1-(tetrahydro-furan-2-yl)methyl]-amide, N-[3-[4-[[4-[(3S)-2,3-dihydro-[1,4]dioxino[2,3-b]pyridin-3-yl]phenyl]methyl]piperazin-1-yl]-3-oxo-propyl]acetamide, N-[1-[[4-[(3S)-2,3-dihydro-[1,4]dioxino[2,3-b]pyridin-3-yl]phenyl]methyl]-4-piperidyl]-2-(2-oxopyrrolidin-1-yl)acetamide, N-[1-[[4-(3S)-2,3-dihydro-[1,4]dioxino[2,3-b]pyridin-3-yl]phenyl]methyl]-4-piperidyl]tetrahydropyran-4-carboxamide, 3-{1-[(S)-4-(2,3-Dihydro-[1,4]dioxino[2,3-b]pyridin-3-yl)-benzyl]-piperidin-4-yl}-[1,3]oxazinan-2-one, 1-{(1S,4S)-5-[(S)-4-(2,3-Dihydro-[1,4]dioxino[2,3-b]pyridin-3-yl)-benzyl]-2,5-diaza-bicyclo[2.2.1]hept-2-yl}-ethanone, (S)-3-{4-[4-(Pyridin-3-yloxy)-piperidin-1-ylmethyl]-phenyl}-2,3-dihydro-[1,4]dioxino[2,3-b]pyridine, 1-[(S)-4-(2,3-Dihydro-[1,4]dioxino[2,3-b]pyridin-3-yl)-benzyl]-4-phenyl-piperidine-4-carboxylic acid, (S)-3-[4-(1-Oxo-1lambda4-thiomorpholin-4-ylmethyl)-phenyl]-2,3-dihydro-[1,4]dioxino[2,3-b]pyridine, and (S)-7-[(S)-4-(2,3-dihydro-[1,4]dioxino[2,3-b]pyridin-3-yl)-benzyl]-hexahydro-oxazolo[3,4-a]pyrazin-3-one, and pharmaceutically acceptable salts thereof.

3. The method of claim 1, wherein said ring B of group A of the compound of formula (I) is a non-aromatic 4 to 8-membered monocyclic radical.

4. The method of claim 3, wherein said non-aromatic 4 to 8-membered monocyclic radical is selected from the group consisting of azetidine, tetrahydropyrrole, piperidine, hexamethyleneimine, 1,2-diazetidine, pyrazolidine, imidazolidine, piperazine, hexahydrodiazepine, isoxazolidine, oxazolidine, tetrahydro-2H-1,3-oxazine, morpholine, and hexahydro-1,4-oxazepine, wherein said non-aromatic 4 to 8-membered monocyclic radical may be further optionally substituted by one to three groups selected from halo, —OH, (=O), —C(O)OH, —C(O)O— ($C_1$-$C_6$)alkyl, and —($C_1$-$C_6$)alkyl.

5. The method of claim 1, wherein said ring B of group A of the compound of formula (I) is a spirocyclic heterocyclic radical.

6. The method of claim 1, wherein said ring B of group A of the compound of formula (I) is a bridged bicyclic radical; or a 6 to 11-membered fused bicyclic radical which may be non-aromatic or have one aromatic ring provided that the aromatic ring of the bicyclic radical, when present, is not attached to the carbon atom 1 of the compound of formula (I).

7. The method of claim 1, wherein said L is —$CH_2$—.

8. The method of claim 1, wherein said L is absent.

9. The method of claim 3, wherein said non-aromatic 4 to 8-membered monocyclic radical is selected from azetidinyl, pyrrolidinyl, piperidinyl and azepanyl;

wherein each of the foregoing azetidinyl, pyrrolidinyl, piperidinyl and azepanyl rings is optionally substituted by one to three groups selected from halo, —OH, (=O), —C(O)OH, C(O)O—($C_1$-$C_6$)alkyl, and —($C_1$-$C_6$)alkyl;

wherein L is absent or a linker selected from —($C_1$-$C_6$) alkylene; and wherein $R^6$ is selected from halo, —OR', —$CF_3$, —CN, —($C_1$-$C_6$)alkyl, —O($C_1$-$C_6$)alkyl, —C(O)$R^7$, —C(O)$_2$$R^7$, —C(O)N($R^7$)$_2$, —N($R^7$)$_2$, —NHC(O)$R^7$, —NHC(O)N($R^7$)$_2$, —S(O)$_2$$R^7$, —NH—S(O)$_2$—$R^7$, —($C_3$-$C_6$) cycloalkyl, -(4- to 11-membered)heterocycloalkyl, —($C_6$-$C_{10}$)aryl, and -(5- to 11-membered)heteroaryl, wherein each of said —($C_1$-$C_6$)alkyl, —O($C_1$-$C_6$)alkyl, —($C_3$-$C_6$)cycloalkyl, -(4- to 11-membered)heterocycloalkyl, —($C_6$-$C_{10}$)aryl, and -(5- to 11-membered) heteroaryl of said $R^6$ group is optionally substituted where possible with one to three groups selected from halo, —OH, —$CF_3$, —CN, (=O), —($C_1$-$C_6$)alkyl, —C(O)OH, —C(O)O—($C_1$-$C_6$)alkyl, —$NH_2$, —NH ($C_1$-$C_6$)alkyl, —N(($C_1$-$C_6$)alkyl)$_2$, —S(O)$_2$($C_1$-$C_6$)alkyl, —($C_3$-$C_6$)cycloalkyl, -(4- to 11-membered)heterocycloalkyl, —($C_6$-$C_{10}$) aryl, and -(5- to 11-membered) heteroaryl.

10. The method of claim 1, wherein said X is N.

11. The method of claim 1, wherein said X is CH.

12. The method of claim 1, wherein the age-related cognitive disease is CADASIL.

13. The method of claim 10, wherein the compound of formula (I) is:

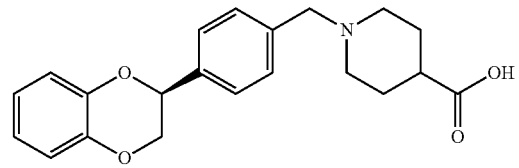

or a pharmaceutically acceptable salt thereof.

* * * * *

UNITED STATES PATENT AND TRADEMARK OFFICE
CERTIFICATE OF CORRECTION

PATENT NO. : 11,957,671 B2  
APPLICATION NO. : 17/977687  
DATED : April 16, 2024  
INVENTOR(S) : Meghan Kerrisk Campbell et al.

Page 1 of 4

It is certified that error appears in the above-identified patent and that said Letters Patent is hereby corrected as shown below:

In the Drawings

Please replace Sheet 43 with attached Sheet 43.

In the Specification

Please replace "(IL-10)" with -- "(IL-1ß) -- (Column 7, Line 33).

Please replace "FIG. 88A" with -- FIG. 88A. -- (Column 10, Line 2).

Please replace "from endothelial" with -- from endothelial cells -- (Column 11, Line 16).

Please replace "wherein each of said," with -- wherein each of said -- (Column 16, Line 67).

Please replace "$R^6$ is elected" with -- $R^6$ is selected -- (Column 20, Line 20).

Please replace "wherein each of said," with -- wherein each of said -- (Column 20, Line 26).

Please replace the following structure for Compound No. 199 in TABLE 1

" 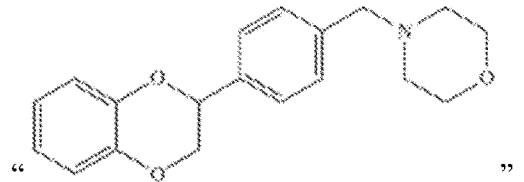 "

with -- 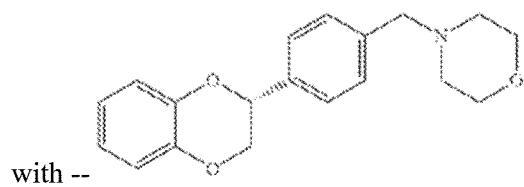 -- (Column 81).

Signed and Sealed this  
First Day of October, 2024

Katherine Kelly Vidal  
*Director of the United States Patent and Trademark Office*

CERTIFICATE OF CORRECTION (continued)
U.S. Pat. No. 11,957,671 B2

Please replace "methyl[" with -- methyl} -- (Column 96, Compound No. 237 in TABLE 1).

Please replace "a pharmaceutically salt" with -- a pharmaceutically acceptable salt -- (Column 98, Line 22).

Please replace "The invention includes the use of any compounds of described above containing one or more asymmetric carbon atoms may occur as racemates and racemic mixtures, single enantiomers, diastereomeric mixtures and individual diastereomers." with -- The invention includes the use of any compounds of described above containing one or more asymmetric carbon atoms. These compounds may occur as racemates and racemic mixtures, single enantiomers, diastereomeric mixtures and individual diastereomers. -- (Column 102, Lines 5-9).

Please replace "effect" with -- effect. -- (Column 102, Line 57).

Please replace "pramipexolole" with -- pramipexole -- (Column 111, Line 21).

Please replace "rotingotine" with -- rotigotine -- (Column 111, Line 22).

Please replace "or" with -- of -- (Column 113, Line 39).

Please replace "complete minutes" with -- complete 5 minutes -- (Column 128, Line 5).

Please replace "(n=13,13,11,12)." with -- (n=13,13,11,12)). -- (Column 133, Line 6).

Please replace "(n=14,13,12,12)." with -- (n=14,13,12,12)). -- (Column 133, Line 13).

Please replace "(n=14,13,12,12)." with -- (n=14,13,12,12)). -- (Column 133, Line 17).

Please replace "(n=14,13,12,12)." with -- (n=14,13,12,12)). -- (Column 133, Lines 20-21).

Please replace "(n=14,13,12,12)." with -- (n=14,13,12,12)). -- (Column 133, Line 24).

Please replace "(n=15,15,15,15)." with -- (n=15,15,15,15)). -- (Column 133, Line 51).

Please replace "the dentate gryus" with -- the dentate gyrus -- (Column 139, Line 60).

Please replace "signaling" with -- signaling. -- (Column 141, Line 56).

Please replace "GO germs" with -- GO terms -- (Column 145, Lines 1-2).

In the Claims

Please replace the following structure in Claim 1

CERTIFICATE OF CORRECTION (continued)
U.S. Pat. No. 11,957,671 B2

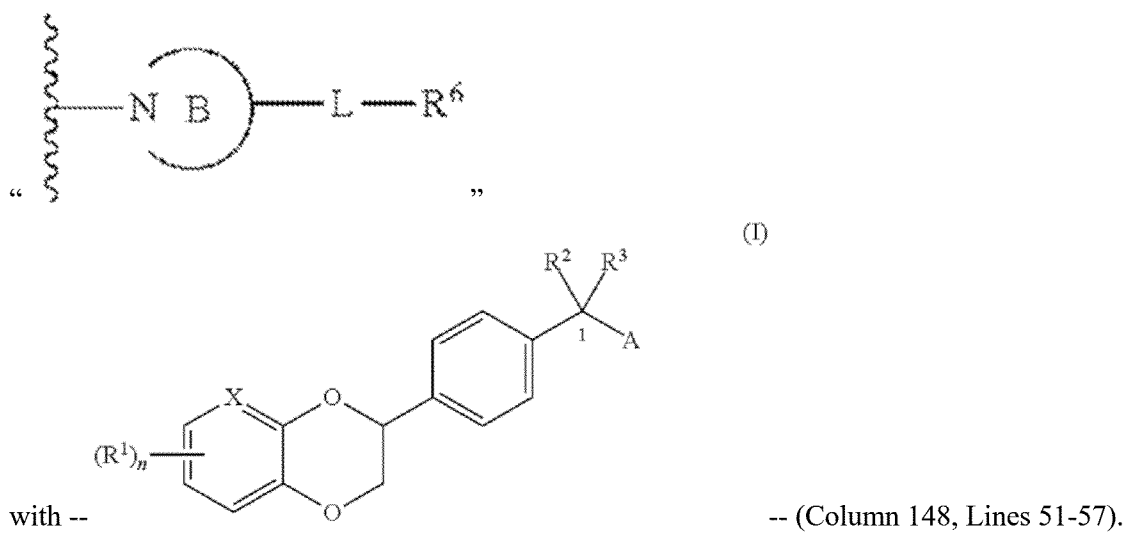

with --            -- (Column 148, Lines 51-57).

Please replace "[(2S)-2,-dihydro-1,4-benzodioxin-2-yl]" in Claim 2 with -- [(2S)-2,3-dihydro-1,4-benzodioxin-2-yl] -- (Column 152, Line 53).

Please replace "[(2S)-2,3-dihydro-1,4-benzodioxin-2yl]" in Claim 2 with -- [(2S)-2,3-dihydro-1,4-benzodioxin-2-yl] -- (Column 153, Lines 7-8).

Please replace "–OR',", with -- –OR$^7$, -- (Column 156, Line 29).